(12) United States Patent
Rabinowitz et al.

(10) Patent No.: US 10,584,132 B2
(45) Date of Patent: Mar. 10, 2020

(54) SHMT INHIBITORS

(71) Applicant: The Trustees of Princeton University, Princeton, NJ (US)

(72) Inventors: Joshua D. Rabinowitz, Princeton, NJ (US); Hahn Kim, Princeton, NJ (US); Gregory S. Ducker, Rocky Hill, NJ (US); Jonathan M. Ghergurovich, Philadelphia, PA (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 16/103,375

(22) Filed: Aug. 14, 2018

(65) Prior Publication Data

US 2018/0354964 A1    Dec. 13, 2018

Related U.S. Application Data

(62) Division of application No. 15/705,200, filed on Sep. 14, 2017, now Pat. No. 10,077,273.

(60) Provisional application No. 62/470,131, filed on Mar. 10, 2017, provisional application No. 62/394,689, filed on Sep. 14, 2016.

(51) Int. Cl.
| | |
|---|---|
| *A61K 31/4162* | (2006.01) |
| *C07D 491/052* | (2006.01) |
| *A61K 31/19* | (2006.01) |
| *A61K 31/496* | (2006.01) |
| *A61K 31/198* | (2006.01) |
| *A61K 45/06* | (2006.01) |

(52) U.S. Cl.
CPC .......... *C07D 491/052* (2013.01); *A61K 31/19* (2013.01); *A61K 31/198* (2013.01); *A61K 31/4162* (2013.01); *A61K 31/496* (2013.01); *A61K 45/06* (2013.01)

(58) Field of Classification Search
CPC ................. C07D 491/052; A61K 31/4162
See application file for complete search history.

(56) References Cited

U.S. PATENT DOCUMENTS

| | | | |
|---|---|---|---|
| 4,918,074 | A | 4/1990 | Tsuda et al. |
| 9,480,259 | B2 | 11/2016 | Witshel et al. |
| 10,077,273 | B2 | 9/2018 | Rabinowitz |
| 2018/0072751 | A1 | 3/2018 | Rabinowitz et al. |
| 2018/0117010 | A1 | 5/2018 | Rabinowitz |

FOREIGN PATENT DOCUMENTS

| | | | |
|---|---|---|---|
| WO | WO 2005/012577 A1 | 2/2005 | |
| WO | WO 2012/078902 A2 | 6/2012 | |
| WO | WO 2013/096820 A1 | 6/2013 | |
| WO | WO 2013/182472 A1 | 12/2013 | |
| WO | WO 2016/007905 A1 | 1/2016 | |
| WO | WO 2016/145252 A1 | 9/2016 | |

OTHER PUBLICATIONS

Non-Final Office Action for U.S. Appl. No. 15/552,442, "SHMT Inhibitors", dated Oct. 19, 2018.
Final Office Action for U.S. Appl. No. 15/552,442, "SHMT Inhibitors", dated Jun. 12, 2019.
Antle, V.D., et al. "Substrate specificity of glycinamide ribonucleotide synthetase from chicken liver", J. Biol. Chem. 271(14):8192-8195 (1996).
Ben-Sahra I., et al., "mTORC1 induces purine synthesis through control of the mitochondrial tetrahydrofolate cycle", Science 351(6274): 728-732 (2016).
Cader, M.Z., et al. :Crystal structure of human wildtype and S581L-mutant glycyl-tRNA synthetase, an enzyme underlying distal spinal muscular atrophy, FEBS Lett. 581(16):2959-2964 (2007).
Clasquin, M.F., et al., "LC-MS Data Processing with MAVEN: a Metabolomic Analysis and Visualization Engine", Curr. Protoc. Bioinformatics Ch. 14, Unit 14.11, doi: 10.1002/0471250953. bi1411s37 (2012).
Cockrell, G.M., et al. "New Paradigm for Allosteric Regulation of *Escherichia coli* Aspartate Transcarbamoylase", Biochemistry 52(45):8036-8047 (2013).
Ducker, G.S., et al., "One-Carbon Metabolism in Health and Disease", Cell Metab. 25, 27-42 (2017).
Ducker, G.S., et al., "Reversal of cytosolic One-Carbon Flux Compensates for Loss of the Mitochondrial Folate Pathway", Cell Metab. 23:1140-1153 (2016).
Eggert, U.S., et al. "Parallel Chemical Genetic and Genome-Wide RNAi Screens Identify Cytokinesis Inhibitors and Targets", Plos Biol 2(12):e379-9 (2004).
Farber, S. "Temporary remissions in acute leukemia in children produced by folid acid antagonist, 4-aminopteroyl-glutamic acid (aminopterin)", New England Journal of Medicine 238(787-793):1-7 (1948).
Ginman, T., et al., Core Refinement toward Permeable β-Secretase (BACE-1) Inhibitors with Low HERG Activity, J. Med. Chem. 56(11): 4181-4205 (2013).
Guertin, D.A., et al. "Ablation in mice of the mTORC components raptor, rictor, or mLST8 reveals that mTORC2 is required for signaling to AKT-FOXO and PKCalpha, but not S6K1", Dev. Cell 11(6):859-871 (2006).
Harvey, R.J., Yee BK "Glycine transporters as novel therapeutic targets in schizophrenia, alcohol dependence and pain", Nat. Rev. Drug Discov. 12(11):866-885 (2013).
International Preliminary Report on Patentability for International Application No. PCT/US2016/021870, "SHMT Inhibitors", dated May 13, 2016.
International Search Report and Written Opinion for International Application No. PCT/US2016/021870, "SHMT Inhibitors", dated May 13, 2016.

(Continued)

*Primary Examiner* — Golam M Shameem
(74) *Attorney, Agent, or Firm* — Hamilton, Brook, Smith & Reynolds, P.C.

(57) ABSTRACT

The disclosure provides compounds of Formulae (I)-(IX). The disclosed compounds are capable of inhibiting a mammalian SHMT. Compounds of the disclosure have numerous uses, such as for treatment of cancer or autoimmue disorders.

22 Claims, 35 Drawing Sheets
(34 of 35 Drawing Sheet(s) Filed in Color)

(56) References Cited

OTHER PUBLICATIONS

Jain M., et al. "Metabolite Profiling Identifies a Key Role for Glycine in Rapid Cancer Cell Proliferation", Science 336(6084):1040-1044 (2012).
Kamel, M.M., "Convenient Synthesis, Characterization, Cytotoxicity and Toxicity of Pyrazole Derivatives", Acta Chim. Slov. 62(1): 136-151 (2015).
Kiriyama, Y., et al. "Biochemical characterization of U937 cells resistant to L-asparaginase: the role of asparagine synthetase", Leukemia 3(4):294-297 (1989).
Komykhov, S.A., et al., "The Reaction of Amino-Imidazoles, -Pyrazoles and -Triazoles with α-β-Unsaturated Nitriles", J. Heterocyclic Chem. 42(6): 1111-1116 (2005).
Labuschagne, C.F., et al., "Serine, but Not Glycine, Supports One-Carbon Metabolism and Proliferation of Cancer Cells", CellReports 7,1248-1258 (2014).
Lamarre, S.G., et al., "An isotope-dilution, GC-MS assay for formate and its application to human and animal metabolism", Amino Acids 46: 1885-1891 (2014).
Lee, G.Y., et al. "Comparative oncogenomics identifies PSMB4 and SHMT2 as potential cancer driver genes", Cancer Res. 74(11):3114-3126 (2014).
Lewis, C.A., et al. "Tracing compartmentalized NADPH metabolism in the cytosol and mitochondria of Mammalian cells" Mol. Cell 55(2):253-263 (2014).
Loayza-Puch, F., et al. "Tumour-specific proline vulnerability uncovered by differential ribosome codon reading", Nature 530(7591):490-494 (2016).
Locasale, J.W., et al. "Phosphoglycerate dehydrogenase diverts glycolytic flux and contributes to oncogenesis" Nat. Genet. 43(9):869-874 (2011).
Longley, D.B., et al., "5-Fluorouracil: mechanisms of action and clinical strategies" Nat. Rev. Cancer 3(5):330-338 (2003).
Lu, W., et al., "Metabolomic Analysis via Reversed-Phase Ion-Pairing Liquid Chromatography Coupled to a Stand Alone Orbitrap Mass Spectrometer", Anal. Chem. 82: 3212-3221 (2010).
Ma, E.H., et al., "Serine Is an Essential Metabolite for Effector T Cell Expansion," Cell Metab. 25,345-357 (2017).
Marani, M., et al., "A pyrazolopyran derivative preferentially inhibits the activity of human cytosolic serine hydroxymethyltransferase and induces cell death in lung cancer cells", Oncotarget 7(4):4570-4583 (2016).
Mullarky, E., et al., "Identification of a small molecule inhibitor of 3-phosphoglycerate dehydrogenase to target serine biosynthesis in cancers", Proc. Natl Acad. Sci. USA 113(7):1778-1783 (2016).
Nilsson, R., et al., Metabolic enzyme expression highlights a key role for MTHFD2 and the mitochondrial folate pathway in cancer. Nat. Commun. 5:3128 (2014).
Nixon, P.F., "Folinic Acid: Pharmacokinetics and Pharmacodynamics", Clinical and Experimental Pharmacology & Physiology Suppl. 5, pp. 35-41 (1979).
Njalsson, R., et al. "Cooperative Binding of γ-Glutamyl Substrate to Human Glutathione Synthetase", Biochemical and Biophysical Research Communications 289(1):80-84 (2001).
Notice of Allowance for U.S. Appl. No. 15/705,200, "SHMT Inhibitors", dated May 7, 2018.
Pacold, M.E., et al. "A PHGDH inhibitor reveals coordination of serine synthesis and one-carbon unit fate", Nat. Chem. Biol. 12(6):452-458 (2016).
Patel, H., et al., "Mammalian fibroblasts lacking mitochondrial NAD+-dependent methylenetetrahydrofolate dehydrogenase-cyclohydrolase are glycine auxotrophs", J. Biol. Chem. 278(21):19436-19441 (2003).
Pavlova, N.N., et al., "The Emerging Hallmarks of Cancer Metabolism", Cell Metab. 23(1):27-47 (2016).
Possemato, R., et al. "Functional genomics reveal that the serine synthesis pathway is essential in breast cancer", Nature 476(7360):346-350 (2011).
Pui, C.-H., et al., "Treatment of acute lymphoblastic leukemia", N. Engl. J. Med. 354(2):166-178 (2006).
Ran, F.A., et al., "Double nicking by RNA-guided CRISPR Cas9 for enhanced genome editing specificity", Cell 154: 1380-1389 (2013).
Ran, F.A., et al., "Genome engineering using the CRISPR-Cas9 system", Nat. Protoc. 8, 2281-2308 (2013).
Schulze, A., Harris, A.L. "How cancer metabolism is tuned for proliferation and vulnerable to disruption", Nature 491(7424):364-373 (2012).
Sirotnak, F.M., et al., "Optimization of High-Dose Methotrexate with Leucovorin Rescue Therapy in the L1210 Leukemia and Sarcoma 180 Murine Tumor Models", Cancer Research 38: 345-353 (1978).
Tibbetts, A.S., et al., "Compartmentalization of Mammalian Folate-Mediated One-Carbon Metabolism", Annu. Rev. Nutr. 30(1):57-81 (2010).
Wang, Q., et al. "Rational Design of Selective Allosteric Inhibitors of PHGDH and Serine Synthesis with Anti-tumor Activity", Cell Chem. Biol. 24(1):55-65 (2017).
Witschel, M.C., et al. "Inhibitors of plasmodial serine hydroxymethyltransferase (SHMT): cocrystal structures of pyrazolopyrans with potent blood- and liver-stage activities" J. Med. Chem. 58(7):3117-3130 (2015).
Yan, C., et al., "Discovery and characterization of small molecules that target the GTPase Ral", Nature 515(7527): 443-447 (2014).
Zhao, R., et al., "Resistance to antifolates", Oncogene (2003) 22, 7431-7457.

SHMT INHIBITORS

RELATED APPLICATIONS

This application is a divisional of U.S. application Ser. No. 15/705,200, filed on Sep. 14, 2017, now U.S. Pat. No. 10,077,273, issued on Sep. 18, 2018, which claims the benefit of U.S. Provisional Application No. 62/470,131, filed on Mar. 10, 2017, and U.S. Provisional Application No. 62/394,689, filed on Sep. 14, 2016. The entire teachings of these applications are incorporated herein by reference.

STATEMENT OF GOVERNMENT SUPPORT

This invention was made with government support under Grant No. CA163591 awarded by the National Institutes of Health. The government has certain rights in the invention.

BACKGROUND OF THE DISCLOSURE

Serine catabolism is initiated by serine hydroxymethyltransferase (SHMT) activity, catalyzed in the cytosol by SHMT1 and in the mitochondria by SHMT2. SHMTs catalyze a reversible reaction converting serine to glycine, with concurrent methylene-tetrahydrofolate (THF) generation. Increased SHMT enzyme activity has been detected in human breast cancer, colon cancer, and in rat sarcoma.

SHMT functions to generate one-carbon units for cellular folate metabolism. Inhibition of other aspects of folate metabolism is an established mechanism of therapy for a variety of cancers and autoimmune diseases. However, existing anti-folates are characterized by dose-limiting toxicity that limits their effectiveness in cancer therapy and their tolerability in autoimmune disease.

Hypoxia occurs in the tumor environment, and the mitochondrial form of SHMT, SHMT2, is induced under hypoxic stress. SHMT expression may help tumor cells survive under hypoxic conditions, thus promoting cancerous cell growth, survival and metastasis. Hypoxic cells are generally more resistant to radiation and chemotherapy treatment, further permitting the tumor to grow and metastasize. SHMT2 overexpression has been observed in various different cancers, including neuroblastoma, bladder cancer, colorectal cancer, kidney cancer, etc.

SUMMARY OF THE DISCLOSURE

There is a need in the art for effective treatments for cancer and other conditions, such as autoimmune disease. Without being bound by theory, SHMT enzymes are an attractive target and SHMT inhibitors, such as inhibitors of SHMT1 and/or SHMT2, (e.g., selective inhibitors of SHMT2 and/or SHMT1) are suitable for a variety of purposes, such as to inhibit SHMT activity in vitro and/or in vivo. Such inhibitors may act additively or synergistically with other anti-folate compounds, such as to treat cancer and autoimmune disease.

The present disclosure provides compounds, compositions, and methods, as described herein. In certain embodiments, the compounds of the disclosure are inhibitors of mammalian SHMT activity, such as mammalian SHMT1 and/or mammalian SHMT2 (e.g., human SHMT1 and/or human SHMT2). Compounds of the disclosure may be provided in isolated or substantially purified form, including as a substantially pure stereoisomer, enantiomer, diastereomer, atropisomer, and a mixture thereof, and/or may be provided as compositions, such as pharmaceutical compositions.

In one aspect, the disclosure provides compounds of the disclosures. Compounds of Formula I (including Ia and Ib), Formula II (including IIa and IIb), and Formula III (including IIIa and IIIb), Formula II' (including IIa' and IIb'), and Formula III' (including IIIa' and IIIb') are exemplary of compounds of the disclosure. The disclosure also provides compounds of any of Formula I-IX (including Ia, Ib, IIa, IIb, IIa', IIb' IIIa, IIIb, IIIa' IIIb', etc., IXa, IXb, and IXc). Compounds described herein include compounds having any combination of structural and/or functional features described herein. Similarly contemplated are pharmaceutical compositions comprising any compounds described herein.

In one aspect, compounds of this discolosure are SHMT inhibitors. In some embodiments, the compound of this disclosure is a selective SHMT inhibitor, such as a SHMT1 inhibitor or a SHMT2 inhibitor. In certain embodiments, the compound of this disclsosure is a dual SHMT inhibitor, such as an SHMT1 and SHMT2 inhibitor. Any of the compounds of the disclosure, including compounds described generally or specifically herein, may be used in any of the in vitro or in vivo methods described herein, such as in a method of treating cancer or an autoimmune condition.

In one aspect, the disclosure provides methods for treating a cancer or autoimmune condition, such as a cancer or autoimmune condition associated with SHMT activity and/or associated with alterations in mitochondrial folate metabolism. In some embodiments, the cancer or autoimmune condition is associated with mitochondrial dysfunction, such as alterations in mitochondrial folate metabolism. In some embodiments, the cancer or autoimmune conditions is characterized by the presence of one or more cells or tissues having mutations in, for example, myc or a protein important for proper mitochondrial function. Exemplary methods include monotherapy, in which a mammalian patient in need thereof is administered an SHMT inhibitor that inhibits activity of a mammalian SMHT2 and/or SHMT1. Further exemplary methods include methods in which an SHMT inhibitor that inhibits activity of a mammalian SHMT2 and/or SHMT1 is administered in a composition and/or as part of a therapeutic regime with one or more additional agents or therapeutic modalities.

In certain embodiments, when multiple agents and/or treatment modalities are used as part of the therapeutic method, each such agent may be administered, independently, at the same or differing times. Similarly, when multiple agents and/or treatment modalities are used as a part of the therapeutic method, each such agent may be administered, independently, using the same or differing routes of administration and/or formulations. All such methods contemplate administration of a compound or a pharmaceutical composition of the disclosure, whether described generally by function as an SHMT inhibitor, or whether described using one or more structural and/or functional features, as set forth herein.

In certain embodiments, this disclosure provides a method of treatment (whether as part of a monotherapy or therapeutic regimen) comprising administering to a mammalian subject in need thereof, a compound of Formula (I) (including Ia or Ib), (II) (including IIa or IIb), (III) (including IIIa or IIIb), Formula II' (including IIa' or IIb'), and Formula III' (including IIIa' or IIIb'), or a pharmaceutically acceptable salt thereof, as described herein. Similarly contemplated are methods in which a pharmaceutical formulation/composition comprising any compound described herein is used. In certain embodiments, this disclosure provides methods comprising administering to a mammalian subject in need thereof a compound of Formula (I) (including Ia or Ib), (II) (including IIa or IIb), (III) (including IIIa or IIIb), Formula II' (including IIa' or IIb'), and Formula III' (including IIIa' or IIIb'), either as a monotherapy or a combination therapy.

In certain embodiments, this disclosure provides a method comprising administration of two or more agents. In certain embodiments, the method comprises administration of a selective SHMT inhibitor, such as an SHMT2 inhibitor, and a second agent or treatment modality. In certain emobidments, the method comprises administration of a dual SHMT inhibitor and a second agent or treatment modality. In certain embodiments, the second agent is another anti-cancer therapeutic agent, such as a chemotherapeutic agent, an anti-folate, radiation therapy, and/or the then standard of care for the particular cancer or autoimmune condition being treated.

In certain embodiments, the second agent is a rescue therapy intended to help reduce toxicity or otherwise limit side effects. Such rescue therapy may be used alone with a selective SHMT inhibitor (e.g., a SHMT2 inhibitor) or a dual SHMT inhibitor or together with another anti-cancer agent, such as a traditional anti-folate. Exemplary rescue therapies and other therapeutic modalities are described herein. In certain embodiments, the second agent is a rescue therapy, such as formate, folinic acid or a derivative thereof (or like compounds, as described herein), but administration of formate, folinic acid (or like compounds) cooperates to increase the anticancer effects of the SHMT inhibitor. In certain embodiments, the addition of formate, folinic acid, or similar compounds improves safety, reduces toxicity or improved the therapeutic index, such as by maintaining or increasing the anti-cancer effect in the cancer cells while not doing so or even decreasing any effect in healthy cells. In other embodiments, the additional of formate decreases toxicity in healthy cells but also in cancerous cells. When multiple agents or treatment modalities are used as part of a therapeutic regimen, they may be administered at the same or differing times. For example, a compound of the disclosure, such as a SHMT inhibitor, may be administered before, at the same time, or following administration of another agent, including a rescue therapy.

In certain embodiments, the cancer is a cancer of a particular tissue, and tumors or cancerour tissue may include cells comprising one or more mutations in, for example, myc or in another gene where the mutation is associated with mitochondrial dysfunction, such as mutations associated with alterations in mitochondrial folate metabolism. It is appreciated that tumors and cancerous tissues are typically heterogenous, such that not all cells in a tumor will have the same mutational status. Rather, one or more cells of the tumor or cancerous tissue contain such a mutation in a mitochondrial enzyme, such as a mitochondrial folate enzyme, or otherwise associated with alterations in mitochondrial metabolism, such as mitochondrial folate metabolism.

In one aspect, the disclosure provides compounds represented by Formula (I) (including Ia or Ib), (II) (including IIa or IIb), (III) (including IIIa or IIIb), Formula II' (including IIa' or IIb'), and Formula III' (including IIIa' or IIIb'), or pharmaceutically acceptable salts or stereoisomers thereof, wherein the variables are defined as described herein. In certain embodiments, such compounds are capable of inhibiting SHMT activity, such as SHMT2 and/or SHMT1 activity (e.g., mammalian SHMT1 and/or mammalian SHMT2, such as human SHMT1 and/or human SHMT2). In certain embodiments, such compounds are selective inhibitors of SHMT2 and/or SHMT1. In certain embodiments, such compounds are dual inhibitors of SHMT1 and SHMT2. Of note, inhibitory activity may be evaluated in vitro and/or in vivo.

In certain embodiments, compounds of any of Formula (I) (including Ia or Ib), (II) (including IIa or IIb), (III) (including IIIa or IIIb), Formula II' (including IIa' or IIb'), and Formula III' (including IIIa' or IIIb'), or a pharmaceutically acceptable salt thereof, may be described based on any combination of structural and/or functional features provided herein.

In another aspect, the disclosure provides pharmaceutical compositions comprising a compound of the disclosure (e.g., a compound of any of Formula (I) (including Ia or Ib), (II) (including IIa or IIb), (III) (including IIIa or IIIb), Formula II' (including IIa' or IIb'), and Formula III' (including IIIa' or IIIb'), or a pharmaceutically acceptable salt thereof, formulated with one or more pharmaceutically acceptable carriers and/or excipients.

In another aspect, the disclosure provides compounds of Formula (I) (including Ia or Ib), (II) (including IIa or IIb), (III) (including IIIa or IIIb), Formula II' (including IIa' or IIb'), and Formula III' (including IIIa' or IIIb'), or stereoisomers thereof, or pharmaceutically acceptable salts thereof, or mixtures of any of the foregoing, or pharmaceutical compositions comprising any one of the foregoing, for use as a medicament.

In another aspect, the disclosure provides numerous methods of using compounds and/or compositions of the disclosure alone or in combination with other agents or treatment modalities. Compounds and/or compositions of the disclosure (e.g., a compound of any of Formula I (Ia, or Ib), II (IIa or IIb), or III (IIIc or IIIb), and/or a pharmaceutically acceptable salt thereof, and/or a composition comprising any one of the foreoging) may be used in any of the in vitro and/or in vivo methods described herein. In certain embodiments, the method is a method of treating cancer. In certain embodiments, the method is a method of treating an autoimmune condition.

In certain embodiments, this disclosure provides a method for treating cancer or an autoimmune disorder. The method comprises administering to a mammalian subject in need thereof an effective amount of a compound of Formula (I) (including Ia or Ib), (II) (including IIa or IIb), (III) (including IIIa or IIIb), Formula II' (including IIa' or IIb'), and Formula III' (including IIIa' or IIIb'), or a pharmaceutically acceptable salt thereof, or a composition comprising any one of the foregoing. In certain such embodiments, the method further comprises administering (either before, at the same time, or after) one or more additional agents (such as a rescue therapy to reduce toxicity) or treatment modalities as part of a therapeutic regimen.

In certain embodiments, SHMT inhibitor is an inhibitor of SHMT2 and/or SHMT1. In certain embodiments, the cancer or autoimmune condition is associated with alterations in mitochondrial folate metabolism.

In certain embodiments, the one or more additional agents comprise a rescue therapy to reduce toxicity. In other embodiments, the one or more additional agents comprise an additional anti-cancer agent. In certain such embodiments, the anti-cancer agent is an anti-folate compound.

In certain embodiments, the subject is a human subject.

In certain embodiments, this disclosre provides a method for treating cancer. In certain embodiments, the cancer comprises a mutation or alteration that affects mitochondrial metabolism, such as a mutation or alteration in a mitochondrial folate pathway gene. By "cancer comprises" it is understood that one or more cells of the tumor or cancerous tissue contain the mutation or alteration. In certain embodiments, the cancer comprises a mutation or alteration in SHMT2, MTHFD2, MTHFD2L, MTHFD1L, fumarate hydratase (FH), SLC25A32, KEAP1, or NRF2, or the patient otherwise has such a mutation or alteration in non-cancerous tissue.

In certain embodiments, the cancer is selected from pediatric or adult leukemia, lymphoma, solid tumors of the lung, non-small cell lung cancer, mesothelioma, solid tumors of the breast, colon cancer, liver cancer, stomach cancer, prostate cancer, pancreatic cancer, ovarian cancer, uterus and female genital tract cancer, bladder cancer, head and neck cancer, osteosarcoma, or trophoblastic neoplasms.

In certain embodiments, the cancer is characterized by a Myc mutation.

In certain embodiments, this disclosure provides a method for treating an autoimmune disorder. In certain such embodiments, the autoimmune disorder is selected from rheumatoid arthritis, dermatomyositis, psoriasis, lupus, sarcoidosis, Crohn's disease, eczema, or vasculitis.

In certain embodiments the subject in need thereof comprises a mutation or alteration that affects mitochondrial metabolism, such as a mutation or alteration in a mitochondrial folate pathway gene. In certain embodiments, the autoimmune disorder comprises a mutation or alteration that affects mitochondrial metabolism, such as a mutation or alteration in a mitochondrial folate pathway gene.

In certain embodiments, the rescue therapy is a formate salt or folinic acid. In other embodiments, the rescue therapy comprises: formate, formate salt, formate ester, or leucovorin. In certain embodiments, the rescue therapy is a formate, formate salt, formate ester, glycine, leucovorin, or a derivative thereof, or a pharmaceutically acceptable salt thereof.

In certain embodiments, the disclosure provides SHMT inhibitors for use in treating a condition, such as lymphoma (e.g., diffuse large B-cell lymphoma). Exemplary SHMT inhibitors are described herein. In certain embodiments, an SHMT inhibitor is a compound of any of Formulae (I)-(IX), including Formulae (Ia), (Ib), (IIa), (IIb), (IIa'), (IIb'), (IIIa), (IIIb), (IIIa'), (IIIb'), etc., (IXa), (IXb), (IXc).

In certain embodiments, the disclosure provides a method for treating lymphoma, such as T-cell lymphoma, B-cell lymphoma, or NK-cell lymphoma, comprising administering to a mammalian subject in need thereof an effective amount of an SHMT inhibitor. In certain such embodiments, the lymphoma is a B-cell lymphoma. In some embodiments, the lymphoma is a diffuse large B-cell lymphoma. In certain embodiments, the disclosure provides a method for inhibiting proliferation or survival of B-cell lymphoma cells, comprising contacting such cells with an effective amount of an SHMT inhibitor and/or a composition comprising such an SHMT inhibitor, e.g., a compound an/or composition of this disclosure. In certain embodiments, the method is an in vivo method. In certain embodiments, the method is an in vitro method. In certain embodiments, the disclosure provides methods for inhibiting growth or promoting growth arrest of B-cell lymphoma cells, comprising contacting such cells with an effective amount of an SHMT inhibitor. In certain embodiments, the method is an in vivo method. In certain embodiments, the method is an in vitro method.

In certain embodiments, the method comprises administering formate or a derivative thereof (as described herein). Although formate alone rescues the effects of an SHMT inhibitor in many cell types, surprisingly, the formate rescue effects were not observed in B-cell lymphomas, such as diffuse large B-cell lymphoma, where a combination of formate and glycine (such as supraphysiologic glycine) is required to so rescue. Rather, although formate (or derivatives thereof, as described herein) is traditionally classified as a rescue therapy, it is suitable for use in combination with an SHMT inhibitor in B-cell lymphoma where it actually further increases the inhibitory effect on the cancerous cells of the SHMT inhibitor. Accordingly, the disclosure provides improved methods of treating B-cell lymphoma, such as diffuse large B-cell lymphoma, using a combination of an SHMT inhibitor (such as a SHMT1 inhibitor, a SHMT2 inhibitor, or a dual SHMT inhibitor) and/or a rescue therapy (e.g., formate, folinic acid, etc.), but wherein the combination actually has increased inhibitory activity against the B-cell lymphoma. In some embodiments, the combination has an improved therapeutic index against cancer, such as B-cell lymphoma.

In certain embodiments, the method further comprises administering (or contacting cells with) at least one additional agent. In certain embodiments, at least one additional agent is a rescue therapy to reduce toxicity. In certain such embodiments, the SHMT inhibitor is a compound of the disclosure (a compound generically or specifically disclosed herein, such as a compound of any of Formulae (I)-(IX), or a pharmaceutical composition comprising a compound of any of Formulae (I)-(IX). In certain embodiments, the SHMT inhibitor is formulated with one or more pharmaceutically acceptable carriers and/or excipients. In certain embodiments, the SHMT inhibitor is a compound of any of Formula (I) (including Ia or Ib), (II) (including IIa or IIb), (III) (including IIIa or IIIb), Formula II' (including IIa' or IIb'), and Formula III' (including IIIa' and IIIb'). In certain embodiments, the SHMT inhibitor is a compound of any of Formulae (IV)-(IX).

In certain embodiments, the rescue therapy is a formate salt or folinic acid, or a derivative thereof. In other embodiments, the rescue therapy comprises: formate, formate salt, formate ester, or leucovorin, or a derivative thereof. In certain embodiments, the rescue therapy is a formate, formate salt, formate ester, glycine, leucovorin, or a derivative thereof, or a pharmaceutically acceptable salt thereof. In certain embodiments, the additional agent is glycine or formate, a derivative thereof, or a pharmaceutically acceptable salt thereof. In some embodiments, the additional agent is glycine, a derivative thereof, or a pharmaceutically acceptable salt thereof. In other embodiments, the additional agent is formate, a derivative thereof, or a pharmaceutically acceptable salt thereof. In yet other embodiments, the rescue theray is a combination of glycine and formate, or derivatives thereof, or pharmaceutically acceptable salts thereof. In some embodiments, the formate and/or glycine rescue is sufficient to restore glycine levels in the normal body (e.g., a healthy cell or tissue) but not in a tumor such as lymphoma.

In certain embodiments, the method further comprises administering (or contacting cells with) a glycine uptake inhibitor, such as RG1678 (Bitopertin), Org 24598, Org 25935, ALX-5407, sarcosine, Org25543, N-arachidonylglycine, amoxapine, or ethanol. In certain such embodiments, the glycine uptake inhibitor is RG1678 (Bitopertin). In certain embodiments, the glycine uptake inhibitor is a glycine transporter (e.g., glycine transporter type-1 (GlyT-1), glycine transporter type-2 (GlyT-2)) inhibitor. In certain embodiments, the glycine uptake inhibitor is a GlyT-1 inhibitor. As used herein, "glycine uptake inhibitor" refers to agents that inhibit the uptake or reuptake of glycine, for example, by inhibiting a glycine transporter.

In certain embodiments, the SHMT inhibitor is an inhibitor of SHMT2 and/or SHMT1.

In certain embodiments, the B-cell lymphoma is a Hodgkin's lymphoma (HL), such as a classical HL or nodular lymphocyte-predominant HL (e.g., nodular sclerosis HL, mixed cellularity HL, lymphocyte-rich HL, or lymphocyte-depleted HL).

In certain embodiments, the B-cell lymphoma is a non-Hodgkin's lymphoma (NHL), such as a diffuse large B-cell lymphoma (e.g., a primary mediastinal large B-cell lymphoma, T-cell/histiocyte-rich large B-cell lymphoma, or intravascular large B-cell lymphoma).

In certain embodiments, the B-cell lymphoma is a diffuse large B-cell lymphoma (DLBC lymphoma or DLBCL), Burkitt lymphoma, follicular lymphoma, marginal zone B-cell lymphoma, extranodal marginal zone lymphoma, mucosa-associated lymphatic tissue lymphoma, small lymphocytic lymphoma, or mantle cell lymphoma. In some embodiments, the B-cell lymphoma is a diffuse large B-cell lymphoma. In other embodiments, the B-cell lymphoma is Burkitt lymphoma.

In certain embodiments, the subject is a human subject (e.g., a human cancer patient).

The disclosure contemplates combinations of any of the aspects and/or embodiments described herein. Compounds of the disclosure may be described based on any suitable combination (e.g., as valence and stability permit) of structural and/or functional properties provided herein. For example, any of the compounds described herein, such as any of the SHMT inhibitors (e.g., compounds that inhibit activity of mammalian SHMT2 and/or SHMT1) described herein, may be used in the treatment of any of the conditions described herein, such as by administering an effective amount to a subject in need thereof. Similarly, any of the compounds described herein may be provided as compositions, such as pharmaceutical compositions, and any such pharmaceutical compositions may be used in the treatment of any of the conditions described herein. Similarly, compounds or compositions of the disclosure may be used in vivo or in vitro, such as in any of the methods, described herein.

DETAILED DESCRIPTION OF THE DRAWINGS

The patent or application file contains at least one drawing executed in color. Copies of this patent or patent application publication with color drawings will be provided by the Office upon request and payment of the necessary fee.

Figure 4A:
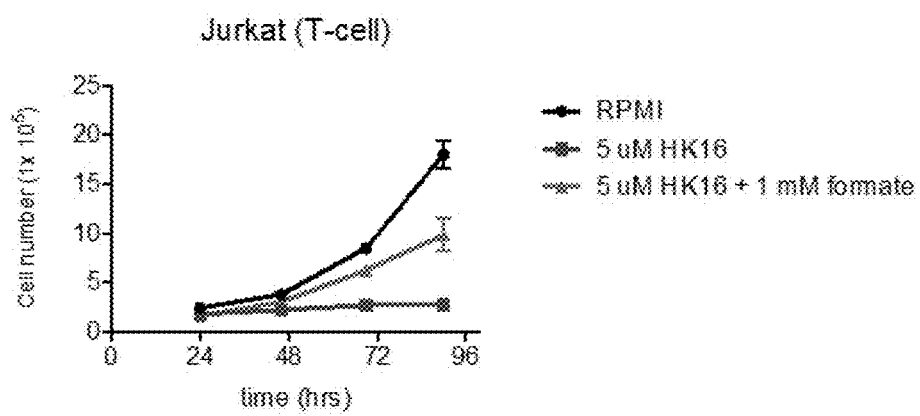
Figure 4B:
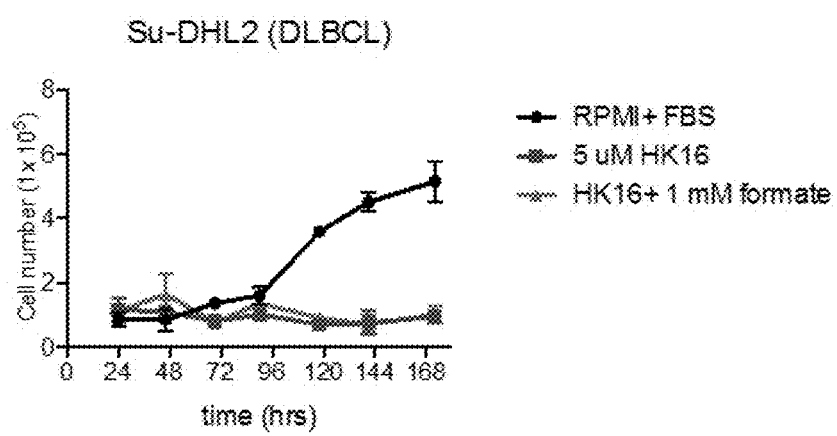

FIG. 4 shows B-cell lymphoma lines are sensitive to SHMT inhibitors and not rescued by formate. The diffuse large B-cell lymphoma cell line, Su-DHL-2, was sensitive to the SHMT inhibitor, (+)-HK-16, and the growth inhibitory effect was not rescuable by formate. In contrast, the Jurkat T cell line was sensitive to the same SHMT inhibitor, but the growth arrest was rescuable by treatment with formate. Compare FIG. 4A (Jurkat cells) with FIG. 4B (Su-DHL-2 cells).

Figure 5:
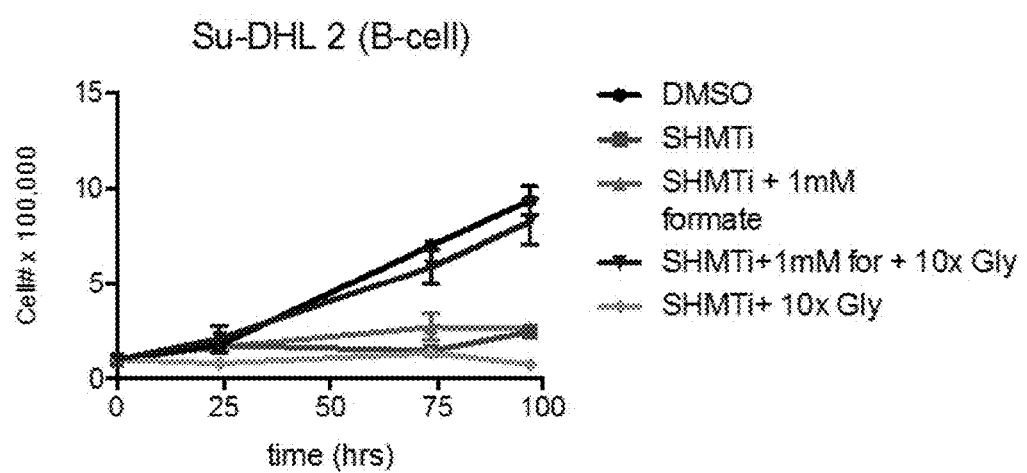

FIG. 5 shows SHMT inhibitor (SHMTi) growth inhibitory activity can be rescued in Su-DHL-2 cells (DLBCL B cell lymphoma cells) with a combination of formate and glycine. Su-DHL-2 cells were cultured with 5 µM of an SHMTi. Growth was rescued by combination with 1 mM sodium formate and 100 mg/L glycine (10× standard RPMI concentration).

Figure 6:
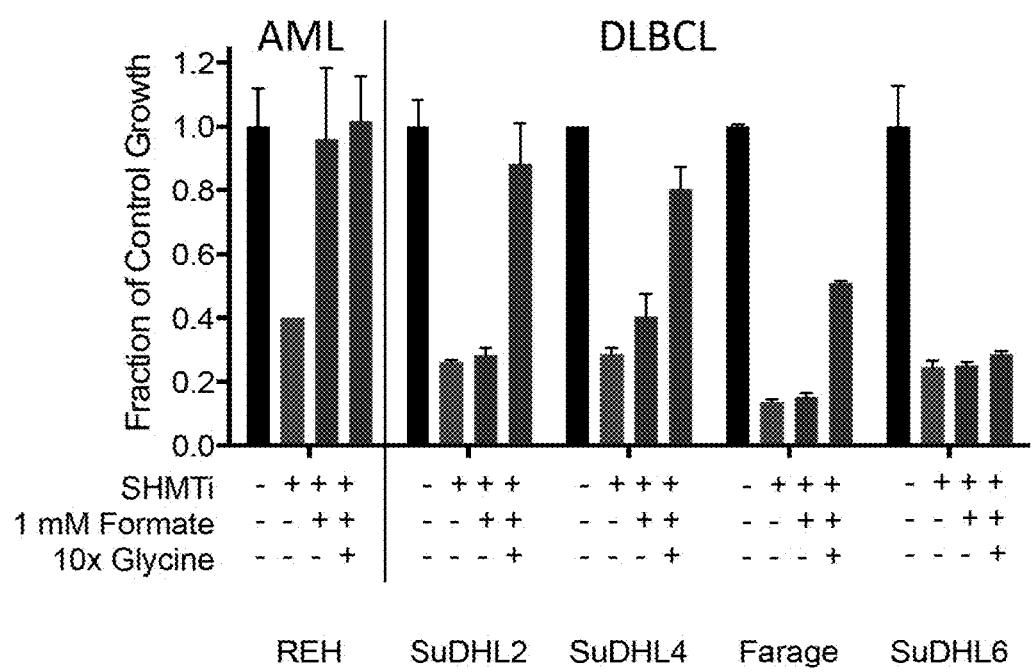

FIG. 6 shows a combination of supplemental formate and glycine is required to rescue B-cell lymphoma lines from SHMTi inhibition. Diffuse large B-cell lymphoma (DLBCL) lines (Su-DHL-2, Su-DHL-4, Farage and Su-DHL-6) were cultured in RPMI with 5 µM of an SHMT inhibitor (SHMTi). Growth was rescued by addition of formate (1 mM sodium formate) AND glycine (100 mg/L). In a representative AML cell line, REH, cell growth was rescued by formate alone.

Figure 7A:
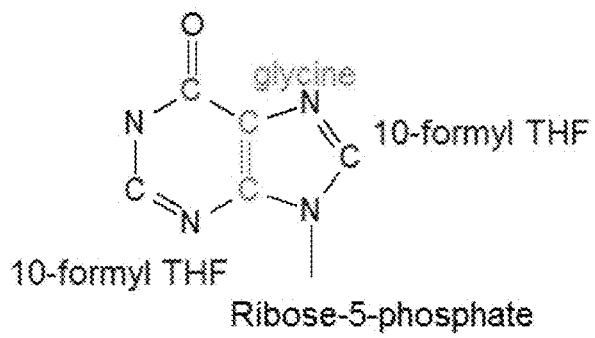
Figure 7B:
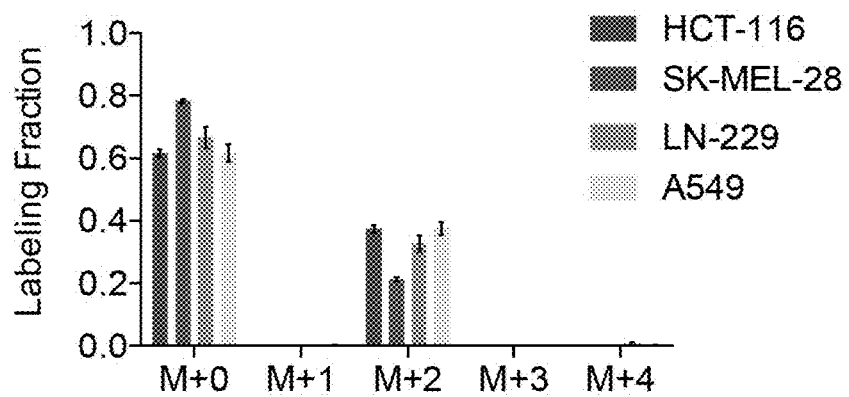
Figure 7C:
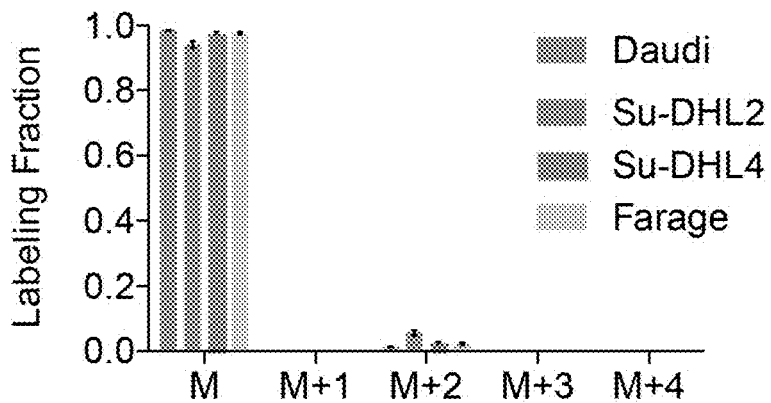

FIG. 7 shows comparison studies of glycine import using ADP labeling in various cell lines to demonstrate impaired glycine uptake in B-cell malignancies. FIG. 7A provides a schematic showing contribution of glycine to de novo synthesis of adenosine ring. FIG. 7B shows the results of isotopic labeling ($^{13}$C) of ADP extracted from various adherent solid tumor derived cancer cell lines incubated with 1,2-$^{13}$C glycine for 48 hours as determined by mass spectrometry. In all such solid tumor cell lines tested, a substantial fraction of ADP is M+2 labeled, indicating incorporation of $^{13}$C glycine from the media. FIG. 7C shows the results of ADP $^{13}$C labeling after 48 hour incubation with 1,2-$^{13}$C glycine in B-cell cancer lines. Results from cell lines from both Burkitt lymphoma and DLBCL reveal nearly no incorporation of exogenous glycine (i.e., imported from outside the cell) into ADP (absence of M+2 labeling in 7C).

FIG. 8 shows SHMT is required for tumor formation in vivo. FIG. 8A shows growth growth of subcutaneous tumors from HCT-116 WT and ΔSHMT2 cells implanted in opposite flanks of nude mice (mean±SEM, n=10, *p<0.05, paired t-test). FIG. 8B shows intratumor abundance of AICAR and serine from xenografted tumors (n=9, ***p<0.001, paired t-test). FIG. 8C shows growth of HCT-116 WT and ΔSHMT1/2 double deletion cells in standard DMEM with and without supplemental 1 mM sodium formate (n>4). FIG. 8D shows tumor growth of subcutaneous tumors from HCT-116 ΔSHMT2 and ΔSHMT1/2 cells implanted in opposite flanks of nude mice (mean±SEM, n=10).

Figure 9A:
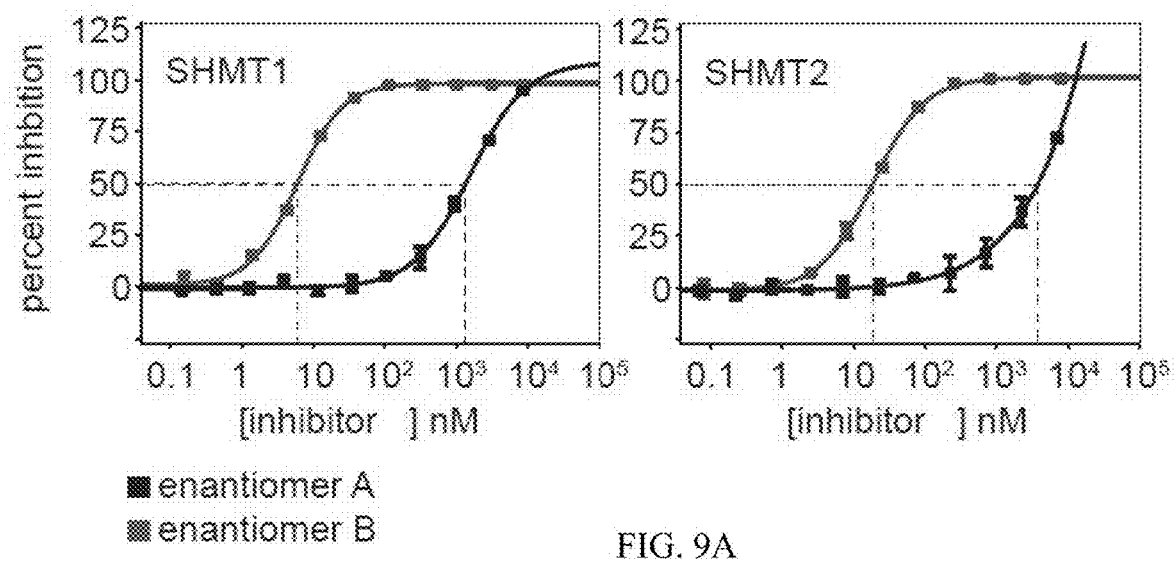

FIG. 9A shows enzymatic inhibition curves for human SHMT1 and SHMT2 with enantiomerically resolved fractions (enantiomer A and enantiomer B) of Compound HK-X1.

Figure 9B:
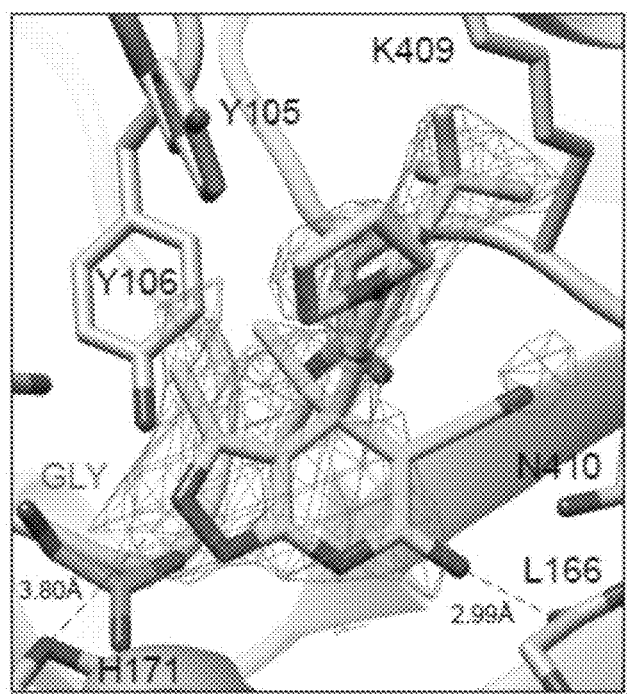

FIG. 9B shows a magnified view of Compound HK-X1 in complex with human SHMT2 as solved in a 2.5 Å resolution x-ray crystal structure. The electron density of the compound is shown as the 2F$_o$-F$_c$ map contoured at 0.5σ and generated with Compound HK-X1 omitted.

Figure 9C:
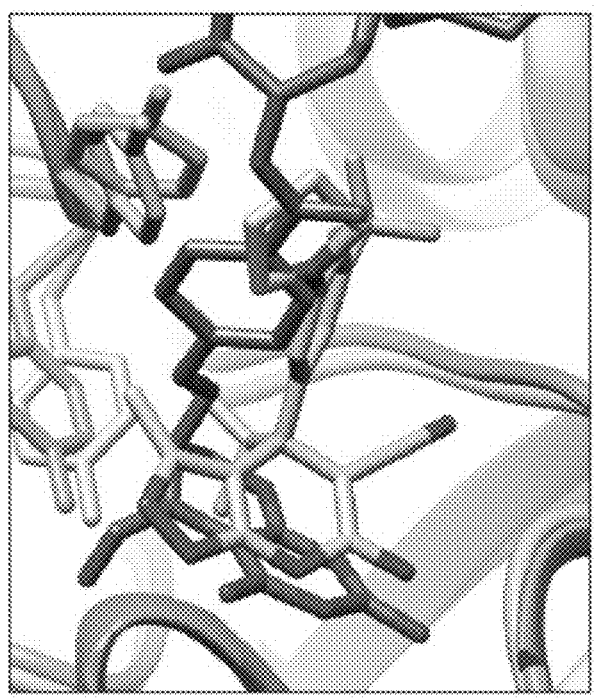

FIG. 9C shows an overlay of the SHMT2/Compound HK-X1 structure from FIG. 9B with the structure of 5-formyl-THF-triglutamate in complex with rabbit SHMT1.

Figure 9D:
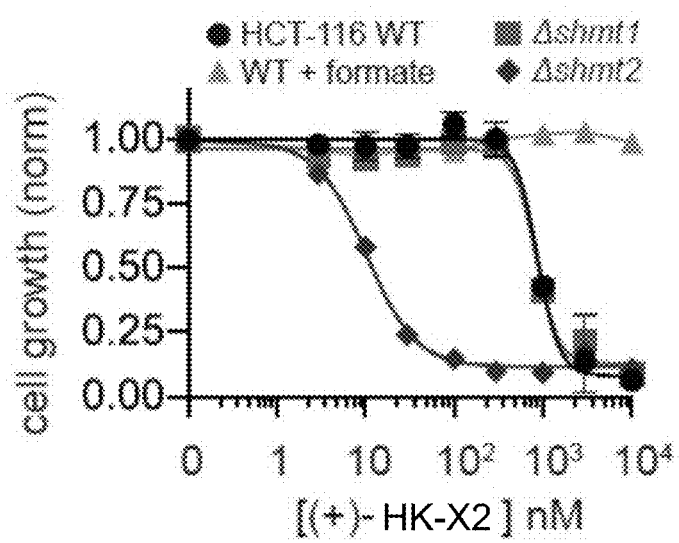

FIG. 9D shows growth of HCT-116 WT±1 mM formate and ASHMT1 and ASHMT2 cell lines in the presence of increasing concentrations of Compound HK-X2 (n>3). Compound HK-X1 and compounds of Fomulae (I)-(III) of this disclosure have shown similar inhibitory effects against HCT-116 WT and ASHMT1 and ASHMT2 cell lines (data not shown).

Figure 9E:
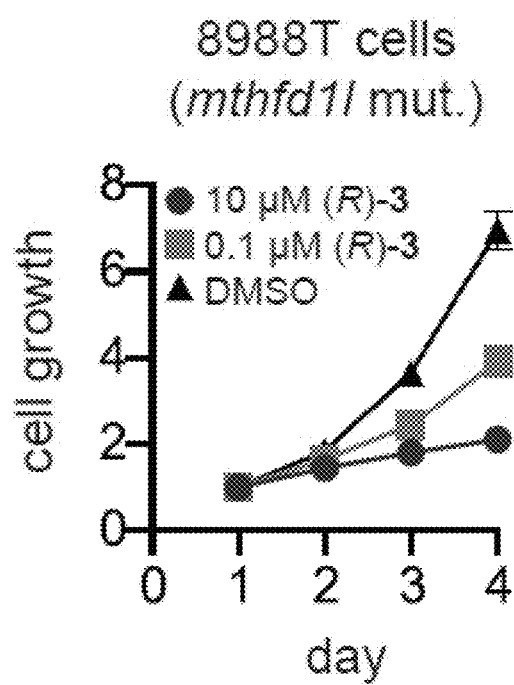

FIG. 9E shows growth of human pancreatic cell line 8988T with indicated concentrations of SHMT inhibitor Compound (+)-HK-16. Compound HK-X1, HK-X2 and compounds of Formulae (I)-(III) of this disclosure have shown similar inhibitory effects against HCT-116 WT and ASHMT1 and ASHMT2 cell lines (data not shown).

FIG. 10 shows Compound (+)-HK-X2 inhibits SHMT1 and SHMT2 in HCT-116 cells. FIG. 10A is a schematic illustration of isotope labeling from U-13C-serine into downstream metabolites. Heavy (13C) atoms are represented by filled in circles. FIG. 10B shows (top) a fraction of original serine remaining in media after 24 hours incubation U-$^{13}$C serine Compound HK-X2 and (bottom) M+1 13C-labeling fraction of media serine after 24 hours (mean±SD, n=3). FIG. 10C shows M+2 $^{13}$C-labeling fraction of intracellular ADP and glutathione after 24 h $^{13}$C-serine co-incubation with DMSO or 5 µM (+)-HK-X2 (mean±SD, n=3). FIG. 10D shows notinalized (to DMSO WT HCT-116 cells) levels of purine biosynthetic pathway intermediates after 24 hours incubation±Compound HK-X2 (mean±SD, n=3). FIG. 10E shows growth of HCT-116 WT cells over 48 hours cultured with varying concentrations of Compound HK-X2±1 mM sodium formate (mean±SD, n=3). FIG. 10F shows total metabolite abundances in HCT-116 cells treated with DMSO versus Compound (+)-HK-X2 for 48 hours. FIG. 10G shows metabolite abundance in HCT-116 cells treated with DMSO or Compound HK-X2 in the presence of 1 mM sodium formate. Metabolites whose abundances differ by more than 4-fold between conditions are highlighted in red (mean, n=3).

FIG. 11 shows SHMT inhibitors are particularly active against B-cell malignancies. FIG. 11A shows ranked IC50 of Compound (+)-HK-X1 for growth inhibition of 298 human cancer cell lines. Lines of B-cell origin are highlighted in red and are enriched among the more sensitive cells (IC50<4 µM). FIG. 11B shows IC50 of (+)-HK-X2, with and without 1 mM formate, for growth inhibition of select hematological cell lines. FIG. 11C shows representative flow cytometry histograms of B-cell line Su-DHL-4 treated with (+)-HK-X2 (5 µM) and formate (1 mM). Etoposide was used as a positive control. Cells were stained with propidium iodide and FITC conjugated Annexin V. 10,000 events shown. FIG. 11D shows fraction of Su-DHL-4 and Jurkat cells that are apoptotic (Annexin V+, PI−) 24 hours after indicated treatment (mean±SD, n>3).

FIG. 12 shows sensitization of malignancies of B-cell origin to co-treatment with Compound HK-X2 and formate due to poor uptake of extracellular glycine. FIG. 12A shows the steady-state labeling fraction of intracellular metabolites synthesized from glycine in select cancer cell lines cultured in RPMI containing U-$^{13}$C-glycine (mean±SD, n=3). FIG. 12B shows intracellular $^{13}$C-glycine assimilation kinetics in Jurkat (fast glycine uptake) and Su-DHL4 (slow glycine uptake) (mean±SD, n=3). FIG. 12C shows doubling times of cells cultured in RPMI with and without glycine and/or formate and Compound HK-X2 at doses of comparable potency for Jurkat (2.5 µM=IC$_{80}$) and SU-DHL4 (5 µM=IC$_{70}$). FIG. 12D shows representative flow cytometry histograms of Su-DHL4 cells treated with indicated combinations of Compound HK-X2 and formate. Cells were stained with propidium iodide and FITC conjugated Annexin V. 10,000 events shown. FIG. 12E shows fraction of Su-DHL4 cells that are apoptotic (Annexin V+, PI−) 24 hours after indicated treatment (mean±SD, n=3). FIG. 12F shows sensitivity of Su-DHL4 cells to Compound HK-X2 is dependent upon media glycine concentration. Cells were cultured in either normal RPMI (10 mg/L glycine) or RPMI containing 10× glycine (100 mg/L) and Compound HK-X2 for 48 hours, and growth was measured by resazurin assay (mean±SD, n=3). FIG. 12G shows cell growth (normalized to DMSO) of diffuse large B-cell lymphoma and other hematopoietic cancer lines with 2.5 µM Compound HK-X2, in RPMI with or without 1 mM formate and 10× physiological glycine (100 mg/L). All conditions included at least normal media glycine (10 mg/L) (mean±SD, n=3).

Figure 13A:
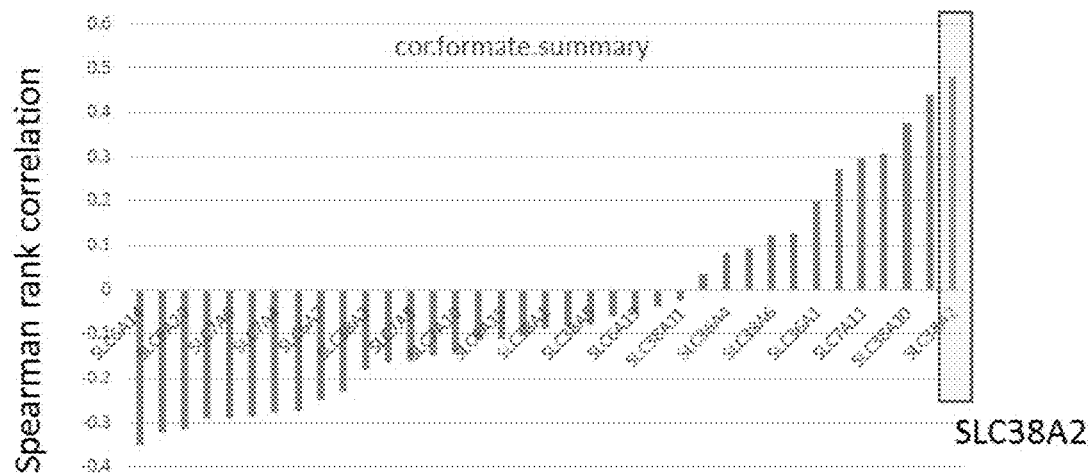

FIG. 13A shows that SLC38A2 loss is correlated with sensitivity to SHMT inhibitor+formate. Spearman rank correlation of mRNA expression (CCLE database) of known amino acid transporters and sensitivity (IC50) of select cancer cell lines (of HEME origin) to inhibition by an SHMT inhibitor with 1 mM sodium formate. Positive correlation is between low expression and low IC50. Loss of this amino acid transporter is hypothesized to impair glycine transport and thus sensitize cells to SHMT inhibition in combination with formate.

Figure 13B:
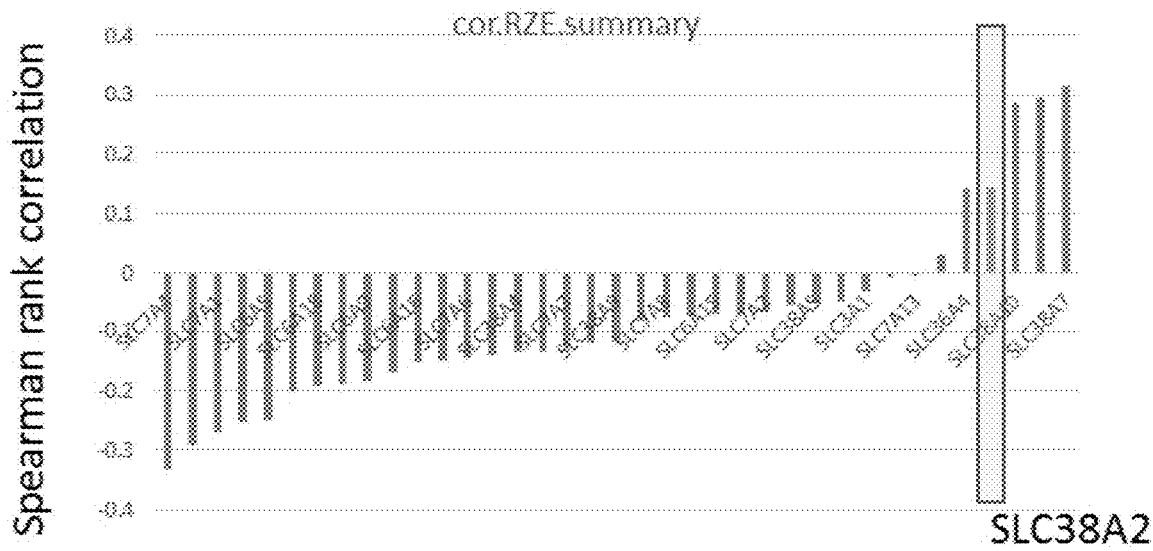

FIG. 13B shows that SLC38A2 expression is weakly correlated with sensitivity to SHMT inhibitor without formate. Spearman rank correlation of mRNA expression (CCLE database) of known amino acid transporters and sensitivity (IC50) of select cancer cell lines (of heme origin) to inhibition by SHMT inhibitor. Positive correlation is between low expression and low IC50.

FIG. 14 shows that glycine made by SHMT is required for B-lymphoma cell line growth. FIG. 14A shows normalized total ion counts of nucleotide triphosphates in Jurkat ALL cells and Su-DHL-4 DLBCL cells after 72 hour (h) treatment with (+)-HK-X2 (5 µM). Co-culture with 1 mM formate restores nucleotide levels selectively in Jurkat cells (mean±SD, n=3-6). FIG. 14B shows normalized glutathione levels from Jurkat and Su-DHL-4 cells treated as in FIG. 14A (mean+SD, n=3-6). FIG. 14C shows growth of Su-DHL-4 cells treated with (+)-HK-X2 and hypoxanthine (100 µM) or thymidine (16 µM) (mean±SD, n=3). FIG. 14D shows intracellular U-$^{13}$C-glycine assimilation kinetics in Jurkat and Su-DHL-4. Note the low uptake in Su-DHL-4 cells (gly=glycine, GSH=glutathione) (mean±SD, n=3). FIG. 14E shows the steady-state labeling fraction of intracellular metabolites synthesized from glycine in cancer cell lines cultured in RPMI containing U-$^{13}$C-glycine (mean±SD, n=3). FIG. 14F shows cell growth (or death) as measured by $\log_2$ fold change in cell number over 48 h in Su-DHL-4 cells cultured in RPMI with and without glycine (10 mg/L), formate (1 mM), the glycine reuptake transporter 1 inhibitor RG1678 (300 nM) and/or (+)-HK-X2 (5 µM) (mean±SD, n=3). FIG. 14G shows a schematic illustrating the proposed glycine vulnerability in B-cells. The SHMT reaction makes two products, 5,10-methyleneTHF and glycine. When SHMT is inhibited, exogenous formate can be incorporated into the 1C cycle whereas in B-cells poor glycine uptake limits the ability of extracellular glycine to rescue. Strategies that further stress glycine availability augment the efficacy of SHMT inhibition.

DETAILED DESCRIPTION OF THE DISCLOSURE

A. Overview

Serine hydroxymethyltransferase (SHMT) is an enzyme which plays an important role in cellular one-carbon pathways by catalyzing the reversible conversions of L-serine to glycine. In addition, SHMT catalyzes the conversion of tetrahydrofolate to 5,10-methylenetetrahydrofolate (e.g., SHMTs catalyze a reversible reaction converting serine to glycine, with concurrent methylene-tetrahydrofolate (meTHF) generation). SHMT enzymatic activity provides the largest part of the one-carbon units available to the cell. In mammals, such as humans, there are two isoforms of SHMT: SHMT1 in the cytosol and SHMT2 in the mitochondria.

The mammalian enzyme is a tetramer of four identical subunits of approximately 50,000 Daltons each. The intact holoenzyme in vivo has a molecular weight of approximately 200,000 Daltons and incorporates four molecules of vitamin $B_6$ as a coenzyme.

Human beings have an absolute dietary requirement for folic acid, the essential cofactor for one-carbon metabolism, and adequate levels are necessary for both normal embryological development and adult tissue function. It has long been recognized that proliferative tissues are particularly dependent upon one-carbon metabolism, and this led to the development of the first effective chemotherapy, the antifolates. These agents, including methotrexate, and the more recently approved pemetrexed, are routinely used in the treatment of a variety of cancers, including non-small cell lung cancer (NSCLC), osteosarcoma, mesothelioma, breast cancer, and multiple hematological malignancies. However, the utility of these medications is limited by toxicities arising from antifolate activity in normal tissue, which include anemia, neutropenia, diarrhea, and alopecia.

These toxicities often necessitate administration of leucovorin as a rescue therapy, although new evidence suggests that folate rescue therapy combined with traditional antifolates may contribute to drug resistance. These traditional antifolate therapies are believed to function mainly through inhibition of the cytosolic folate enzymes dihydrofolate reductase (DHFR) and thymidylate synthetase (TS), resulting in impaired DNA synthesis and impaired cellular replication. This model is consistent with the toxicity profiles observed in patients who receive antifolate therapies. In contrast, modulation of serine flux and/or folate metabolism via inhibition of SHMT may provide the benefits of traditional antifolate therapies without the deficiencies of an approach based on inhibiting DHFR and/or TS (e.g., traditional antifolates; alternative anti-folates). Moreover, rescue therapy can still be used, in combination, to help further decrease or manage toxicity.

The present disclosure provides compounds, compositions, and methods suitable for treating cancer and autoimmune conditions, including in subjects having mutations or alterations affecting native mitochondrial function or a native mitochondrial folate pathway. Without being bound by theory, even in subjects without known alterations in mitochondrial metabolism, SHMT inhibitors are suitable for altering folate metabolism, and thus, depriving cells of the energy necessary to fuel pathological growth and activity. Accordingly, these agents that modulate folate metabolism in the mitochondria and, potentially, in the cytoplasm, have significant utility in modulating cell behavior in numerous contexts including cancer and autoimmune conditions.

Folate metabolism occurs as a cycle between two interconnected pathways: one in the cytosol, which directly contributes one-carbon (1C) units to cellular biosynthetic processes, and one in the mitochondria. The pathways are connected by the metabolites serine, glycine, and formate. Since most studies on folate metabolism initially revolved around the actions of antifolate therapy and the cellular pathophysiology of folate/vitamin B12 deficiency, both of which were believed to involve cytosolic enzymes, the role of the mitochondrial pathway in regulating 1C metabolism was underappreciated until much later. Since its elucidation, however, it has been shown that folate metabolism in the mitochondrial compartment is central to eukaryotic 1C metabolism and is an original source for the majority of 1C units in the tissue systems studied to date.

Cancer growth and proliferation are supported by disease-specific metabolic processes. In cancer, these include enhanced glucose uptake, aerobic glycolysis (the Warburg effect), and folate-dependent one-carbon (1C) flux. The predominant source of 1C units in cancer cells is the amino acid serine. The enzyme SHMT catalyzes the conversion of serine and tetrahydrofolate (THF) into glycine and 5,10-methylene-THF (meTHF). Increases in the synthesis and consumption of serine and glycine have been identified in many transformed cells and cancers. In cancer, mitochondrial serine hydroxymethyl transferase (SHMT2) and the immediate downstream enzyme, mitochondrial methylene tetrahydrofolate dehydrogenase (MTHFD2), which forms the core of the mitochondrial pathway, are highly expressed in multiple cancer types and sit in the center of the cancer-induced 1C metabolic network, linking higher serine synthesis by phosphoglycerate dehydrogenase (PHGDH) to the mitochondrial production and subsequent cytosolic utilization of 1C units for nucleotide synthesis. Comparative oncogenomics identifies PSMB4 and SHMT2 as potential cancer driver genes. Metabolic enzyme expression highlights a key role for MTHFD2 and the mitochondrial folate pathway in cancer. In contrast, expression of SHMT2 in normal adult tissue was found to be consistently low, even in most rapidly proliferating tissues examined. In a separate study, high SHMT2 expression correlated with lower overall survival in lung cancer patients, and overexpression of this pathway was associated with a poor prognosis in breast cancer.

High expression of SHMT2 and MTHFD2 is linked to rapid catabolism of serine into glycine and folate associated 1C units. In contrast, cytosolic 1C metabolism is not consistently upregulated in cancer. This reflects most cancer cells defaulting to mitochondrial serine catabolism by SHMT2, with the cytosolic isozyme SHMT1 playing a minimal role (and actually not consuming 1C units to synthesize serine), as demonstrated by isotope tracer studies with 2H-serine tracer, which can distinguish 1C units generated by mitochondrial versus cytosolic serine catabolism. Without being bound by theory, high expression of core mitochondrial folate enzymes in cancer is consistent with the role of serine flux (which provides these 1C units) through the mitochondria in cancer. A potential outcome of higher serine flux through this compartment is increased export of formate from the mitochondria, effectively augmenting the cytosolic 1C pool.

While the mitochondrial pathway usually supplies all of the 1C units in rapidly proliferating cells, it is not essential in nutrient replete conditions, as evidenced by the viability of SHMT2 and MTHFD2 deletion cell lines. In such deletion cells, SHMT1 reverses direction and produces 1C units required for purine and thymidine synthesis. In the absence of exogenous glycine, however, this flux is not sufficient to meet glycine demand and these and all mitochondrial folate mutant cell lines are glycine auxotrophs.

1C metabolism is targeted therapeutically by folate analogues, including the common clinical agents pemetrexed and methotrexate. These drugs mimic folate and broadly block folate metabolism. Another common chemotherapeutic drug, 5-fluorouracil, specifically targets 1C utilization to make thymidine (in addition to thymidine incorporation into DNA). No existing antifolates are thought to specifically target the production of 1C units from serine, the primary source of 1C in tumors. Efforts to block serine synthesis through inhibition of PHGDH have been largely unsuccessful as tumor cells avidly uptake environmental serine, bypassing the requirement for PHGDH.

In addition, and without being bound by theory, roles for SHMT2 in cancer may also include a non-biosynthetic role of mitochondrial folate metabolism in cancer as a redox defense through generation of NADPH within the mitochondria (e.g., such as a defense to hypoxic conditions). In addition, and without being bound by theory, the role for SHMT2 in cancer may also include 5,10-methyleneTHF dependent translation of mitochondrial proteins and maintenance of mitochondrial electron transport function, oxidative phosphorylation and organelle specific metabolic activity. In addition, and without being bound by theory, the role for SHMT2 in cancer may also include a non-1C metabolism biosynthetic contribution in the form of glycine generation both specifically localized to within the mitochondria and in the cytosol. Glycine synthesis can support mitochondrial health and function as well as the redox state of the entire cell.

Modulation of folate metabolism is suitable for therapeutic intervention, such as in cancer. The present disclosure provides inhibitors of SHMT2 and/or SHMT1. Such inhibitors represent an alternative to traditional anti-folates or anti-folates that directly inhibit DHFR or TS for modulating folate metabolism in cells in vitro and/or in vivo. Thus, in certain embodiments, the disclosure provides compounds, compositions and methods for modulation of serine flux and/or folate metabolism using inhibitors, such as selective inhibitors, of mammalian SHMT enzymes. In certain embodiments, the disclosure provides compounds, compositions, and methods to modulate (e.g., inhibit) serine flux and/or the mitochondrial folate pathway by inhibiting SHMT2 (e.g., using inhibitors of SHMT2; providing compounds capable of inhibiting SHMT2). Such inhibitors may optionally also inhibit SHMT1. Similarly, in certain embodiments, the disclosure provides compounds, compositions, and methods to modulate (e.g., inhibit) generation of NADPH by inhibiting SHMT2 (e.g., using inhibitors of SHMT2; providing compounds capable of inhibiting SHMT2). Such inhibitors may optionally also inhibit SHMT1.

In certain embodiments, the disclosure provides compounds, compositions, and methods for modulating (e.g., inhibiting) glycine generation in the mitochondria and/or cytosol in cells. Accordingly, the disclosure provides, in certain embodiments, compounds and/or compositions capable of inhibiting a mammalian SHMT enzyme (e.g., SHMT2 and/or SHMT1), as well as methods for using such compounds. In certain embodiments, such inhibitors of a mammalian SHMT2 and/or SHMT1 are selective inhibitors for SHMT enzymes (e.g., the compounds show selectivity for SHMT enzymes over DHFR and/or TS and/or MTHFD2). In certain embodiments, suitable inhibitors of mammalian SHMT2 and/or SHMT1 do not substantially inhibit the activity of DHFR and/or TS and/or MTHFD2.

In one aspect, the present disclosure provides SHMT inhibitors, including selective and dual SHMT (SHMT1 and SHMT2) inhibitors. It has been shown that dual SHMT1/2 knockout prevents xenograft formation according to Examples of this disclosure. Dual SHMT inhibition blocks cell growth in a formate rescuable fashion and phenocopies genetic knockout. However, in some hematological cell lines, for example B-cell lymphoma lines such as diffuse large-cell B-cell lymphomas (DLBCL), formate alone did not rescue, but rather synergized with an SHMT inhibitor (such as an SHMT inhibitor described herein) as shown in the Examples of this disclosure. This unexpected outcome reflects the inability of these cells to uptake glycine, a required product of the SHMT reaction. Without being bound by theory, defective glycine uptake renders DLBCL cells (as well as other cancers in which formate fails to rescue following treatment with an SHMT inhibitor) uniquely sensitive to SHMT inhibition (alone or in combination with formate or a formate derivative).

These SHMT inhibitors are useful in numerous in vitro and in vivo applications, as described herein, including in the treatment of cancer and other hyperproliferative conditions, as well as in the treatment of autoimmune disorders, particularly those caused or exacerbated by proliferation or increased metabolic activity of immune cells. In certain embodiments, SHMT inhibitors are useful in cancers or other contexts that are associated with alterations in mitochondrial metabolism, such as mitochondrial folate metabolism (e.g., cancers that contain alterations in genes associated with mitochondrial metabolism). Without being bound by theory, such cancers seem to be particularly sensitized to SHMT inhibitors.

B. Definitions

Unless otherwise defined herein, scientific and technical terms used in this disclosure shall have the meanings that are commonly understood by those of ordinary skill in the art. Generally, nomenclature used in connection with, and techniques of, chemistry, cell and tissue culture, molecular biology, cell and cancer biology, immunology, and pharmacology, described herein, are those well known and commonly used in the art.

Chemistry terms used herein are used according to conventional usage in the art, for example as exemplified by "The McGraw-Hill Dictionary of Chemical Terms", Parker S., Ed., McGraw-Hill, San Francisco, Calif. (1985).

All of the above, and any other publications, patents and published patent applications referred to in this disclosure are specifically incorporated by reference herein. In case of conflict, the present disclosure, including its specific definitions, will control.

It is to be understood that the present desclosure is not limited to particular embodiments described, as such may, of course, vary. It is also to be understood that the terminology used herein is for the purpose of describing particular embodiments only, and is not intended to be limiting.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Any formula depicted herein is intended to represent a compound of that structural formula as well as certain variations or forms. For example, a formula given herein is intended to include a racemic form, or one or more enantiomeric, diastereomeric, or geometric isomers, or tautomeric forms, or a mixture thereof. Additionally, any formula given herein is intended to refer also to a solvate, such as a hydrate, solvate, or polymorph of such a compound, or a mixture thereof. Any formula given herein is intended to refer to amorphous and/or crystalline physical forms of the compound. The compounds described herein may be analytically pure, or a mixture in which the compound comprises at least 50%, at least 70%, at least 80%, at least 90%, at least 95%, or at least 98% by weight of the mixture.

In addition, where features or aspects of the embodiments of this disclosure are described in terms of Markush groups, those skilled in the art will recognize that embodiments described herein is also thereby described in teiins of any individual member or subgroup of members of the Markush group. For example, if X is described as selected from the group consisting of bromine, chlorine, and iodine, claims for X being bromine and claims for X being bromine and chlorine are fully described.

The term "herein" refers to the entire disclosure.

As used herein, the terms "including," "containing," "comprises," and "comprising" are used in their open, non-limiting sense.

The term "alkoxy" refers to an oxygen atom having an alkyl group attached thereto. Representative alkoxy groups include methoxy, ethoxy, propoxy, tert-butoxy and the like. In some embodiments, a straight chain or branched chain alkoxy has 30 or fewer carbon atoms, and preferably 20 or fewer, such as $C_1$-$C_{10}$ alkoxy, $C_1$-$C_8$ alkoxy, or $C_1$-$C_6$ alkoxy.

The term "alkenyl" refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. In some embodiments, a straight chain or branched chain alkenyl has 30 or fewer carbon atoms, and preferably 20 or fewer, such as $C_2$-$C_{10}$ alkenyl or $C_2$-$C_8$ alkenyl.

The term "alkynyl" refers to an aliphatic group containing at least one triple bond and is intended to include both "unsubstituted alkynyls" and "substituted alkynyls," the latter of which refers to alkynyl moieties having substituents replacing one or more hydrogens on one or more carbons of the alkynyl group. Such substituents may occur on one or more carbons that are included or not included in one or more triple bonds. Moreover, such substituents include all those contemplated for alkyl groups, as discussed below, except where stability is prohibitive. For example, substitution of alkynyl groups by one or more alkyl, carbocyclyl, aryl, heterocyclyl, or heteroaryl groups is contemplated. In some embodiments, a straight chain or branched chain alkynyl has 30 or fewer carbon atoms, and preferably 20 or fewer, such as $C_2$-$C_{10}$ alkynyl or $C_2$-$C_8$ alkynyl.

The term "alkyl" refers to a saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g., methyl, ethyl, n-propyl, i-propyl, n-butyl and n-pentyl. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In some embodiments, the chain has eight or fewer carbon ($C_1$-$C_8$) atoms. In other embodiments, the chain has six or fewer carbon ($C_1$-$C_6$) atoms in its backbone. A $C_1$-$C_6$ straight chained or branched alkyl group is also referred to as a "lower alkyl" group. Moreover, the term "alkyl" (or "lower alkyl") as used throughout the disclosure, examples, and claims is intended to include both "unsubstituted alkyls" and "substituted alkyls", the latter of which refers to alkyl moieties having substituents replacing a hydrogen on one or more carbons of the hydrocarbon backbone.

Such substituents can include, but not limited to, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety. It will be understood by those skilled in the art that the moieties substituted on the hydrocarbon chain can themselves be substituted, if appropriate. For instance, the substituents of a substituted alkyl may include substituted and unsubstituted forms of hydroxyl, halo, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "arylkyl", as used herein, refers to an alkyl group substituted with one or more aryl groups.

The term "aryl", as used herein, includes substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like.

The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "amine" and "amino" are art-recognized and refer to both unsubstituted and substituted amines and salts thereof, e.g., a moiety that can be represented by

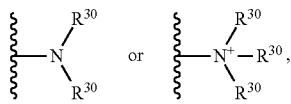

wherein each $R^{30}$ independently represents a hydrogen or a hydrocarbyl group, or two $R^{30}$ are taken together with the N atom to which they are attached complete a heterocycle having from 4 to 8 atoms in the ring structure.

The term "aminoalkyl" refers to an alkyl group substituted with an amino group.

The term "amide" refers to a group:

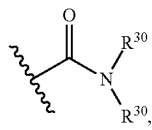

wherein each $R^{30}$ independently represent a hydrogen or hydrocarbyl group, or two $R^{30}$ are taken together with the N atom to which they are attached complete a heterocycle having from 4 to 8 atoms in the ring structure.

The terms "nitrile" or "cyano," as used herein, refers to CN.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be susbstituted at any one or more positions capable of bearing a hydrogen atom.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated, and aromatic rings.

A "cycloalkenyl" group, as used herein, refers to a cyclic hydrocarbon containing one or more double bonds. A "cycloalkynyl" group is a cyclic hydrocarbon containing one or more triple bonds.

The terms "polycyclyl", "polycycle", and "polycyclic", as used herein, refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The terms "halo" and "halogen", as used herein, means halogen and includes chloro, fluoro, bromo, and iodo.

The twin "haloalkyl", as used herein, means an alkyl group substituted with one or more halogens. When more than one halogen is present, the halogens may be the same or different. For examples, haloalkyl groups include, but are not limited to, fluoromethyl, difluoromethyl, trifluoromethyl, chlorodifluoromethyl, 2,2,2-trifluoroethyl, pentafluoroethyl, and the like.

The term "haloalkoxy", as used herein, means an alkoxy group substituted with one or more halogens. When more than one halogen is present, the halogens may be the same or different. For examples, haloalkyl groups include, but are not limited to, difluoromethoxy, trifluoromethoxy, 2,2,2-trifluoroethoxy, pentafluoroethoxy, and the like.

The term "heteroarylakyl", as used herein, refers to an alkyl group substituted with a heteroaryl group.

The term "heteroaryl" includes substituted or unsubstituted aromatic single ring structures, preferably 5- to 7-membered rings, more preferably 5- to 6-membered rings, whose ring structures include at least one heteroatom (e.g., O, N, or S), preferably one to four, or one to 3 heteroatoms, more preferably one or two heteroatoms. When two or more heteroatoms are present in a heteroaryl ring, they may be the same or different. For examples, heteroaryl groups include, but are not limited to, pyrrole, furan, thiophene, imidazole, tetrazole, oxazole, thiazole, pyrazole, pyridine, pyrazine, pyridazine, pyrimidine, and the like. The term "heteroaryl" also include substituted or unsubstituted "polycyclic" ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls.

The term "heteroatom", as used herein, means an atom of any element other than carbon or hydrogen. Exemplary heteroatoms include but are not limited to nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. In certain embodiments, the ring structure is saturated, such as heterocycloalkyls; in other embodiments, the ring structure is unsaturated, such as heterocycloalkenyls or heterocycloalkynyls. The terms "heterocyclyl" and "heterocyclic" also include substituted or unsubstituted polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. In certain embodiments, the ring structure can have two cyclic rings. In some embodiments, the two cyclic rings can have two or more atoms in common, e.g., the rings are "fused rings." Heterocyclyl groups include, but no Emitted to, for example, piperidine, piperazine, pyrrolidine, morpholine, lactones, lactams, and the like.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Accordingly, substituents can further include an acetamide, for example.

Unless specifically stated as "unsubstituted," references to chemical moieties herein are understood to include substituted variants. For example, reference to an "alkyl" group or moiety implicitly includes both substituted and unsubstituted variants. The term "unsubstituted" refers to that the specified group bears no substituents.

The term "optionally substituted", as used herein, means that substitution is optional and therefore it is possible for the designated atom or moiety to be unsubstituted.

The term "ring" or "ring system", unless context indicates otherwise, may include monocyclic rings or polycyclic rings, such as bicyclic rings. When the term ring refers to a polycyclic or bicyclic ring, each ring is independently selected from saturated or unsaturated, and either or both rings may contain one or more heteroatoms, preferably a total of 0, 1, 2, 3 or 4 heteroatoms across the ring system.

A "pharmaceutically active metabolite" or "metabolite" refers to a pharmacologically active product of metabolism/ biochemical modification of a compound described herein, e.g., a compound of of Formula (I) (including Ia and Ib), (II) (including IIa and IIb), (III) (including IIIa and IIIb), Formula II' (including IIa' and IIb'), and Formula III' (including IIIa' and IIIb') or salt thereof, under physiological conditions, e.g., through certain enzymatic pathway. For example, an oxidative metabolite is formed by oxidation of the parent compound during metabolism, such as the oxidation of a pyridine ring to pyridine-N-oxide. In another example, an oxidative metabolite is formed by demethylation of a methoxy group to result in a hydroxyl group.

Compounds of this disclosure can also exist as various "solvates" or "hydrates." A "hydrate" is a compound that exists in a composition with water molecules. The composition can include water in stoichiometic quantities, such as a monohydrate or a dihydrate, or can include water in random amounts. A "solvate" is a similar composition except that a solvent other that water, such as with methanol, ethanol, dimethylformamide, diethyl ether and the like replaces the water. For example, methanol or ethanol can form an "alcoholate," which can again be stoichiometic or non-stoichiometric. Mixtures of such solvates or hydrates can also be prepared. The source of such solvate or hydrate can be from the solvent of crystallization, inherent in the solvent of preparation or crystallization, or adventitious to such solvent.

The compounds of the disclosure, including their pharmaceutically acceptable salts and prodrugs, can exist as various polymorphs, pseudo-polymorphs, or in amorphous state. The term "polymorph", as used herein, refers to different crystalline forms of the same compound and other solid state molecular forms including pseudo-polymorphs, such as hydrates, solvates, or salts of the same compound. Different crystalline polymorphs have different crystal structures due to a different packing of molecules in the lattice, as a result of changes in temperature, pressure, or variations in the crystallization process. Polymorphs differ from each other in their physical properties, such as x-ray diffraction characteristics, stability, melting points, solubility, or rates of dissolution in certain solvents. Thus crystalline polymorphic forms are important aspects in the development of suitable dosage forms in pharmaceutical industry.

In certain embodiments, a "pharmaceutically acceptable" substance is suitable for use in contact with cells, tissues or organs of animals or humans without excessive toxicity, irritation, allergic response, immunogenicity or other adverse reactions, in the amount used in the dosage form according to the dosing schedule, and commensurate with a reasonable benefit/risk ratio. In certain embodiments, a "pharmaceutically acceptable" substance that is a component of a pharmaceutical composition is, in addition, compatible with the other ingredient(s) of the composition.

The terms "pharmaceutically acceptable excipient", "pharmaceutically acceptable carrier" and "pharmaceutically acceptable diluent" encompass, without limitation, pharmaceutically acceptable inactive ingredients, materials, compositions and vehicles, such as liquid fillers, solid fillers, diluents, excipients, carriers, solvents and encapsulating materials. Carriers, diluents and excipients also include all pharmaceutically acceptable dispersion media, coatings, buffers, isotonic agents, stabilizers, absorption delaying agents, antimicrobial agents, antibacterial agents, antifungal agents, adjuvants, and so on. Except insofar as any conventional excipient, carrier or diluent is incompatible with the active ingredient, the present disclosure encompasses the use of conventional excipients, carriers and diluents in pharmaceutical compositions. See, e.g., Remington: The Science and Practice of Pharmacy, 21st Ed., Lippincott Williams & Wilkins (Philadelphia, Pa., 2005); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla., 2004). A "pharmaceutically acceptable salt" is a salt of a compound that is suitable for pharmaceutical use, including but not limited to metal salts (e.g., sodium, potassium, magnesium, calcium, etc.), acid addition salts (e.g., mineral acids, carboxylic acids, etc.), and base addition salts (e.g., ammonia, organic amines, etc.).

"Pharmaceutically acceptable salt" or "salt" is used herein to refer to an agent or a compound according to the disclosure that is a therapeutically active, non-toxic base and acid salt form of the compounds. The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like. See, e.g., WO 01/062726. Some pharmaceutically acceptable salts listed by Berge et al., *Journal of Pharmaceutical Sciences*, 66: 1-19 (1977), incorporated herein by reference in its entirety.

Compounds containing acidic protons may be converted into their therapeutically active, non-toxic base addition salt form, e.g. metal or amine salts, by treatment with appropriate organic and inorganic bases. Appropriate base salt forms include, for example, ammonium salts, alkali and earth alkaline metal salts, e.g., lithium, sodium, potassium, magnesium, calcium salts and the like, salts with organic bases, e.g. N-methyl-D-glucamine, hydrabamine salts, and salts with amino acids such as, for example, arginine, lysine and the like. Conversely, said salt forms can be converted into the free forms by treatment with an appropriate base or acid. Compounds and their salts can be in the form of a solvate, which is included within the scope of the present disclosure. Such solvates include for example hydrates, alcoholates and the like. See, e.g., WO 01/062726.

Other examples of pharmaceutically acceptable salts include, but are not limited to, camsylate, sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

The neutral font's of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent faint of the compound for the purposes of the present disclosure.

The term "pharmaceutical composition" refers to a composition suitable for pharmaceutical use in a subject animal, including humans and mammals, e.g., combined with one or more pharmaceutically acceptable carriers, excipients or solvents. Such a composition may also contain diluents, fillers, salts, buffers, stabilizers, solubilizers, and other materials well known in the art. In certain embodiments, a pharmaceutical composition encompasses a composition comprising the active ingredient(s), and the inert ingredient(s) that make up the excipient, carrier or diluent, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and one or more pharmaceutically acceptable excipient(s), carrier(s) and/or diluent(s).

Accordingly, the pharmaceutical compositions of the present disclosure encompass any composition made by admixing a compound of the disclosure and one or more pharmaceutically acceptable excipient(s), carrier(s) and/or diluent(s).

The disclosure further provides pharmaceutical compositions comprising one or more compounds of the disclosure together with a pharmaceutically acceptable carrier or excipient. Compounds or pharmaceutical compositions of the disclosure may be used in vitro or in vivo.

Isomerism and Tautomerism in Described Compounds
Tautomerism

Within the present disclosure it is to be understood that a compound described herein or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric form. However, it is also to be understood that the disclosure encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

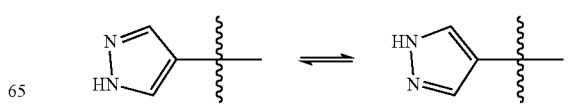

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

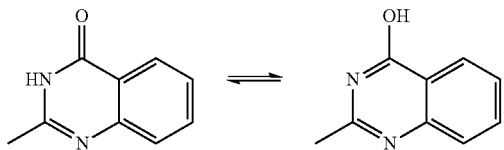

is an example of tautomerism. Accordingly, a structure depicted herein as one tautomer is intended to also include the other tautomer.

Optical Isomerism

It will be understood that when compounds of the present disclosure contain one or more chiral centers, the compounds may exist in, and may be isolated as pure enantiomeric or diastereomeric forms or as racemic mixtures. The present disclosure therefore includes any possible enantiomers, diastereomers, racemates in their pure forms or mixtures thereof, and salts thereof, of the compounds of the disclosure.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

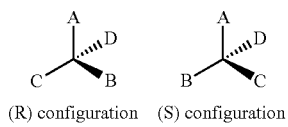

(R) configuration   (S) configuration

In certain embodiments, the therapeutic preparation may be enriched to provide predominantly one enantiomer of a compound (e.g., of formula (I), (Ia), or (Ib)). An enantiomerically enriched mixture may comprise, for example, at least 60 mol percent of one enantiomer, or more preferably at least 75, 90, 95, or even 99 mol percent. In certain embodiments, a compound of the invention may have greater than 30% ee, 40% ee, 50% ee, 60% ee, 70% ee, 80% ee, 90% ee, or even 95% or greater ee. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, compounds of the disclosure may have more than one stereocenter. In certain such embodiments, compounds of the disclosure may be enriched in one or more diastereomer. For example, a compound of the disclosure may have greater than 30% de, 40% de, 50% de, 60% de, 70% de, 80% de, 90% de, or even 95% or greater de.

Isolated optical isomers may be purified from racemic mixtures by well-known chiral separation techniques, such as but not limited to, normal and reverse phase chromatography, and crystallization. According to one such method, a racemic mixture of a compound of the disclosure, or a chiral intermediate thereof, is separated using a chiral salt or carried out on a Chiralcell OD column. The column is operated according to the manufacturer's instructions.

Isolated optical isomers (enantiomerically pure compounds) can also be prepared by the use of chiral intermediates or catalysts in synthesis. When a chiral synthetic intermediate is used, the optical center (chiral center) can be preserved without racemization throughout the remainder of the preparative procedure, as is well known in the art. Chiral catalyst can be used to impart at least some degree of enantiomeric purity to products of reactions catalyzed by the chiral catalyst. And, in some cases, compounds having at least some degree of enantiomeric enrichment can be obtained by physical processes such as selective crystallization of salts or complexes formed with chiral adjuvants.

A variety of compounds in the present disclosure may exist in particular geometric or stereoisomeric forms. The present disclosure takes into account all such compounds, including tautomers, cis- and trans-isomers, R- and S-enantiomers, diastereomers, (D)-isomers, (L)-isomers, the racemic mixtures thereof, and other mixtures thereof, as being covered within the scope of this disclosure. All tautomeric farms are encompassed in the present disclosure. Additional asymmetric carbon atoms may be present in a substituent such as an alkyl group. All such isomers, as well as mixtures thereof, are intended to be included in this disclosure, unless the stereochemistry or isomeric form is specifically indicated.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present disclosure therefore includes any possible stable rotamers of formula (I) which are biologically active in the treatment of cancer or other proliferative disease states.

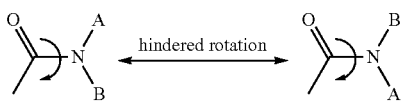

Regioisomerism

The compounds of the disclosure have a particular spatial arrangement of substituents on the aromatic rings, which are related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

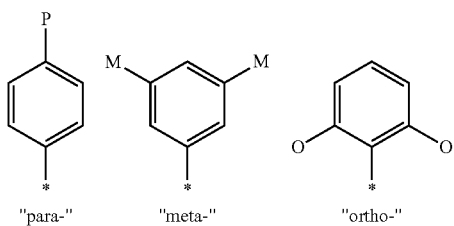

In various embodiments, the compound or set of compounds, such as are used in the disclosed methods, can be any one of any of the combinations and/or sub-combinations of the above-listed embodiments.

Cis-, Trans-Isomerism or E/Z Isomerism

In som embodiments, the compounds of the disclosure may contain a double bond. It is understood that cis/trans isomers are configurational isomers having different orientation at the double bond. In certain such embodiments, the compounds of this disclosure can be in either cis- or trans-formation. In the present disclosure, the term "cis" is equivalently used for "Z" and vice versa "trans" for "E" and vice versa.

A "patient," "subject," or "individual" are used interchangeably and refer to to both mammals and non-mammals. Mammals include, for example, humans; non-human primates either a human or a non-human animal. These terms include mammals, such as humans, non-human primates, e.g. apes and monkeys; and non-primates, e.g. mice, rats, rabbits, dogs, cats, cattle, horses, sheep, and goats. In certain embodiments, the patient or subject is a human patient or subject, such as a human patient having a condition associated with SHMT activity and in need of treatment.

"SHMT" refers to serine hydroxymethyltransferase. Such enzymes are known and, in mammals, both SHMT1 and SHMT2 are expressed and active. Exemplary SHMTs include mammalian SHMT1 and SHMT2, such as human SHMT1 and SHMT2. Further structural information regarding human SHMT1 can be found at NCBI entrez ID number 6470. Further structural information regarding human SHMT2 can be found at NCBI entrez ID number 6472.

"Inhibitor" as used herein refers to any molecule that is capable of interacting directly or indirectly with another molecule (e.g., an enzyme or receptor) and causing a decrease in a biological activity of that other molecule. In certain embodiments, the compounds of the present disclosure inhibit mammalian SHMT enzyme activity (e.g., SHMT1 and/or SHMT2). In certain embodiments the inhibitors are selective inhibitors of SHMT enzyme activity (e.g., SHMT1 and/or SHMT2). In certain embodiments, the inhibitors bind to SHMT1 and/or SHMT2 (e.g., bind to the enzyme). In certain embodiments, the SHMT inhibitor is an inhibitor of SHMT2 and does not inhibit or inhibits with a significantly lower $IC_{50}$ an activity of SHMT1. In certain embodiments, the SHMT inhibitor inhibits an activity of SHMT2 and, optionally, SHMT1. In certain embodiments, the SHMT inhibitor inhibits both SHMT1 and SHMT2 (e.g., either with approximately the same $IC_{50}$ or within 2, 3 or 4-fold). In certain embodiments, the compounds of the disclosure (such as compounds of Formulae (I)-(IX) (including compounds of Formulae (I)-(IX), and pharmaceutically acceptable salts thereof, as well as the individual compounds disclosed herein) are used as inhibitors of SHMT activity (e.g., enzyme activity). In certain embodiments, compounds of the disclosure are SHMT inhibitors, such as selective SHMT inhibitors (SHMT1 and/or SHMT2). It should be noted that a compound may be characterized as an SHMT1 and/or SHMT2 inhibitor by evaluation in an in vitro assay. This gives an accurate characterization. However, in vivo, the compound's mechanism of action may be primarily via its effect on one but not both enzymes. For example, when used in a subject or cell line deficient in SHMT2, the compound's effect on cell proliferation may be primarily through its effect as an SHMT1 inhibitor. Similarly, in some systems, a compound may have poor penetration or accessibility to the mitochondria, and thus, the effect of the compound may be primarily through its effect on SHMT1 despite its high intrinsic activity against SHMT2. Regardless of the particular mechanism of action at play in any particular in vivo system, inhibitors may be characterized as SHMT2 and/or SHMT1 inhibitors based on activity in one or more in vitro assays, as described herein.

In certain embodiments, by "SHMT activity" is meant a native function of a mammalian SHMT enzyme, such its native enzymatic activity. In certain embodiments, SHMT activity refers to the function of mammalian SHMT to catalyze a reversible reaction converting serine to glycine. In certain embodiments, SHMT activity refers to the function of mammalian SHMT to catalyze a reversible reaction converting serine to glycine with concurrent methylene-tetrahydrofolate (meTHF) generation. In certain embodiments, SHMT activity refers to the generation of 1C units. SHMT activity may be assayed or evaluated in numerous ways, such as is described herein. SHMT activity may be evaluated by evaluating serine flux and/or folate metabolism, such as mitochondrial serine flux, glycine synthesis, NADPH generation, generation and excretion of formate or mitochondrial folate metabolism.

The term "compounds of the disclosure" refers to any of the compounds described herein based on any combination of structural and/or functional features, including compounds of Formulae (I)-(IX), wherein the variables are defined as provided herein, as well as to any of the specific compounds described herein. The term "compounds of the disclosure" refers, unless context indicates otherwise, to salts of such compounds, such as pharmaceutically acceptable salts. In certain embodiments, compounds of the disclosure are capable of inhibiting SHMT activity, such as enzyme activity. In certain embodiments, compounds of the disclosure are inhibitors of SHMT2 and/or SHMT1. In certain embodiments, compounds of the disclosure are selective inhibitors of SHMT (e.g., SHMT1 and/or 2). In certain embodiments, compounds of the disclosure are dual inhibitors of SHMT1 and SHMT2. In certain embodiments, compounds of the disclosure are selective for SHMT over MTHFD2 and/or DHFR and/or TS. For example, in certain embodiments, compounds of the disclosure either do not inhibit or inhibit one or more of MTHFD2, DHFR, FH, TS and/or another protein involved in mitochondrial folate metabolism with an IC50 at least 25 fold, at least 50 fold, at least 75 fold, at least 100 fold, at least 200 fold, at least 500 fold, at least 1000 fold, or greater than 1000 fold less than that for SHMT2 and/or SHMT1.

In certain embodiments, compounds of the disclosure include compounds provided as a pharmaceutical composition.

Compounds of the disclosure also include tautomeric founts, such as keto-enol tautomers, prototropic tautomers, and the like, for example annular tautomers wherein a proton can occupy two or more positions on a heteroaryl system. Tautomeric forms can be in equilibrium or sterically locked into one form by appropriate substitution. It is understood that the various tautomeric forms are within the scope of the compounds of the present disclosure.

Compounds of the disclosure also include all isotopes of atoms occurring in the intermediates and/or final compounds. Isotopes include those atoms having the same atomic number but different mass numbers. For example, isotopes of hydrogen include deuterium and tritium.

Compounds of Formulae (I)-(IX) (and the other compounds of the disclosure) have one or more chiral centers and therefore can exist as enantiomers and/or diastereomers. Compounds of Formulae (I)-(IX) (and the other compounds of the disclosure) may also exist as stereoisomers, for example atropisomers, resulting from hindered rotation about a single bond. The compound of the disclosure are understood to extend to, and embrace all such enantiomers, diastereomers, atropisomers, stereoisomers, and mixtures thereof; including but not limited to racemates. Formulae (I)-(IX) (and the other compounds of the disclosure) used throughout this disclosure are intended to represent all individual stereoisomers and mixtures thereof, unless stated or shown otherwise.

"Treating" a condition or patient refers to taking steps to obtain beneficial or desired results, including clinical results. Beneficial or desired clinical results include, but are not limited to, alleviation, amelioration, or slowing the progression, of one or more symptoms associated with a condition, such as cancer. Exemplary beneficial clinical results are described herein.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. When a method is part of a therapeutic regimen involving more than one agent or treatment modality, the disclosure contemplates that the agents may be administered at the same or differing times and via the same or differing routes of administration.

Appropriate methods of administering a substance, a compound or an agent to a subject will also depend, for example, on the age of the subject, whether the subject is active or inactive at the time of administering, whether the subject is cognitively impaired at the time of administering, the extent of the impairment, and the chemical and biological properties of the compound or agent (e.g. solubility, digestibility, bioavailability, stability and toxicity).

A "therapeutically effective amount" or a "therapeutically effective dose" of a drug or agent is an amount of a drug or an agent that, when administered to a subject will have the intended therapeutic effect, sufficient to show a meaningful patient benefit, e.g., treatment, healing, inhibition or amelioration of a physiological response or condition, etc. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of disease, the therapeutics or combination of therapeutics selected for administration, and the mode of administration. The skilled worker can readily determine the effective amount for a given situation by routine experimentation.

C. Compounds

The present disclosure provides a compound of Formula (I):

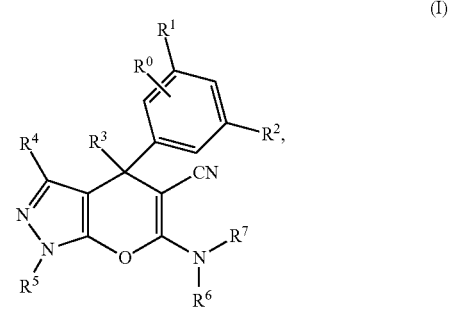

or a pharmaceutically acceptable salt thereof, wherein:
$R^0$, $R^1$ and $R^2$ are each independently selected from the group consisting of —H, halogen (such as F, Br, or Cl), hydroxyl, nitro, nitrile, —SOR$^{11}$, —S(O)$_2$R$^{11}$, —S(O)$_2$R$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted alkyl (such as C$_1$-C$_8$ alkyl or C$_1$-C$_6$ alkyl; e.g., methyl, ethyl, or iso-propyl), substituted or unsubstituted alkenyl (such as C$_2$-C$_8$ alkenyl), substituted or unsubstituted alkynyl (such as C$_2$-C$_8$ alkynyl), substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl (such as C$_1$-C$_8$ haloalkyl or C$_1$-C$_6$ haloalkyl; e.g., trifluoromethyl), and substituted or unsubstituted haloalkoxy (such as C$_1$-C$_8$ haloalkoxy or C$_1$-C$_6$ haloalkoxy); provided that, at least one of $R^0$, $R^1$ and $R^2$ is selected from the group consisting of substituted or unsubstituted alkenyl (such as C$_2$-C$_8$ alkenyl), and substituted or unsubstituted alkynyl (such as C$_2$-C$_8$ alkynyl);
$R^3$ is selected from the group consisting of —H, halogen, hydroxyl, nitro, nitrile, —SOR$^{11}$, —S(O)$_2$R$^{11}$, —S(O)$_2$R$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$_{10}$R$^{12}$, —N(R$^{12}$)C(O)R$^{11}$, —NS(O)$_2$R$^{12}$, substituted or unsubstituted alkyl (such as C$_1$-C$_8$ alkyl or C$_1$-C$_6$ alkyl; e.g., methyl, ethyl, or iso-propyl), substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl (such as C$_1$-C$_8$ haloalkyl or C$_1$-C$_6$ haloalkyl; e.g., trifluoromethyl), and substituted or unsubstituted haloalkoxy (such as C$_1$-C$_8$ haloalkoxy or C$_1$-C$_6$ haloalkoxy);

R$^4$ is selected from the group consisting of —H, substituted or unsubstituted alkyl (such as C$_1$-C$_8$ alkyl; e.g., methyl, ethyl, or iso-propyl), substituted or unsubstituted cycloalkyl (such as C$_3$-C$_7$ cycloalkyl; e.g., cyclopropyl or cyclobutyl), substituted or unsubstituted aryl, substituted or unsubstituted heteroaryl, substituted or unsubstituted arylalkyl, and substituted or unsubstituted heteroarylalkyl;

R$^5$, R$^6$ and R$^7$ are each independently selected from the group consisting of —H, —C(O)R$^{11}$, substituted or unsubstituted alkyl (such as C$_1$-C$_8$ alkyl or C$_1$-C$_6$ alkyl; e.g., methyl, ethyl, or iso-propyl), substituted or unsubstituted cycloalkyl (such as C$_3$-C$_7$ cycloalkyl; e.g., cyclopropyl or cyclobutyl), substituted or unsubstituted aryl, substituted or unsubstituted heteroaryl, substituted or unsubstituted arylalkyl, and substituted or unsubstituted heteroarylalkyl; or R$^5$ is selected from any of the foregoing and R$^6$ and R$^7$ taken together with the nitrogen atom to which they are attached form a substituted or unsubstituted 3-6 membered ring;

each occurrence of R$^{11}$ is independently selected from the group consisting of substituted or unsubstituted alkyl (such as C$_1$-C$_8$ alkyl or C$_1$-C$_6$ alkyl; e.g., methyl, ethyl, or iso-propyl), substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, and substituted or unsubstituted heteroaryl; and each occurrence of R$^{10}$ and R$^{12}$ is independently selected from the group consisting of —H, substituted or unsubstituted alkyl (such as C$_1$-C$_8$ alkyl or C$_1$-C$_6$ alkyl; e.g., methyl, ethyl, or iso-propyl), substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, and substituted or unsubstituted heteroaryl.

In some embodiments, the compound of this disclosure is represented by Formula (Ia):

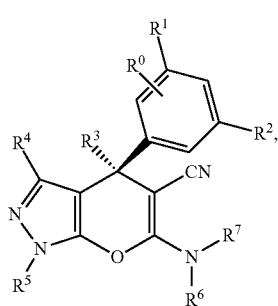

(Ia)

or a pharmaceutically acceptable salt there.

In certain embodiments, the compound of this disclosure is represented by Formula (Ib):

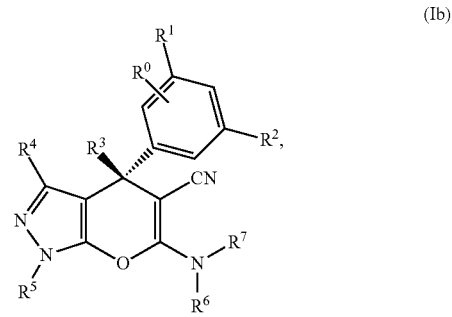

(Ib)

or a pharmaceutically acceptable salt thereof.

In certain embodiments of any of the foregoing or following, R$^0$, R$^1$ and R$^2$ are each independently selected from the group consisting of —H, halogen, hydroxyl, nitro, nitrile, —SOR$^{11}$, —S(O)$_2$R$^{11}$, —S(O)$_2$NR$^{10}$R$^{12}$, —OR$^{11}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted alkyl (such as C$_1$-C$_8$ alkyl or C$_1$-C$_6$ alkyl; e.g., methyl, ethyl, or iso-propyl), substituted or unsubstituted alkenyl (such as C$_2$-C$_8$ alkenyl), substituted or unsubstituted alkynyl (such as C$_2$-C$_8$ alkynyl), substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl (such as C$_1$-C$_8$ haloalkyl or C$_1$-C$_6$ haloalkyl; e.g., trifluoromethyl), and substituted or unsubstituted haloalkoxy (such as C$_1$-C$_8$ haloalkoxy or C$_1$-C$_6$ haloalkoxy); provided that, at least one of R$^0$, R$^1$ and R$^2$ is independently selected from the group consisting of substituted or unsubstituted alkenyl, and substituted or unsubstituted alkynyl.

In certain embodiments of any of the foregoing or following, one of R$^1$ and R$^2$ is selected from the group consisting of substituted or unsubstituted alkenyl (such as C$_2$-C$_8$ alkenyl), and substituted or unsubstituted alkynyl (such as C$_2$-C$_8$ alkynyl); the other is independently selected from the group consisting of —H, halogen, hydroxyl, nitro, nitrile, —SOR$^{11}$, —S(O)$_2$R$^{11}$, —S(O)$_2$NR$^{10}$R$^{12}$, —OR$^{11}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted alkyl (such as C$_1$-C$_8$ alkyl or C$_1$-C$_6$ alkyl; e.g., methyl, ethyl, or iso-propyl), substituted or unsubstituted alkenyl (such as C$_2$-C$_8$ alkenyl), substituted or unsubstituted alkynyl (such as C$_2$-C$_8$ alkynyl), substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl (such as C$_1$-C$_8$ haloalkyl or C$_1$-C$_6$ haloalkyl; e.g., trifluoromethyl), and substituted or unsubstituted haloalkoxy (such as C$_1$-C$_8$ haloalkoxy or C$_1$-C$_6$ haloalkoxy).

In other embodiments of any of the foregoing or following, one of R$^1$ and R$^2$ is selected from the group consisting of substituted or unsubstituted alkenyl (such as C$_2$-C$_8$ alkenyl), and substituted or unsubstituted alkynyl (such as C$_2$-C$_8$ alkynyl); the other is independently selected from the group consisting of —H, halogen, hydroxyl, nitro, nitrile, —OR$^{11}$, substituted or unsubstituted alkyl, substituted or unsubstituted alkenyl, substituted or unsubstituted alkynyl, substituted or unsubstituted haloalkyl (such as C$_1$-C$_8$ haloalkyl or C$_1$-C$_6$ haloalkyl; e.g., trifluoromethyl), and substituted or unsubstituted haloalkoxy (such as C$_1$-C$_8$ haloalkoxy or C$_1$-C$_6$ haloalkoxy).

In certain embodiments of any of the foregoing or following, one of R$^1$ and R$^2$ is substituted or unsubstituted alkynyl (such as C$_2$-C$_8$ alkynyl), the other is not. In other embodiments, both R$^1$ and R$^2$ are substituted or unsubstituted alkynyl (such as C$_2$-C$_8$ alkynyl).

In some embodiments of any of the foregoing of following, one of R$^1$ and R$^2$ is substituted or unsubstituted alkenyl (such as C$_2$-C$_8$ alkenyl), the other is not. In other embodiments, both R$^1$ and R$^2$ are substituted or unsubstituted alkenyl (such as C$_2$-C$_8$ alkenyl).

In certain embodiments of any of the foregoing or following, R$^1$ is substituted or unsubstituted alkynyl and R$^2$ is not a substituted or unsubstituted alkynyl (such as C$_2$-C$_8$ alkynyl). In other embodiments, R$^2$ is substituted or unsubstituted alkynyl and R$^1$ is not a substituted or unsubstituted alkynyl (such as C$_2$-C$_8$ alkynyl).

In certain embodiments of any of the foregoing or following, R$^1$ is substituted or unsubstituted alkenyl and R$^2$ is not a substituted or unsubstituted alkenyl (such as C$_2$-C$_8$ alkenyl). In other embodiments, R$^2$ is substituted or unsubstituted alkenyl and R$^1$ is not a substituted or unsubstituted alkenyl (such as C$_2$-C$_8$ alkenyl).

In certain embodiments of any of the foregoing or following, the alkenyl (such as C$_2$-C$_8$ alkenyl) or alkynyl (such as C$_2$-C$_8$ alkynyl), when substituted, is substituted with one or more substituents independently selected from the group consisting of halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, optionally substituted aryl, and optionally substituted heteroaryl comprising 1-4N atoms; or two of the substituents together with the atoms to which they are attached faun an optionally substituted ring.

In certain such embodiments of any of the foregoing or following, alkenyl (such as C2-C8 alkenyl) or alkynyl (such as C2-C8 alkynyl), when substituted, is substituted with one or more substituents independently selected from the group consisting of OH, halogen, —OR11, —C(O)OR12, —C(O)NR10R12, —NR10R12, optionally substituted aryl, and optionally substituted heteroaryl comprising 1-4N atoms; or two of the substituents together with the atoms to which they are attached faint an optionally substituted ring.

In certain embodiments of any of the foregoing or following, R0 is selected from the group consisting of hydroxyl, —S(O)2R11, —S(O)2NR10R12, —OR11, —C(O)NR10R12, —NR10R12, —N(R12)C(O)R11, and —NS(O)2R12. In certain such embodiments, R0 is H.

In certain embodiments of any of the foregoing or following, R3 is selected from the group consisting of methyl, ethyl, propyl, isopropyl, cyclopropyl, and cyclobutyl. In certain such embodiments, R3 is selected from the group consisting of isopropyl, cyclopropyl, and cyclobutyl. In some embodiments, R3 is isopropyl.

In certain embodiments of any of the foregoing or following, R4 is selected from the group consisting of methyl, ethyl, isopropyl, cyclopropyl, cyclobutyl, cyclopentyl, cyclohexyl, phenyl, and benzyl. In certain such embodiments, R4 is methyl or isopropyl. In some embodiments, R4 is methyl.

In certain embodiments of any of the foregoing or following, R5, R6, and R7 are each independently selected from the group consisting of —H, methyl, ethyl, isopropyl, cyclopropyl, cyclobutyl, cyclopentyl, cyclohexyl, phenyl, benzyl, and —COCH3. In certain such embodiments, R5, R6 and R7 are each independently selected from the group consisting of —H, methyl, phenyl, and —COCH3. In some embodiments, R5 and R6 are each independently selected from the group consisting of —H, methyl, and phenyl.

In certain embodiments of any of the foregoing or following, R7 is —H.

In certain embodiments of any of the foregoing or following, R5 is selected from the group consisting of —H, methyl, ethyl, isopropyl, cyclopropyl, cyclobutyl, cyclopentyl, cyclohexyl, phenyl, benzyl, and —COCH3; and R6 and R7 taken together with the nitrogen atom to which they are attached form a substituted or unsubstituted ring selected from the group consisting of:

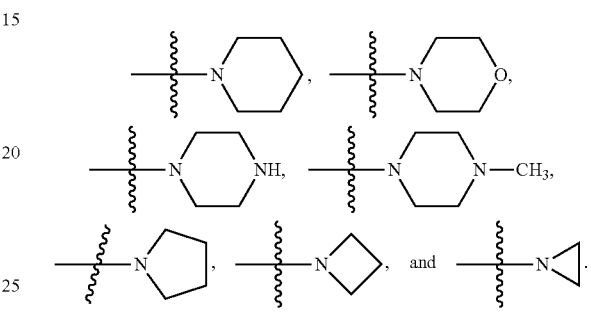

In ceratin emobidments of any of the foregoing or following, R$^5$ is selected from the group consisting of —H, methyl, phenyl, and —COCH$_3$; and R$^6$ and R$^7$ taken together with the nitrogen atom to which they are attached form a substituted or unsubstituted ring selected from the group consisting of:

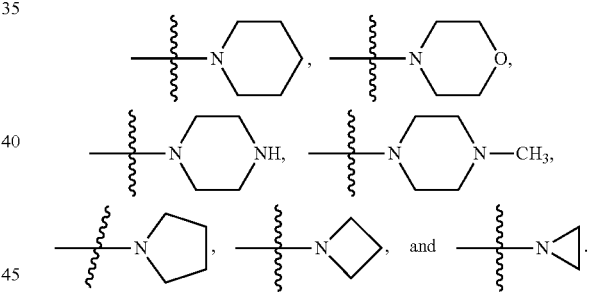

In certain embodiments of any of the foregoing or following, R$^0$ is selected from the group consisting of —H, halogen, hydroxyl, nitro, nitrile, —S(O)$_2$R$^{11}$, —S(O)$_2$R$^{10}$R$^{12}$, —OR$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted alkyl (such as C$_1$-C$_8$ alkyl; e.g., methyl, ethyl, or iso-propyl), substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl (such as C$_1$-C$_8$ haloalkyl or C$_1$-C$_6$ haloalkyl; e.g., trifluoromethyl), and substituted or unsubstituted haloalkoxy (such as C$_1$-C$_8$ haloalkoxy or C$_1$-C$_6$ haloalkoxy);

one of R$^1$ and R$^2$ is substituted or unsubstituted alkenyl (such as C$_2$-C$_8$ alkenyl), or substituted or unsubstituted alkynyl (such as C$_2$-C$_8$ alkynyl); the other is independently selected from the group consisting of —H, halogen, hydroxyl, nitro, nitrile, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted alkyl (such as C$_1$-C$_8$ alkyl; e.g., methyl, ethyl, or iso-propyl), unsubstituted or unsubstituted alkenyl (such as C$_2$-C$_8$ alkenyl), substituted or unsubstituted alkynyl (such as C$_2$-C$_8$ alkynyl), substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl (such as C$_1$-C$_8$ haloalkyl or C$_1$-C$_6$ haloalkyl); e.g., trifluoromethyl), and substituted or unsubstituted haloalkoxy (such as C$_1$-C$_8$ haloalkoxy or C$_1$-C$_6$ haloalkoxy);

R$^3$ is selected from the group consisting of methyl, ethyl, propyl, isopropyl, cyclopropyl, and cyclobutyl;

R$^4$ is selected from the group consisting of methyl, ethyl, isopropyl, cyclopropyl, cyclobutyl, cyclopentyl, cyclohexyl, phenyl and benzyl; and R$^5$, R$^6$ and R$^7$ are each independently selected from the group consisting of —H, methyl, ethyl, isopropyl, cyclopropyl, cyclobutyl, cyclopentyl, cyclohexyl, phenyl, benzyl, and —COCH$_3$.

In certain embodiments of any of the foregoing of following, R$^0$ is —H;

one of R$^1$ and R$^2$ is substituted or unsubstituted alkenyl (such as C$_2$-C$_8$ alkenyl), or substituted or unsubstituted alkynyl (such as C$_2$-C$_8$ alkynyl); the other is independently selected from the group consisting of —H, halogen, hydroxyl, nitro, nitrile, —OR$^{11}$, substituted or unsubstituted alkyl (such as C$_1$-C$_8$ alkyl C$_1$-C$_6$ alkyl); e.g., methyl, ethyl, or iso-propyl), substituted or unsubstituted alkenyl (such as C$_2$-C$_8$ alkenyl), substituted or unsubstituted alkynyl (such as C$_2$-C$_8$ alkynyl), substituted or unsubstituted haloalkyl (such as C$_1$-C$_8$ haloalkyl or C$_1$-C$_6$ haloalkyl); e.g., trifluoromethyl), or substituted or unsubstituted haloalkoxy (such as C$_1$-C$_8$ haloalkoxy or C$_1$-C$_6$ haloalkoxy);

R$^3$ is selected from the group consisting of isopropyl, cyclopropyl, and cyclobutyl;

R$^4$ is methyl or isopropyl; and

R$^5$, R$^6$ and R$^7$ are each independently selected from the group consisting of —H, alkyl (such as C$_1$-C$_8$ alkyl C$_1$-C$_6$ alkyl); e.g., methyl, ethyl, or iso-propyl), phenyl, and —COCH$_3$.

In certain embodiments, R$^0$ is —H;

one of R$^1$ and R$^2$ is substituted or unsubstituted alkenyl (such as C$_2$-C$_8$ alkenyl), or substituted or unsubstituted alkynyl (such as C$_2$-C$_8$ alkynyl); the other is independently selected from the group consisting of —H, methoxy, fluoro, chloro, bromo, hydroxyl, nitro, nitrile, alkyl, —CCl$_3$, and —CF$_3$;

R$^3$ is cyclobutyl or iso-propyl;

R$^4$ is methyl;

R$^5$ and R$^6$ are each independently selected from the group consisting of —H, alkyl (such as C$_1$-C$_6$alkyl; e.g., methyl, ethyl, or iso-propyl), and phenyl; and R$^7$ is H.

In certain embodiments of any of the foregoing or following, R$^0$ is selected from the group consisting of —H, hydroxyl, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, and —NS(O)$_2$$^{12}$;

one of R$^1$ and R$^2$ is substituted or unsubstituted alkynyl (such as C$_2$-C$_8$ alkynyl); the other is nitro, —Cl, —OCH$_3$, or —CF$_3$; R$^3$ is iso-propyl; R$^4$ is methyl; and R$^5$, R$^6$, and R$^7$ are H.

The disclosure contemplates compounds have any combination of any of the foregoing or following structural and/or functional characteristics.

In certain embodiments, this disclosure provides a compound of Formula (II):

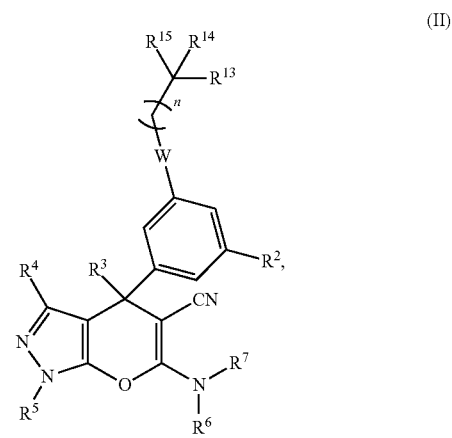

(II)

or a pharmaceutically acceptable salt thereof, wherein

R$^2$, R$^3$, R$^4$, R$^5$, R$^6$, and R$^7$ are as defined herein;

W represents —CR$^{16}$=CR$^{16}$— or —C≡C—;

n is 0, 1, 2, 3, or 4;

R$^{13}$, R$^{14}$, and R$^{15}$ are independently selected from the group consisting of hydrogen, —OH, halogen, optionally substituted alkyl (such as C$_1$-C$_8$ alkyl or C$_1$-C$_6$ alkyl); e.g., methyl, ethyl, or iso-propyl), optionally substituted haloalkyl (such as C$_1$-C$_8$ haloalkyl or C$_1$-C$_6$ haloalkyl; e.g., trifluoromethyl), —OR$^a$, —OC(O)R$^b$, —C(O)NR$^a$R$^b$, and —NR$^a$R$^b$; or R$^{13}$ and R$^{14}$ together with the atom to which they are attached form a 4-7 membered heterocyclic ring comprising 1 or 2 heteroatoms selected from the group consisting of NR$^a$, O, S, or SO, or SO$_2$; wherein the heterocyclic ring is optionally substituted with one or more substituents independently selected from the group consisting of oxo and optionally substituted alkyl; and R$^{16}$, R$^a$ and R$^b$, independently at each occurrence, are H or optionally substituted alkyl (such as C$_1$-C$_8$ alkyl or C$_1$-C$_6$ alkyl; e.g., methyl, ethyl, or iso-propyl).

In certain embodiments, the compound of Formula (II) can be represented by Formula (IIa) or (Ib):

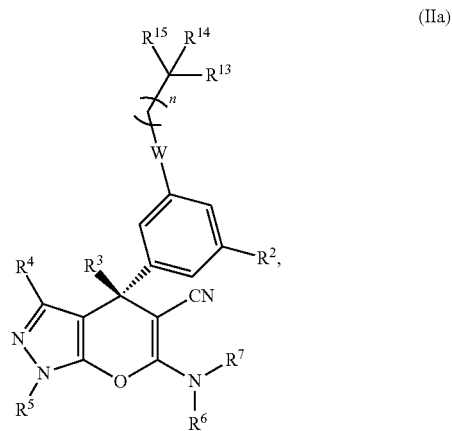

(IIa)

-continued

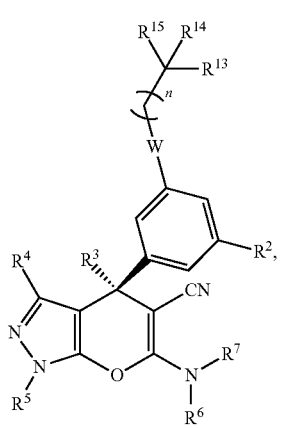

(IIb)

or a pharmaceutically acceptable salt thereof.

In certain embodiments of any of the foregoing or following, W is —CR$^{16}$=CR$^{16}$ in cis- or trans-formation. In other embodiments, W is —C≡C—.

In certain embodiments of any of the foregoing of following, R$^{13}$, R$^{14}$, and R$^{15}$ are independently selected from the group consisting of hydrogen, —OH, halogen, optionally substituted alkyl (such as C$_1$-C$_8$ alkyl or C$_1$-C$_6$ alkyl; e.g., methyl, ethyl, or iso-propyl), optionally substituted haloalkyl (such as C$_1$-C$_8$ haloalkyl or C$_1$-C$_6$ haloalkyl; e.g., trifluoromethyl), —OR$^a$, —OC(O)R$^b$, —C(O)NR$^a$R$^b$, and —NR$^a$R$^b$, and wherein R$^a$ and R$^b$, independently at each occurrence, are H or optionally substituted alkyl ((such as C$_1$-C$_8$ alkyl or C$_1$-C$_6$ alkyl; e.g., methyl, ethyl, or iso-propyl).

In certain embodiments of any of the foregoing or following, n is 0; R$^{13}$ and R$^{14}$ together with the atom to which they are attached form a 4-7 membered heterocyclic ring comprising 1 or 2 heteroatoms selected from the group consisting of NR$^a$, and O; wherein the heterocyclic ring is optionally substituted with one or more substituents independently selected from the group consisting of oxo and optionally substituted alkyl; and R$^{15}$ is H. The disclosure contemplates compounds have any combination of any of the foregoing or following structural and/or functional characteristics.

In certain embodiments of any of the foregoing or following, this disclosure provides a compound of Formula (III):

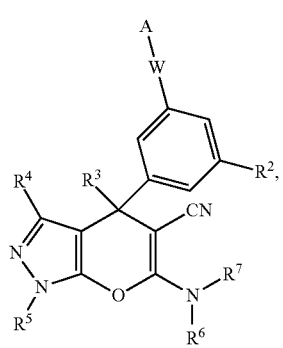

(III)

or a pharmaceutically acceptable salt thereof, wherein
R$^2$, R$^3$, R$^4$, R$^5$, R$^6$, and R$^7$ are as defined herein;
W represents —CR$^{16}$=CR$^{16}$ or —C≡C—;
R$^{16}$ is H or optionally substituted alkyl (such as C$_1$-C$_8$ alkyl or C$_1$-C$_6$ alkyl; e.g., methyl, ethyl, or iso-propyl); and
A represents optionally substituted aryl or optionally substituted heteroaryl.

In certain embodiments, the compound of Formula (III) can be represented by Formula (IIIa) or (IIIb):

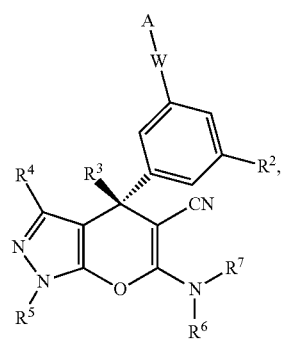

(IIIa)

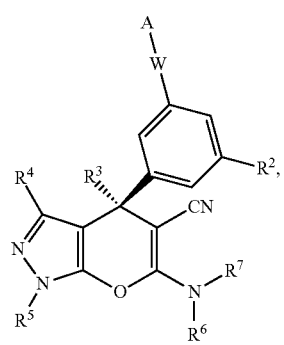

(IIIb)

or a pharmaceutically acceptable salt thereof.

In certain embodiments of any of the foregoing or following, W is —C≡C—. In other embodiments, W is —CR$^{16}$=CR$^{16}$ in cis- or trans-formation.

In certain embodiments of any of the foregoing or following, A is aryl, optionally substituted with one or more substituents independently selected from the group consisting of —OH, halogen, optionally substituted alkyl (such as C$_1$-C$_9$ alkyl or C$_1$-C$_6$ alkyl; e.g., methyl, ethyl, or iso-propyl), optionally substituted haloalkyl (such as C$_1$-C$_8$ haloalkyl or C$_1$-C$_6$ haloalkyl; e.g., trifluoromethyl), —OR$^a$, —OC(O)R$^b$, —C(O)NR$^a$R$^b$, and —NR$^a$R$^b$, and wherein R$^a$ and R$^b$, independently at each occurrence, are H or optionally substituted alkyl. In certain such embodiments, A is phenyl, optionally substituted with one or more substituents independently selected from the group consisting of —CH$_2$OH, —OH, —CF$_3$, —COOH, —F, —CH$_2$NH$_2$, —CONH$_2$, and —NH$_2$.

In certain embodiments of any of the foregoing or following, A is heteroaryl, optionally substituted with one or more substituents independently selected from the group consisting of —OH, halogen, optionally substituted alkyl (such as C$_1$-C$_8$ alkyl or C$_1$-C$_6$ alkyl; e.g., methyl, ethyl, or iso-propyl), optionally substituted haloalkyl (such as C$_1$-C$_8$ haloalkyl or C$_1$-C$_6$ haloalkyl; e.g., trifluoromethyl), —OR$^a$, —OC(O)R$^b$, —C(O)NR$^a$R$^b$, and —NR$^a$R$^b$, and wherein R$^a$ and R$^b$, independently at each occurrence, are H or optionally substituted alkyl (such as C$_1$-C$_8$ alkyl or C$_1$-C$_6$ alkyl; e.g., methyl, ethyl, or iso-propyl).

In certain such embodiments, A is an optionally substituted heteroaryl containing 1-4 N atoms.

In some embodiments of any of the foregoing or following, A is an optionally substituted tetrazolyl or optionally substituted triazolyl.

In certain embodiments of any of the foregoing or following, A is pyridinyl, optionally substituted with one or more substituents independently selected from the group consisting of —H, —CH$_2$OH, —OH, —CF$_3$, —COOH, —F, —CH$_2$NH$_2$, —CONH$_2$, and —NH$_2$.

In certain embodiments of any of the foregoing or following, R$^2$ is nitro, —F, —Cl, —OCH$_3$, CCl$_3$, or —CF$_3$; R$^3$ is selected from the group consisting of isopropyl, cyclopropyl, and cyclobutyl; R$^4$ is methyl or isopropyl; and R$^5$, R$^6$ and R$^7$ are each independently selected from the group consisting of —H, alkyl (such as C$_1$-C$_8$ alkyl or C$_1$-C$_6$ alkyl; e.g., methyl, ethyl, or iso-propyl), phenyl, and —COCH$_3$.

In certain embodiments of any of the foregoing or following, R$^2$ is CF$_3$; R$^3$ is iso-propyl; R$^4$ is methyl; and R$^5$, R$^6$, and R$^7$ are H.

In certain embodiments, this disclosure provides a compound of Formula (II'):

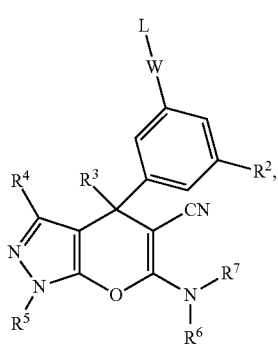

(II')

or a pharmaceutically acceptable salt thereof, wherein:
R$^2$ and R$^3$ are each independently selected for each occurrence from the group consisting of —H, halogen (such as F, Br, or Cl), hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted alkyl (such as C$_1$-C$_8$ alkyl or C$_1$-C$_6$ alkyl; e.g., methyl, ethyl, or iso-propyl), substituted or unsubstituted alkenyl, substituted or unsubstituted alkynyl, substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl (such as C$_1$-C$_8$ haloalkyl or C$_1$-C$_6$ haloalkyl; e.g., trifluoromethyl), and substituted or unsubstituted haloalkoxy (such as C$_1$-C$_8$ haloalkoxy or C$_1$-C$_6$ haloalkoxy);

R$^4$ is selected from the group consisting of —H, substituted or unsubstituted alkyl (such as C$_1$-C$_8$ alkyl; e.g., methyl, ethyl, or iso-propyl), substituted or unsubstituted alkenyl, substituted or unsubstituted alkynyl, substituted or unsubstituted cycloalkyl (such as C$_3$-C$_7$ cycloalkyl; e.g., cyclopropyl or cyclobutyl), substituted or unsubstituted aryl, substituted or unsubstituted heteroaryl, substituted or unsubstituted arylalkyl, and substituted or unsubstituted heteroarylalkyl;

R$^5$, R$^6$ and R$^7$ are each independently selected from the group consisting of —H, —C(O)R$^{11}$, substituted or unsubstituted alkyl (such as C$_1$-C$_8$ alkyl or C$_1$-C$_6$ alkyl; e.g., methyl, ethyl, or iso-propyl), substituted or unsubstituted alkenyl, substituted or unsubstituted alkynyl, substituted or unsubstituted cycloalkyl (such as C$_3$-C$_7$ cycloalkyl; e.g., cyclopropyl or cyclobutyl), substituted or unsubstituted aryl, substituted or unsubstituted heteroaryl, substituted or unsubstituted arylalkyl, and substituted or unsubstituted heteroarylalkyl; or R$^5$ is selected from any of the foregoing and R$^6$ and R$^7$ taken together with the nitrogen atom to which they are attached form a substituted or unsubstituted 3-6 membered ring;

each occurrence of R$^{11}$ is independently selected from the group consisting of substituted or unsubstituted alkyl (such as C$_1$-C$_8$ alkyl or C$_1$-C$_6$ alkyl; e.g., methyl, ethyl, or iso-propyl), substituted or unsubstituted alkenyl, substituted or unsubstituted alkynyl, substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, and substituted or unsubstituted heteroaryl; and each occurrence of R$^{10}$ and R$^{12}$ is independently selected from the group consisting of —H, substituted or unsubstituted alkyl (such as C$_1$-C$_8$ alkyl or C$_1$-C$_6$ alkyl; e.g., methyl, ethyl, or iso-propyl), substituted or unsubstituted alkenyl, substituted or unsubstituted alkynyl, substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, and substituted or unsubstituted heteroaryl.

W represents —CR$^{16}$=CR$^{16}$— or —C≡C—;

R$^{16}$ is H or optionally substituted alkyl (such as C$_1$-C$_8$ alkyl or C$_1$-C$_6$ alkyl; e.g., methyl, ethyl, or iso-propyl); and L is selected from the group consisting of —H, substituted or unsubstituted alkyl (such as C$_1$-C$_{12}$ alkyl or C$_1$-C$_8$ alkyl; e.g., methyl, ethyl, iso-propyl, n-butyl, or n-proypl), substituted or unsubstituted alkenyl, substituted or unsubstituted alkynyl, substituted or unsubstituted cycloalkyl (such as C$_3$-C$_7$ cycloalkyl; e.g., cyclopropyl or cyclobutyl), substituted or unsubstituted heterocyclyl, substituted or unsubstituted arylalkyl, substituted or unsubstituted heteroarylalkyl.

In certain embodiments, the compound of Formula (II') can be represented by Formula (IIa') or (IIb'):

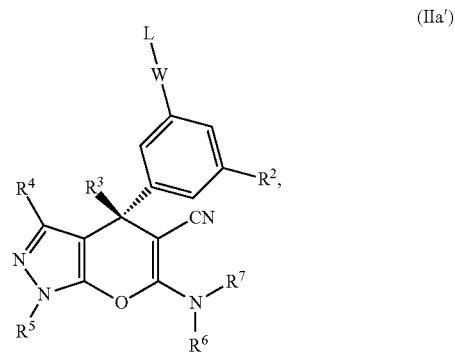

(IIa')

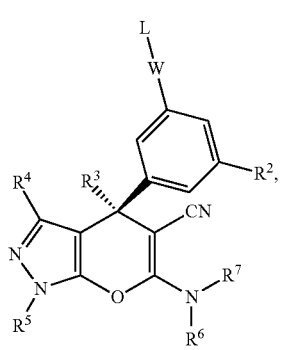 (IIb')

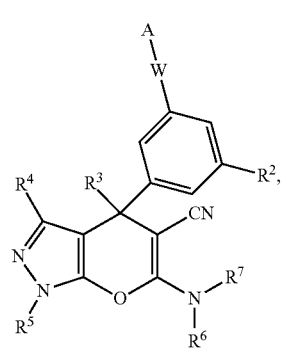 (III')

or a pharmaceutically acceptable salt thereof.

In certain embodiments of any of the foregoing or following, W is —CR$^{16}$=CR$^{16}$ in a cis-formation. In certain embodiments, W is —CR$^{16}$=CR$^{16}$ in a trans-formation. In some embodiments, W is —C≡C—.

In certain embodiments of any of the foregoing or following, L is alkyl, optionally substituted with one or more substituents selected from the group consisting of halogen, hydroxyl, nitro, nitrile, —SOR$^{11}$, —S(O)$_2$R$^{11}$, —S(O)$_2$N$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted alkyl (such as C$_1$-C$_{12}$ alkyl or C$_1$-C$_8$ alkyl; e.g., methyl, ethyl, iso-propyl, or n-butyl), substituted or unsubstituted cycloalkyl (such as C$_3$-C$_7$ cycloalkyl; e.g., cyclopropyl or cyclobutyl), substituted or unsubstituted heterocyclyl ring, substituted or unsubstituted aryl, substituted or unsubstituted heteroaryl, substituted or unsubstituted arylalkyl, substituted or unsubstituted heteroarylalkyl, substituted or unsubstituted haloalkyl (such as C$_1$-C$_8$ haloalkyl or C$_1$-C$_6$ haloalkyl; e.g., trifluoromethyl), and substituted or unsubstituted haloalkoxy (such as C$_1$-C$_8$ haloalkoxy or C$_1$-C$_6$ haloalkoxy);

In certain embodiments of any of the foregoing or following, L is alkyl optionally substituted with one or more substituents independently selected from the group consisting of hydrogen, —OH, halogen, optionally substituted alkyl (such as C$_1$-C$_{12}$ alkyl or C$_1$-C$_8$ alkyl; e.g., methyl, ethyl, iso-propyl, n-butyl), substituted or unsubstituted heteroaryl, optionally substituted haloalkyl (such as C$_1$-C$_8$ haloalkyl or C$_1$-C$_6$ haloalkyl; e.g., trifluoromethyl), —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$;

In certain embodiments of any of the foregoing or following, L is cycloalkyl or heterocyclyl ring, optionally substituted with one or more substituents selected from the group consisting of halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted alkyl, and oxo.

In certain embodiments of any of the foregoing or following, L is a four to seven membered heterocyclyl ring comprising one to three heteroatoms selected from the group consisting of NR$^{10}$, O, S, SO, or SO$_2$.

In certain embodiments of any of the foregoing or following, L is H.

In certain embodiments of any of the foregoing or following, this disclosure provides a compound of Formula (III'):

or a pharmaceutically acceptable salt thereof,
wherein:
R$^2$ and R$^3$ are each independently selected for each occurrence from the group consisting of —H, halogen (such as F, Br, or Cl), hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted alkyl (such as C$_1$-C$_8$ alkyl or C$_1$-C$_6$ alkyl; e.g., methyl, ethyl, or iso-propyl), substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl (such as C$_1$-C$_8$ haloalkyl or C$_1$-C$_6$ haloalkyl; e.g., trifluoromethyl), and substituted or unsubstituted haloalkoxy (such as C$_1$-C$_8$ haloalkoxy or C$_1$-C$_6$ haloalkoxy);

R$^4$ is selected from the group consisting of —H, substituted or unsubstituted alkyl (such as C$_1$-C$_8$ alkyl; e.g., methyl, ethyl, or iso-propyl), substituted or unsubstituted cycloalkyl (such as C$_3$-C$_7$ cycloalkyl; e.g., cyclopropyl or cyclobutyl), substituted or unsubstituted aryl, substituted or unsubstituted heteroaryl, substituted or unsubstituted arylalkyl, and substituted or unsubstituted heteroarylalkyl;

R$^5$, R$^6$ and R$^7$ are each independently selected from the group consisting of —H, —C(O)R$^{11}$, substituted or unsubstituted alkyl (such as C$_1$-C$_8$ alkyl or C$_1$-C$_6$ alkyl; e.g., methyl, ethyl, or iso-propyl), substituted or unsubstituted cycloalkyl (such as C$_3$-C$_7$ cycloalkyl; e.g., cyclopropyl or cyclobutyl), substituted or unsubstituted aryl, substituted or unsubstituted heteroaryl, substituted or unsubstituted arylalkyl, and substituted or unsubstituted heteroarylalkyl; or R$^5$ is selected from any of the foregoing and R$^6$ and R$^7$ taken together with the nitrogen atom to which they are attached form a substituted or unsubstituted 3-6 membered ring;

each occurrence of R$^{11}$ is independently selected from the group consisting of substituted or unsubstituted alkyl (such as C$_1$-C$_8$ alkyl or C$_1$-C$_6$ alkyl; e.g., methyl, ethyl, or iso-propyl), substituted or unsubstituted alkenyl, substituted or unsubstituted alkynyl, substituted or unsubstituted cycloalkyl (such as C$_3$-C$_7$ cycloalkyl; e.g., cyclopropyl or cyclobutyl), substituted or unsubstituted heterocyclyl, substituted or unsubstituted aryl, and substituted or unsubstituted heteroaryl; and each occurrence of R$^{10}$ and R$^{12}$ is independently selected from the group consisting of H, substituted or unsubstituted alkyl (such as C$_1$-C$_8$ alkyl or C$_1$-C$_6$ alkyl; e.g., methyl, ethyl, or iso-propyl), substituted or unsubstituted alkenyl, substituted or unsubstituted alkynyl, substituted or unsubstituted cycloalkyl (such as $C_3$-$C_7$ cycloalkyl; e.g., cyclopropyl or cyclobutyl), substituted or unsubstituted heterocyclyl, substituted or unsubstituted aryl, and substituted or unsubstituted heteroaryl.

W represents —$CR^{16}$=$CR^{16}$ or —C≡C—;

$R^{16}$ is H or optionally substituted alkyl (such as $C_1$-$C_8$ alkyl or $C_1$-$C_6$ alkyl; e.g., methyl, ethyl, or iso-propyl); and A represents optionally substituted aryl or optionally substituted heteroaryl.

In certain embodiments, the compound of Formula (III) can be represented by Formula (IIIa') or

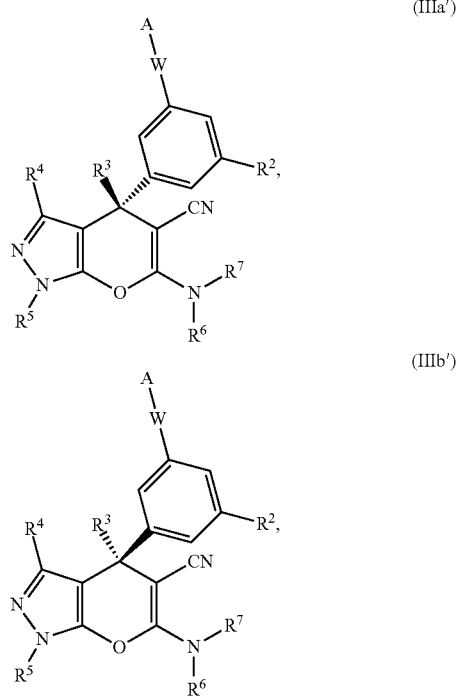

or a pharmaceutically acceptable salt thereof.

In certain embodiments of any of the foregoing or following, W is —C≡C—. In some embodiments, W is —$CR^{16}$=$CR^{16}$ in a cis-formation. In some embodiments, W is in a trans-formation.

In certain embodiments of any of the foregoing or following, A is aryl, optionally substituted with one or more substituents independently selected from the group consisting of halogen (such as F, Br, or Cl), hydroxyl, nitro, nitrile, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted alkyl (such as $C_1$-$C_8$ alkyl or $C_1$-$C_6$ alkyl; e.g., methyl, ethyl, or iso-propyl), substituted or unsubstituted alkenyl, substituted or unsubstituted alkynyl, substituted or unsubstituted cycloalkyl (such as $C_3$-$C_7$ cycloalkyl; e.g., cyclopropyl or cyclobutyl), substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl (such as $C_1$-$C_8$ haloalkyl or $C_1$-$C_6$ haloalkyl; e.g., trifluoromethyl), and substituted or unsubstituted haloalkoxy (such as $C_1$-$C_8$ haloalkoxy or $C_1$-$C_6$ haloalkoxy);

In certain such embodiments, A is phenyl, optionally substituted with one or more substituents independently selected from the group consisting of —$CH_2OH$, —OH, —$CF_3$, —COOH, —F, —$CH_2NH_2$, —$CONH_2$, and —$NH_2$.

In certain embodiments of any of the foregoing or following, A is heteroaryl, optionally substituted with one or more substituents independently selected from the group consisting of halogen (such as F, Br, or Cl), hydroxyl, nitro, nitrile, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted alkyl (such as $C_1$-$C_8$ alkyl or $C_1$-$C_6$ alkyl; e.g., methyl, ethyl, or iso-propyl), substituted or unsubstituted alkenyl, substituted or unsubstituted alkynyl, substituted or unsubstituted cycloalkyl (such as $C_3$-$C_7$ cycloalkyl; e.g., cyclopropyl or cyclobutyl), substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl (such as $C_1$-$C_8$ haloalkyl or $C_1$-$C_6$ haloalkyl; e.g., trifluoromethyl), and substituted or unsubstituted haloalkoxy (such as $C_1$-$C_8$ haloalkoxy or $C_1$-$C_6$ haloalkoxy);

In certain embodiments of any of the foregoing or following, A is heteroaryl, optionally substituted with one or more substituents independently selected from the group consisting of —OH, halogen, optionally substituted alkyl (such as $C_1$-$C_8$ alkyl or $C_1$-$C_6$ alkyl; e.g., methyl, ethyl, or iso-propyl), optionally substituted haloalkyl (such as $C_1$-$C_8$ haloalkyl or $C_1$-$C_6$ haloalkyl; e.g., trifluoromethyl), —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$.

In certain such embodiments, A is an optionally substituted heteroaryl containing 1-4N atoms.

In some embodiments of any of the foregoing or following, A is an optionally substituted tetrazolyl or optionally substituted triazolyl.

In certain embodiments of any of the foregoing or following, A is pyridinyl, optionally substituted with one or more substituents independently selected from the group consisting of —H, —$CH_2OH$, —OH, —$CF_3$, —COOH, —F, —$CH_2NH_2$, —$CONH_2$, and —$NH_2$.

In certain embodiments of any of the foregoing or following, $R^2$ is nitro, —F, —Cl, —$OCH_3$, $CCl_3$, or —$CF_3$; $R^3$ is selected from the group consisting of isopropyl, cyclopropyl, and cyclobutyl; $R^4$ is methyl or isopropyl; and $R^5$, $R^6$ and $R^7$ are each independently selected from the group consisting of —H, alkyl (such as $C_1$-$C_8$ alkyl or $C_1$-$C_6$ alkyl; e.g., methyl, ethyl, or iso-propyl), phenyl, and —$COCH_3$.

In certain embodiments of any of the foregoing or following, $R^2$ is —$CF_3$; $R^3$ is iso-propyl; $R^4$ is methyl; and $R^5$, $R^6$, and $R^7$ are H.

In certain embodiments of any of the foregoing or following, this disclosure provides a compound selected from any compounds described herein, such as the group consisting of compounds as shown in Table 1 or 3, and pharmaceutically acceptable salts thereof. Such compounds may be used in any of the methods described herein, such as for the treatment of a lymphoma, such as a B cell lymphoma, or to inhibit growth, proliferation and/or survival of a lymphoma cell.

In certain embodiments of any of the foregoing or following, this disclosure provides a pharmaceutical composition comprising (a) a compound described in this disclosure; and (b) one or more pharmaceutically acceptable carriers and/or excipients.

In certain embodiments of any of the foregoing or following, the compound of disclosure is selected from Table 1, and pharmaceutical acceptable salts thereof.
TABLE 1
1,4-dihydropyrano[2,3-c]pyrazole derivatives as SHMT inhibitors
| Compound # | Chemical Structure |
|---|---|
| 1 | 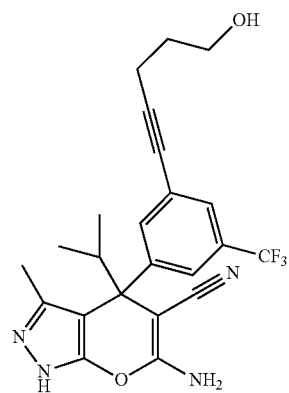 [SMILES: Cc1n[nH]c2c1C(c1cc(C#CCCCO)cc(C(F)(F)F)c1)(C(C)C)C(C#N)=C(N)O2] |
| 2 | 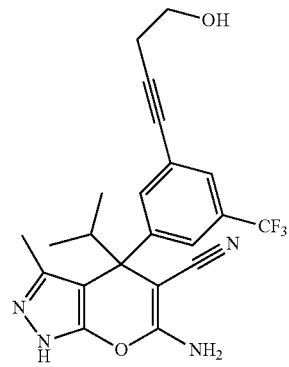 [SMILES: Cc1n[nH]c2c1C(c1cc(C#CCCO)cc(C(F)(F)F)c1)(C(C)C)C(C#N)=C(N)O2] |
| 3 | 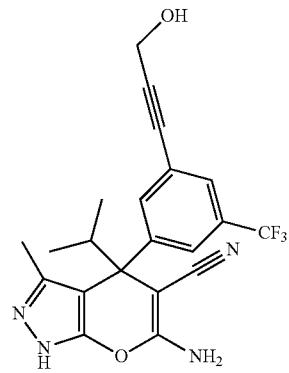 |

TABLE 1-continued
1,4-dihydropyrano[2,3-c]pyrazole derivatives as SHMT inhibitors
| Compound # | Chemical Structure |
|---|---|
| 4 | 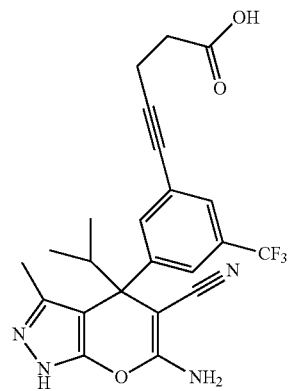 [SMILES: Cc1n[nH]c2c1C(c1cc(C#CCCC(=O)O)cc(C(F)(F)F)c1)(C(C)C)C(C#N)=C(N)O2] |
| 5 | 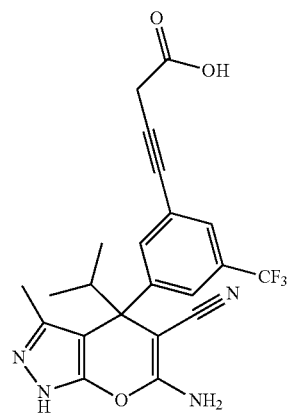 [SMILES: Cc1n[nH]c2c1C(c1cc(C#CCC(=O)O)cc(C(F)(F)F)c1)(C(C)C)C(C#N)=C(N)O2] |
| 6 | 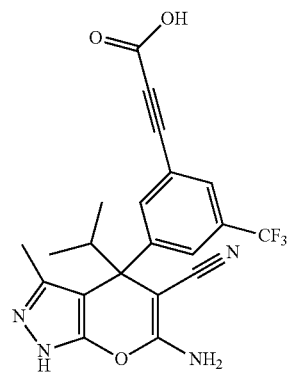 [SMILES: Cc1n[nH]c2c1C(c1cc(C#CC(=O)O)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 7 | 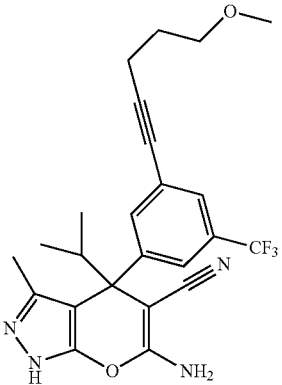 [SMILES: COCCCC#Cc1cc(C(F)(F)F)cc(C2(C(C)C)C(C#N)=C(N)Oc3[nH]nc(C)c32)c1] |
| 8 | 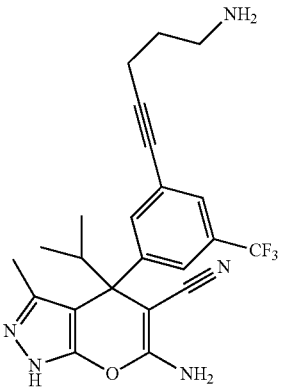 [SMILES: Cc1n[nH]c2c1C(c1cc(C#CCCCN)cc(C(F)(F)F)c1)(C(C)C)C(C#N)=C(N)O2] |
| 9 | 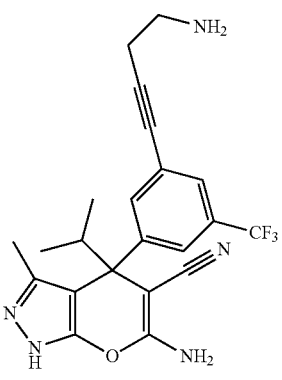 [SMILES: Cc1n[nH]c2c1C(c1cc(C#CCCN)cc(C(F)(F)F)c1)(C(C)C)C(C#N)=C(N)O2] |
| 10 | 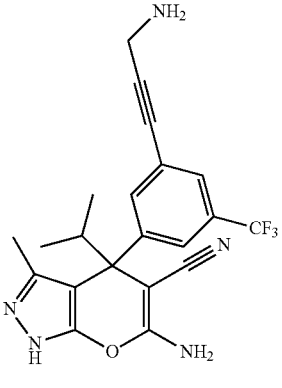 [SMILES: Cc1n[nH]c2c1C(c1cc(C#CCN)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 11 | 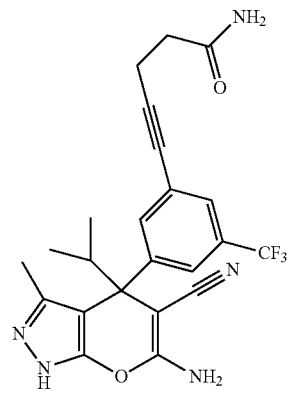 [SMILES: Cc1n[nH]c2c1C(c1cc(C#CCCC(N)=O)cc(C(F)(F)F)c1)(C(C)C)C(C#N)=C(N)O2] |
| 12 | 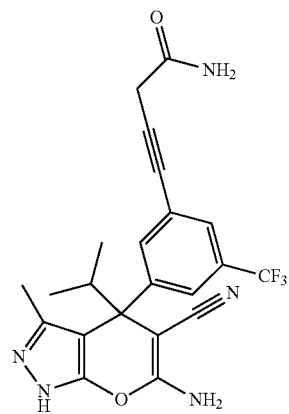 [SMILES: Cc1n[nH]c2c1C(c1cc(C#CCC(N)=O)cc(C(F)(F)F)c1)(C(C)C)C(C#N)=C(N)O2] |
| 13 | 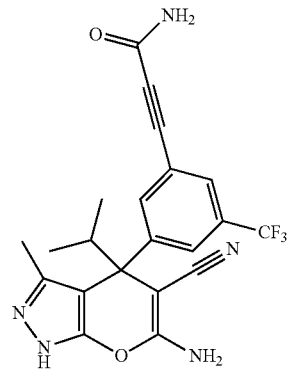 [SMILES: Cc1n[nH]c2c1C(c1cc(C#CC(N)=O)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 14 | 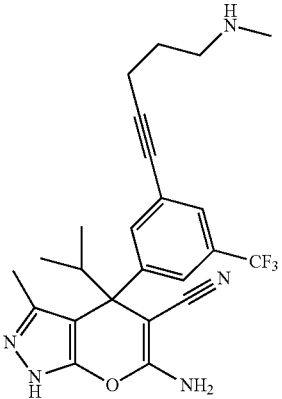 [SMILES: CNCCCC#Cc1cc(C(F)(F)F)cc(C2(C(C)C)C(C#N)=C(N)Oc3[nH]nc(C)c32)c1] |
| 15 | 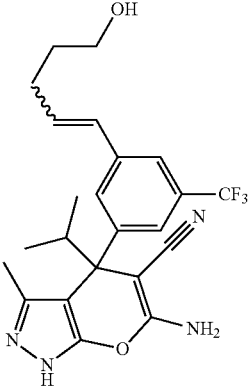 [SMILES: Cc1n[nH]c2c1C(c1cc(C=CCCCO)cc(C(F)(F)F)c1)(C(C)C)C(C#N)=C(N)O2] |
| 16 | 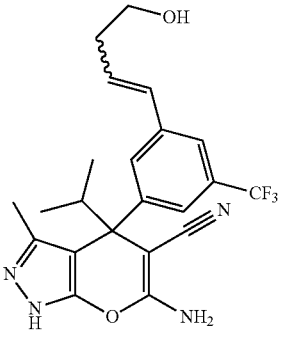 [SMILES: Cc1n[nH]c2c1C(c1cc(C=CCCO)cc(C(F)(F)F)c1)(C(C)C)C(C#N)=C(N)O2] |
| 17 | 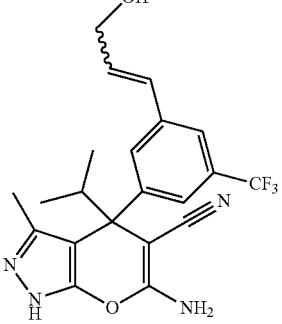 |

TABLE 1-continued
1,4-dihydropyrano[2,3-c]pyrazole derivatives as SHMT inhibitors
| Compound # | Chemical Structure |
| --- | --- |
| 18 | 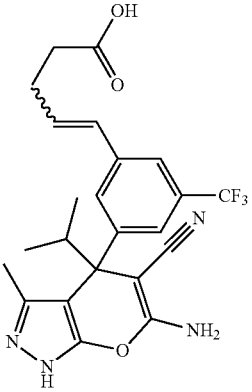 [SMILES: Cc1n[nH]c2c1C(c1cc(C=CCCC(=O)O)cc(C(F)(F)F)c1)(C(C)C)C(C#N)=C(N)O2] |
| 19 | 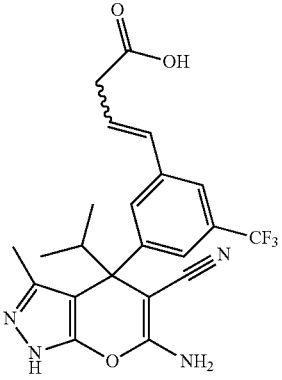 |
| 20 | 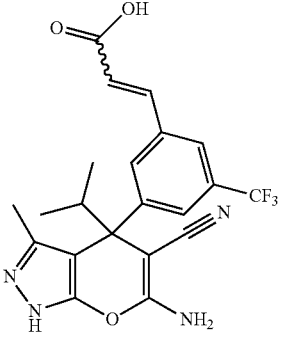 [SMILES: Cc1n[nH]c2c1C(c1cc(C=CC(=O)O)cc(C(F)(F)F)c1)(C(C)C)C(C#N)=C(N)O2] |
| 21 | 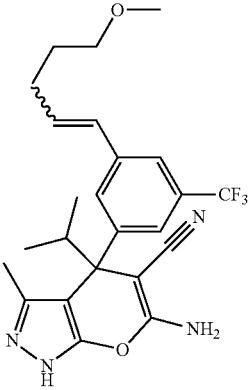 [SMILES: COCCCC=Cc1cc(C(F)(F)F)cc(C2(C(C)C)C(C#N)=C(N)Oc3[nH]nc(C)c32)c1] |

TABLE 1-continued
1,4-dihydropyrano[2,3-c]pyrazole derivatives as SHMT inhibitors
| Compound # | Chemical Structure |
|---|---|
| 22 | 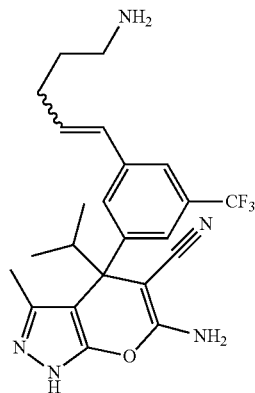 [SMILES: Cc1n[nH]c2c1C(c1cc(C=CCCCN)cc(C(F)(F)F)c1)(C(C)C)C(C#N)=C(N)O2] |
| 23 | 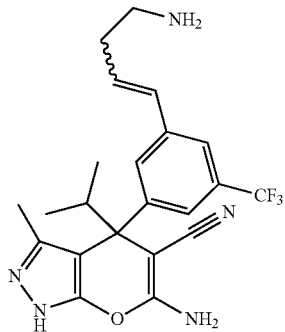 [SMILES: Cc1n[nH]c2c1C(c1cc(C=CCCN)cc(C(F)(F)F)c1)(C(C)C)C(C#N)=C(N)O2] |
| 24 | 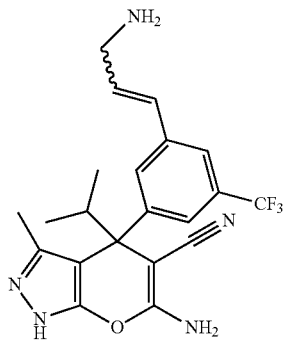 [SMILES: Cc1n[nH]c2c1C(c1cc(C=CCN)cc(C(F)(F)F)c1)(C(C)C)C(C#N)=C(N)O2] |
| 25 | 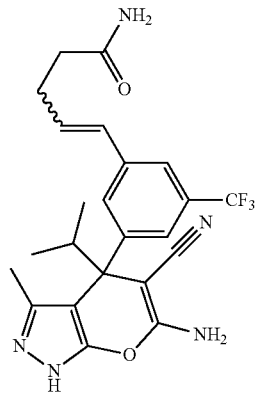 [SMILES: Cc1n[nH]c2c1C(c1cc(C=CCCC(N)=O)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 26 | 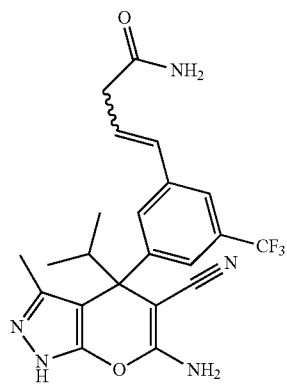 [SMILES: Cc1n[nH]c2c1C(c1cc(C=CCC(N)=O)cc(C(F)(F)F)c1)(C(C)C)C(C#N)=C(N)O2] |
| 27 | 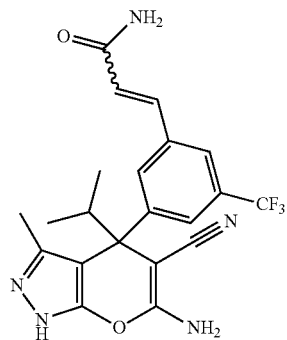 [SMILES: Cc1n[nH]c2c1C(c1cc(C=CC(N)=O)cc(C(F)(F)F)c1)(C(C)C)C(C#N)=C(N)O2] |
| 28 | 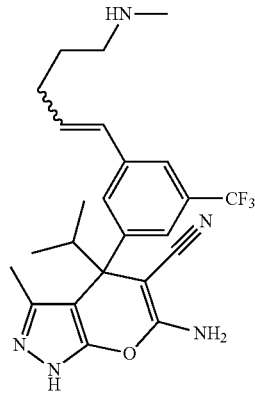 [SMILES: CNCCCC=Cc1cc(C(F)(F)F)cc(C2(C(C)C)C(C#N)=C(N)Oc3[nH]nc(C)c32)c1] |

TABLE 1-continued
1,4-dihydropyrano[2,3-c]pyrazole derivatives as SHMT inhibitors
| Compound # | Chemical Structure |
|---|---|
| 29 | 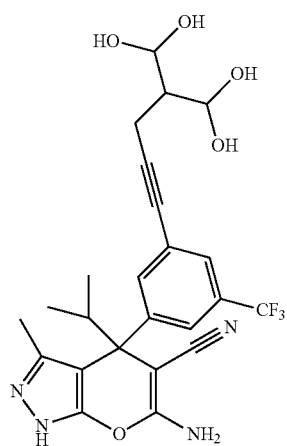 [SMILES: Cc1n[nH]c2c1C(c1cc(C#CCC(C(O)O)C(O)O)cc(C(F)(F)F)c1)(C(C)C)C(C#N)=C(N)O2] |
| 30 | 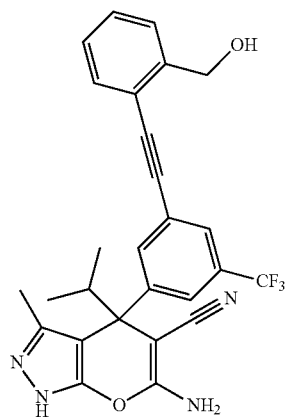 [SMILES: Cc1n[nH]c2c1C(c1cc(C#Cc3ccccc3CO)cc(C(F)(F)F)c1)(C(C)C)C(C#N)=C(N)O2] |
| 31 | 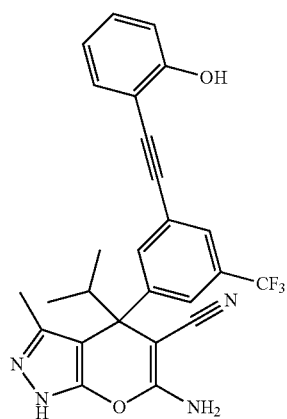 [SMILES: Cc1n[nH]c2c1C(c1cc(C#Cc3ccccc3O)cc(C(F)(F)F)c1)(C(C)C)C(C#N)=C(N)O2] |

TABLE 1-continued 1,4-dihydropyrano[2,3-c]pyrazole derivatives as SHMT inhibitors

| Compound # | Chemical Structure |
|---|---|
| 32 | 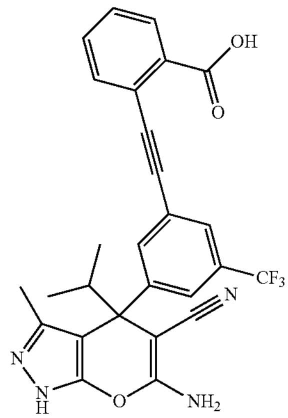 [SMILES: Cc1n[nH]c2c1C(c1cc(C#Cc3ccccc3C(=O)O)cc(C(F)(F)F)c1)(C(C)C)C(C#N)=C(N)O2] |
| 33 | 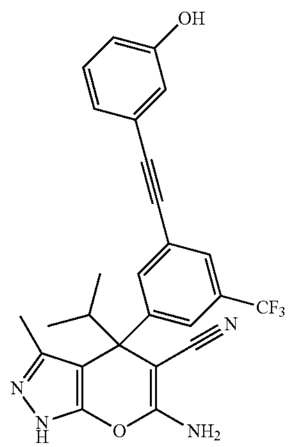 [SMILES: Cc1n[nH]c2c1C(c1cc(C#Cc3cccc(O)c3)cc(C(F)(F)F)c1)(C(C)C)C(C#N)=C(N)O2] |
| 34 | 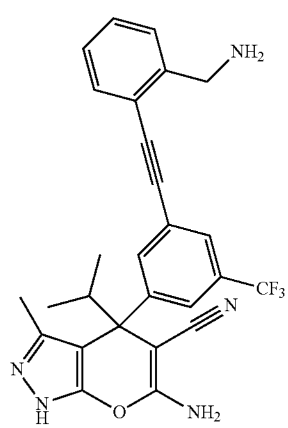 [SMILES: Cc1n[nH]c2c1C(c1cc(C#Cc3ccccc3CN)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 35 | 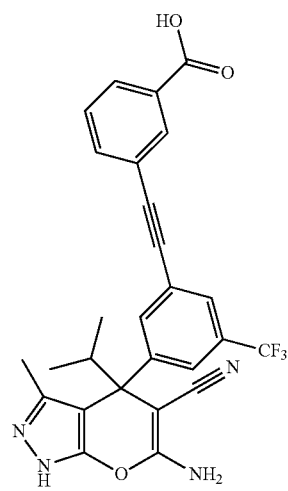 [SMILES: Cc1n[nH]c2c1C(c1cc(C#Cc3cccc(C(=O)O)c3)cc(C(F)(F)F)c1)(C(C)C)C(C#N)=C(N)O2] |
| 36 | 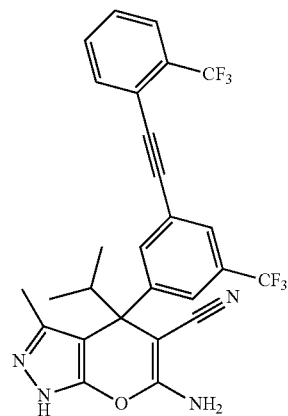 [SMILES: Cc1n[nH]c2c1C(c1cc(C#Cc3ccccc3C(F)(F)F)cc(C(F)(F)F)c1)(C(C)C)C(C#N)=C(N)O2] |
| 37 | 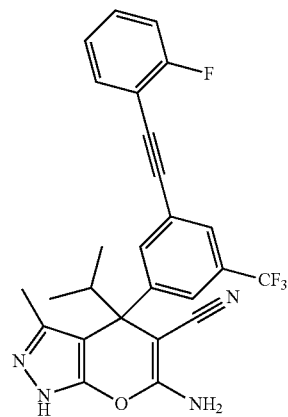 [SMILES: Cc1n[nH]c2c1C(c1cc(C#Cc3ccccc3F)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 38 | 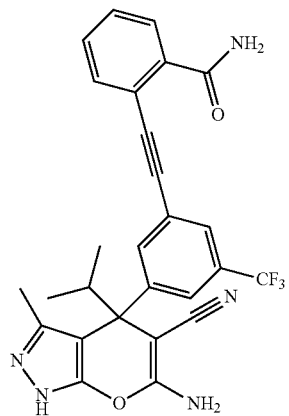 [SMILES: Cc1n[nH]c2c1C(c1cc(C#Cc3ccccc3C(N)=O)cc(C(F)(F)F)c1)(C(C)C)C(C#N)=C(N)O2] |
| 39 | 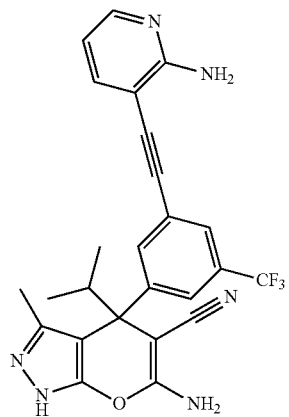 [SMILES: Cc1n[nH]c2c1C(c1cc(C#Cc3cccnc3N)cc(C(F)(F)F)c1)(C(C)C)C(C#N)=C(N)O2] |
| 40 | 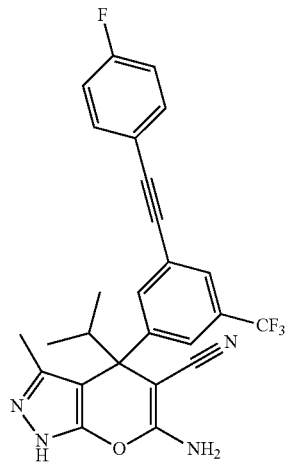 [SMILES: Cc1n[nH]c2c1C(c1cc(C#Cc3ccc(F)cc3)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 41 | 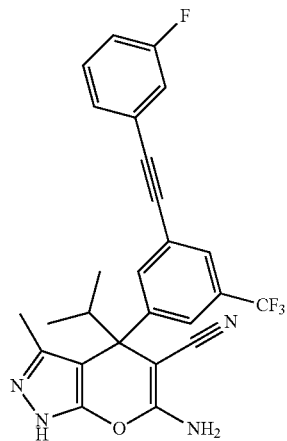 [SMILES: Cc1n[nH]c2c1C(c1cc(C#Cc3cccc(F)c3)cc(C(F)(F)F)c1)(C(C)C)C(C#N)=C(N)O2] |
| 42 | 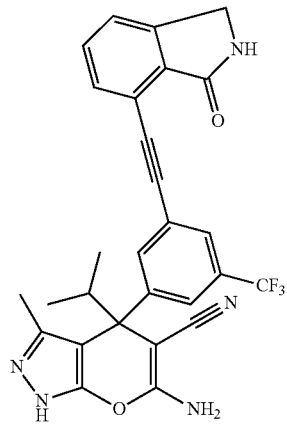 [SMILES: Cc1n[nH]c2c1C(c1cc(C#Cc3cccc4c3C(=O)NC4)cc(C(F)(F)F)c1)(C(C)C)C(C#N)=C(N)O2] |
| 43 | 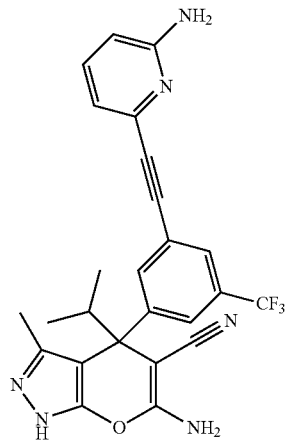 [SMILES: Cc1n[nH]c2c1C(c1cc(C#Cc3cccc(N)n3)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 44 | 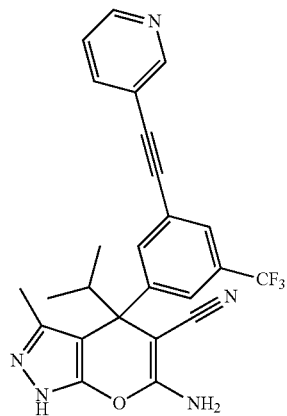 [SMILES: Cc1n[nH]c2c1C(c1cc(C#Cc3cccnc3)cc(C(F)(F)F)c1)(C(C)C)C(C#N)=C(N)O2] |
| 45 | 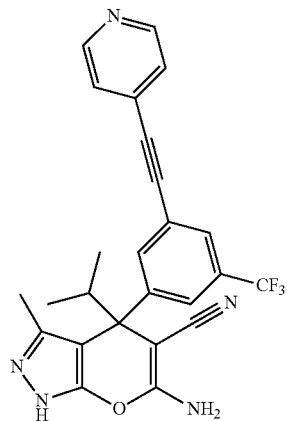 [SMILES: Cc1n[nH]c2c1C(c1cc(C#Cc3ccncc3)cc(C(F)(F)F)c1)(C(C)C)C(C#N)=C(N)O2] |
| 46 | 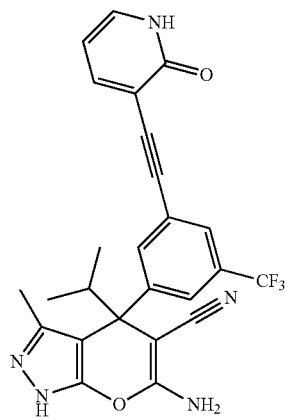 [SMILES: Cc1n[nH]c2c1C(c1cc(C#Cc3ccc[nH]c3=O)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 47 | 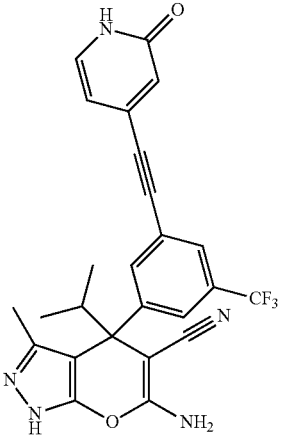 [SMILES: Cc1n[nH]c2c1C(c1cc(C#Cc3cc[nH]c(=O)c3)cc(C(F)(F)F)c1)(C(C)C)C(C#N)=C(N)O2] |
| 48 | 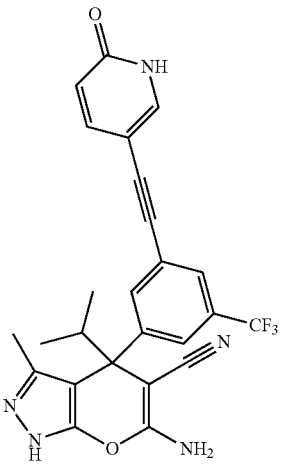 [SMILES: Cc1n[nH]c2c1C(c1cc(C#Cc3ccc(=O)[nH]c3)cc(C(F)(F)F)c1)(C(C)C)C(C#N)=C(N)O2] |
| 49 | 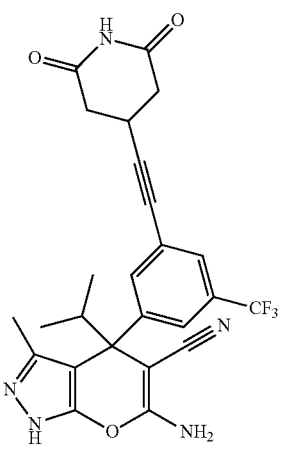 [SMILES: Cc1n[nH]c2c1C(c1cc(C#CC3CC(=O)NC(=O)C3)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 50 | 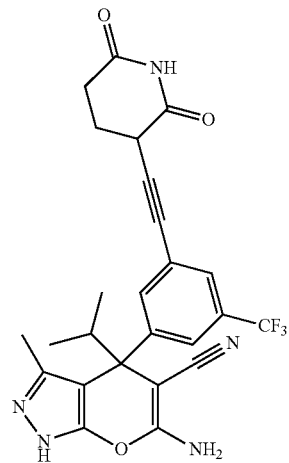 [SMILES: Cc1n[nH]c2c1C(c1cc(C#CC3CCC(=O)NC3=O)cc(C(F)(F)F)c1)(C(C)C)C(C#N)=C(N)O2] |
| 51 | 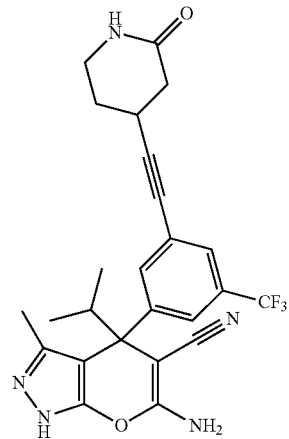 [SMILES: Cc1n[nH]c2c1C(c1cc(C#CC3CCNC(=O)C3)cc(C(F)(F)F)c1)(C(C)C)C(C#N)=C(N)O2] |
| 52 | 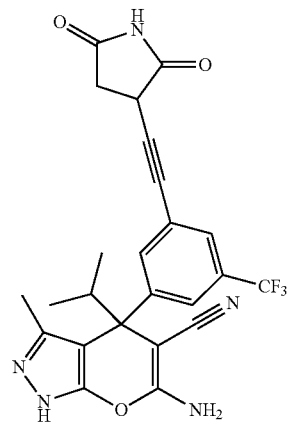 [SMILES: Cc1n[nH]c2c1C(c1cc(C#CC3CC(=O)NC3=O)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 53 | 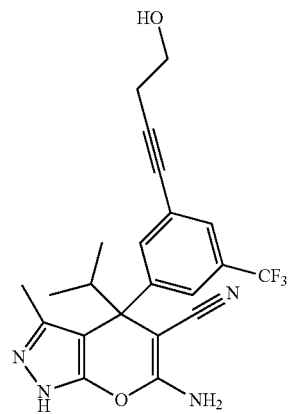 [SMILES: Cc1n[nH]c2c1C(c1cc(C#CCCO)cc(C(F)(F)F)c1)(C(C)C)C(C#N)=C(N)O2] |
| 54 | 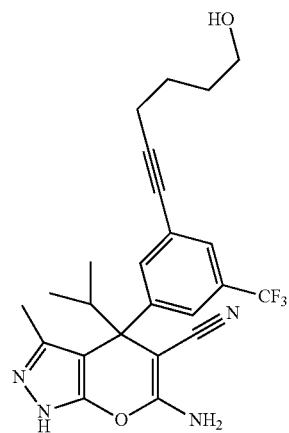 [SMILES: Cc1n[nH]c2c1C(c1cc(C#CCCCCO)cc(C(F)(F)F)c1)(C(C)C)C(C#N)=C(N)O2] |
| 55 | 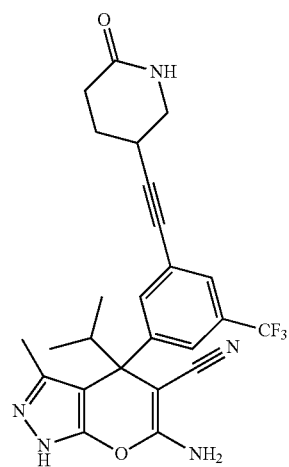 [SMILES: Cc1n[nH]c2c1C(c1cc(C#CC3CCC(=O)NC3)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 56 | 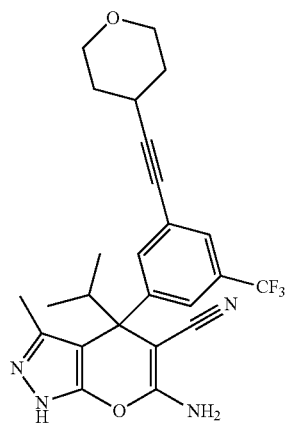 [SMILES: Cc1n[nH]c2c1C(c1cc(C#CC3CCOCC3)cc(C(F)(F)F)c1)(C(C)C)C(C#N)=C(N)O2] |
| 57 | 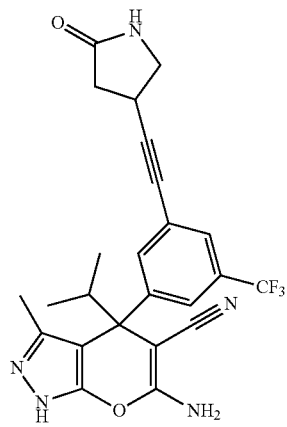 [SMILES: Cc1n[nH]c2c1C(c1cc(C#CC3CNC(=O)C3)cc(C(F)(F)F)c1)(C(C)C)C(C#N)=C(N)O2] |
| 58 | 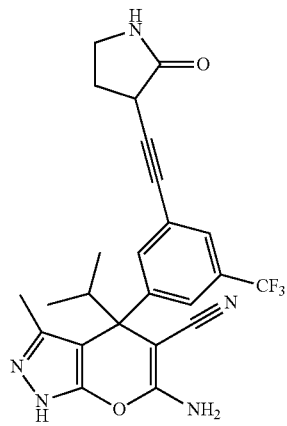 [SMILES: Cc1n[nH]c2c1C(c1cc(C#CC3CCNC3=O)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 59 | 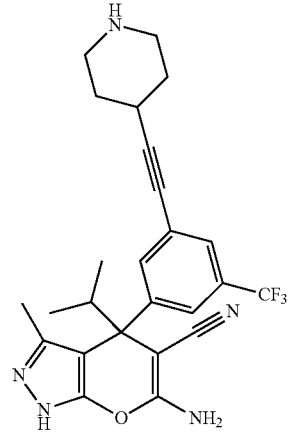 [SMILES: Cc1n[nH]c2c1C(c1cc(C#CC3CCNCC3)cc(C(F)(F)F)c1)(C(C)C)C(C#N)=C(N)O2] |
| 60 | 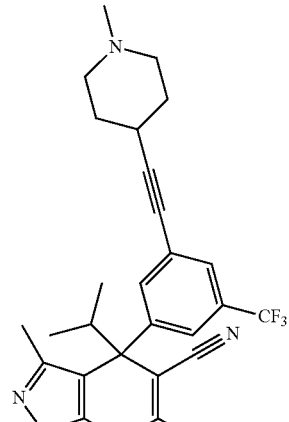 |
| 61 | 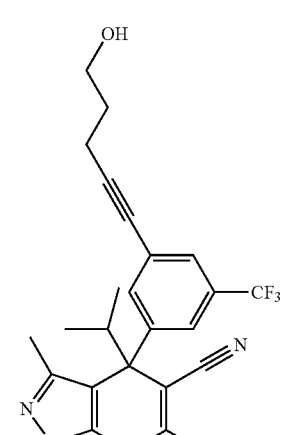 |

TABLE 1-continued
1,4-dihydropyrano[2,3-c]pyrazole derivatives as SHMT inhibitors
| Compound # | Chemical Structure |
|---|---|
| 62 | 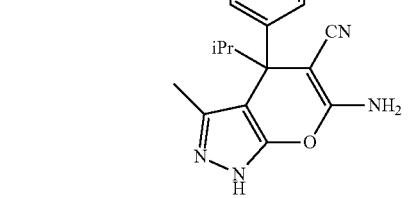 |
| 63 | 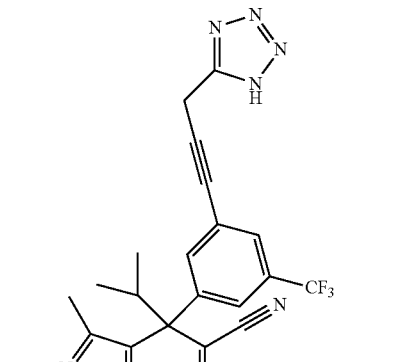 |
| 64 | 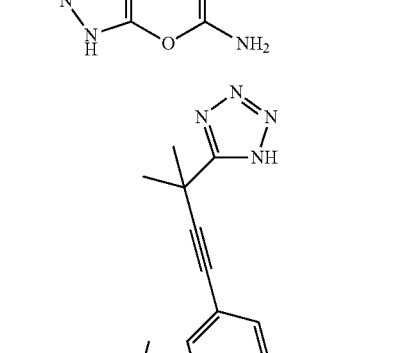 |
| 65 | 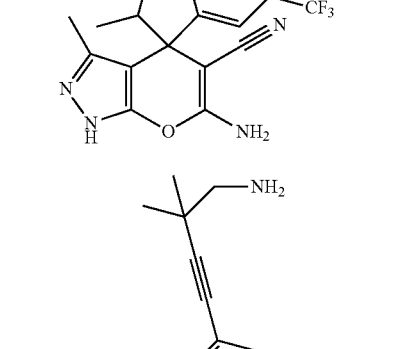 |

TABLE 1-continued
1,4-dihydropyrano[2,3-c]pyrazole derivatives as SHMT inhibitors
| Compound # | Chemical Structure |
|---|---|
| 66 | 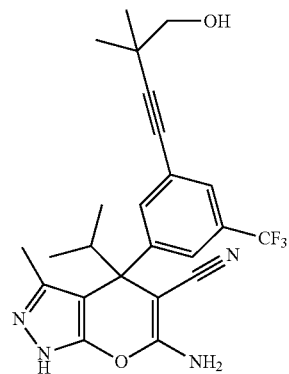 [SMILES: Cc1n[nH]c2c1C(c1cc(C#CC(C)(C)CO)cc(C(F)(F)F)c1)(C(C)C)C(C#N)=C(N)O2] |
| 67 | 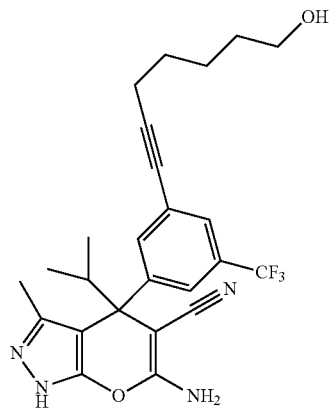 [SMILES: Cc1n[nH]c2c1C(c1cc(C#CCCCCCO)cc(C(F)(F)F)c1)(C(C)C)C(C#N)=C(N)O2] |
| 68 | 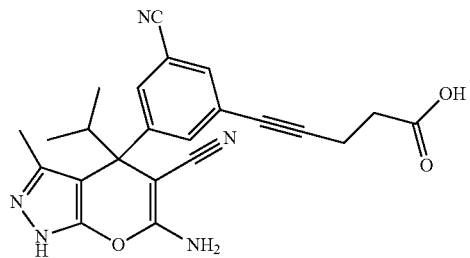 [SMILES: Cc1n[nH]c2c1C(c1cc(C#N)cc(C#CCCC(=O)O)c1)(C(C)C)C(C#N)=C(N)O2] |
| 69 | 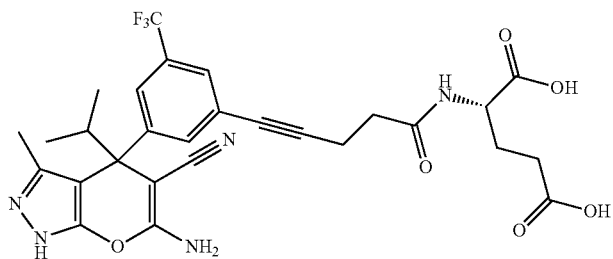 [SMILES: Cc1n[nH]c2c1C(c1cc(C#CCCC(=O)N[C@@H](CCC(=O)O)C(=O)O)cc(C(F)(F)F)c1)(C(C)C)C(C#N)=C(N)O2] |

TABLE 1-continued
1,4-dihydropyrano[2,3-c]pyrazole derivatives as SHMT inhibitors
| Compound # | Chemical Structure |
|---|---|
| 70 | 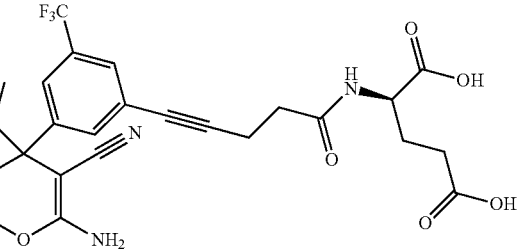 |
| 71 | 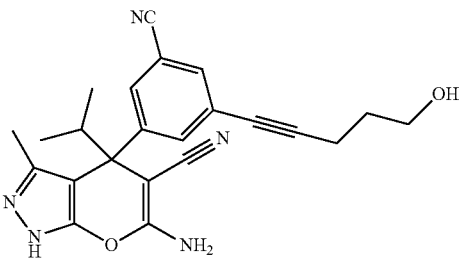 [SMILES: Cc1n[nH]c2c1C(c1cc(C#N)cc(C#CCCCO)c1)(C(C)C)C(C#N)=C(N)O2] |
| 72 | 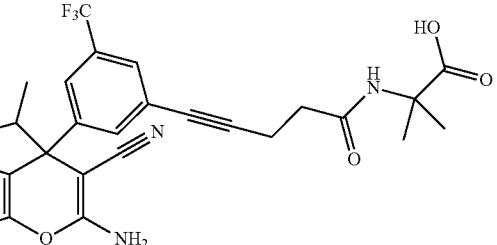 |
| 73 | 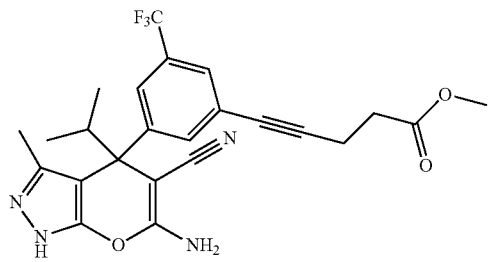 [SMILES: COC(=O)CCC#Cc1cc(C(F)(F)F)cc(C2(C(C)C)C(C#N)=C(N)Oc3[nH]nc(C)c32)c1] |
| 74 | 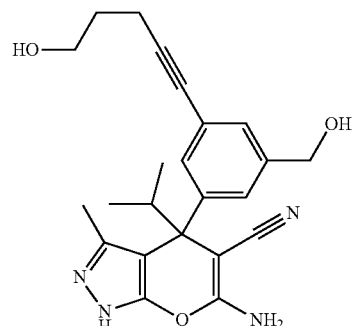 |
Certain compounds of the disclosure (e.g., Compounds of Formula (I), (II), and (II') and their corresponding inhibitory activity values are shown in Table 2 below. The assay used to evaluate activity is described in the Examples.

TABLE 2

| Compound # | Structure | LogP Value | SHMT2 IC50 (μM) | SHMT1 IC50 (μM) | HCT Cell IC50 (μM) | % formate rescue |
|---|---|---|---|---|---|---|
| 4 | 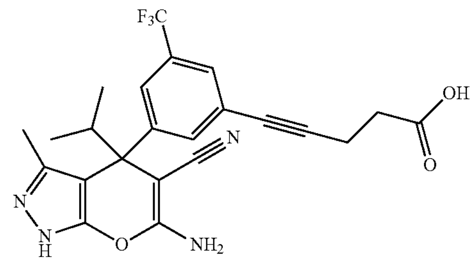 [SMILES: Cc1n[nH]c2c1C(c1cc(C#CCCC(=O)O)cc(C(F)(F)F)c1)(C(C)C)C(C#N)=C(N)O2] | 3.56 | 0.00017 | — | 15.10 | 93.35 |
| 68 | 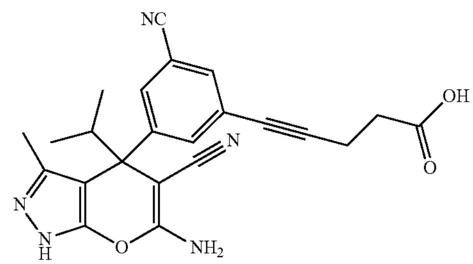 [SMILES: Cc1n[nH]c2c1C(c1cc(C#N)cc(C#CCCC(=O)O)c1)(C(C)C)C(C#N)=C(N)O2] | 2.37 | 0.0004 | 0.0017 | 100.00 | 106.02 |
| 1 (enantiomeric mixture) | 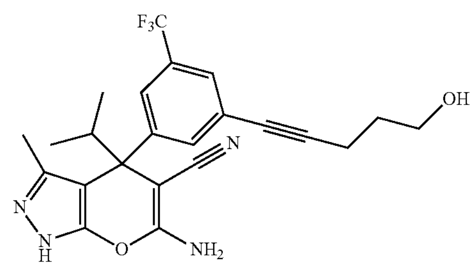 [SMILES: Cc1n[nH]c2c1C(c1cc(C#CCCCO)cc(C(F)(F)F)c1)(C(C)C)C(C#N)=C(N)O2] | 3.91 | 0.00065 | — | — | — |
| 1 (enatio-merically active peak) | 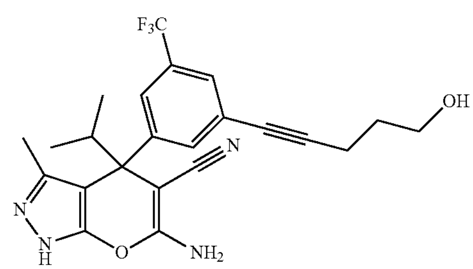 [SMILES: Cc1n[nH]c2c1C(c1cc(C#CCCCO)cc(C(F)(F)F)c1)(C(C)C)C(C#N)=C(N)O2] | 3.91 | 0.00079 | — | 1.36 | 94.96 |
| 69 | 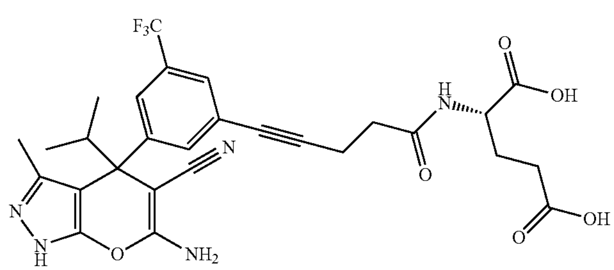 [SMILES: Cc1n[nH]c2c1C(c1cc(C#CCCC(=O)N[C@@H](CCC(=O)O)C(=O)O)cc(C(F)(F)F)c1)(C(C)C)C(C#N)=C(N)O2] | 2.49 | 0.0008 | — | 100.00 | 96.41 |

TABLE 2-continued

| Compound # | Structure | LogP Value | SHMT2 IC50 (μM) | SHMT1 IC50 (μM) | HCT Cell IC50 (μM) | % formate rescue |
|---|---|---|---|---|---|---|
| 70 | 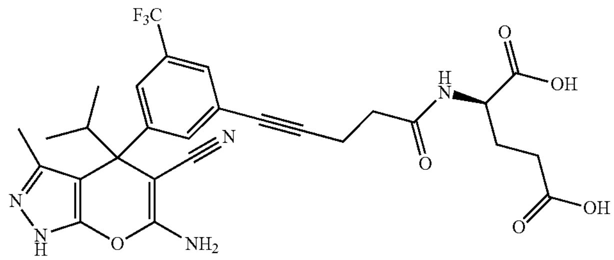 [SMILES: Cc1n[nH]c2c1C(c1cc(C#CCCC(=O)N[C@H](CCC(=O)O)C(=O)O)cc(C(F)(F)F)c1)(C(C)C)C(C#N)=C(N)O2] | 2.49 | 0.001 | — | 100.00 | 94.89 |
| 11 | 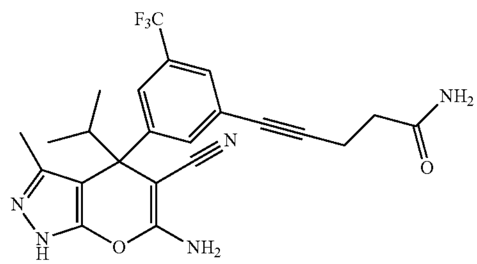 [SMILES: Cc1n[nH]c2c1C(c1cc(C#CCCC(N)=O)cc(C(F)(F)F)c1)(C(C)C)C(C#N)=C(N)O2] | 3.22 | 0.0014 | 0.0004 | 5.98 | 96.98 |
| 71 | 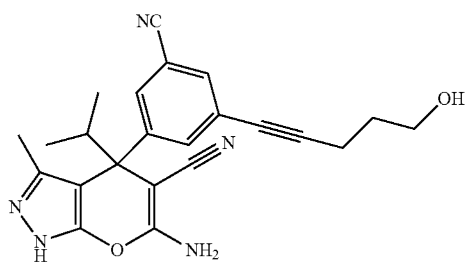 [SMILES: Cc1n[nH]c2c1C(c1cc(C#N)cc(C#CCCCO)c1)(C(C)C)C(C#N)=C(N)O2] | 2.89 | 0.0017 | 0.0024 | 4.96 | 97.81 |
| 72 | 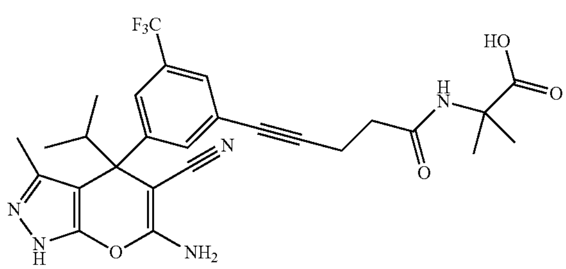 [SMILES: Cc1n[nH]c2c1C(c1cc(C#CCCC(=O)NC(C)(C)C(=O)O)cc(C(F)(F)F)c1)(C(C)C)C(C#N)=C(N)O2] | 3.38 | 0.002 | 0.004 | 200.00 | 98.35 |
| 2 | 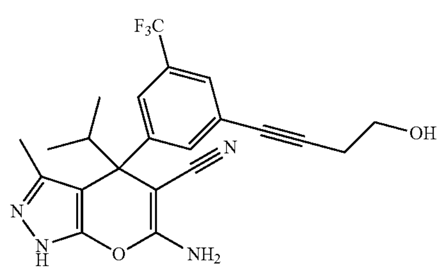 [SMILES: Cc1n[nH]c2c1C(c1cc(C#CCCO)cc(C(F)(F)F)c1)(C(C)C)C(C#N)=C(N)O2] | 3.46 | 0.004 | 0.002 | 6.90 | 100.58 |

TABLE 2-continued

| Compound # | Structure | LogP Value | SHMT2 IC50 (μM) | SHMT1 IC50 (μM) | HCT Cell IC50 (μM) | % formate rescue |
|---|---|---|---|---|---|---|
| 73 | 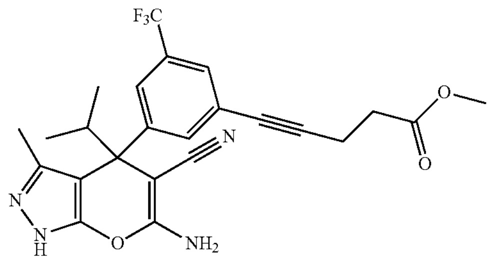 [SMILES: COC(=O)CCC#Cc1cc(C(F)(F)F)cc(C2(C(C)C)C(C#N)=C(N)Oc3[nH]nc(C)c32)c1] | 4.17 | 0.0075 | — | 11.10 | 97.33 |
| 8 | 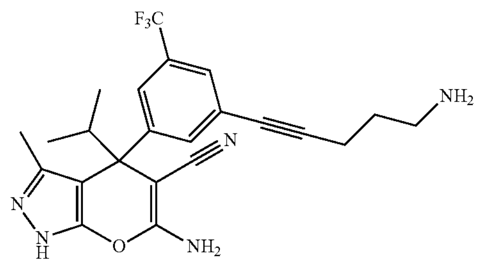 [SMILES: Cc1n[nH]c2c1C(c1cc(C#CCCCN)cc(C(F)(F)F)c1)(C(C)C)C(C#N)=C(N)O2] | 2.72 | 0.043 | 0.008 | 2.04 | 80.65 |
| 74 | 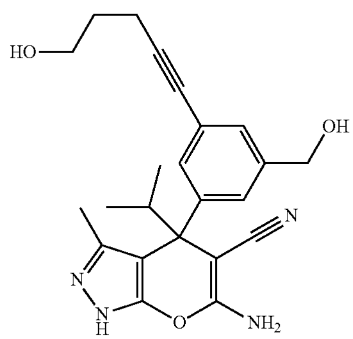 [SMILES: Cc1n[nH]c2c1C(c1cc(C#CCCCO)cc(CO)c1)(C(C)C)C(C#N)=C(N)O2] | | 0.019 | 0.017 | | |

D. More Compounds

In one aspect, the disclosure provides compounds represented by general Formula IV:

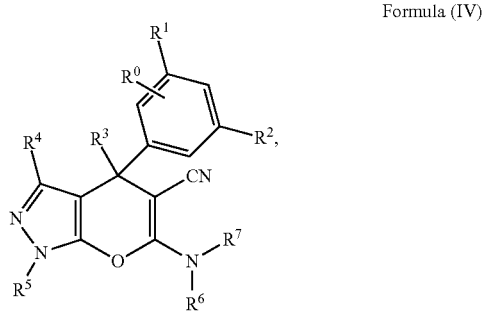

Formula (IV)

wherein:

$R^0$, $R^1$ and $R^2$ are each independently selected from —H, halogen, hydroxyl, nitro, nitrile, —SOR$^{11}$, —S(O)$_2$R$^{11}$, —S(O)$_2$NR$^{10}$R$^{12}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C$_1$-C$_6$ haloalkyl, or substituted or unsubstituted C$_1$-C$_6$ haloalkoxy;

$R^3$ is selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C$_1$-C$_6$ haloalkyl, or substituted or unsubstituted C$_1$-C$_6$ haloalkoxy; $R^4$ is selected from H, substituted or unsubstituted C$_1$-C$_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

$R^5$, $R^6$ and $R^7$ are each independently selected from —H, —C(O)R$^{11}$, substituted or unsubstituted C$_1$-C$_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or $R^5$ is selected from any of the foregoing and $R^6$ and $R^7$ taken together with the nitrogen atom to which they are attached form a substituted or unsubstituted 3-6 membered ring; with the proviso that the occurrences of $R^5$, $R^6$ and $R^7$ are not all H simultaneously;

each occurrence of $R^{11}$ is independently selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl; and each occurrence of $R^{10}$ and $R^{12}$ is each independently selected from H, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl, or a pharmaceutically acceptable salt thereof.

In certain embodiments, the compounds of the disclosure, or a pharmaceutically acceptable salt thereof, are represented by Formula (IVa) (wherein the R groups are as described above for Formula (IV)):

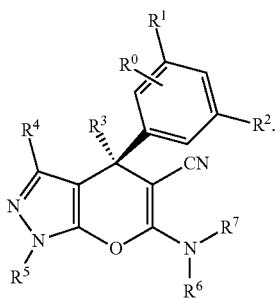

Formula (IVa)

In certain embodiments, the compounds of the disclosure, or a pharmaceutically acceptable salt thereof, are represented by Formula (IVb) (wherein the R groups are as described above for Formula (IV)):

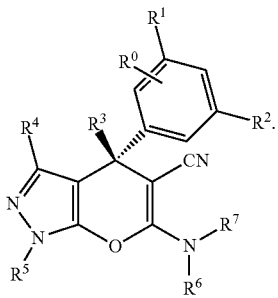

Formula (IVb)

In certain embodiments of any of the foregoing or following, $R^0$, $R^1$ and $R^2$ are each independently selected from —H, halogen, hydroxyl, nitro, nitrile, —$SOR^{11}$, —$S(O)_2R^{11}$, —$S(O)_2NR^{10}R^{12}$, —$OR^{11}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy.

In certain embodiments of any of the foregoing or following, $R^0$ is selected from hydroxyl, —$S(O)_2R^{11}$, —$S(O)_2NR_{10}R^{12}$, —$OR11$, —$C(O)NR^{10}R^{12}$, —$NR^{10}R^{12}$, —$N(R^{12})C(O)R^{11}$, or —$NS(O)_2R^{12}$. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ (and, optionally $R^0$) are each independently selected from —H, halogen, hydroxyl, nitro, nitrile, —$OR^{11}$, substituted or unsubstituted $C_1$-$C_6$ alkyl, substituted or unsubstituted $C_1$-$C_6$ haloalkyl, or substituted or unsubstituted $C_1$-$C_6$ haloalkoxy. In other embodiments, $R^1$ and $R^2$ (and, optionally $R^0$) are each independently selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl.

In certain embodiments of any of the foregoing or following, $R^1$ and $R^2$ (and, optionally $R^0$) are each independently selected from —H, methoxy, fluoro, chloro, bromo, hydroxyl, nitro, nitrile, methyl, trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ (and, optionally $R^0$) are each independently selected from —H, methoxy, chloro, nitro, nitrile, or trifluoromethyl. In other embodiments, $R^0$ is selected from H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ (and, optionally, $R^0$) are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^3$ is selected from —H, halogen, hydroxyl, nitro, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from substituted or unsubstituted $C_1$-$C_6$ alkyl, or substituted or unsubstituted cycloalkyl.

In certain embodiments of any of the foregoing or following, $R^3$ is selected from methyl, ethyl, propyl, isopropyl, cyclopropyl, or cyclobutyl. In certain embodiments, any of the foregoing may be optionally substituted.

In certain embodiments of any of the foregoing or following, $R^3$ is selected from isopropyl, cyclopropyl, or cyclobutyl. In certain embodiments, any of the foregoing may be optionally substituted.

In certain embodiments of any of the foregoing or following, $R^3$ is cyclobutyl. In certain embodiments, acyclobutyl may be optionally substituted.

In certain embodiments of any of the foregoing or following, $R^4$ is selected from —H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^4$ is selected from —H, substituted or unsubstituted $C_1$-$C_6$ alkyl, substituted or unsubstituted cycloalkyl, substituted or unsubstituted aryl, or substituted or unsubstituted arylalkyl.

In certain embodiments of any of the foregoing or following, $R^4$ is selected from methyl, ethyl, isopropyl, cyclopropyl, cyclobutyl, cyclopentyl, cyclohexyl, phenyl or benzyl. In certain embodiments, any of the foregoing may be optionally substituted.

In certain embodiments of any of the foregoing or following, $R^4$ is methyl or isopropyl. In certain embodiments, any of the foregoing may be optionally substituted.

In certain embodiments of any of the foregoing or following, $R^4$ is methyl. In certain embodiments, methyl may be optionally substituted.

In certain embodiments of any of the foregoing or following, $R^5$, $R^6$ and $R^7$ are each independently selected from —H, —C(O)$R^{11}$, substituted or unsubstituted $C_1$-$C_6$ alkyl, substituted or unsubstituted cycloalkyl, substituted or unsubstituted aryl, substituted or unsubstituted arylalkyl, or $R^5$ is selected from any of the foregoing and $R^6$ and $R^7$ taken together with the nitrogen atom to which they are attached form a substituted or unsubstituted 3-6 membered ring.

In certain embodiments of any of the foregoing or following, $R^5$, $R^6$ and $R^7$ are each independently selected from —H, —C(O)$R^{11}$, substituted or unsubstituted $C_1$-$C_6$ alkyl, substituted or unsubstituted cycloalkyl, substituted or unsubstituted aryl, or substituted or unsubstituted arylalkyl.

In certain embodiments of any of the foregoing or following, $R^5$, $R^6$ and $R^7$ are each independently selected from —H, methyl, ethyl, isopropyl, cyclopropyl, cyclobutyl, cyclopentyl, cyclohexyl, phenyl, benzyl, or —COCH$_3$. In certain embodiments, any of the foregoing, except —H, may be optionally substituted.

In certain embodiments of any of the foregoing or following, $R^5$, $R^6$ and $R^7$ are each independently selected from —H, methyl, phenyl, or —COCH$_3$. In certain embodiments, any of the foregoing, except —H, may be optionally substituted.

In certain embodiments of any of the foregoing or following, $R^5$ and $R^6$ are each independently selected from —H, methyl or phenyl. In certain embodiments, any of the foregoing, except —H, may be optionally substituted.

In certain embodiments of any of the foregoing or following, $R^7$ is —H.

In certain embodiments of any of the foregoing or following, $R^6$ and $R^7$ taken together with the nitrogen atom to which they are attached form a substituted or unsubstituted 3-6 membered ring. In certain embodiments the 3-6 membered ring is a monocylic ring. In certain embodiments, the 3-6 membered ring may be saturated or unsaturated (e.g., contain at least one double bond). In certain embodiments, the 3-6 membered ring may contain one or two additional heteroatoms, other than the nitrogen atom to which $R^6$ and $R^7$ are attached.

In certain embodiments of any of the foregoing or following, $R^5$ is selected from —H, methyl, ethyl, isopropyl, cyclopropyl, cyclobutyl, cyclopentyl, cyclohexyl, phenyl, benzyl, or —COCH$_3$, and $R^6$ and $R^7$ taken together with the nitrogen atom to which they are attached faun a substituted or unsubstituted ring selected from:

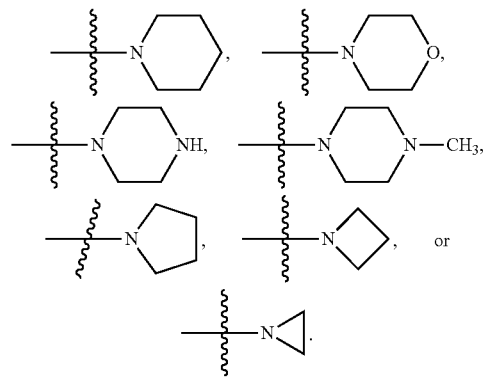

In certain embodiments of any of the foregoing or following, $R^5$ is selected from —H, methyl, phenyl, or —COCH$_3$, and $R^6$ and $R^7$ taken together with the nitrogen atom to which they are attached form a substituted or unsubstituted ring selected from:

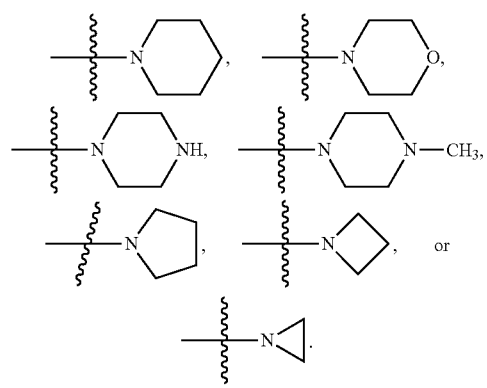

In certain embodiments of any of the foregoing or following, each occurrence of $R^{11}$ is independently selected from substituted or unsubstituted $C_1$-$C_6$ alkyl or substituted or unsubstituted cycloalkyl. In certain embodiments, there is no occurrence of $R^{11}$.

In certain embodiments of any of the foregoing or following, each occurrence of $R^{10}$ and $R^{12}$ is each independently selected from H, substituted or unsubstituted $C_1$-$C_6$ alkyl, or substituted or unsubstituted cycloalkyl, such as from H, or substituted or unsubstituted $C_1$-$C_6$ alkyl. In certain embodiments, each occurrence of $R^{10}$ and $R^{12}$ is —H. In certain embodiments, there is no occurrence of $R^{10}$ and/or $R^{12}$.

In certain embodiments of any of the foregoing or following, $R^0$ is selected from —H, halogen, hydroxyl, nitro, nitrile, —S(O)$_2$$R^{11}$, —S(O)$_2$N$R^{10}$$R^{12}$, —O$R^{11}$, —C(O)N$R^{10}$$R^{12}$, —N$R^{10}$$R^{12}$, —N($R^{12}$)C(O)$R^{11}$, —NS(O)$_2$$R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;

$R^1$ and $R^2$ are each independently selected from —H, methoxy, fluoro, chloro, bromo, hydroxyl, nitro, nitrile, methyl, or trifluoromethyl;

$R^3$ is selected from methyl, ethyl, propyl, isopropyl, cyclopropyl, or cyclobutyl;
$R^4$ is selected from methyl, ethyl, isopropyl, cyclopropyl, cyclobutyl, cyclopentyl, cyclohexyl, phenyl or benzyl; and
$R^5$, $R^6$ and $R^7$ are each independently selected from —H, methyl, ethyl, isopropyl, cyclopropyl, cyclobutyl, cyclopentyl, cyclohexyl, phenyl, benzyl, or —COCH$_3$.

In certain embodiments of any of the foregoing or following, $R^0$ is selected from —H, hydroxyl, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$;
$R^1$ and $R^2$ are each independently selected from —H, methoxy, chloro, nitro, nitrile, or trifluoromethyl;
$R^3$ is selected from isopropyl, cyclopropyl, or cyclobutyl;
$R^4$ is methyl or isopropyl; and
$R^5$, $R^6$ and $R^7$ are each independently selected from —H, methyl, phenyl, or —COCH$_3$.

In certain embodiments of any of the foregoing or following, $R^0$ is selected from —H, hydroxyl, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$;
$R^1$ and $R^2$ are each —CF$_3$;
$R^3$ is cyclobutyl;
$R^4$ is methyl;
$R^5$ and $R^6$ are each independently selected from H, methyl or phenyl; and
$R^7$ is H.

In certain embodiments, the compound is selected from the group consisting of:

or a pharmaceutically acceptable salt thereof.

In certain embodiments of any of the foregoing or following, the disclosure provides a pharmaceutically acceptable salt thereof or an enantiomer thereof.

In certain embodiments of any of the foregoing or following, the $R^0$, $R^1$ and $R^2$ are not all simultaneously —H. In other embodiments, $R^0$ is —H and the ring to which it is attached, is substituted with a single substituent (other than —H) at one of $R^1$ or $R^2$. In certain embodiments, $R^0$ is —H, and $R^1$ and $R^2$ are not —H. In other embodiments, $R^1$ is —H and the ring to which it is attached is substituted with a single substituent (other than H) at one of $R^0$ or $R^2$. In certain embodiments, $R^1$ is —H, and $R^0$ and $R^2$ are not —H. In other embodiments, $R^2$ is —H and the ring to which it is attached is substituted with a single substituent (other than —H) at one of $R^0$ or $R^1$. In certain embodiments, $R^2$ is —H, and $R^0$ and $R^1$ are not —H. In other embodiments, $R^0$, $R^1$ and $R^2$ are not —H.

In one aspect, the disclosure provides compounds represented by general Formula (V):

Formula (V)

wherein:
Z is N or CR$^4$;
X is O, S, CH$_2$, or NR$^6$;
$R^0$, $R^1$ and $R^2$ are each independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O) R$^{11}$, —NS(O)$_2$R$^{12}$, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C$_1$-C$_6$ haloalkyl, or substituted or unsubstituted C$_1$-C$_6$ haloalkoxy;
$R^3$ is selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR¹⁰R¹², —N(R¹²)C(O)R¹¹, —NS(O)₂R¹², substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy; $R^4$ is selected from —H, —NR¹⁰R¹², —C(O)NR¹⁰R¹², —N(R¹²)C(O)R¹¹, nitrile, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

$R^5$ is selected from —H, —NR¹⁰R¹², —C(O)NR¹⁰R¹², —N(R¹²)C(O)R¹¹, nitrile, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or $R^5$ and $R^4$ taken together with the respective carbon atom to which they are attached form a substituted or unsubstituted 4-12 membered ring; $R^6$ is selected from H, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, or substituted or unsubstituted heteroarylalkyl;

$R^7$ and $R^8$ are each independently selected from —H, —NR¹⁰R¹², —C(O)NR¹⁰R¹², —N(R¹²)C(O)R¹¹, nitrile, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

each occurrence of $R^{11}$ is independently selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl; and each occurrence of $R^{10}$ and $R^{12}$ is each independently selected from —H, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl, or a pharmaceutically acceptable salt thereof.

In certain embodiments, the compounds of the disclosure, or a pharmaceutically acceptable salt thereof, are represented by Formula (Va) (wherein the R groups are as described above for Formula (V)):

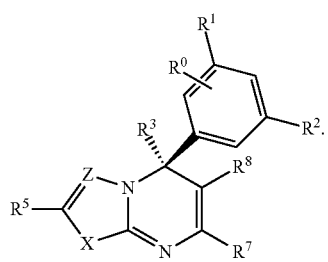

Formula (Va)

In certain embodiments, the compounds of the disclosure, or a pharmaceutically acceptable salt thereof, are represented Formula (Vb) (wherein the R groups are as described above for Formula (V)):

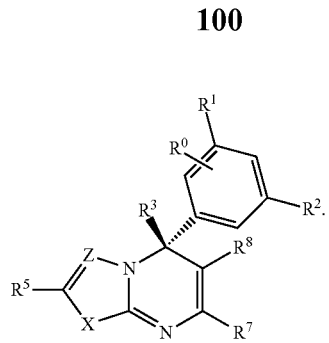

Formula (Vb)

In certain embodiments of any of the foregoing or following, $R^0$, $R^1$ and $R^2$ are each independently selected from —H, halogen, hydroxyl, nitro, nitrile, —SOR¹¹, —S(O)₂R¹¹, —S(O)₂NR¹⁰R¹², —OR¹¹, —C(O)OR¹², —C(O)R¹¹, —C(O)NR¹⁰R¹², —NR¹⁰R¹², —N(R¹²)C(O)R¹¹, —NS(O)₂R¹², substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy.

In certain embodiments of any of the foregoing or following, $R^0$ is selected from hydroxyl, —S(O)₂R¹¹, —S(O)₂NR¹⁰R¹², —OR¹¹, —C(O)NR¹⁰R¹², —NR¹⁰R¹², —N(R¹²)C(O)R¹¹, or —NS(O)₂R¹². In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from H, halogen, hydroxyl, nitro, nitrile, —OR¹¹, substituted or unsubstituted $C_1$-$C_6$ alkyl, substituted or unsubstituted $C_1$-$C_6$ haloalkyl, substituted or unsubstituted $C_1$-$C_6$ haloalkoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, methoxy, fluoro, chloro, bromo, hydroxyl, nitro, nitrile, methyl, trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^3$ is selected from —H, halogen, hydroxyl, nitro, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from methyl, ethyl, propyl, isopropyl, cyclopropyl, or cyclobutyl. In certain embodiments, any of the foregoing may be optionally substituted.

In certain embodiments of any of the foregoing or following, $R^3$ is isopropyl or cyclopropyl. In certain embodiments, any of the foregoing may be optionally substituted.

In certain embodiments of any of the foregoing or following, $R^4$ and $R^5$ are each independently selected from —H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^4$ and $R^5$ are each independently selected from —H, substituted or unsubstituted $C_1$-$C_6$ alkyl, substituted or unsubstituted cycloalkyl, substituted or unsubstituted aryl, or substituted or unsubstituted arylalkyl.

In certain embodiments of any of the foregoing or following, $R^4$ and $R^5$ are each independently selected from —H, methyl, ethyl, propyl, isopropyl, cyclopropyl, cyclobutyl, cyclopentyl, cyclohexyl, phenyl or benzyl. In certain embodiments, any of the foregoing, except —H, may be optionally substituted.

In certain embodiments of any of the foregoing or following, $R^4$ and $R^5$ are independently —H or methyl. In certain embodiments, methyl may be optionally substituted.

In certain embodiments of any of the foregoing or following, $R^5$ and $R^4$ taken together with the respective carbon atom to which they are attached form a 4-12 membered ring selected from substituted or unsubstituted aryl, or substituted or unsubstituted heteroaryl.

In certain embodiments of any of the foregoing or following, $R^5$ and $R^4$ taken together with the respective carbon atom to which they are attached form a substituted or unsubstituted 4-12 membered ring containing 0-4 heteroatoms (0, 1, 2, 3 or 4) independently selected from N, O, or S.

In certain embodiments of any of the foregoing or following, the 4-12 membered ring is a monocyclic ring. In certain embodiments of any of the foregoing or following, the 4-12 membered ring is a polycyclic ring. In certain embodiments of any of the foregoing or following, the 4-12 membered ring is a bicyclic ring. In certain embodiments of any of the foregoing or following, when the 4-12 membered ring is a polycyclic ring, each ring is independently selected from saturated or unsaturated, and each ring may independently contain one or more heteroatoms (e.g., for a total of 1, 2, 3, 4 or 4 heteroatoms).

In certain embodiments of any of the foregoing or following, $R^5$ and $R^4$ taken together with the respective carbon atom to which they are attached form a phenyl ring. In certain embodiments, the phenyl ring may be optionally substituted.

In certain embodiments of any of the foregoing or following, $R^6$ is selected from H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^6$ is selected from —H, methyl, ethyl, isopropyl, cyclopropyl, cyclobutyl, cyclopentyl, cyclohexyl, phenyl, pyridyl, or benzyl. In certain embodiments, any of the foregoing may be optionally substituted.

In certain embodiments of any of the foregoing or following, $R^6$ is —H.

In certain embodiments of any of the foregoing or following, $R^7$ and $R^8$ are each independently selected from —H, —$NR^{10}R^{12}$, —$C(O)NR^{10}R^{12}$, —$N(R^{12})C(O)R^{11}$, nitrile, methyl, ethyl, isopropyl, cyclopropyl, cyclobutyl, cyclopentyl, cyclohexyl, phenyl, or benzyl.

In certain embodiments of any of the foregoing or following, $R^7$ is selected from —H, —$NH_2$, methyl, or phenyl. In certain embodiments, any of the foregoing except —H, may be optionally substituted.

In certain embodiments of any of the foregoing or following, $R^8$ is selected from —H, nitrile, or —$C(O)NH_2$. In certain embodiments, —$C(O)NH_2$ may be optionally substituted.

In certain embodiments of any of the foregoing or following, each occurrence of $R^{11}$ is independently selected from substituted or unsubstituted $C_1$-$C_6$ alkyl or substituted or unsubstituted cycloalkyl. In certain embodiments, there is no occurrence of $R^{11}$.

In certain embodiments of any of the foregoing or following, each occurrence of $R^{10}$ and $R^{12}$ is each independently selected from —H, substituted or unsubstituted $C_1$-$C_6$ alkyl, or substituted or unsubstituted cycloalkyl, such as from —H, or substituted or unsubstituted $C_1$-$C_6$ alkyl. In certain embodiments, each occurrence of $R^{10}$ and $R^{12}$ is H. In certain embodiments, there is no occurrence of $R^{10}$ and/or $R^{12}$.

In certain embodiments of any of the foregoing or following, the disclosure provides a pharmaceutically acceptable salt thereof or an enantiomer thereof.

In certain embodiments of any of the foregoing or following, the $R^0$, $R^1$ and $R^2$ are not all simultaneously —H. In other embodiments, $R^0$ is —H and the ring to which it is attached, is substituted with a single substituent (other than —H) at one of $R^1$ or $R^2$. In certain embodiments, $R^0$ is —H, and $R^1$ and $R^2$ are not —H. In other embodiments, $R^1$ is —H and the ring to which it is attached is substituted with a single substituent (other than —H) at one of $R^0$ or $R^2$. In certain embodiments, $R^1$ is —H, and $R^0$ and $R^2$ are not —H. In other embodiments, $R^2$ is —H and the ring to which it is attached is substituted with a single substituent (other than —H) at one of $R^0$ or $R^1$. In certain embodiments, $R^2$ is —H, and $R^0$ and $R^1$ are not —H. In other embodiments, $R^0$, $R^1$ and $R^2$ are not —H.

In certain embodiments, when Z is N, and $R^8$ is H, $R^7$ cannot be substituted or unsubstituted aryl.

In certain embodiments, the compound of Formulae (V), (Va), or (Vb) is not

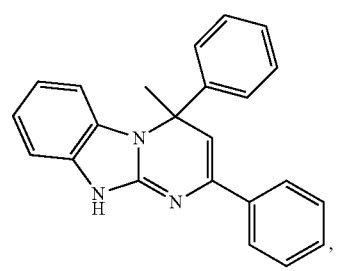

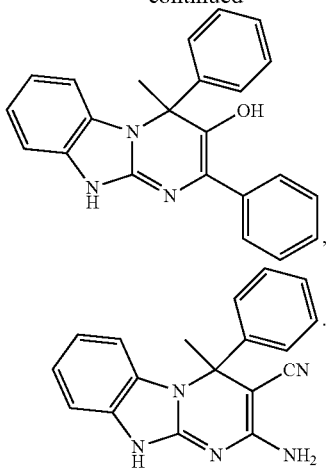

In certain embodiments, when R⁴ and R⁵ taken together with the respective carbon atoms to which they are attached for a substituted aryl ring, R⁸ is not —H, —OH, or —CN.

In certain embodiments, the compound of Formulae (V), (Va), or (Vb) is:

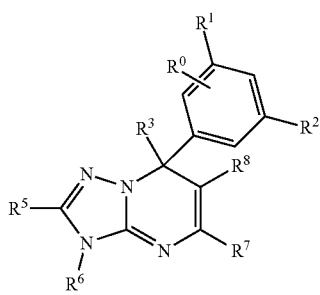

or a pharmaceutically acceptable salt thereof.

In one aspect, the disclosure provides compounds represented by general by Formula (VI):

Formula (VI)

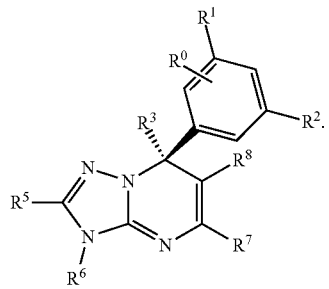

wherein:
R⁰, R¹ and R² are each independently selected from —H, halogen, hydroxyl, nitro, nitrile, —SOR¹¹, —S(O)₂R¹¹, —S(O)₂NR¹⁰R¹², —OR¹¹, —OC(O)R¹², —C(O)OR¹², —C(O)R¹¹, —C(O)NR¹⁰R¹², —NR¹⁰R¹², —N(R¹²)C(O)R¹¹, —NS(O)₂R¹², substituted or unsubstituted C₁-C₆ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C₁-C₆ haloalkyl, or substituted or unsubstituted C₁-C₆ haloalkoxy;

R³ is selected from —H, halogen, hydroxyl, nitro, nitrile, —SOR¹¹, —S(O)₂R¹¹, —S(O)₂NR¹⁰R¹², —OR¹¹, —C(O)R¹², —C(O)OR¹², —C(O)R¹¹, —C(O)NR¹⁰R¹², —NR¹⁰R¹², —N(R¹²)C(O)R¹¹, —NS(O)₂R¹², substituted or unsubstituted C₁-C₆ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C₁-C₆ haloalkyl, or substituted or unsubstituted C₁-C₆ haloalkoxy; R⁵ is selected from —H, —NR¹⁰R¹², —C(O)NR¹⁰R¹², —N(R¹²)C(O)R¹¹, nitrile, substituted or unsubstituted C₁-C₆ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

R⁶ is selected from —H, substituted or unsubstituted C₁-C₆ alkyl, substituted or unsubstituted cycloalkyl, substituted or unsubstituted heterocyclyl, substituted or unsubstituted aryl, substituted or unsubstituted heteroaryl substituted or unsubstituted arylalkyl, or substituted or unsubstituted heteroarylalkyl;

R⁷ and R⁸ are each independently selected from H, —NR¹⁰R¹², —C(O)NR¹⁰R¹², —N(R¹²)C(O)R¹¹, nitrile, substituted or unsubstituted C₁-C₆ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

each occurrence of R¹¹ is independently selected from substituted or unsubstituted C₁-C₆ alkyl, substituted or unsubstituted cycloalkyl, substituted or unsubstituted heterocyclyl, substituted or unsubstituted aryl, or substituted or unsubstituted heteroaryl; and each occurrence of R¹⁰ and R¹² is each independently selected from —H, substituted or unsubstituted C₁-C₆ alkyl, substituted or unsubstituted cycloalkyl, substituted or unsubstituted heterocyclyl, substituted or unsubstituted aryl, or substituted or unsubstituted heteroaryl, or a pharmaceutically acceptable salt thereof.

In certain embodiments, the compounds of the disclosure, or a pharmaceutically acceptable salt thereof, are represented by Formula (VIa) (wherein the R groups are as described above for Formula (VI)):

Formula (VIa)

In certain embodiments, the compounds of the disclosure, or a pharmaceutically acceptable salt thereof, are represented by Formula (VIb) (wherein the R groups are as described above for Formula (VI)):

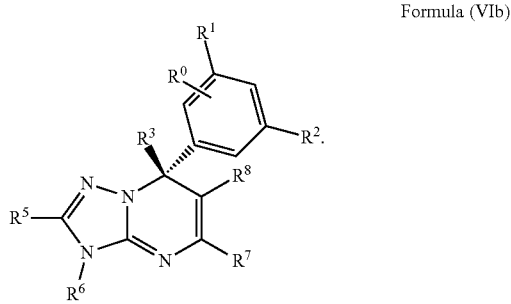

Formula (VIb)

In certain embodiments of any of the foregoing or following, $R^0$, $R^1$ and $R^2$ are each independently selected from —H, halogen, hydroxyl, nitro, nitrile, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$, substituted or unsubstituted C$_1$-C$_6$ alkyl, substituted or unsubstituted cycloalkyl, substituted or unsubstituted C$_1$-C$_6$ haloalkyl, or substituted or unsubstituted C$_1$-C$_6$ haloalkoxy.

In certain embodiments of any of the foregoing or following, $R^0$ is selected from hydroxyl, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$. In other embodiments, $R^0$ is selected from H, halogen, substituted or unsubstituted C$_1$-C$_6$ haloalkyl, substituted or unsubstituted C$_1$-C$_6$ haloalkoxy, or substituted or unsubstituted C$_1$-C$_6$ alkyl. In other embodiments $R^0$ is —H.

In certain embodiments of any of the foregoing or following, $R^1$ and $R^2$ are each independently selected from —H, halogen, hydroxyl, nitro, nitrile, —OR$^{11}$, substituted or unsubstituted C$_1$-C$_6$ alkyl, substituted or unsubstituted C$_1$-C$_6$ haloalkyl, or substituted or unsubstituted C$_1$-C$_6$ haloalkoxy. In other embodiments, $R^0$ is selected from —H, halogen, substituted or unsubstituted C$_1$-C$_6$ haloalkyl, substituted or unsubstituted C$_1$-C$_6$ haloalkoxy, or substituted or unsubstituted C$_1$-C$_6$ alkyl. In other embodiments $R^0$ is —H.

In certain embodiments of any of the foregoing or following, $R^1$ and $R^2$ are each independently selected from —H, methoxy, fluoro, chloro, bromo, hydroxyl, nitro, nitrile, methyl, trifluoromethyl, or trifluoromethoxy. In other embodiments, $R^0$ is selected from —H, halogen, substituted or unsubstituted C$_1$-C$_6$ haloalkyl, substituted or unsubstituted C$_1$-C$_6$ haloalkoxy, or substituted or unsubstituted C$_1$-C$_6$ alkyl. In other embodiments $R^0$ is —H.

In certain embodiments of any of the foregoing or following, $R^1$ and $R^2$ are each trifluoromethyl. In other embodiments, $R^0$ is selected from H, halogen, substituted or unsubstituted C$_1$-C$_6$ haloalkyl, substituted or unsubstituted C$_1$-C$_6$ haloalkoxy, or substituted or unsubstituted C$_1$-C$_6$ alkyl. In other embodiments $R^0$ is —H.

In certain embodiments of any of the foregoing or following, $R^3$ is selected from —H, halogen, hydroxyl, nitro, nitrile, substituted or unsubstituted C$_1$-C$_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected substituted or unsubstituted C$_1$-C$_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from methyl, ethyl, propyl, isopropyl, cyclopropyl, or cyclobutyl. In certain embodiments, any of the foregoing may be optionally substituted.

In certain embodiments of any of the foregoing or following, $R^3$ is isopropyl or cyclopropyl. In certain embodiments, any of the foregoing may be optionally substituted.

In certain embodiments of any of the foregoing or following, $R^5$ is selected from —H, methyl, ethyl, propyl, isopropyl, cyclopropyl, cyclobutyl, cyclopentyl, cyclohexyl, phenyl or benzyl. In certain embodiments, any of the foregoing except —H, may be optionally substituted.

In certain embodiments of any of the foregoing or following, $R^5$ is —H.

In certain embodiments of any of the foregoing or following, $R^6$ is selected from H, substituted or unsubstituted C$_1$-C$_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^6$ is selected from —H, methyl, ethyl, isopropyl, cyclopropyl, cyclobutyl, cyclopentyl, cyclohexyl, phenyl, pyridyl or benzyl. In certain embodiments, any of the foregoing except H, may be optionally substituted.

In certain embodiments of any of the foregoing or following, $R^6$ is —H.

In certain embodiments of any of the foregoing or following, $R^7$ and $R^8$ are each independently selected from —H, —NR$^{10}$R$^{12}$, —C(O)NR$^{10}$R$^{12}$, —N(R$^{12}$)C(O)R$^{11}$, nitrile, methyl, ethyl, isopropyl, cyclopropryl, cyclobutyl, cyclopentyl, cyclohexyl, phenyl, or benzyl.

In certain embodiments of any of the foregoing or following, $R^7$ is selected from —NH$_2$, methyl, or phenyl. In certain embodiments, any of the foregoing, may be optionally substituted.

In certain embodiments of any of the foregoing or following, $R^8$ is selected from —H, nitrile, or —C(O)NH$_2$. In certain embodiments, —C(O)NH$_2$ may be optionally substituted.

In certain embodiments of any of the foregoing or following, each occurrence of $R^{11}$ is independently selected from substituted or unsubstituted C$_1$-C$_6$ alkyl or substituted or unsubstituted cycloalkyl. In certain embodiments, there is no occurrence of $R^{11}$.

In certain embodiments of any of the foregoing or following, each occurrence of $R^{10}$ and $R^{12}$ is each independently selected from H, substituted or unsubstituted C$_1$-C$_6$ alkyl, or substituted or unsubstituted cycloalkyl, such as from H, or substituted or unsubstituted C$_1$-C$_6$ alkyl. In certain embodiments, each occurrence of $R^{10}$ and $R^{12}$ is —H. In certain embodiments, there is no occurrence of $R^{10}$ and/or $R^{12}$.

In certain embodiments of any of the foregoing or following, $R^0$ is selected from —H, halogen, hydroxyl, nitro, nitrile, —S(O)$_2$R$^{11}$, —S(O)$_2$NR$^{10}$R$^{12}$, —OR$^{11}$, —C(O)NR$^{10}$R$^{12}$, —NR$^{10}$R$^{12}$, —N(R$^{12}$)C(O)R$^{11}$, or —NS(O)$_2$R$^{12}$, substituted or unsubstituted C$_1$-C$_6$ alkyl, substituted or unsubstituted C$_1$-C$_6$ haloalkyl, or substituted or unsubstituted C$_1$-C$_6$ haloalkoxy;

$R^1$ and $R^2$ are each independently selected from —H, methoxy, fluoro, chloro, bromo, hydroxyl, nitro, nitrile, methyl, or trifluoromethyl;

$R^3$ is selected from methyl, ethyl, propyl, isopropyl, cyclopropyl, or cyclobutyl;

$R^5$ is selected from —H, methyl, ethyl, propyl or isopropyl;

R⁶ is selected from —H, methyl, ethyl, isopropyl, cyclopropyl, cyclobutyl, cyclopentyl, cyclohexyl, phenyl or benzyl; and R⁷ and R⁸ are each independently selected from —H, —NH₂, —C(O)NH₂, nitrile, methyl, ethyl, isopropyl, cyclopropyl, cyclobutyl, cyclopentyl, cyclohexyl, phenyl, or benzyl.

In certain embodiments of any of the foregoing or following, R⁰ is selected from —H, hydroxyl, —S(O)₂R¹¹, —S(O)₂NR¹⁰R¹², —OR¹¹, —C(O)NR¹⁰R¹², —NR¹⁰R¹², —N(R¹²)C(O)R¹¹, or —NS(O)₂R¹²;
R¹ and R² are each trifluoromethyl;
R³ is isopropyl or cyclopropyl;
R⁵ is —H;
R⁶ is —H;
R⁷ is selected from —NH₂, methyl, or phenyl; and
R⁸ is selected from H, nitrile, or —C(O)NH₂.

In certain embodiments, the compound is selected from:

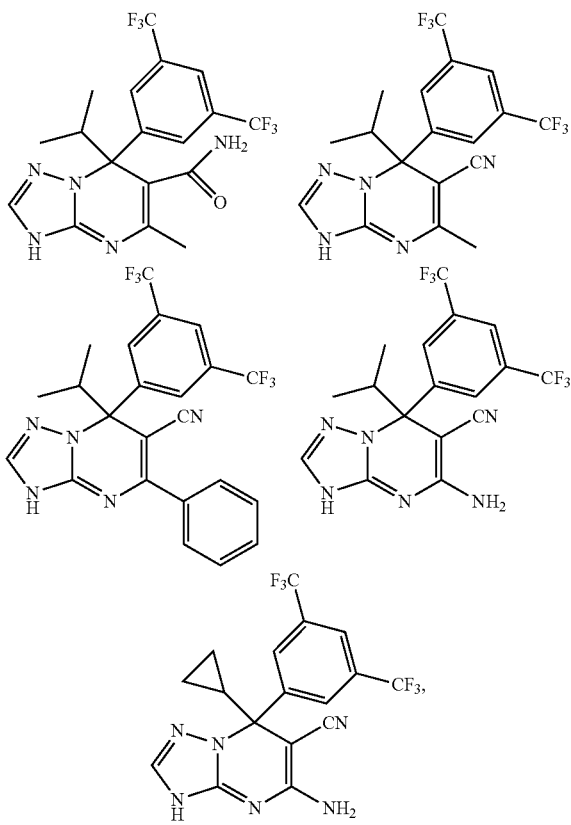

or a pharmaceutically acceptable salt thereof.

In certain embodiments of any of the foregoing or following, the disclosure provides a pharmaceutically acceptable salt thereof or an enantiomer thereof.

In certain embodiments of any of the foregoing or following, the R⁰, R¹ and R² are not all simultaneously —H. In other embodiments, R⁰ is —H and the ring to which it is attached, is substituted with a single substituent (other than —H) at one of R¹ or R². In certain embodiments, R⁰ is —H, and R¹ and R² are not —H. In other embodiments, R¹ is —H and the ring to which it is attached is substituted with a single substituent (other than —H) at one of R⁰ or R². In certain embodiments, R¹ is —H, and R⁰ and R² are not —H. In other embodiments, R² is —H and the ring to which it is attached is substituted with a single substituent (other than —H) at one of R⁰ or R¹. In certain embodiments, R² is —H, and R⁰ and R¹ are not —H. In other embodiments, R⁰, R¹ and R² are not —H.

In certain embodiments, when R⁸ is H, R⁷ is not a substituted or unsubstituted aryl.

In one aspect, the disclosure provides compounds represented by general Formula (VII):

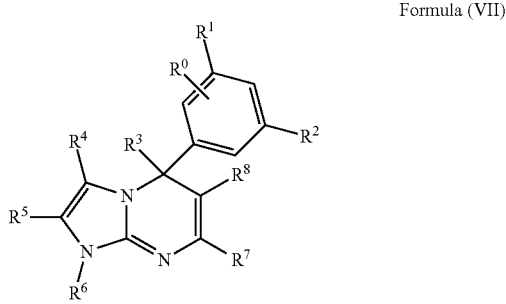

Formula (VII)

wherein:
R⁰, R¹ and R² are each independently selected from —H, halogen, hydroxyl, nitro, nitrile, —SOR¹¹, —S(O)₂R¹¹, —S(O)₂NR¹⁰R¹², —OR¹¹, —OC(O)R¹², —C(O)OR¹², —C(O)R¹¹, —C(ONR¹⁰R¹², —NR¹⁰R¹², —N(R¹²)C(O)R¹¹, —NS(O)₂R¹², substituted or unsubstituted C₁-C₆ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C₁-C₆ haloalkyl, or substituted or unsubstituted C₁-C₆ haloalkoxy;

R³ is selected from —H, halogen, hydroxyl, nitro, nitrile, —SOR¹¹, —S(O)₂R¹¹, —S(O)₂NR¹⁰R¹², —OR¹¹, —OC(O)R¹², —C(O)OR¹², —C(O)R¹¹, —C(O)NR¹⁰R¹², —NR¹⁰R¹², —N(R¹²)C(O)R¹¹, —NS(O)₂R¹², substituted or unsubstituted C₁-C₆ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C₁-C₆ haloalkyl, or substituted or unsubstituted C₁-C₆ haloalkoxy; R⁴ and R⁵ are independently selected from H, —NR¹⁰R¹², —C(O)NR¹⁰R¹², —N(R¹²)C(O)R¹¹, nitrile, substituted or unsubstituted C₁-C₆ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or R⁵ and R⁴ taken together with the respective carbon atom to which they are attached form a substituted or unsubstituted 4-12 membered ring;

R⁶ is selected from —H, substituted or unsubstituted C₁-C₆ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, or substituted or unsubstituted heteroarylalkyl;

R⁷ and R⁸ are each independently selected from —H, —NR¹⁰R¹², —C(O)NR¹⁰R¹², —N(R¹²)C(O)R¹¹, nitrile, substituted or unsubstituted C₁-C₆ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

each occurrence of $R^{11}$ is independently selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl; and each occurrence of $R^{10}$ and $R^{12}$ is each independently selected from —H, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl, or a pharmaceutically acceptable salt thereof.

In certain embodiments of any of the foregoing or following, the compounds of the disclosure, or a pharmaceutically acceptable salt thereof, are represented by Formula (VIIa) (wherein the R groups are as described above for Formula (VII)):

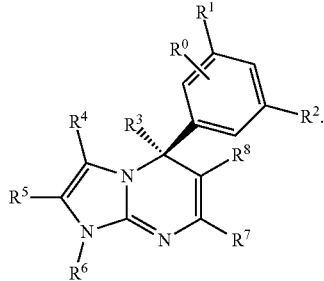

Formula (VIIa)

In certain embodiments of any of the foregoing or following, the compounds of the disclosure, or a pharmaceutically acceptable salt thereof, are represented by Formula (VIIb) (wherein the R groups are as described above for Formula (VII)):

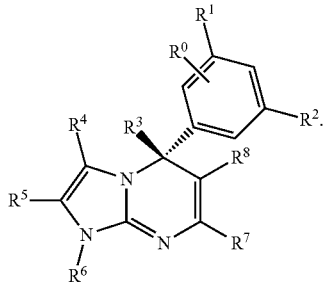

Formula (VIIb)

In certain embodiments of any of the foregoing or following, $R^0$, $R^1$ and $R^2$ are each independently selected from —H, halogen, hydroxyl, nitro, nitrile, —$SOR^{11}$, —$S(O)_2R^{11}$, —$S(O)_2NR^{10}R^{12}$, —$OR^{11}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy.

In certain embodiments of any of the foregoing or following, $R^0$ is selected from hydroxyl, —$S(O)_2R^{11}$, —$S(O)_2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, hydroxyl, —$S(O)_2R^{11}$, —$S(O)_2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$.

In certain embodiments of any of the foregoing or following, $R^1$ and $R^2$ are each independently selected from —H, methoxy, fluoro, chloro, bromo, hydroxyl, nitro, nitrile, methyl, trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is H.

In certain embodiments of any of the foregoing or following, $R^3$ is selected from —H, halogen, hydroxyl, nitro, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from methyl, ethyl, propyl, isopropyl, cyclopropyl, or cyclobutyl. In certain embodiments, any of the foregoing, may be optionally substituted.

In certain embodiments of any of the foregoing or following, $R^3$ is isopropyl. In certain embodiments, isopropyl may be optionally substituted.

In certain embodiments of any of the foregoing or following, $R^4$ and $R^5$ are independently selected from H, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl.

In certain embodiments of any of the foregoing or following, $R^4$ and $R^5$ are each independently selected from —H, methyl, ethyl, propyl, isopropyl, cyclopropyl, cyclobutyl, cyclopentyl, cyclohexyl, phenyl or benzyl. In certain embodiments, any of the foregoing except H, may be optionally substituted.

In certain embodiments of any of the foregoing or following, $R^4$ and $R^5$ are each independently —H or methyl. In certain embodiments, methyl may be optionally substituted.

In certain embodiments of any of the foregoing or following, $R^5$ and $R^4$ taken together with the respective carbon atoms to which they are attached faun a substituted or unsubstituted 4-12 membered ring.

In certain embodiments of any of the foregoing or following, $R^5$ and $R^4$ taken together with the respective carbon atom to which they are attached form a 4-12 membered ring selected from substituted or unsubstituted aryl or substituted or unsubstituted heteroaryl.

In certain embodiments of any of the foregoing or following, $R^5$ and $R^4$ taken together with the respective carbon atom to which they are attached form a substituted or unsubstituted 4-12 membered ring containing 0-4 heteroatoms (0, 1, 2, 3 or 4) independently selected from N, O, or S.

In certain embodiments of any of the foregoing or following, the 4-12 membered ring is a monocyclic ring. In certain embodiments of any of the foregoing or following, the 4-12 membered ring is a polycyclic ring. In certain embodiments of any of the foregoing or following, the 4-12 membered ring is a bicyclic ring. In certain embodiments of any of the foregoing or following, when the 4-12 membered ring is a polycyclic ring, each ring is independently selected from saturated or unsaturated, and each ring may independently contain one or more heteroatoms.

In certain embodiments of any of the foregoing or following, $R^5$ and $R^4$ taken together with the respective carbon atom to which they are attached form a phenyl ring. In certain embodiments, the phenyl ring may be optionally substituted.

In certain embodiments of any of the foregoing or following, $R^6$ is selected from H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^6$ is selected from —H, methyl, ethyl, isopropyl, cyclopropyl, cyclobutyl, cyclopentyl, cyclohexyl, phenyl, pyridyl, or benzyl. In certain embodiments, any of the foregoing except —H, may be optionally substituted.

In certain embodiments of any of the foregoing or following, $R^6$ is —H.

In certain embodiments of any of the foregoing or following, $R^7$ and $R^8$ are each independently selected from —H, —NR$^{10}$R$^{12}$, —C(O)NR$^{10}$R$^{12}$, —N(R$^{12}$)C(O)R$^{11}$, nitrile, methyl, ethyl, isopropyl, cyclopropryl, cyclobutyl, cyclopentyl, cyclohexyl, phenyl, or benzyl.

In certain embodiments of any of the foregoing or following, $R^7$ is selected from —H, —NH$_2$, methyl, or phenyl. In certain embodiments, any of the foregoing except —H, may be optionally substituted.

In certain embodiments of any of the foregoing or following, $R^8$ is selected from —H, nitrile, or —C(O)NH$_2$. In certain embodiments, —C(O)NH$_2$ may be optionally substituted.

In certain embodiments of any of the foregoing or following, each occurrence of $R^{11}$ is independently selected from substituted or unsubstituted $C_1$-$C_6$ alkyl or substituted or unsubstituted cycloalkyl. In certain embodiments, there is no occurrence of $R^{11}$.

In certain embodiments of any of the foregoing or following, each occurrence of $R^{10}$ and $R^{12}$ is each independently selected from —H, substituted or unsubstituted $C_1$-$C_6$ alkyl, or substituted or unsubstituted cycloalkyl, such as from —H, or substituted or unsubstituted $C_1$-$C_6$ alkyl. In certain embodiments, each occurrence of $R^{10}$ and $R^{12}$ is —H. In certain embodiments, there is no occurrence of $R^{10}$ and/or $R^{12}$.

In certain embodiments, the compound is selected from:

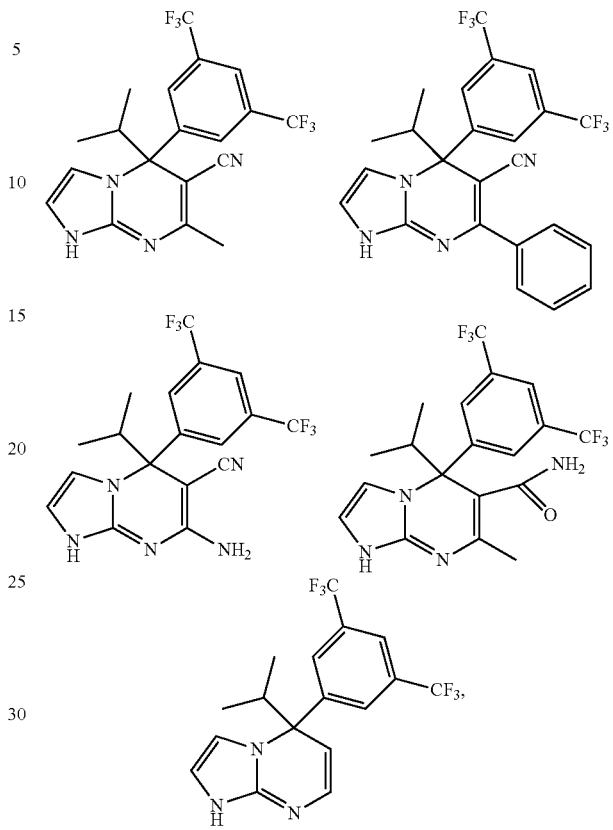

or a pharmaceutically acceptable salt thereof.

In certain emobidments, the compound of Formula (VII), (VIIa), or (VIIb) is:

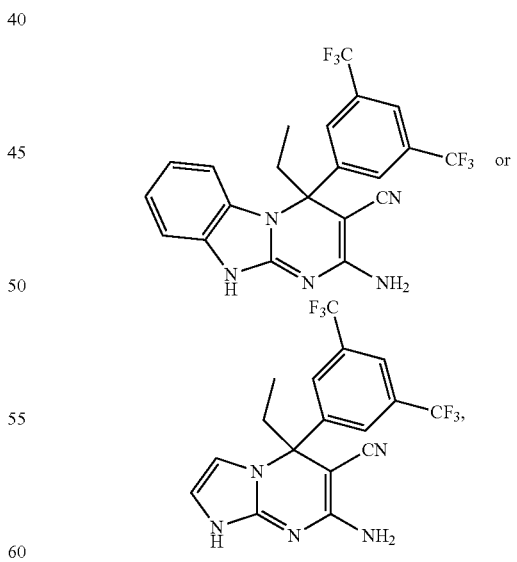

or a pharmaceutically acceptable salt thereof.

In certain embodiments of any of the foregoing or following, the $R^0$, $R^1$ and $R^2$ are not all simultaneously —H. In other embodiments, $R^0$ is —H and the ring to which it is attached, is substituted with a single substituent (other than —H) at one of $R^1$ or $R^2$. In certain embodiments, $R^0$ is —H, and $R^1$ and $R^2$ are not —H. In other embodiments, $R^1$ is —H and the ring to which it is attached is substituted with a single substituent (other than —H) at one of $R^0$ or $R^2$. In certain embodiments, $R^1$ is —H, and $R^0$ and $R^2$ are not —H. In other embodiments, $R^2$ is —H and the ring to which it is attached is substituted with a single substituent (other than —H) at one of $R^0$ or $R^1$. In certain embodiments, $R^2$ is —H, and $R^0$ and $R^1$ are not —H. In other embodiments, $R^0$, $R^1$ and $R^2$ are not —H.

In certain embodiments, the compound of Formula (VII), (VIIa), or (VIIb) is not

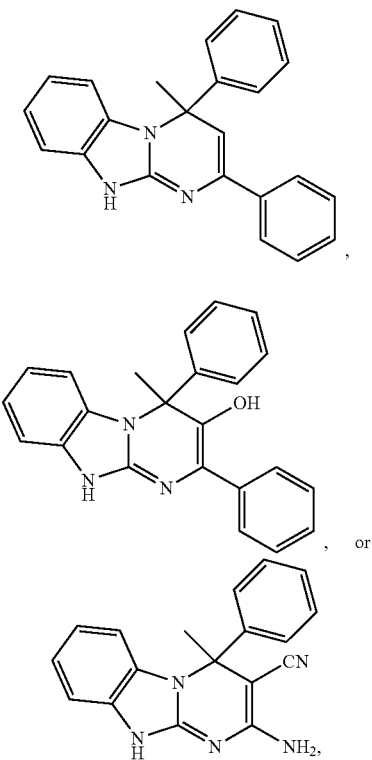

In one aspect, the disclosure provides compounds represented by general Formula (VIII):

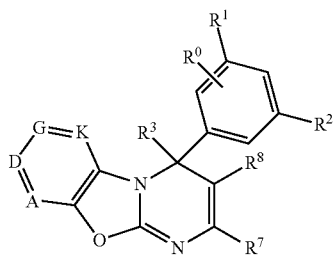

Formula (VIII)

wherein:
A, D, G and K are each independently N or $CR^{15}$, provided that no more than two of A, D, G, and K are N simultaneously;
$R^0$, $R^1$ and $R^2$ are each independently selected from —H, halogen, hydroxyl, nitro, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$ substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy;

$R^3$ is selected from —H, halogen, hydroxyl, nitro, nitrile, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)_{NR}{}^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy; $R^7$ and $R^8$ are each independently selected from —H, —$NR^{10}R^{12}$, —$C(O)NR^{10}R^{12}$, —$N(R^{12})C(O)R^{11}$, nitrile, substituted or unsubstituted $C_1$-$C_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

each occurrence of $R^{11}$ is independently selected from substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl;

each occurrence of $R^{10}$ and $R^{12}$ is each independently selected from —H, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl; and each occurrence of $R^{15}$ is independently selected from —H, halogen, hydroxyl, nitro, nitrile, substituted or unsubstituted $C_1$-$C_6$ alkoxy, substituted or unsubstituted $C_1$-$C_6$ alkyl, or substituted or unsubstituted $C_1$-$C_6$ haloalkyl, substituted or unsubstituted $C_1$-$C_6$ haloalkoxy, or a pharmaceutically acceptable salt thereof.

In certain embodiments, the compounds of the disclosure, or a pharmaceutically acceptable salt thereof, are represented by Formula (VIIIa) (wherein the R groups are as described above for Formula (VIII)):

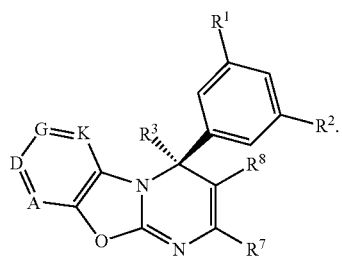

Formula (VIIIa)

In certain embodiments, the compounds of the disclosure, or a pharmaceutically acceptable salt thereof, are represented by Formula (VIIIb) (wherein the R groups are as described above for Formula (VIII)):

Formula (VIIIb)

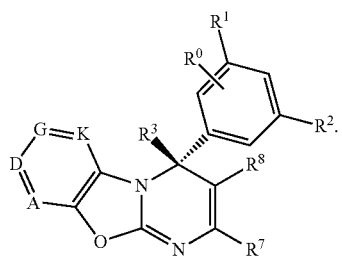

In certain embodiments of any of the foregoing or following, $R^0$, $R^1$, and $R^2$, are each independently selected from —H, halogen, hydroxyl, nitro, nitrile, —$SOR^{11}$, —$S(O)_2R^{11}$, —$S(O)_2NR^{10}R^{12}$, —$OR^{11}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy.

In certain embodiments of any of the foregoing or following, $R^0$ is selected from —H, hydroxyl, —$S(O)_2R^{11}$, —$S(O)_2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, halogen, hydroxyl, nitro, nitrile, —$OR_{11}$, substituted or unsubstituted $C_1$-$C_6$ alkyl, or substituted or unsubstituted $C_1$-$C_6$ haloalkyl, substituted or unsubstituted $C_1$-$C_6$ haloalkoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each independently selected from —H, methoxy, fluoro, chloro, bromo, hydroxyl, nitro, nitrile, methyl, or trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^1$ and $R^2$ are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is H.

In certain embodiments of any of the foregoing or following, $R^3$ is selected from —H, halogen, hydroxyl, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected from methyl, ethyl, propyl, isopropyl, cyclopropyl, or cyclobutyl. In certain embodiments, any of the foregoing, may be optionally substituted.

In certain embodiments, in of any of the foregoing or following, $R^3$ is isopropyl. In certain embodiments, isopropyl may be optionally substituted.

In certain embodiments of any of the foregoing or following, $R^7$ and $R^8$ are each independently selected from —H, —$NR^{10}R^{12}$, —$C(O)NR^{10}R^{12}$, —$N(R^{12})C(O)R^{11}$, nitrile, methyl, ethyl, isopropyl, cyclopropryl, cyclobutyl, cyclopentyl, cyclohexyl, phenyl, or benzyl. In certain embodiments, any of the foregoing except —H, may be optionally substituted.

In certain embodiments of any of the foregoing or following, $R^7$ is methyl or phenyl. In certain embodiments, any of the foregoing may be optionally substituted.

In certain embodiments of any of the foregoing or following, $R^8$ is nitrile or —$C(O)NH_2$. In certain embodiments, —$C(O)NH_2$ may be optionally substituted.

In certain embodiments of any of the foregoing or following, each occurrence of $R^{11}$ is independently selected from substituted or unsubstituted $C_1$-$C_6$ alkyl or substituted or unsubstituted cycloalkyl. In certain embodiments, there is no occurrence of $R^{11}$.

In certain embodiments of any of the foregoing or following, each occurrence of $R^{10}$ and $R^{12}$ is each independently selected from —H, substituted or unsubstituted $C_1$-$C_6$ alkyl, or substituted or unsubstituted cycloalkyl, such as from —H, or substituted or unsubstituted $C_1$-$C_6$ alkyl. In certain embodiments, each occurrence of $R^{10}$ and $R^{12}$ is —H. In certain embodiments, there is no occurrence of $R^{10}$ and/or $R^{12}$.

In certain embodiments of any of the foregoing or following, $R^0$ is independently selected from —H, halogen, hydroxyl, nitro, nitrile, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy; $R^1$ and $R^2$ are each independently selected from —H, methoxy, fluoro, chloro, bromo, hydroxyl, nitro, nitrile, methyl, or trifluoromethyl;

$R^3$ is selected from methyl, ethyl, propyl, isopropyl, cyclopropyl, or cyclobutyl;

$R^7$ and $R^8$ are each independently selected from —H, —$NH_2$, —$C(O)NH_2$, nitrile, methyl, ethyl, isopropyl, cyclopropryl, cyclobutyl, cyclopentyl, cyclohexyl, phenyl, or benzyl; and A, D, G and K is each independently selected from N or $CR^{15}$, wherein each occurrence of $R^{15}$ is independently selected from —H, halogen, hydroxyl, nitro, nitrile, substituted or unsubstituted $C_1$-$C_6$ alkoxy, substituted or unsubstituted $C_1$-$C_6$ alkyl, or substituted or unsubstituted $C_1$-$C_6$ haloalkyl, substituted or unsubstituted $C_1$-$C_6$ haloalkoxy.

In certain embodiments of any of the foregoing or following, $R^0$ is selected from —H, hydroxyl, —$S(O)_2R^{11}$, —$S(O)^2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$;

$R^1$ and $R^2$ are each trifluoromethyl;

$R^3$ is isopropyl;

$R^7$ is —$NH_2$, methyl or phenyl;

$R^8$ is nitrile or —$C(O)NH_2$; and

A, D, G and K is each independently selected from N or CR$^{15}$, wherein each occurrence of R$^{15}$ is independently selected from —H, halogen, hydroxyl, nitro, nitrile, substituted or unsubstituted C$_1$-C$_6$ alkoxy, substituted or unsubstituted C$_1$-C$_6$ alkyl, or substituted or unsubstituted C$_1$-C$_6$ haloalkyl, substituted or unsubstituted C$_1$-C$_6$ haloalkoxy.

In certain embodiments, the compound is selected from:

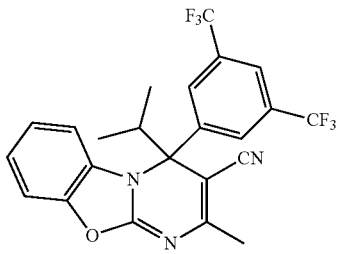

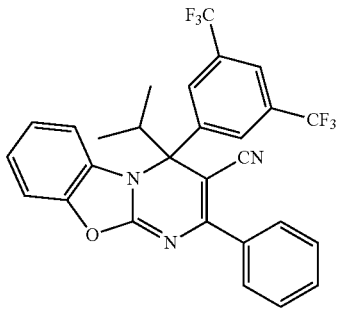

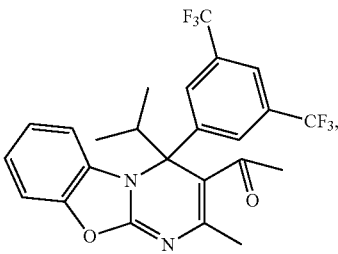

or a pharmaceutically acceptable salt thereof.

In certain embodiments of any of the foregoing or following, the R$^0$, R$^1$ and R$^2$ are not all simultaneously —H. In other embodiments, R$^0$ is —H and the ring to which it is attached, is substituted with a single substituent (other than —H) at one of R$^1$ or R$^2$. In certain embodiments, R$^0$ is —H, and R$^1$ and R$^2$ are not —H. In other embodiments, R$^1$ is H and the ring to which it is attached is substituted with a single substituent (other than —H) at one of R$^0$ or R$^2$. In certain embodiments, R$^1$ is —H, and R$^0$ and R$^2$ are not —H. In other embodiments, R$^2$ is —H and the ring to which it is attached is substituted with a single substituent (other than —H) at one of R$^0$ or R$^1$. In certain embodiments, R$^2$ is —H, and R$^0$ and R$^1$ are not —H. In other embodiments, R$^0$, R$^1$ and R$^2$ are not —H.

In one aspect, the compounds of the disclosure, or a pharmaceutically acceptable salt thereof, are represented by Formula (IX):

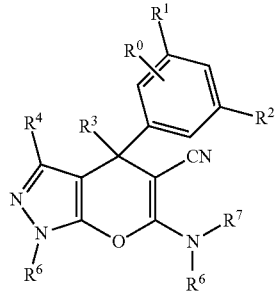

Formula (IX)

wherein:

R$^0$, R$^1$ and R$^2$ are each independently selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O) R$^{11}$, —NS(O)$_2$R$^{12}$, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl substituted or unsubstituted arylalkyl, substituted or unsubstituted heteroarylalkyl, substituted or unsubstituted C$_1$-C$_6$ haloalkyl, or substituted or unsubstituted C$_1$-C$_6$ haloalkoxy;

R$^3$ is selected from —H, halogen, hydroxyl, nitro, nitrile, —SOR$^{11}$, —S(O)$_2$R$^{11}$, —S(O)$_2$NR$^{10}$R$^{12}$, —OR$^{11}$, —OC(O)R$^{12}$, —C(O)OR$^{12}$, —C(O)R$^{11}$, —C(O)NR$^{10}$R$^{12}$, —NR$^{10}$R$^{12}$, —N(R$^{12}$)C(O)R$^{11}$, —NS(O)$_2$R$^{12}$, substituted or unsubstituted C$_1$-C$_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted C$_1$-C$_6$ haloalkyl, or substituted or unsubstituted C$_1$-C$_6$ haloalkoxy; R$^4$ is selected from H, substituted or unsubstituted C$_1$-C$_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl;

R$^5$, R$^6$ and R$^7$ are each independently selected from —H, —C(O)R$^{11}$, substituted or unsubstituted C$_1$-C$_6$ alkyl, substituted or unsubstituted cycloalkyl, substituted or unsubstituted aryl, substituted or unsubstituted heteroaryl, substituted or unsubstituted arylalkyl, or substituted or unsubstituted heteroarylalkyl, or R$^5$ is selected from any of the foregoing and R$^6$ and R$^7$ taken together with the nitrogen atom to which they are attached form a substituted or unsubstituted 3-6 membered ring;

each occurrence of R$^{11}$ is independently selected from substituted or unsubstituted C$_1$-C$_6$ alkyl, substituted or unsubstituted cycloalkyl, substituted or unsubstituted heterocyclyl, substituted or unsubstituted aryl, or substituted or unsubstituted heteroaryl; and each occurrence of R$^{10}$ and R$^{12}$ is each independently selected from —H, substituted or unsubstituted C$_1$-C$_6$ alkyl, substituted or unsubstituted cycloalkyl, substituted or unsubstituted heterocyclyl, substituted or unsubstituted aryl, or substituted or unsubstituted heteroaryl.

In some embodiments, the compound is represented by Formula (IXa) (wherein the R groups are as described above for Formula (IX)):

Formula (IXa)

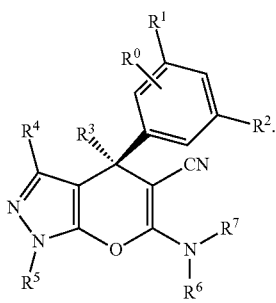

In certain embodiments, the compound is represented by Formula (IXb) (wherein the R groups are as described above for Formula (IX)):

Formula (IXb)

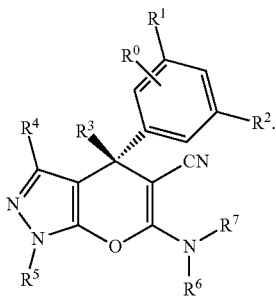

In some embodiments, of any of the foregoing or following, $R^0$, $R^1$ and $R^2$ are each independently selected from —H, halogen, hydroxyl, nitro, nitrile, —$SOR^{11}$, —$S(O)_2R^{11}$, —$S(O)_2NR^{10}R^{12}$, —$OR^{11}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted $C_1$-$C_6$ alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted $C_1$-$C_6$ haloalkyl, or substituted or unsubstituted $C_1$-$C_6$ haloalkoxy.

In some embodiments, of any of the foregoing or following, $R^0$ is selected from hydroxyl, —$S(O)_2R^{11}$, —$S(O)_2NR^{10}R^{12}$, —$OR^{11}$, —$C(O)NR^{10}R^{12}$, —$NR^{10}R^{12}$, —$N(R^{12})C(O)R^{11}$, or —$NS(O)_2R^{12}$. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In some embodiments, of any of the foregoing or following, $R^1$ and $R^2$ are each independently selected from —H, halogen, hydroxyl, nitro, nitrile, —$OR^{11}$, substituted or unsubstituted $C_1$-$C_6$ alkyl, or substituted or unsubstituted $C_1$-$C_6$ haloalkyl, or substituted or unsubstituted $C_1$-$C_6$ haloalkoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In some embodiments, of any of the foregoing or following, $R^1$ and $R^2$ are each independently selected from —H, methoxy, fluoro, chloro, bromo, hydroxyl, nitro, nitrile, methyl, trifluoromethyl, or trifluoromethoxy. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In some embodiments, of any of the foregoing or following, $R^1$ and $R^2$ are each independently selected from H, methoxy, chloro, nitro, nitrile, or trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In some embodiments, of any of the foregoing or following, R1 and $R^2$ are each trifluoromethyl. In other embodiments, $R^0$ is selected from —H, halogen, substituted or unsubstituted $C_1$-$C_6$ haloalkyl, substituted or unsubstituted $C_1$-$C_6$ haloalkoxy, or substituted or unsubstituted $C_1$-$C_6$ alkyl. In other embodiments $R^0$ is —H.

In certain embodiments of any of the foregoing or following, $R^3$ is selected from —H, halogen, hydroxyl, nitro, nitrile, substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In certain embodiments of any of the foregoing or following, $R^3$ is selected substituted or unsubstituted $C_1$-$C_6$ alkyl, substituted or unsubstituted cycloalkyl, substituted or unsubstituted heterocyclyl, substituted or unsubstituted aryl, or substituted or unsubstituted heteroaryl.

In some embodiments of any of the foregoing or following, $R^3$ is selected from methyl, ethyl, propyl, isopropyl, cyclopropyl, or cyclobutyl. In certain embodiments, any of the foregoing may be optionally substituted.

In some embodiments of any of the foregoing or following, $R^3$ is selected from isopropyl, cyclopropyl, or cyclobutyl. In certain embodiments, any of the foregoing may be optionally substituted.

In some embodiments of any of the foregoing or following, $R^3$ is cyclobutyl. In certain embodiments, cyclobutyl may be optionally substituted.

In certain embodiments of any of the foregoing or following, $R^4$ is selected from —H, substituted or unsubstituted $C_1$-$C_6$ alkyl, substituted or unsubstituted cycloalkyl, substituted or unsubstituted aryl, substituted or unsubstituted heteroaryl, or substituted or unsubstituted arylalkyl.

In certain embodiments of any of the foregoing or following, $R^4$ is selected from —H, substituted or unsubstituted $C_1$-$C_6$ alkyl, substituted or unsubstituted cycloalkyl, substituted or unsubstituted aryl, or substituted or unsubstituted arylalkyl.

In some embodiments of any of the foregoing or following, $R^4$ is selected from methyl, ethyl, isopropyl, cyclopropyl, cyclobutyl, cyclopentyl, cyclohexyl, phenyl or benzyl. In certain embodiments, any of the foregoing may be optionally substituted.

In some embodiments of any of the foregoing or following, $R^4$ is methyl or isopropyl. In certain embodiments, any of the foregoing may be optionally substituted.

In some embodiments of any of the foregoing or following, $R^4$ is methyl. In certain embodiments, methyl may be optionally substituted.

In certain embodiments of any of the foregoing or following, $R^5$, $R^6$ and $R^7$ are each independently selected from —H, —$C(O)R^{11}$, substituted or unsubstituted $C_1$-$C_6$ alkyl, substituted or unsubstituted cycloalkyl, substituted or unsubstituted aryl, substituted or unsubstituted arylalkyl, or $R^5$ is selected from any of the foregoing and $R^6$ and $R^7$ taken together with the nitrogen atom to which they are attached form a substituted or unsubstituted 3-6 membered ring.

In certain embodiments of any of the foregoing or following, $R^5$, $R^6$ and $R^7$ are each independently selected from —H, —C(O)$R^{11}$, substituted or unsubstituted $C_1$-$C_6$ alkyl, substituted or unsubstituted cycloalkyl, substituted or unsubstituted aryl, or substituted or unsubstituted arylalkyl.

In some embodiments of any of the foregoing or following, $R^5$, $R^6$ and $R^7$ are each independently selected from —H, methyl, ethyl, isopropyl, cyclopropyl, cyclobutyl, cyclopentyl, cyclohexyl, phenyl, benzyl, or COCH$_3$. In certain embodiments, any of the foregoing, except —H, may be optionally substituted.

In some embodiments of any of the foregoing or following, $R^5$, $R^6$ and $R^7$ are each independently selected from H, methyl, phenyl, or COCH$_3$. In certain embodiments, any of the foregoing, except —H, may be optionally substituted.

In some embodiments of any of the foregoing or following, $R^5$ and $R^6$ are each independent selected from H, methyl or phenyl. In certain embodiments, any of the foregoing, except —H, may be optionally substituted.

In some embodiments of any of the foregoing or following, $R^7$ is H.

In some embodiments of any of the foregoing or following, the compound is selected from:

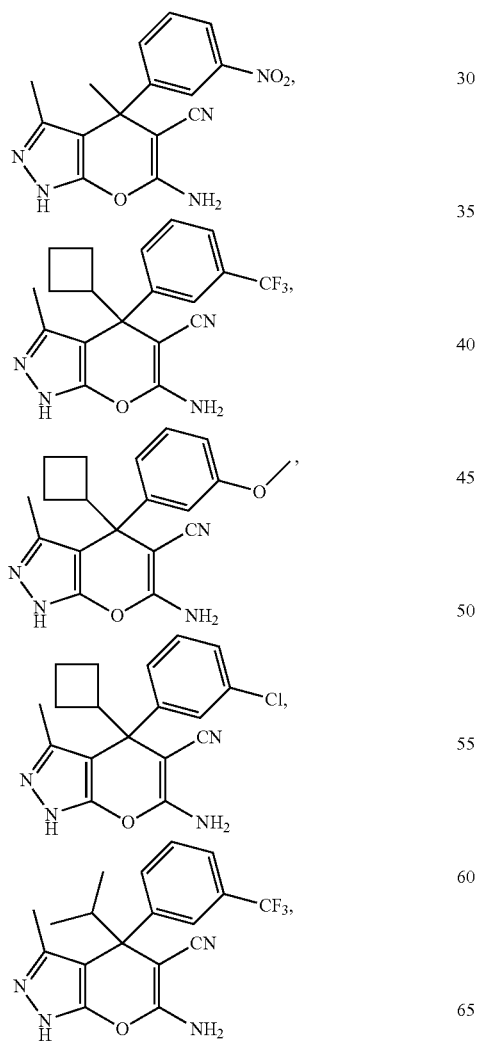

-continued

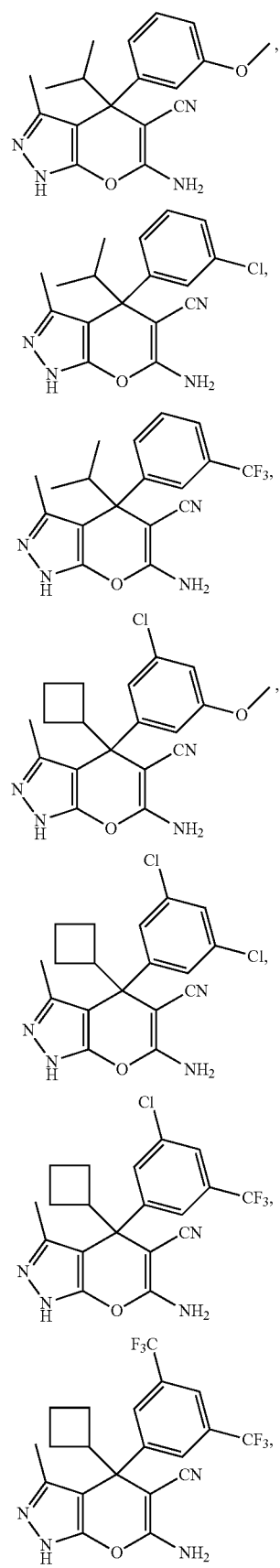

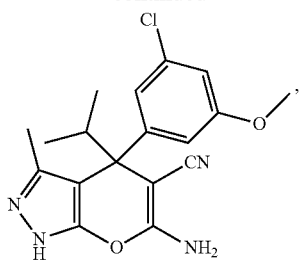
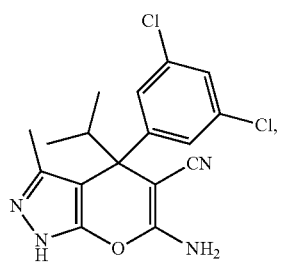
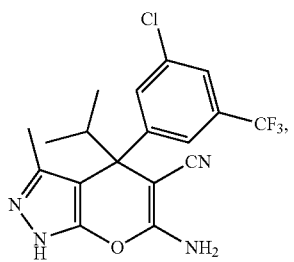
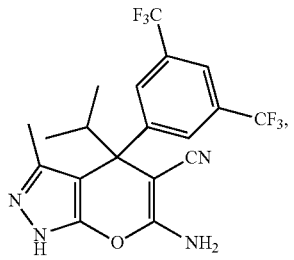
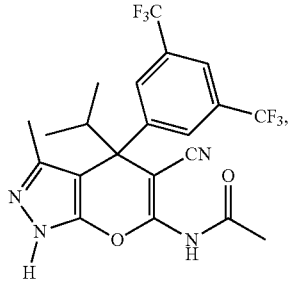
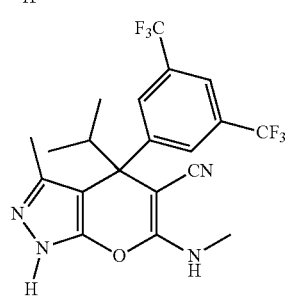
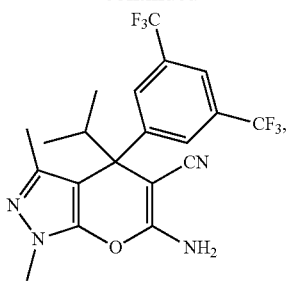
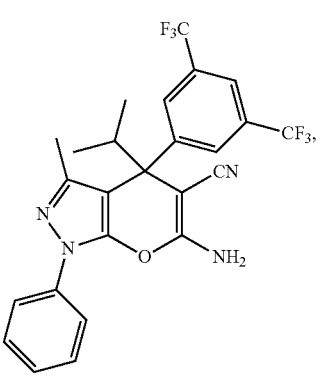 [SMILES: Cc1nn(-c2ccccc2)c2c1C(c1cc(C(F)(F)F)cc(C(F)(F)F)c1)(C(C)C)C(C#N)=C(N)O2]
or a pharmaceutically acceptable salt thereof.
In certain embodiments of any of the foregoing or following, the compound is selected from the group consisting of
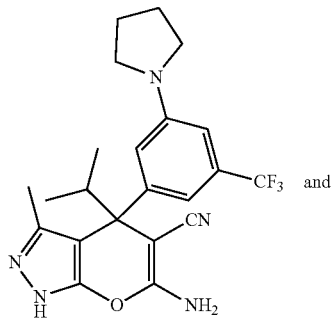
and
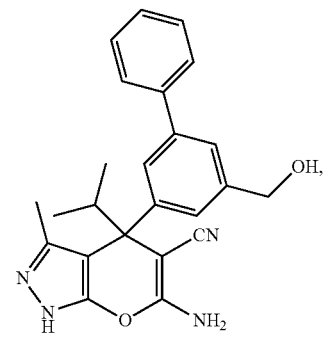 [SMILES: Cc1n[nH]c2c1C(c1cc(CO)cc(-c3ccccc3)c1)(C(C)C)C(C#N)=C(N)O2]
or a pharmacetutically acceptable salt thereof.
In certain embodiments of any of the foregoing or following, the compound is

125

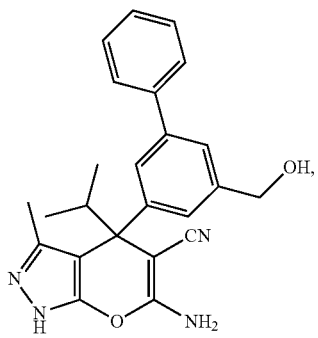

or a pharmaceutically acceptable salt thereof. In certain such embodiments, the compound is:

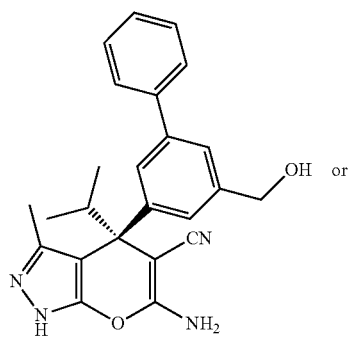

or a pharmaceutically acceptable salt thereof.

In certain embodiments of any of the foregoing or following, the compound is,

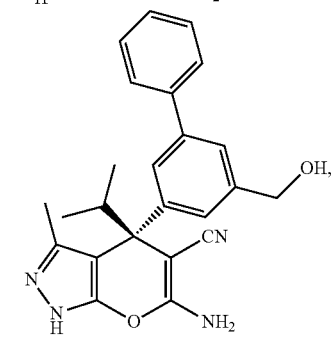

or a pharmaceutically acceptable salt thereof.

In certain embodiments of any of the foregoing or following, the compound is:

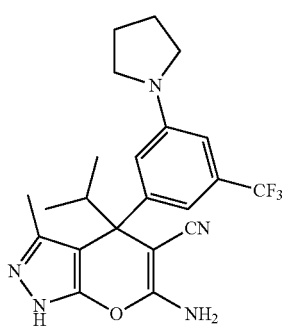 [SMILES: Cc1n[nH]c2c1C(c1cc(N3CCCC3)cc(C(F)(F)F)c1)(C(C)C)C(C#N)=C(N)O2]

or a pharmaceutically acceptable salt thereof. In certain such embodiments, the compound is:

126

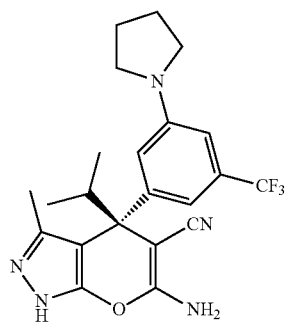 or

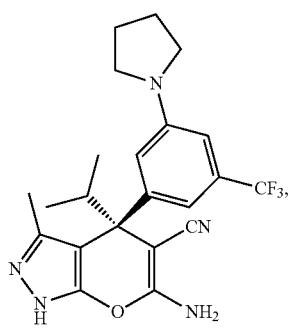

or a pharmaceutically acceptable salt thereof.

In certain embodiments of any of the foregoing or following, the compound is;

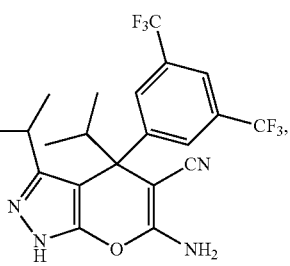

or a pharmaceutically acceptable salt thereof.

In certain embodiments of any of the foregoing or following, the compound is:

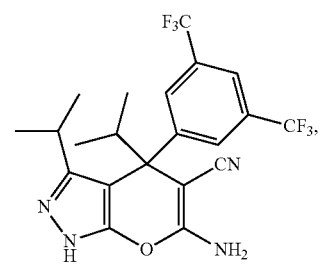 [SMILES: CC(C)c1n[nH]c2c1C(c1cc(C(F)(F)F)cc(C(F)(F)F)c1)(C(C)C)C(C#N)=C(N)O2]

or an enantiomer thereof, or a pharmaceutically acceptable salt of any one of the foregoing. In certain such embodiment, the compound is:

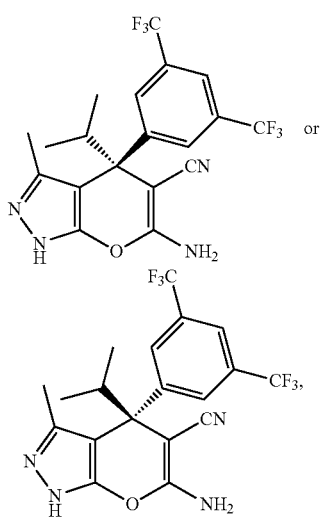

or a pharmaceutically acceptable salt thereof.

In certain embodiments of any of the foregoing or following, the $R^0$, $R^1$ and $R^2$ are not all simultaneously —H. In other embodiments, $R^0$ is —H and the ring to which it is attached, is substituted with a single substituent (other than —H) at one of $R^1$ or $R^2$. In certain embodiments, $R^0$ is —H, and $R^1$ and $R^2$ are not —H. In other embodiments, $R^1$ is —H and the ring to which it is attached is substituted with a single substituent (other than —H) at one of $R^0$ or $R^2$. In certain embodiments, $R^1$ is —H, and $R^0$ and $R^2$ are not —H. In other embodiments, $R^2$ is —H and the ring to which it is attached is substituted with a single substituent (other than —H) at one of $R^0$ or $R^1$. In certain embodiments, $R^2$ is —H, and $R^0$ and $R^1$ are not —H. In other embodiments, $R^0$, $R^1$ and $R^2$ are not —H.

The disclosure also provides variants of Formulae (IV), (V), (VI), (VII), (VIII), and (IX), wherein

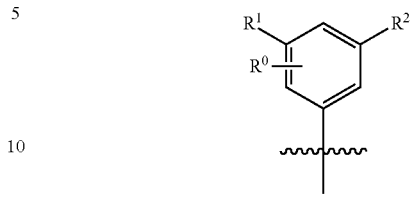

contains 1 to 3 heteroatoms (e.g., 1, 2 or 3 heteroatoms) independently selected from O or N.

Certain compounds of the disclosure (e.g., Compounds of Formula (IXc), wherein Formula (IXc) is a sub-genus of Formula (IX)) and their corresponding inhibitory activity values are shown in Table 3 below. The assay used to evaluate activity is described in the Examples.

Formula (IXc)

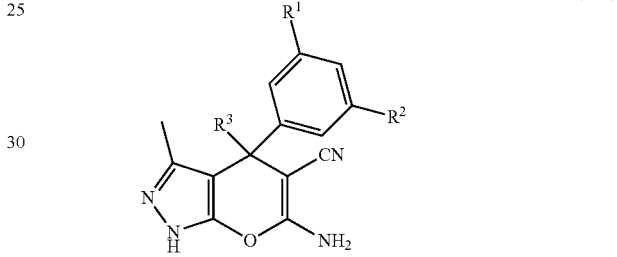

TABLE 3

| | $R^3$ | $R^2$ | $R^1$ | SHMT2 IC$_{50}$ (nM) | SHMT1 IC$_{50}$ (nM) |
|---|---|---|---|---|---|
| GD-07 | —CH$_3$ | —NO$_2$ | —H | >5000 | — |
| HK-1 | -cyclobutane | —CF$_3$ | —H | >5000 | — |
| HK-2 | -cyclobutane | —OMe | —H | >5000 | >5000 |
| HK-3 | -cyclobutane | —Cl | —H | 1191 | — |
| HK-4 | -cyclobutane | —CF$_3$ | —H | 1768 | — |
| HK-5 | —CH(CH$_3$)$_2$ | —CF$_3$ | —H | 756 | — |
| HK-6 | —CH(CH$_3$)$_2$ | —OMe | —H | 4580 | — |
| HK-7 | —CH(CH$_3$)$_2$ | —Cl | —H | 400.5 | — |
| HK-8 | —CH(CH$_3$)$_2$ | —CF$_3$ | —H | 400.5 | — |
| HK-9 | -cyclobutane | —Cl | —OMe | 3464 | — |
| HK-10 | -cyclobutane | —Cl | —Cl | 1193 | 593 |
| HK-11 | -cyclobutane | —Cl | —CF$_3$ | 100 | — |
| HK-12 | -cyclobutane | —CF$_3$ | —CF$_3$ | 168 | 205.7 |
| HK-13 | —CH(CH$_3$)$_2$ | —Cl | —OMe | 500 | — |
| HK-14 | —CH(CH$_3$)$_2$ | —Cl | —Cl | 131 | 67 |
| HK-15 | —CH(CH$_3$)$_2$ | —Cl | —CF$_3$ | 35 | 20 |
| HK-16 (racemic mxture) | —CH(CH$_3$)$_2$ | —CF$_3$ | —CF$_3$ | 27 | 21 |
| HK-16 (PK-1) | —CH(CH$_3$)$_2$ | —CF$_3$ | —CF$_3$ | >5000 | >5000 |
| HK-16 (PK-2) | —CH(CH$_3$)$_2$ | —CF$_3$ | —CF$_3$ | 15 | 5 |
| HK-X1 | —CH(CH$_3$)$_2$ | —CF$_3$ | pyrrolidinyl | 66 | 13 |
| HK-X2 | —CH(CH$_3$)$_2$ | —CH$_2$OH | —C$_6$H$_5$ (phenyl) | 13 | 5 |

TABLE 3-continued

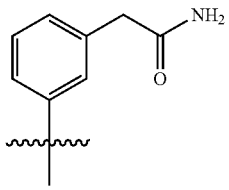 [SMILES: *c1cccc(CC(N)=O)c1]

| | R³ | R² | R¹ | SHMT2 IC₅₀ (nM) | SHMT1 IC₅₀ (nM) |
|---|---|---|---|---|---|
| HK-X3 | —CH(CH₃)₂ | —CH₂OH | | 7.8 | 16.9 |
| Compound a | —CH(CH₃)₂ | —CF₃ | —Br | 42 | — |

HK-16 (PK2), enriched for an enantiomer of HK-16 (see, for example Formula (IXa) and (IXb)), was used in Example 11 and FIG. 4. As shown in Example 11 and FIG. 4, HK-16 (PK2) is not only highly active against SHMT it also is highly active in terms of its growth inhibitory effect on the tested cancer cell lines.

In certain embodiments, the disclosure provides a pharmaceutically acceptable salt of any of the compounds of the disclosure. In certain embodiments, any of the compounds of Formulae (I)-(IX) described herein, or a pharmaceutically acceptable salt thereof, are capable of inhibiting activity of an SHMT enzyme (e.g., are SHMT inhibitors, such as an SHMT2 inhibitor). Any such compounds described based on any of the structural features described herein may, in certain embodiments, also be described based on any of the functional features described herein (e.g., binding affinity for SHMT1 and/or SHMT 2, IC50, selectivity, inhibitory effect on serine flux or mitochondrial serine flux, etc.).

In certain embodiments of any of the foregoing or following, a compound of the disclosure is provided in isolated or substantially purified form, such as a substantially purified stereoisomer of a compound of the disclosure. Without being bound by theory, compounds of the disclosure have a stereocenter. Thus, in certain embodiments, substantially purified stereoisomers are provided and are suitable in any of the methods described herein.

In certain embodiments of any of the foregoing, compounds of this disclosure, such as compounds of Formulae (I)-(IX) and others, described using any combination of structural and/or functional activity, including any combination of one or more features described above or herein, are provided (and may be provided as an isolated or purified form or as a pharmaceutical composition). In certain embodiments, any such compounds of the disclosure may be used in any of the methods described herein, such as to inhibit SHMT activity in vitro or in vivo, or to treat cancer.

In another aspect of any of the foregoing or following, the disclosure provides a method of inhibiting the activity of a mammalian serine hydroxymethyl transferase (SHMT) enzyme, comprising contacting the enzyme or a cell expressing the enzyme with a compound, or a pharmaceutically acceptable salt thereof, or a pharmaceutical composition as described herein. In certain embodiments of any of the foregoing or following, the mammalian SHMT enzyme is a human SHMT enzyme, such as SHMT1, SHMT2, or both. In certain embodiments of any of the foregoing or following, the SHMT enzyme is SHMT2.

In certain embodiments of any of the foregoing or following, the method is an in vitro method comprising contacting the cell with the compound.

In certain embodiments of any of the foregoing, compounds of this disclosure, such as those of Formulae (I)-(IX) and others, are inhibitors of SHMT, such as are capable of inhibiting an activity of an SHMT enzyme. In certain embodiments, compounds of Formulae (I)-(IX) are SHMT2 inhibitors and, optionally, are also inhibitors of SHMT1. In certain embodiments, compounds of Formulae (I)-(IX) are SHMT2 inhibitors, but do not inhibit SHMT1. In certain embodiments, compounds of Formulae (I)-(IX) are dual SHMT inhibitors. In certain embodiments, compounds of Formulae (I)-(IX) inhibit SHMT2 with an IC50 of less than 5000 nM and, optionally, inhibit SHMT1 with an IC50 of less than 5000 nM. In certain embodiments, compound of Formulae (I)-(IX) inhibit SHMT2 with an IC50 of less than 2000 nM, less than 1500 nM, less than 800 nM, less than 500 nM, less than 250 nM, less than 150 nM, or less than 50 nM. In certain embodiments, such compounds also inhibit SHMT1 with an IC50 of less than 5000 nM. In certain embodiments, such compounds inhibit SHMT1 with an IC50 of less than 1000 nM, less than 750 nM, less than 500 nM, less than 250 nM, less than 100 nM, or less than 50 nM.

In one aspect, the disclosure further provides pharmaceutical compositions comprising one or more compounds of the disclosure together with a pharmaceutically acceptable carrier or excipient. Compounds or pharmaceutical compositions of the disclosure may be used in vitro or in vivo. Exemplary compounds of the disclosure, including examples of SHMT inhibitors, are provided herein. SHMT inhibitors may include any such compounds, as well as other compounds described structurally and/or functionally. The disclosure contemplates compounds have any combination of any of the foregoing structural and/or functional characteristics.

E. Exemplary Uses

In certain aspects, compounds of the disclosure, such as compounds and compositions as described herein, can be used for a variety of in vitro or in vivo uses. In other words, in certain embodiments, compounds of the disclosure, which may include mammalian SHMT inhibitors, such as SHMT2 inhibitors, such as inhibitors that inhibit both mammalian SHMT2 and SHMT1, can be used for a variety of in vitro and/or in vivo uses. Exemplary SHMT inhibitors are described herein. In certain embodiments, the SHMT2 inhibitor is a small organic molecule. In some embodiments, the SHMT2 inhibitor is not an antibody. Compounds of the disclosure (e.g., SHMT inhibitors, such as any of the inhibitors described herein based on structure and/or function) are suitable to inhibit SHMT activity, such as enzyme activity, in vitro or in vivo. In vitro uses include for studying SHMT function and/or serine flux and/or folate metabolism and/or NADPH generation and/or glycine generation in, for example, healthy cells, cancerous cells and/or in hypoxic cells. Similarly, folate metabolism, NADPH generation, and/or SHMT activity can be assessed in mutant cell lines, such as cells in which the activity of MTHFD1, MTHFD1L, MTHFD2, MTHFD2L, SHMT1, SHMT2, MTHFR, ALDH1L1, ALDHL2, FH, KEAP1 is or has been inhibited, disregulated or knocked out, or cells having certain hyper-activating mutations in any of the foregoing or in NRF2. Evaluation of compounds in such mutant or knock out cell lines, or in cell lines harboring mutations affecting mitochondrial metabolism or a mitochondrial folate pathway is also useful for identifying cell types and cancer types in which compounds of the disclosure would be particularly useful, have increased anti-proliferative activity and/or improved activity at a lower dose. This can be seen in the examples.

In vivo uses include for studying SHMT activity and/or folate metabolism and/or serine flux and/or NADPH generation in animal models of disease, such as in animal cancer models, such as mouse xenografts. In certain embodiments, compounds of the disclosure are useful for evaluating the impact of hypoxic conditions to growth, survival and migration of cells, such as the tolerance of cells to hypoxic conditions. In certain embodiments, the cells or animal model comprise a mutation in Myc.

Suitable in vivo uses include treating cancer or an autoimmune condition. For example, suitable in vivo uses include treating a condition associated with SHMT activity and/or associated with alterations in mitochondrial metabolism, such as mitochondrial folate metabolism. For example, compounds of the disclosure, such as SHMT2 inhibitors, or such as any of the compounds described herein based on structure and/or function, are suitable for use in conditions in which increased mitochondrial activity is necessary or useful for disease progression, and/or SHMT expression or activity (e.g., SHMT2) is elevated in the disease state versus the healthy state and/or in which there is an alteration in mitochondrial metabolism, such as mitochondrial folate metabolism (e.g., via mutations or alterations in, for example, cancer cells).

Exemplary genes or proteins that may be disregulated in, for example, cancer cells, are described above and include, for example, MTHFD1, MTHFD1L, MTHFD2, MTHFD2L, SHMT1, SHMT2, MTHFR, ALDH1L1, ALDHL2, SLC25A32 (also known as the mitochondrial folate transporter MFT), FH, KEAP1, and/or NRF2. Accordingly, the disclosure provides methods of treating cancer in a mammalian subject in need thereof, such as by inhibiting SHMT in a mammalian subject in need thereof, such as a subject with a condition associated with SHMT activity and/or associated with alterations in mitochondrial metabolism, such as mitochondrial folate metabolism.

In certain embodiments, the disclosure provides compounds, compositions, and methods of treating malignancies (such as malignancies of B-cell origin, e.g., cancer of B-cell origin) in which the SLC38A2 gene is disregulated (e.g., down-regulated). In certain embodiments, the disclosure provides compounds, compositions, and methods of treating lymphoma (e.g., B-cell lymphoma) in which the SLC38A2 gene is disregulated (e.g., down-regulated). Moreover, and as shown in the FIG. 13, we observed that decreased expression of SLC38A2, as assessed by mRNA expression, is correlated with sensitivity to a combination of an SHMT inhibitor+formate.

Accordingly, the disclosure provides methods of treating lymphomoas in a subject in need thereof, such as B-cell lymphomas, wherein the lymphoma is characterized by decreased expression of SLC38A2 (e.g., relative to healthy control cells, such as control cells of the same or an adjacent cell type from the same person or against a standard). In certain embodiments, the patient in need thereof is a patient having a lymphoma that can be characterized by decreased expression of SLC38A2, such as a B-cell lymphoma, such as diffuse large B-cell lymphoma having such decreased expression. In certain embodiments, the expression of SLC38A2 is mRNA expression. In certain embodiments, the expression is protein expression. Without being bound by theory, such cancers having a loss of or decreased expression of SLC38A2 represent a subset of B-cell lymphomas and identify a distinct patient population particular suitable for and sensitive to treatment with a combination of an (i) SHMT inhibitor (SHMT 1, SHMT2, or dual inhibitor) and (ii) formate, folinic acid, or a derivative or related compound thereof, as described herein.

In certain embodiments, the method comprises administering a therapeutically effective amount of a compound of the disclosure. In certain embodiments, administration of the compound improves one or more symptoms of the disease or condition. In the case of cancer, such improvement in symptoms may include, for example, decrease in tumor size, decrease in disease progression, increased time to progression, increased overall patient survival, decrease in metastasis or decrease in time to metastasis, and the like. In certain embodiments, improvement in these symptoms is evaluated versus a control (e.g., an untreated patient or a patient receiving the standard of care).

Similarly, as demonstrated in the examples, compounds of the disclosure, such as SHMT inhibitors are useful to treat conditions in which there is a mutation or dysfunction in mitochondrial metabolism, such as a mitochondrial folate pathway. These may include activating mutations or upregulating of enzymes in the pathway. However, this may also include loss of function mutations that lead to dysregulation. Without wishing to be bound by theory, such dysregulation may sensitize cells to SHMT inhibitors, particularly inhibitors of the present disclosure capable of inhibiting both SHMT2 and SHMT1. Such conditions are not the only conditions in which compounds of the disclosure are effective (as shown herein). However, they may represent a category of conditions that are particularly sensitive to this approach.

In certain embodiments, the disclosure provides a method for treating cancer. In certain embodiments, the cancer is associated with SHMT activity. In certain embodiments, the method comprises administering an effective amount of a compound or composition of the disclosure, such as an SHMT2 inhibitor, such as any of the compounds described herein based on structure and/or function. SHMT inhibitors may be administered as a monotherapy or in combination with one or more additional agents or therapeutic modalities as part of a therapeutic regimen. In certain embodiments, administration of the compound (alone or as part of the therapeutic regimen) improves one or more symptoms of the disease or condition. In the case of cancer, such improvement in symptoms may include, for example, decrease in tumor size, decrease in pain, decrease in disease progression, increased time to progression, increased overall patient survival, decrease in metastasis or decrease in time to metastasis, and the like. In certain embodiments, improvement in these symptoms is evaluated versus a control (e.g., an untreated patient or a patient receiving the standard of care).

In certain embodiments, this disclosure provides a method for treating lymphoma, such as T-cell lymphoma, B-cell lymphoma, or NK-cell lymphoma, comprising administering to a mammalian subject in need thereof an effective amount of an SHMT inhibitor. In certain such embodiments, the lymphoma is a B-cell lymphoma. In certain embodiments, the B-cell lymphoma is diffuse large B-cell lymphoma or Burkitt lymphoma. In certain embodiments, the B-cell lymphoma is characterized as having the following in vitro activity: growth sensitivity to an SHMT inhibitor in vitro that is not rescueable by formate but is rescuable by a combination of formate and glycine, wherein growth sensitivity is assessed by cell count in vitro. In some embodiments, the glycine rescue is sufficient to restore glycine levels in the normal body (e.g., a healthy cell or tissue) but not in the tumor or lymphoma.

In certain embodiments, the disclosure provides a method for treating an autoimmune disorder. In certain embodiments, the autoimmune disorder is associated with SHMT activity. In certain embodiments, the method comprises administering an effective amount of a compound or composition of the disclosure, such as an SHMT2 inhibitor, or any of the inhibitors compounds herein based on structure and/or function. SHMT inhibitors may be administered as a monotherapy or in combination with one or more additional agents or therapeutic modalities as part of a therapeutic regimen. In certain embodiments, administration of the compound (alone or as part of the therapeutic regimen) improves one or more symptoms of the disease or condition. In the case of an autoimmune disorder, such improvement in symptoms may include, for example, decrease in inflammatory markers, decrease in inflammation, decrease in pain, increased mobility and/or range of motion, and improvements in patient reports on quality of life measures. The particular symptoms improved will vary based on the autoimmune condition. In certain embodiments, improvement in these symptoms is evaluated versus a control (e.g., an untreated patient or a patient receiving the standard of care).

In certain aspects, the disclosure contemplates that any of the compounds of the disclosure (and pharmaceutical compositions) may be used in any of the in vitro or in vivo methods provided herein. In certain embodiments, compounds of the disclosure are SHMT inhibitors and are suitable for inhibiting SHMT activity, such as SHMT2 and, optionally, SHMT1 activity. In certain embodiments, such compounds are suitable for modulating SHMT activity in vitro, such as to manipulate serine flux and/or folate metabolism. Such in vitro methods may be useful for identifying other components of folate metabolic pathways. In other embodiments, such compounds are suitable for modulating SHMT activity in vivo, such to treat a patient suffering from a SHMT-related condition or a condition that can be ameliorated by inhibiting SHMT activity and/or a condition associated with alterations in mitochondrial metabolism, such as mitochondrial folate metabolism, such as cancer and autoimmune disorders.

Moreover, any of the compounds of the disclosure may be formulated as a pharmaceutical composition comprising a compound and one or more acceptable carriers and/or excipients. Compositions, such as pharmaceutical compositions, may be used in any of the in vitro or in vivo methods described herein, such has to treat any one or more of the diseases or conditions described herein.

Accordingly, the disclosure contemplates methods of treating (decreasing the frequency or severity of or otherwise alleviating one or more symptoms of the condition) a subject in need thereof (e.g., a subject having any of the conditions described herein, including any of the autoimmune conditions described herein or any of the forms of cancer described herein) by administering a compound of the disclosure (e.g., SHMT inhibitors, such as any of the inhibitors described herein based on structure and/or function), such as an effective amount of a compound of the disclosure.

Cancers and Proliferative Disorders

In certain embodiments, compounds and compositions of the disclosure are useful to treat cancer, such as to reduce cancer cell growth, survival and/or metastasis. Such cancers include, for example, solid tumors and hematological malignancies (both adult and pediatric). Exemplary cancers include, but are not limited to, leukemia (including, but not limited to, acute lymphoblastic leukemia (ALL), acute myelogenous leukemia (AML), chronic lymphocytic leukemia (CLL), chronic myelogenous leukemia (CML), acute monocytic leukemia (AMoL)), lymphoma (non-Hodgkin's lymphoma or Hodgkin's lymphoma), lung cancer (including non-small lung cancer), mesothelioma, breast cancer (including other solid tumors of the breast), liver cancer (including other solid tumors of the liver), colon or colorectal cancer (including other solid tumors of the colon and/or rectum), stomach cancer (including other solid tumors of the stomach), prostate cancer (including other solid tumors of the prostate), pancreatic cancer (including other solid tumors of the pancreas), ovarian cancer (including other solid tumors of the ovary), solid tumors of the uterus or female genital tract, bladder cancer (including other solid tumors of the bladder), head and neck cancers, glioblastoma and other brain tumors, and trophoblastic neoplasms. In certain embodiments, the cancer is a lymphoma, preferably a B-cell lymphoma. In certain embodiments, the B-cell lymphoma is a diffuse large B-cell lymphoma or a Burkitt lymphoma.

Although the high metabolic needs of cancer cells make all cancers good candidates for treatment with SHMT inhibitors, certain cancers may be particularly susceptible to treatment or may be sensitized to treatment due to their underlying mitochondrial activity or mutational status. By way of non-limiting example, in certain embodiments, the cancer comprises cells having a mutation affecting mitochondrial metabolism or the mitochondrial folate pathway. One class of cancers has high expression levels of SHMT2 or upregulation in a component of the mitochondrial folate pathway. However, other mutations may impair mitochondrial metabolism or the mitochondrial folate pathway, and thus, sensitize cancers to SHMT inhibition. Examples of such sensitization are provided herein. Examples of such sensitization are provided herein. Exemplary genes or proteins that may be disregulated in, for example, cancer cells, are described above and include, for example, MTHFD1, MTHFD1L, MTHFD2, MTHFD2L, SHMT1, SHMT2, MTHFR, ALDH1L1, ALDHL2, SLC25A32 (also known as the mitochondrial folate transporter MFT), FH, KEAP1, and/or NRF2.

Other classes of cancers that may be particularly susceptible to treatment with an SHMT inhibitor are cancers comprising mutations that inactivate KEAP1 (either by, for example, somatic mutation or epigenetic silencing). Such mutations may result in aberrant NRF2 activity and nuclear function. Additionally or alternatively, suitable cancers may additionally have mutations in NRF2 itself with or without KEAP1 mutation. Cancers may additionally have alterations in mitochondrial metabolism including mutations to fumarate hydratase (FH) that lead to activation of NRF2. Loss of FH activity may potentiate cells to SHMT inhibitors by additional mechanisms as well. Without being bound by theory, cancers may have aberrant activation of NRF2 via other mechanisms. Aberrant NRF2 activation leads to altered transcription of mitochondrial and one carbon metabolism genes through the activity of ATF4. Activation of the 1c pathway and mitochondrial folate metabolism by NRF2 may also occur via ATF4 independent mechanisms.

Exemplary cancers with identified mutations in the KEAP1-NRF2-ATF4 pathway include non-small cell lung cancer, squamous cell lung carcinoma, prostate cancer, head and neck cancer (KEAP1 mutations, NRF2 mutations), hereditary papillary renal carcinoma, Hereditary leiomyomatosis and renal cell cancer (FH mutations). Furthermore, as described herein, there are identified cancers with elevated SHMT2 levels and/or mutations in other folate pathway components.

Without being bound by theory, the present disclosure provides methods for treating cancer and autoimmune conditions, such as cancers and conditions associated with SHMT activity. In some embodiments, particularly susceptible cancers or autoimmune conditions are those in which SHMT2 or another mitochondrial folate pathway enzyme or another gene is upregulated or activated. In other embodiments, particularly susceptible cancers or autoimmune conditions are those in which SHMT2 or another mitochondrial folate pathway component are knocked out or downregulated, thereby increasing the susceptibility of cells to treatment.

In certain embodiments, a compound of the disclosure is administered as a monotherapy. In other embodiments, compounds of the disclosure are used in combination with one or more other agents and/or therapeutic modalities (e.g., dietary regimen). When more than one agent is administered, the agents may be administered at the same or varying times, and by the same or differing routes of administration.

In certain embodiments, compounds of the disclosure are used in combination with the then current standard of care of the particular condition as part of a therapeutic regimen. In other embodiments, the therapeutic regimen includes one or more antifolates (e.g., other than a compound of the disclosure; an antifolate that is not selective for SHMT1 and/or SHMT2), such as traditional antifolates, such as methotrexate or pemetrexed or another compound that is an inhibitor of DHFR and/or TS. In other embodiments, the therapeutic regimen includes an additional anti-cancer agent, such as 5FU or other chemotherapeutic or radiotherapy regimen. In certain embodiments, the therapeutic regimen includes rescue therapy, such as leucovorin, formate or pharmaceutical salts, esters or derivatives of formate. In certain embodiments, rescue therapy refers to administration of folinic acid (leucovorin), formate and/or a pharmaceutical salt of formate. In certain embodiments, administration of rescue therapy provide rescue of SHMT activity in non-cancerous tissues, reducing systemic toxicity and increasing therapeutic index. In certain embodiments, such as in the context of a B cell neoplasia, the inhibition activity of an SHMT inhibitor may be enhanced when administered in combination with rescue therapy, such as formate, glycine, folinic acid (leucovorin) or a pharmaceutically acceptable salt, ester, or derivative thereof.

Without being bound by theory, use of rescue therapy to reduce toxicity and/or side effects may be used when SHMT inhibitors are used alone, as well as when they are used as part of a therapeutic regimen with one or more additional agents or therapeutic modalities. Rescue therapy is routinely used currently in patients receiving, for example, methotrexate. Accordingly, its use can be readily adapted to this context. For example, the dose of rescue therapy can be tittered to decrease toxicity without abrogating therapeutic efficacy. Similarly, rescue therapy may be administered at the same time, or following administration of an SHMT inhibitor to manage any toxicity (if any) while maintaining an acceptable therapeutic profile. In other embodiments, use of rescue therapy is unnecessary because the safety and toxicity profile is acceptable.

In certain embodiments, co-administration results in an additive or synergistic effect versus administration of at least one of the compounds alone. In certain embodiments, co-administration permits administration of a lower dose of the non-SHMT inhibitor compound (e.g., effectiveness is reached at a lower dose of, for example, methotrexate) or of a higher dose of the SHMT inhibitor or other agent by, for example, reducing side effects. In certain embodiments, the combination therapy improves the therapeutic window of one or both compounds or reduces side effects associated with one or both compounds.

In other embodiments, a compound of the disclosure is administered with a glycine containing composition. In other embodiments, the therapeutic regimen includes a dietary regimen, such as a regimen in which dietary levels of methionine, serine, and/or choline are reduced and/or dietary levels of glycine are increased.

In certain embodiments, the cancer is pancreatic cancer or colon cancer. In certain embodiments, the cancer is a cancer comprising (e.g., in which one or more cells of the tumor or cancer have) a mutation in the mitochondrial folate pathway. For example, in certain embodiments, the compounds of the disclosure, such as SHMT inhibitors are used to treat a cancer comprising a mutation in the mitochondrial folate pathway, such as mutation in mitochondrial serine hydroxymethyl transferase (SHMT2), mitochondrial methylene tetrahydrofolate dehydrogenase (MTHFD2), MTHFD1L or FH.

The disclosure contemplates combinations of any of the foregoing embodiments and aspects. In other words, the disclosure contemplates that any of the compounds of the disclosure, including any inhibitor of mammalian SHMT2 (and, in certain embodiments also SHMT1), may be used in any of the in vitro or in vivo methods, including methods of treatment. Moreover, such compounds and pharmaceutical compositions may be used as a monotherapy or as part of a therapeutic regimen with one or more other agents or treatment modalities, including but not limited to chemotherapy, anti-folate agent, rescue therapy, glycine, radiation therapy, nutritional therapy, and/or the standard of care for the particular cancer. Exemplary categories of compounds for use in treating cancer or autoimmune condition are, for example, Compounds of Formulae (I)-(IX), or any of the compounds described based on a combination of structural and/or functional characteristics herein.

Autoimmune Conditions

In other embodiments, the disclosure provides methods of treating an autoimmune condition by administering a compound of the disclosure. Such diseases or disorders include, but are not limited to, rheumatoid arthritis, multiple sclerosis, systemic lupus erythematosus, myasthenia gravis, inflammatory bowel disease (e.g., Crohn's disease or ulcerative colitis), polymyositis, dermatomyositis, inflammatory myositis, ankylosing spondolytis, and ulcerative colitis. Similar to as described above for cancer, autoimmune disorders, as well as other conditions, may be treated based on administering a compound of the disclosure as a monotherapy or as a combination therapy, as described above.

As noted above, in certain embodiments, compounds of the disclosure may be particularly suitable for use in subjects having one or more mutations that impact mitochondrial metabolism, as described above. Such as contemplated here. Additionally or alternatively, in autoimmune conditions the mitochondrial foliate pathway may be activated, and thus, compounds of the disclosure offer a mechanism for regulating this inappropriate activation or dysregulation of mitochondrial metabolism.

The disclosure contemplates combinations of any of the foregoing embodiments and aspects. In other words, the disclosure contemplates that any of the compounds of the disclosure, including any inhibitor of mammalian SHMT2 (and, in certain embodiments also SHMT1), may be used in any of the in vitro or in vivo methods, including methods of treatment. Moreover, such compounds and pharmaceutical compositions may be used as a monotherapy or as part of a therapeutic regimen with one or more other agents or treatment modalities, including but not limited to chemotherapy, anti-folate agent, rescue therapy, glycine, radiation therapy, nutritional therapy, and/or the standard of care for the particular cancer. Exemplary categories of compounds for use in treating cancer or autoimmune condition are, for example, compounds of Formulae (I)-(IX), or any of the compounds described based on a combination of structural and/or functional characteristics herein.

F. Compositions and Modes of Administration

In some embodiments of this disclosure, a compound of the present disclosure is formulated with one or more pharmaceutically acceptable carriers, excipients and/or solvents. The disclosure provides such compositions and pharmaceutical compositions. Any of the compounds of the disclosure may be provided in isolated or purified form and/or as a pharmaceutical composition. The compound may be formulated for administration in any convenient way for use in human medicine. Any compound of the disclosure or salt or enantiomer thereof can be provided as a composition, such as a pharmaceutical composition, such as a composition having any of the features described herein. Any such compound of the disclosure or composition of the disclosure may be used in any of the in vitro or in vivo methods described herein.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The characteristics of the carrier will depend on the route of administration. Each of the methods or uses of the present disclosure, as described herein, comprises administering to a mammal in need of such treatment or use an effective amount, such as a pharmaceutically or therapeutically effective amount, of a compound of the disclosure, or a pharmaceutically acceptable salt thereof. Compounds may be administered alone or in combination with other agents.

Compounds or pharmaceutical compositions of the disclosure may be administered to cells in vitro, such as by addition to culture media. Additionally or alternatively, compounds or pharmaceutical compositions may be administered to route of administration, such as oral, parenteral, intravenous, intra-arterial, cutaneous, subcutaneous, intramuscular, topical, intracranial, intraorbital, ophthalmic, intravitreal, intraventricular, intracapsular, intraspinal, intracisternal, intraperitoneal, intranasal, aerosol, central nervous system (CNS) administration, or administration by suppository. In some embodiments, the therapeutic methods of the disclosure include administering the composition of a compound topically, systemically, or locally. For example, therapeutic compositions of compounds of the disclosure may be formulated for administration by, for example, injection (e.g., intravenously, subcutaneously, or intramuscularly), inhalation or insufflation (either through the mouth or the nose) or oral, buccal, sublingual, transdermal, nasal, or parenteral administration. The compositions of compounds described herein may be formulated as part of an implant or device, or formulated for slow or extended release. When administered parenterally, e.g., by intravenous, cutaneous or subcutaneous injection, the therapeutic composition of compounds for use in this disclosure is preferably in a pyrogen-free, physiologically acceptable form.

A preferred pharmaceutical composition for intravenous, cutaneous, or subcutaneous injection should contain, in addition to the toxicity-reducing compounds, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the compound of the present disclosure may also contain stabilizers, preservatives, buffers, antioxidants, or other additives known to those of skill in the art. Techniques and formulations generally may be found in Remington's Pharmaceutical Sciences, Meade Publishing Co., Easton, Pa.

A composition comprising a compound of the present disclosure may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

When an effective amount of a compound(s) of the present disclosure is administered orally, compound(s) of the present disclosure may be in the form of a tablet, capsule, powder, solution or elixir. When administered in tablet form, the pharmaceutical composition may additionally contain a solid carrier such as a gelatin or an adjuvant. The tablet, capsule, and powder may contain from about 5 to 95% of a compound of the present disclosure, and preferably from about 10% to 90% of a compound of the present disclosure. When administered in liquid form, a liquid carrier such as water, petroleum, oils of animal or plant origin such as peanut oil, mineral oils, phospholipids, tweens, triglycerides, including medium chain triglycerides, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition typically contains from about 0.5 to 90% by weight of a compound of the present disclosure, and preferably from about 1 to 50% by weight of a compound of the present disclosure.

In solid dosage forms for oral administration (capsules, tablets, pills, dragees, powders, granules, and the like), one or more compositions comprising the compound of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the compound of the present disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

The pharmaceutical compositions may be in the form of a liposome or micelles in which the toxicity-reducing compounds are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

Suspensions, in addition to the active compounds may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The amount of compound(s) of the present disclosure in the pharmaceutical composition will depend upon the nature and severity of the condition being treated, on the amount of the compound of the present disclosure used, and on the nature of prior treatments the patient has undergone. Ultimately, the practitioner will decide the amount of the compound of the present disclosure with which to treat each individual patient. Representative doses of the present disclosure include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during one day, especially when relatively large amounts are deemed to be needed. It is contemplated that the various pharmaceutical compositions used to practice the methods of the present disclosure should contain about 0.1 µg to about 100 mg (preferably about 0.1 mg to about 50 mg, more preferably about 1 mg to about 2 mg) of compound per kg body weight.

The desired dose may conveniently be presented in a single dose or as divided doses administered at appropriate intervals, for example, as 2, 3, 4 or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

This disclosure will be better understood from the Experimental Details which follow. However, one skilled in the art will readily appreciate that the specific methods and results discussed are merely illustrative of the disclosure as described more fully in the embodiments which follow thereafter.

EXEMPLIFICATION

The subject matter of this disclosure now being generally described, it will be more readily understood by reference to the following examples which are included merely for purposes of illustration of certain aspects and embodiments of the present disclosure, and are not intended to limit the subject matter of this disclosure.

Example 1: General Synthetic Scheme

The compounds of this disclosure may be prepared in general by methods known to those skilled in the art. Schemes 1-3 below illustrate general synthetic routes to the compounds of the present disclosure according to certain embodiments. Other equivalent schemes, which will be readily apparent to the ordinary skilled organic chemist, may alternatively be used to synthesize various portions of the molecules as illustrated by the general scheme below.

Compounds of Formulae (I), (Ia or Ib); (II), (IIa or IIb); (III) (IIIa or IIIb); or (II') (IIa' or IIb') can be prepared according to the following Schemes 1-3.

Scheme 1

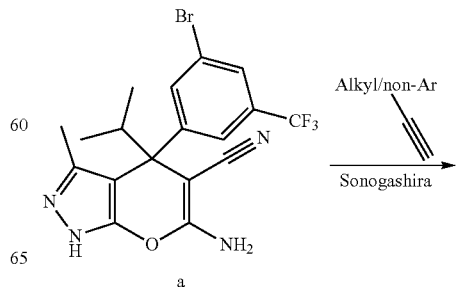

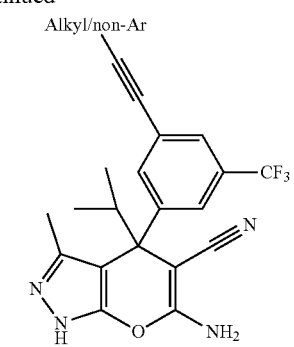
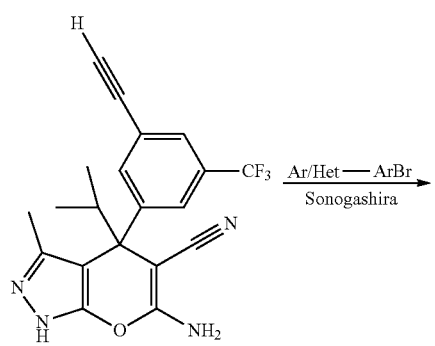
Scheme 2
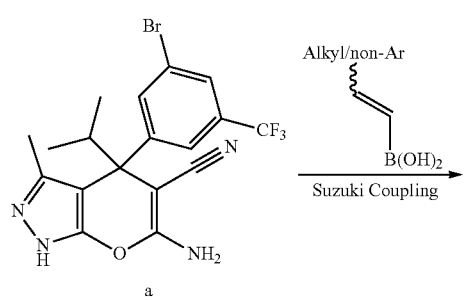
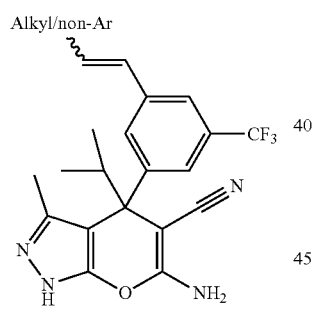
Example 2: Preparation of 6-amino-4-(3-bromo-5-(trifluoromethyl)phenyl)-4-isopropyl-3-methyl-1,4-dihydropyrano[2,3-c]pyrazole-5-carbonitrile (compound a) via the Following Scheme 4
Scheme 4
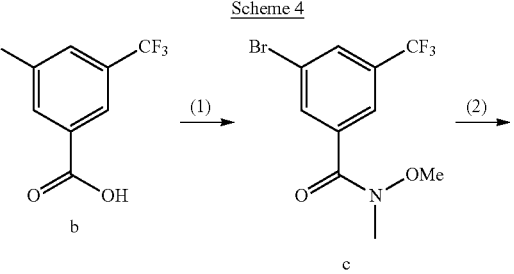
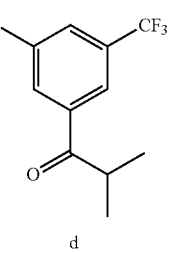
Scheme 3
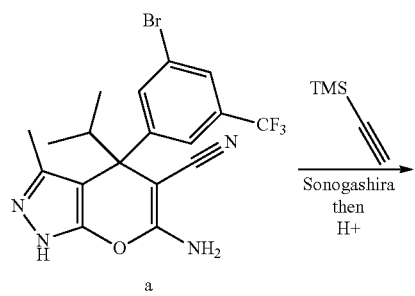

143
-continued

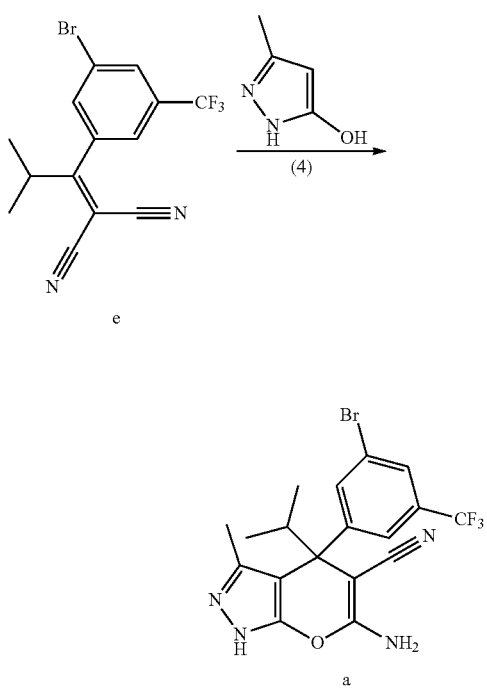

Scheme 4. Reagents and conditions: (1) carbonyldiimidazole, methoxymethylamine, dichloromethane, room temperature, 18 h; (2) i-PrMgCl, Et₂O, room temperature, overnight; (3) CHCl₃, malodinitrile, Ti(Cl)₄, pyridine, reflux, 48 h; (4) EtOH/dioxane (1:1), piperidine, 100° C./microwave, 12 h.

A solution of compound a (500 mg, 1.4 mmol) and 3-hydroxy-5-methylpyrazole (286.5 mg, 2.9 mmol) in ethanol (5 ml) dioxane (5 ml) and piperidine (12.4 mg, 0.146 mmol) is heated for 12 h at 100° C. in the microwave. After cooling water is added and extracted with ethylacetate. The organic phase is dried with sodium sulfate and the solvents evaporated. The residue was purified by pre-chromatographed on silica with PE/EA=1:1 to yield 0.66 g of (a) (24% yield) as white solid which was used for the next step.

Example 3: Preparation of Compound 61, 2, 4, 8, 11, 69, 70, 71, 72, and 73

Scheme 5

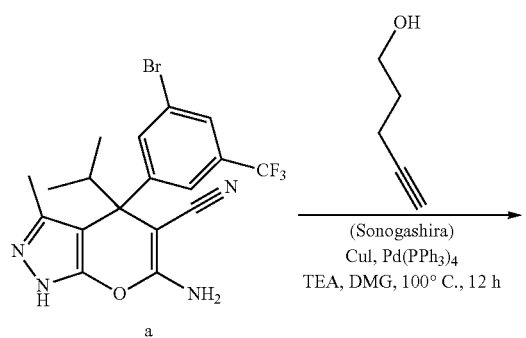

144
-continued

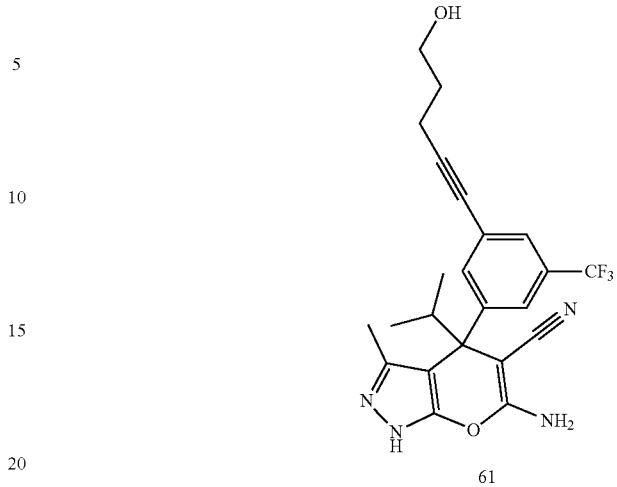

To a solution of Compound a (300 mg, 679.9 umol) in trietheyl amine (9 mL) and DMF (3 mL) at 50° C. was added Ph(PPh₃)₂Cl₂ (47.7 mg, 67.9 umol) and CuI (25.9 mg, 135.9 umol). The reaction mixture was slowly warmed to 100° C. before the addition of pent-4-yn-1-ol (74.3 mg, 883.8 umol). The reaction mixture was allowed to stir at 100° C. for 12 hours until LCMS indicated formation of the product. The solvent as removed in vacuo to give the crude residue. The crude residue was purified by pre-thin layer chromatography on silica (DCM:MeOH=20:1) and pre-HPLC (column: Waters, XBridge 150×25 5μ; mobile phase: solvent A: NH₄HCO₃ aqeous solution (10 mM); solvent B: acetonitrile; gradient B %: 30-45%) to give the product 6-amino-4-(3-(5-hydroxypent-1-yn-1-yl)-5-(trifluoromethyl)phenyl)-4-isopropyl-3-methyl-1,4-dihydropyrano[2,3-c]pyrazole-5-carbonitrile Compound 61 (87.5 mg, 28.9%) as white solid when solidified. ¹H NMR (CDCl₃, 400 MHz), δ 9.19 (s, 1H), 7.58 (s, 1H), 7.54 (s, 1H), 7.50 (s, 1H), 4.75 (s, 2H), 3.82 (t, J=6.4 Hz, 2H), 2.82-2.78 (m, 1H), 2.55 (t, J=14.0 Hz, 2H), 1.91-1.86 (m, 2H), 1.83 (s, 3H), 1.26 (s, 1H), 1.02 (d, J=6.8 Hz, 2H), 3.82 (d, J=6.4 Hz, 2H). LC-MS (m/z): 445 [M+H]⁺.

Compounds 2, 4, 8, 71, and 73 were prepared in a manner analogous to that shown above for Compound 61.

Compound 2 was prepared with Compound a reacting with 3-butyn-1-ol.

Compound 4 was prepared with Compound a reacting with ethyl ester of 1-pentyn-5-carboxylic acid, followed by hydrolysis using LiOH/THF.

Compound 8 was prepared with Compound a reacting with mono Boc-protected 5-pentyn-1-amine, followed by TFA deprotection of the Boc group to yield the the HCl salt of Compound 8 as a white solid salt after purification.

Compound 71 was prepared with 6-amino-4-(3-bromo-5-cyanophenyl)-4-isopropyl-3-methyl-1,4-dihydropyrano[2,3-c]pyrazole-5-carbonitrile (a derivative of Compound a) as the starting material.

Compound 73 was prepared with Compound a reacting with 1-pentyn-5-ethyl ester. Compound 73 was isolated as a white solid after purification.

Compounds 11, 69, 70, and 72 were prepared with Compound 4 as the starting material and their preparations are described as follows:

Compound 11 was prepared with Compound 4 reacting with ammonium hydroxide under the amide coupling reaction conditions with HATU. Compound 11 was purified in the form of a HCl salt as a while solid.

Compound 69 was prepared with Compound 4 reacting with t-butyl-ester protected (S)-gluamic acid under amid coupling reaction conditions with HATU, followed by acid deprotection of the t-butyl groups using TFA. Compound 69 was purified in the form of a HCl salt as a white solid.

Compound 70 was prepared following similar protocol as Compound 69 using the t-butyl-ester protected (R)-glutamic acid. Compound 70 was purified in the form of a HCl salt as a white solid.

Compound 72 was prepared with Compound 4 reacting with t-butyl-ester protected dimethyl amino acid followed by acid deprotecion of the t-butyl group TFA. Compound 72 was purified in the form of a HCl salt as a white solid.

Characterizations of exemplary compounds of this disclosure are included in Table 4 below.

TABLE 4

| Compound # | LC-MS (m/z) [M + H]$^+$ | NMR Characterization |
|---|---|---|
| 61 | 445.1 | $^1$H NMR (d$^6$-DMSO, 300 MHz), δ 12.24 (S, 1H), 7.61(S, 1H), 7.56(S, 1H), 7.52(S, 1H), 7.01(S, 1H), 4.54(t, J = 5.4 Hz, 1H), 3.43 (m, 2H), 2.75 (m, 1H), 2.52-2.46(m, 2H), 1.74-1.67 (m, 5H), 0.89 (d, J = 6 Hz, 3H), 0.76 (d, J = 6 Hz, 3H) |
| 2 | 472.1 | $^1$H NMR (CD$_3$OD, 300 MHz), δ 7.68 (s, 1H), 7.59-7.58 (m, 2H), 3.75 (t, J = 6 Hz, 2H), 2.84(m, 1H), 2.68(t, J = 6 Hz, 2H), 1.80 (s, 3H), 1.02 (d, J = 6 Hz, 3H), 0.89 (d, J = 6 Hz, 3H) |
| 4 | 459.1 | $^1$H NMR (d$^6$-DMSO, 300 MHz), δ 12.25 (S, 1H), 7.59(S, 1H), 7.55(S, 1H), 7.53(S, 1H), 7.01(S, 1H), 2.77 (m, 1H), 2.65-2.60(m, 2H), 2.51-2.45(m, 2H), 1.70 (s, 3H), 0.88 (d, J = 6 Hz, 3H), 0.76 (d, J = 6 Hz, 3H) |
| 8 | 444.2 | $^1$H NMR (d$^6$-DMSO, 300 MHz), δ 12.27 (S, 1H), 7.80 (br s, 2H), 7.65(S, 1H), 7.57(m, 2H), 7.03(S, 2H), 2.94-2.90 (m, 2H), 2.78-2.74 (m, 1H), 2.60-2.50(m, 2H), 1.86-1.81(m, 2H), 1.70 (s, 3H), 0.89 (d, J = 6 Hz, 3H), 0.77 (d, J = 6 Hz, 3H) |
| 11 | 458.1 | $^1$H NMR (d$^6$-DMSO, 300 MHz), δ 12.24 (S, 1H), 7.59(s, 1H), 7.55(s, 1H), 7.53(s, 1H), 7.39(s, 1H), 7.06(br s, 2H), 6.96(br s, 1H), 2.80-2.73 (m, 1H), 2.63(t, J = 7.2 Hz, 2H), 2.39(t, J = 7.2 Hz, 2H), 1.70 (s, 3H), 0.89 (d, J = 6 Hz, 3H), 0.76 (d, J = 6 Hz, 3H) |
| 69 | 588.2 | $^1$H NMR (d$^6$-DMSO, 300 MHz), δ12.25 (S, 1H), 8.24(d, J = 7.5 Hz, 1H), 7.61(s, 1H), 7.58(s, 1H), 7.51(s, 1H), 7.01(br s, 2H), 4.25-4.21(br s, 1H), 2.79-2.75 (m, 1H), 2.67-2.63(m, 2H), 2.51(m, 2H), 2.33-2.25 (m, 2H), 1.99-1.96(m, 1H), 1.79-1.70(m, 1H), 1.70 (s, 3H), 0.89 (d, J = 6 Hz, 3H), 0.76 (d, J = 6 Hz, 3H) |
| 70 | 588.2 | $^1$H NMR (CD$_3$OD, 300 MHz), δ 7.70(s, 1H), 7.58(s, 1H), 4.52-4.47(m, 1H), 2.88-2.81(m, 1H), 2.79-2.71(m, 2H), 2.60-2.55(m, 2H), 2.44-2.39 (m, 2H), 2.27-2.18(m, 1H), 2.00-1.90(m, 1H), 1.80 (s, 3H), 1.03 (d, J = 6 Hz, 3H), 0.90 (d, J = 6 Hz, 3H) |
| 71 | 402.3 | $^1$H NMR (d$^6$-DMSO, 300 MHz), δ 12.23 (S, 1H), 7.76(br S, 2H), 7.53(S, 1H), 7.09(S, 1H), 3.50 (t, J = 6 Hz, 2H), 2.75 (m, 1H), 2.52-2.45(m, 2H), 1.71(s, 3H), 1.70-1.67 (m, 2H), 0.89 (d, J = 6 Hz, 3H), 0.76 (d, J = 6 Hz, 3H) |
| 72 | 544.2 | $^1$H NMR (CD$_3$OD, 300 MHz), δ 7.65 (s, 1H), 7.59-7.57 (m, 2H), 2.87-2.85(m, 1H), 2.81(t, J = 6 Hz, 2H), 2.70(t, J = 6 Hz, 2H), 1.78 (s, 3H), 1.46 (s, 6H), 1.02 (d, J = 6 Hz, 3H), 0.89 (d, J = 9 Hz, 3H) |
| 73 | 473.1 | $^1$H NMR (d$^6$-DMSO, 300 MHz), δ 12.24 (S, 1H), 7.60(br S, 1H), 7.55(br S, 2H), 7.01(S, 2H), 3.63 (s, 3), 2.82-2.65 (m, 5H), 1.70 (s, 3H), 0.89 (d, J = 6 Hz, 3H), 0.76 (d, J = 6 Hz, 3H) |

Example 4: Preparation of Compound 62: 6-amino-4-(3-(5-bromopent-1-yn-1-yl)-5-(trifluoromethyl)phenyl)-4-isopropyl-3-methyl-1,4-dihydropyrano[2,3-c]pyrazole-5-carbonitrile

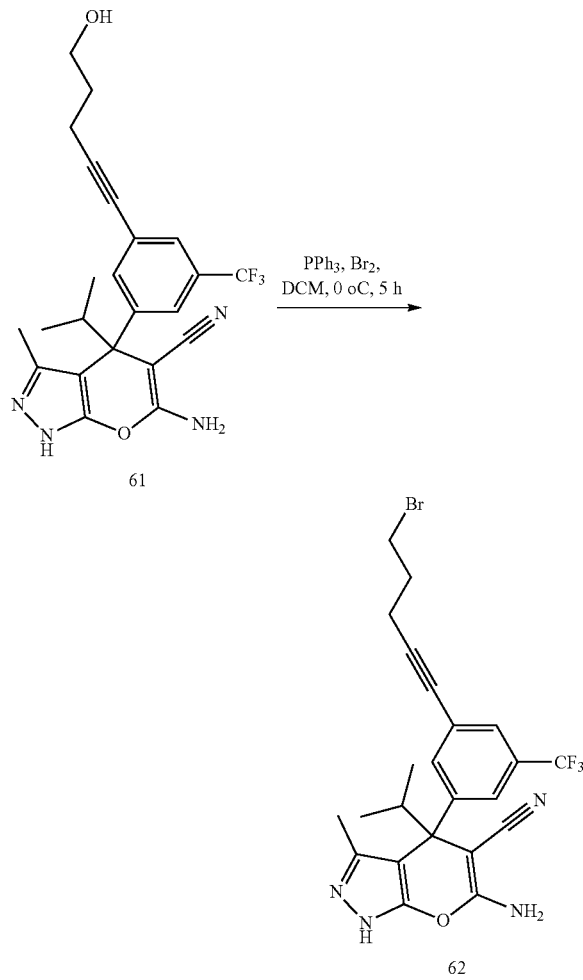

In a 10 mL round bottom flask, $PPh_3$ (70.8 mg, 270 μmol) was dissolved in 5 mL of anhydrous dichloromethane (DCM) under $N_2$ protection. After cooling the solution to 0° C., $Br_2$ (43.1 mg, 270 μmol) was added slowly and the reaction mixture was stirred for 30 min at 0° C. before slowly adding Compound 61 (100 mg, 225 μmol). The reaction mixture was allowed to warm to 25° C. and stirred for 5 hours until LC-MS showed the formation of the product. The reaction mixture was then concentrated in vacuo and compound 62 (30 mg, crude) was obtained as light yellow solid (30 mg) and used directly in the next reaction. LC-MS (m/z): 508 [M+11]$^+$.

Example 5: Labeled dTTP ((2'-deoxythymidine 5'-triphosphate)

Figure 1A:
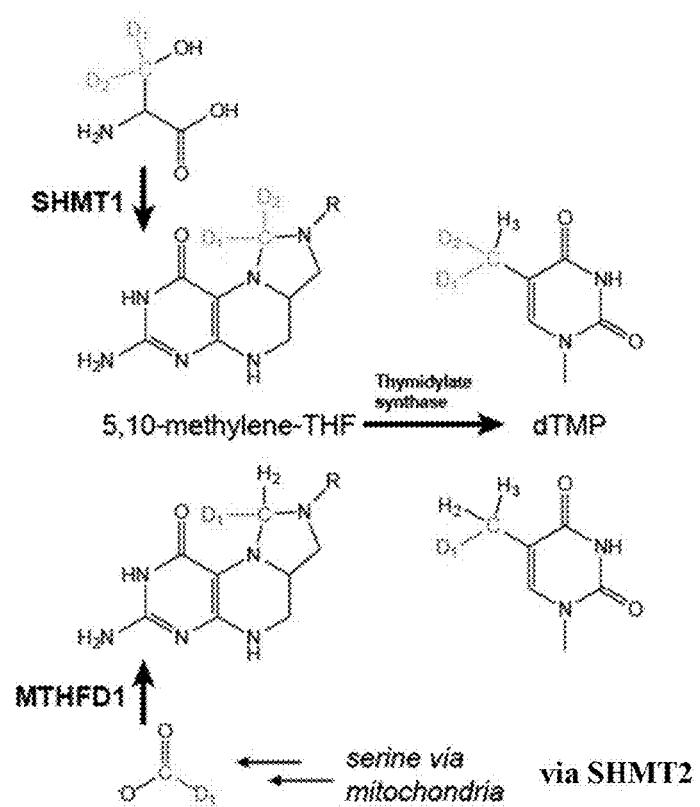
FIG. 1A illustrates that deuterated serine (2,3,3-$^2$H$_3$ serine, (D3-serine)) isotopic labeling into deoxythymidine phosphates reveals mitochondrial versus cytosolic compartmentalization of serine metabolism.
Figure 1B:
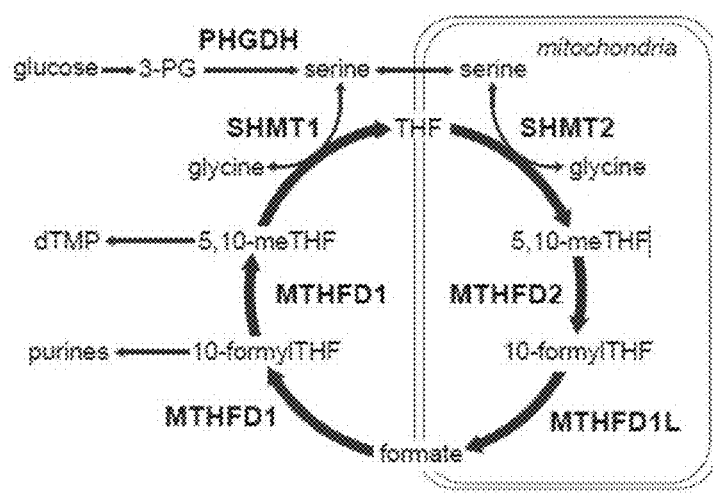
FIG. 1B illustrates that serine synthesis and catabolism occur in an inter-compartmental cycle mediated by cytosolic and mitochondrial SHMT activity. Key enzymes mediating these transformations are highlighted in capital letters.

Using 2,3,3-$^2H_3$-serine (D3-serine) as a tracer, mitochondrial flux is measured by quantifying the labeling pattern of dTTP, a downstream product of dTMP. Two-labeled (M+2) dTTP can only arise from cytosolic flux, since 1C units from the mitochondria enter the cytosol as formate, which can only retain one deuterium (FIG. 1A). Essentially all de novo dTTP is M+1, implying nearly all 1C units originate in the mitochondria. In contrast, most de novo dTTP in ΔMTHFD2 cells (cells engineered with a deletion in MTHFD2) is M+2, meaning its 1C units derive from the cytosolic pathway. This assay is used to examine mitochondrial serine flux and the effect of compounds of the disclosure on mitochondrial serine flux, in either wildtype or mutant cells.

Methods: Isotope Labeling Experiments:

HEK-293T cells are cultured in 6-well plates in Dulbecco's modified eagle media (DMEM) without pyruvate with 10% dialysed fetal bovine serum in 5% $CO_2$ at 37° C. Cells are treated with media containing uniformly labeled $^{13}C$ serine or 2,3,3-$^2H_3$ serine (D3-serine) and, for inhibitor experiments, either DMSO (vehicle) or compound of this disclosure (an inhibitor of SHMT2; racemic mixture or enatiomerically resolved). Growth is quenched and metabolites extracted by aspirating media, washing cells with cold PBS, and immediately adding MeOH/water (80:20 at −80° C.). Supernatants from two rounds of extraction are combined, dried under $N_2$, resuspended in water, placed in a 4° C. autosampler, and analyzed by reverse-phase ion-paring chromatography negative-mode electrospray-ionization high-resolution MS on a stand-alone orbitrap.

Deletion Cell Lines:

HEK293T cell lines (or other cell lines) mutant for SHMT1 and SHMT2 are created using the CRISPR-Cas9 system following standard published protocols. Single clones from successful transfections are grown up, genotyped and characterized.

Example 6: Measurement of 5-Aminoimidazole-4-carboxamide ribonucleotide (AICAR)

Generation of AICAR provides an assay to evaluate one-carbon unit stress. Inhibition of SHMT2 in cells decreases serine metabolism and leads to one-carbon stress. Such cells show high constitutive levels of 5-aminoimidazole-4-carboxamide ribonucleotide (AICAR), a marker for one-carbon unit stress, when cultured in media. This can be rescued by exogenous treatment with sodium formate. Human cells expressing SHMT2 are treated with control or increasing concentrations of an SHMT inhibitor, such as one in this disclosure.

Generation of AICAR provides an assay for evaluating compounds of the disclosure. Compounds of the disclosure are evaluated in such an assay.

Example 7: Inhibition of Human SHMT

Figure 2A:
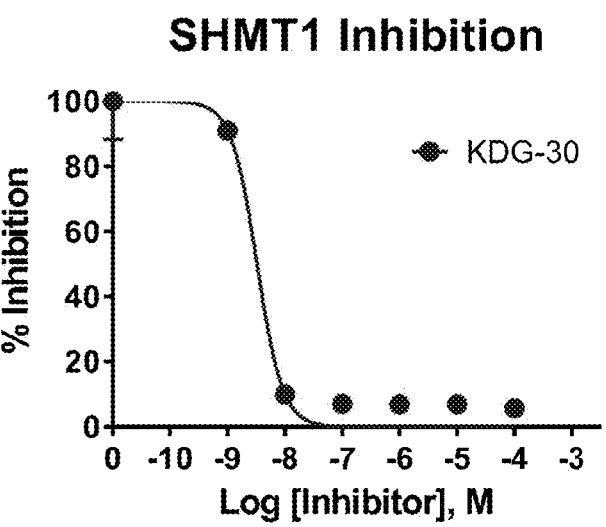
FIG. 2 shows inhibition of human SHMT enzyme activity (using calculated percent inhibition) by potent pyrazolopyran compound described in this disclosure against human SHMT1 (FIG. 2A) and SHMT 2 (FIG. 2B) in an in vitro assay.
Figure 2B:
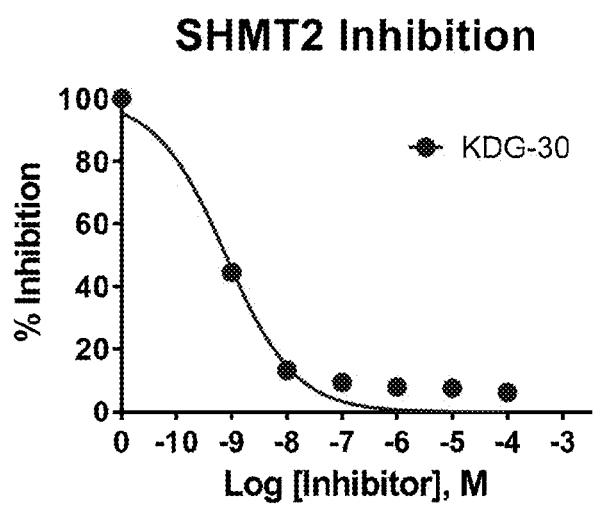

Inhibition of human SHMT by compounds in this disclosure is evaluated, for example, in their racemic forms in an in vitro assay. For example, Compound 61 (also referred to as KDG-30) was tested and demonstrated inhibition in vitro for both SHMT1 and SHMT2 with IC50 values at 3.2 nM and 0.78 nM respectively, shown in FIGS. 2A and 2B.

Of note, certain compounds in this disclosure are selective for SHMT. These compounds show activity against SHMT2 in vitro but do not inhibit human MTHFD2 in enzymatic assays.

Enzymatic Assays:

For the SHMT1 and SHMT2 in vitro enzymatic assays, the rate of 5,10-methylene tetrahydrofolate formation catalyzed by SHMT1/2 was indirectly evaluated by coupling with excess MTHFD2, which converts NAD+ to NADH allowing for reaction monitoring by absorption at 340 nm. The reaction was started by addition of serine (1 mM final) to either human SHMT1 or human SHMT2 (2 mcg/mL), and human MTHFD2 (25 mcg/mL) in a buffer of 50 mM potassium phosphate (pH 7.4), 0.3 mM tetrahydrofolate, 7.5 mM dithiothreitol, 1.25 mM NAD+, and 4% DMSO. Inhibition of initial reaction velocity was determined by adding various inhibitors at different concentrations and monitored as described. IC50 may be calculated based on this assay.

For the MTHFD2 in vitro assay, the rate of NADH formation is directly monitored at 340 nm. The reaction is started by addition of 0.125 uM (final) of 5,10 methylene tetrahydrofolate to MTHFD2 (2.5 mcg/mL), 50 mM potassium phosphate (pH 7.4), 7.5 mM dithiothreitol, 1.25 mM NAD$^+$, and 4% DMSO.

Example 8: Inhibition of Cancer Cell Growth

Figure 3A:
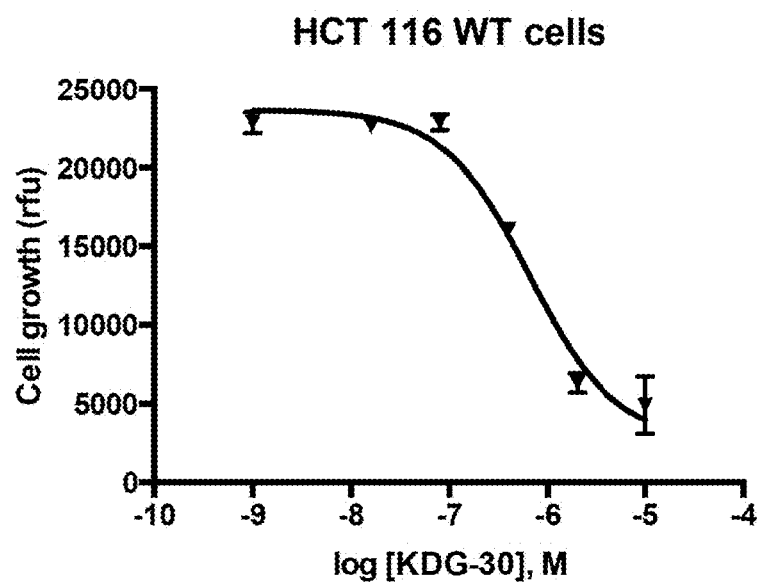
FIG. 3 shows cancer cell growth inhibition of potent pyrazolopyran compounds described in this disclosure. Compounds of this disclosure demonstrated different inhibition effects against wildtype (FIG. 3A) and SHMT2 knock-out (FIG. 3B) human colon carcinoma HCT-116 cells.
Figure 3B:
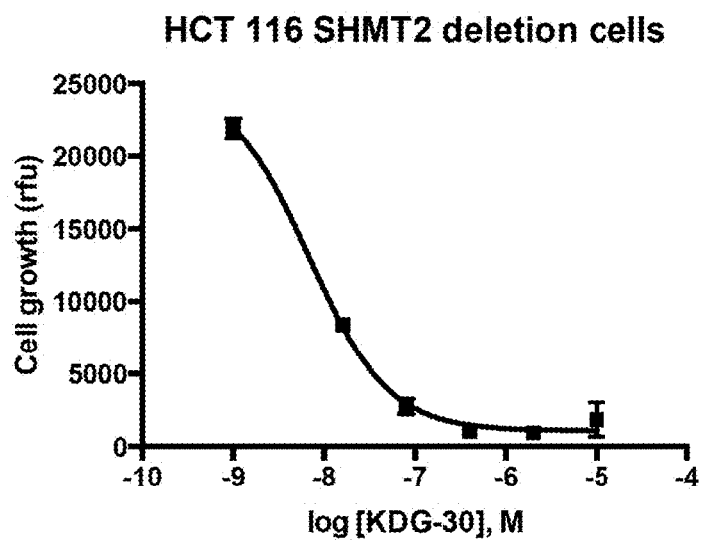

Inhibitors of SHMT were evelauted in various cancer cell lines, in the presence and absence of mutations in mitochondrial folate pathway enzymes. In this example, compound 61 (also referred to as KDG-30) inhibited growth (proliferation) of human colon carcinoma cells HCT116. The inhibitory activity of compound 61 was increased or potentiated in the presence of a mutation in a mitochondrial folate pathway enzyme, specifically in SHMT2 knock-out HCT116 cells. As shown in FIG. 3A and FIG. 3B, compound 61 inhibited growth of both the native and knockout HCT116 cancer cells, albeit with increased potency versus the SHMT2 knock-out HCT116 cells.

Example 9: Inhibition of Human Cell Growth

Inhibitors of SHMT can be evaluated in cells in culture, such as transformed cells or cancerous cells, to evaluate inhibition of cell growth.

For example, Human Embryonic Kidney_HEK293T cells (e.g., wild-type HEK293T, SHMT2 knock-out HEK293T cells, and MTHFD2 knock-out HEK293T cells) are cultured in 96-well plates in Dulbecco's modified eagle media (DMEM) without pyruvate with 10% dialysed fetal bovine serum (Invitrogen) in 5% CO$_2$ at 37° C. 24 hours after plating, cells are treated with various concentrations of an inhibitor. Growth was serially assessed using the resazurin ('AlamarBlue') assay.

Example 10: Formate Rescue Assays

Application of formate is shown to rescue the anti-growth effect in certain human cells treated with SHMT inhibitors in a cell growth assay.

Cell Growth Assays

The described cell lines for Examples 8 and 9 are cultured in 96-well plates in Dulbecco's modified eagle media (DMEM) without pyruvate (CELLGRO) with 10% dialysed fetal bovine serum (Invitrogen) in 5% CO$_2$ at 37° C. Approximately 2,500 cells are plated in each well in 90 uL of media. After 24 hours cells are treated with various concentrations of inhibitor (time=0 hours), with or without formate. Growth was assessed at multiple time points (time=0, 24, 48, 72 hours) through measurement of fluorescence at 595 nm (excitation at 535 nm) on a BioTek micro titer plate reader after incubation with resazurin (0.01 mg/mL for 1.5 hours). IC50 curves are generated from percent inhibition of growth at 72 hours.

Example 11: SHMT Inhibitor Effective in Hematological Malignancies

Cell lines derived from neoplasias of hematological origin are sensitive to the effects of SHMT inhibition. For example, growth (e.g., growth, proliferation and/or survival), as assessed by cell count, of both the T-cell leukemia line, Jurkat, and the diffuse large B cell lymphoma (DLBCL) line, Su-DHL-2, was inhibited by treatment with 5 μM of the SHMT inhibitor, HK-16 (PK2). For Jurkat cells, this inhibition is significantly rescued by addition of 1 mM sodium formate to the growth media. In contrast, the DLBCL line Su-DHL-2 was not rescued by 1 mM formate. (FIGS. 4A and 4B).

Example 12: SHMT Inhibitor (SHMTi) Activity can be Rescued in Su-DHL-2 Cells with Formate and Glycine The inhibitory effects on growth of Su-DHL-2 cells was rescued by supplementation with additional glycine (10× the standard RPMI concentration, 100 mg/L total) and sodium formate (1 mM). A similar pattern was observed in a larger group of DLBCL lines (FIGS. 5 and 6). In all DLBCL lines tested, treatment with an SHMT inhibitor inhibited cell growth (e.g., inhibited growth, proliferation and/or survival), and formate did not rescue this inhibitory effect. But, addition of both formate and 10× glycine did rescue in approximately ¾ of the B cell lines tested.

Example 13: Supplemental Formate and Glycine Required to Rescue B-Cell Lymphoma Lines from SHMTi Inhibition Diffuse large B-cell lymphoma (DLBCL) lines (Su-DHL-2, Su-DHL-4, Farage and Su-DHL-6) were cultured in RPMI with 5 uM of an SHMTi, and inhibition of growth (e.g., inhibition of growth, proliferation and/or survival), as measured by cell count, was observed. This inhibition was not rescued by addition of formate to the culture media, but was largely rescued by addition of both formate (1 mM sodium formate) AND glycine (100 mg/L). By comparison, in a representative AML cell line, such as REH, cell growth was rescued by addition of formate alone. Results are shown in FIG. 6.

Cellular Growth Assays:

Jurkat, REH, Farage, Daudi, Su-DHL2, Su-DHL-4, Su-DHL-6 cells were purchased from ATCC. Cells were subcultured in RPMI supplemented with 10% FBS. For growth assays, cells were seeded at 2×10^5/mL in 5 mL growth media in 12.5 cm flasks. Media was supplemented with sodium formate (1 mM), additional glycine (100 mg/L) and an SHMTi (5 uM). Cells were sampled daily, and counted using trypan blue staining and light microscopy.

Example 14: Glycine Uptake is Impaired in B-Cell Malignancies 1,2-13C Glycine Labeling Assays:

FIG. 7B shows the results of isotopic labeling ($^{13}$C) of ADP extracted from various adherent solid tumor derived cancer cell lines incubated with 1,2-$^{13}$C glycine for 48 hours as determined by mass spectrometry. Cell lines were cultured in standard culture media (RPMI for suspension lines, DMEM for adherent lines), supplemented with 10% dialyzed FBS. Cells were grown in 1,2-$^{13}$C glycine (replacing unlabeled glycine in media) containing media for 48 hr before harvesting for polar metabolites. Suspension cells were pelleted, washed with PBS once and metabolism quenched with −80 C lysis buffer (80:20 methanol:water).

Metabolites were analyzed on a ThermoFisher Orbitrap mass spectrometer operating in negative ion mode as previously described. Peak identities were confirmed using external standards and quantified using the MAVEN software suite6. In all adherent, solid tumor cell lines tested, a substantial fraction of ADP is M+2 labeled, indicating incorporation of $^{13}$C glycine from the media. In contrast, cell lines from both Burkitt lymphoma and DLBCL showed nearly no incorporation of glycine into ADP (see M+2 results in FIG. 7C).

These data suggested that when compared to adherent cultured cancer cell lines, B-cell derived cell lines do not import glycine from the media into biomolecules. The synthesis of the adenine ring in ADP involves 1 glycine molecule and 2 carbons atoms from 2 equivalents of 10-formyl-THF (FIG. 7A). In adherent cells, replacement of glycine in standard cell culture media with labeled 1,2-$^{13}$C glycine leads to generation of the M+2 labeling isomer of ADP. However, when the experiment was repeated in B-cell derived cancer cell lines (including Burkitt lymphoma (Daudi) and DLBCL), no labeling into ADP was observed from 1,2-$^{13}$C glycine. When 10× glycine was used, labeling was observed continuing that the method of rescue was glycine import into these cells (Data not shown).

Example 15: Requirement for SHMT Activity in HCT-116 Xenograft Formation

Figure 8A:
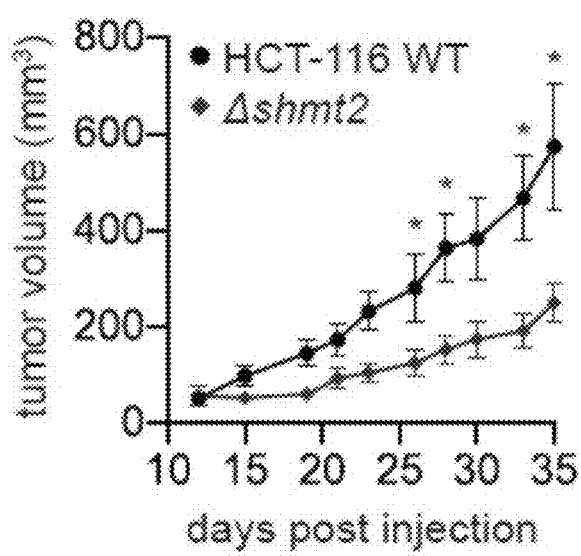
Figure 8B:
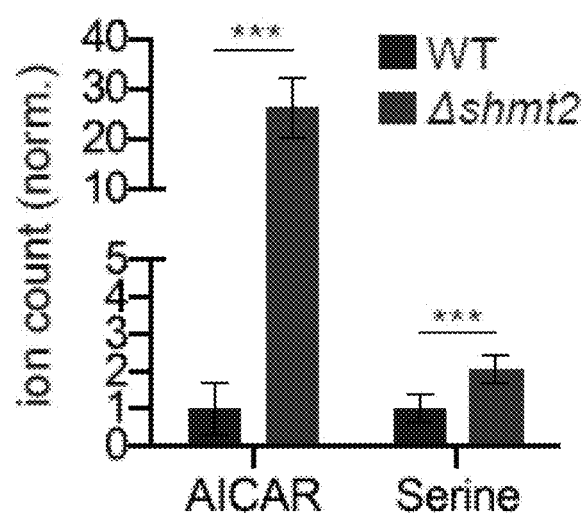

Clonal deletion cell lines of SHMT1, SHMT2, and SHMT1/2 were generated from the human colorectal carcinoma cell line HCT-116. Paired Cas9 nickase (Cas9n) containing constructs that encoded single-guide RNA sequences targeting SHMT1 or 2 were transiently transfected into cells, and mutant colonies from single clones were picked as described in Ducker et al., (2016) Reversal of Cytosolic One-Carbon Flux Compensates for Loss of the Mitochondrial Folate Pathway, Cell Metab 23, 1140-1153. SHMT1 deletion had no effect on cell growth either in cell culture or as subcutaneous xenografts in nude mice. In contrast, SHMT2 deletion cells grew slower in culture and as xenografts (FIG. 8A). Liquid chromatography-mass spectrometry (LC-MS) analysis of the soluble metabolites extracted from SHMT2 deletion tumors revealed characteristic signs of defective serine catabolism (FIG. 8B): serine levels were increased approximately 2-fold and the purine intermediate aminoimidazole carboxamide ribotide (AICAR), whose consumption requires 10-formyl-THF, was elevated approximately 25-fold.

Figure 8C:
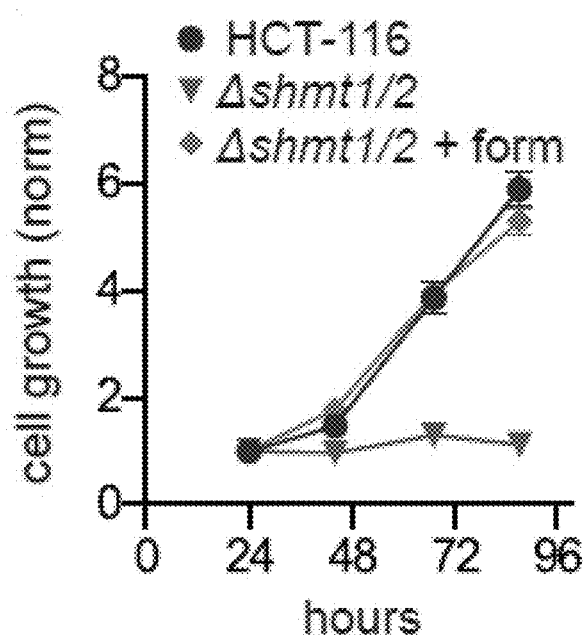
Figure 8D:
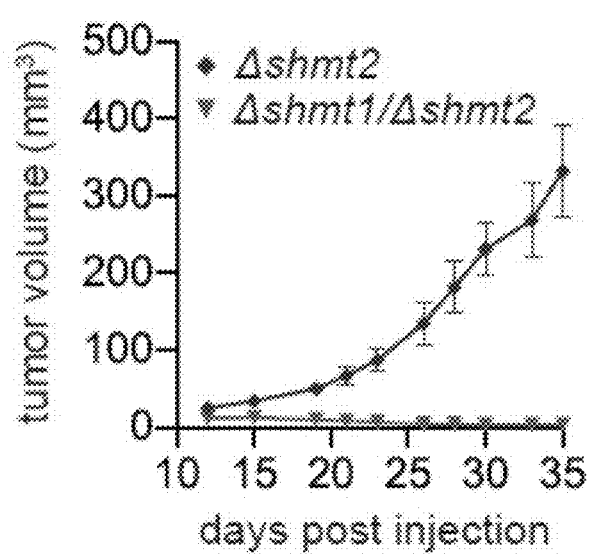

To generate dual SHMT1/SHMT2 double deletion cell lines, SHMT2 deletion cells were transfected with Cas9 and guide RNA sequences targeting SHMT1 in the presence of 1 mM sodium formate. Isolated clones cultured in formate grew at rates comparable to wild-type parental cells; as predicted no growth was observed in media without formate (FIG. 8C). To test whether circulating nucleotides and 1C sources in vivo could support the growth of SHMT1/SHMT2 double deletion cells, we xenografted them into nude mice. No tumors were observed from the SHMT1/SHMT2 double deletion cells (FIG. 8D). Thus, in HCT-116 xenografts, circulating alternative 1C donors (e.g. betaine, sarcosine, formate) and nucleotides are together insufficient to support intracellular 1C metabolism required for tumorigenesis.

Example 16: Small Molecule Inhibitors of Human SHMT1/2

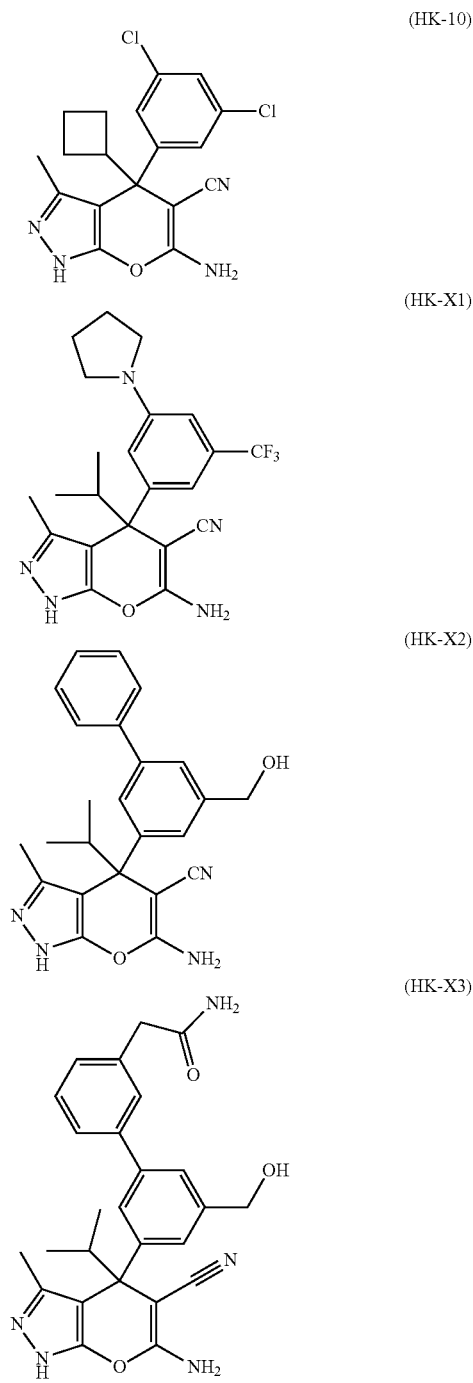

This disclosure provides compounds with improved inhibition properties for human SHMT1 and/or SHMT2. These compounds were modestly more potent in vitro against SHMT1 than SHMT2. Changes that improve potency against both human isoforms include introduction of an isopropyl group at the chiral 4-carbon of the pyrano ring and adding steric bulk to the meta substitutions on the phenyl ring (Compound HK-X1). Aromatic substitution at this position further increased potency yielding Compound HK-X2, which inhibits T cell proliferation.

To understand the binding mode of these inhibitors, a 2.47 Å structure of human SHMT2 as a dimer in complex with glycine, PLP and racemic HK-X1 (FIG. 9B) (PDB 5V7I). Electron density was identified in both binding pockets of the protein dimer, but in only one active site was it well resolved. Hydrogen binding contacts with the exocyclic amine are made with the amide backbone of L166 and between the pyrazole and H171. Overlaying this inhibitor-bound structure with a previously solved structure of rabbit SHMT1 bound to 5-formyl-THF triglutamate (PDB 1LS3) revealed that the bicyclic ring system of HK-X1 and pteridine moiety of folate occupy the same space, but at a different angle (FIG. 9C). The substituted phenyl ring and associated pyrrolidine of HK-X1 trace along the para-aminobenzoic acid (PABA) moiety of folate as it exits the pteridine binding pocket towards the solvent exposed folate polyglutamate side chain. Directly adjacent to the pyrrolidine lies a tyrosine residue that is well positioned to form a pi-stacking interaction with the phenyl of HK-X2, potentially contributing to the improved potency of this compound. Compared to the position of the folate pteridine ring, the pyrazolopyran ring of HK-X1 is rotated approximately 60° out of plane. However, hydrogen bond contacts are preserved, and engage the inhibitor at several core positions including the exocyclic amine and the pyrazole nitrogens. Given the conserved nature of the SHMT active site, these compounds are likely to inhibit SHMT enzymes not only of humans, but also other mammals.

Both Compounds HK-X1 and HK-X2 contain a single chiral center. Although crystallization was performed with racemic HK-X1, the electron density was consistent with only a single enantiomer binding to the enzyme. Using chiral chromatography, HK-X1 was separated, and enantioselective enzyme inhibition was confirmed (FIG. 9A). Thus, these pyrazolopyrans are potent, folate-competitive, enantioselective mammalian SHMT1/2 inhibitors.

Vibrational circular dichroism spectroscopy (VCD) will be used to determine the absolute stereochemistry of the active enantiomer. However, it has been found that the active enantiomer of Compound HK-X1 has a (+) optical rotation, and by structural analogy, it is expected that the active isomer of Compound HK-X2 will also have a (+) optical rotation.

The activity of Compound HK-X1 and HK-X2 against cytosolic and mitochondrial SHMT isoforms in cultured cells was investigated. The inactive (−) enantiomer of HK-X2 had no significant effect on growth in HCT-116 cells at doses up to 30 µM, whereas the active (+) enantiomer blocked growth with half-maximal inhibitory constants ($IC_{50}$) of 870 nM (FIG. 9D, Table 5). To analyze the effects of inhibition on each isoform independently, SHMT1 and SHMT2 HCT-116 deletion clones were used. The active enantiomers of both compounds, (+)-HK-X1 and (+)-HK-X2, were potent against cytosolic SHMT1, as evidenced by $IC_{50}$s for growth of less than 50 nM in SHMT2 deletion cells (FIG. 9D, Table 5). In contrast, SHMT1 deletion cells showed indistinguishable sensitivity from wild-type (WT), confirming that mitochondrial SHMT inhibition is limiting for compound efficacy (Table 5).

As HK-X1 and HK-X2 both have similar biochemical activities against SHMT1 and SHMT2, the much higher doses required for functional inhibition of cellular SHMT2 likely reflects a combination of imperfect mitochondrial penetration and greater intrinsic cellular SHMT2 activity (i.e., a substantial functional reserve due to high SHMT2 expression). Importantly, the effects on cell growth of HK-X1 and HK-X2 could be rescued by addition of formate, indicating that they inhibit cell growth through on-target depletion of cellular 1C pools (Table 5). However, as glycine is also a product of the SHMT reaction, formate can only rescue cell growth when this amino acid is present in the media.

TABLE 5

| | Cellular $IC_{50}$ (nM) | | | |
|---|---|---|---|---|
| Compound | WT | +formate | ΔSHMT1 | ΔSHMT2 |
| (+)-HK-X1 | 2300 | 13500 | 2800 | 36 |
| (+)-HK-X2 | 870 | >50000 | 840 | 10 |

Notably, while most cancers have high mitochondrial 1C pathway activity, certain cancer cells, such as the pancreatic cancer cell line 8988T, harbor genetic lesions in the mitochondrial folate pathway activity and therefore rely on SHMT1 to generate 1C units. In such cells, HK-X2 impairs cell growth at concentrations <100 nM due to its potent engagement of cellular SHMT1 (FIG. 9E).

Example 17: Metabolic Readouts for Target Engagement

Figure 10A:
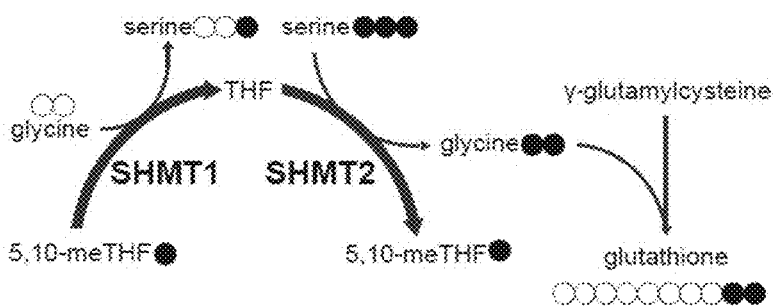
Figure 10B:
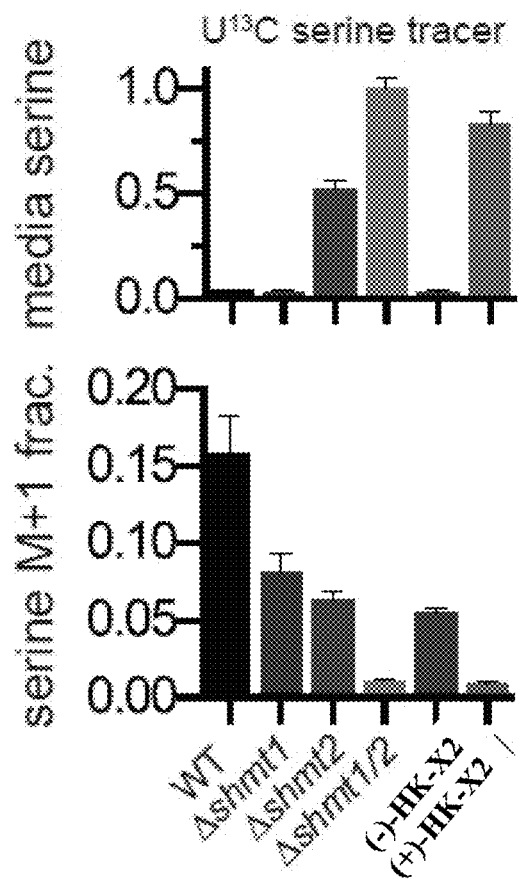
Figure 10C:
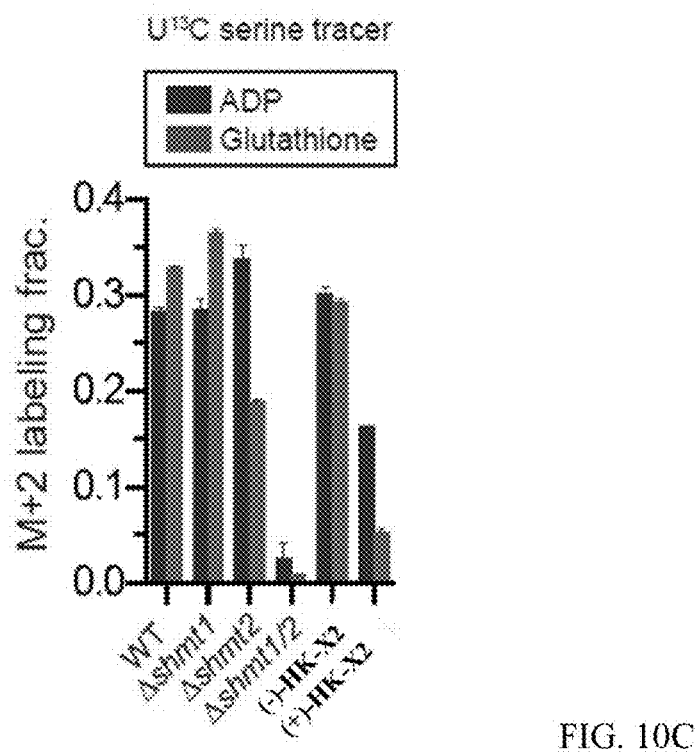
Figure 10D:
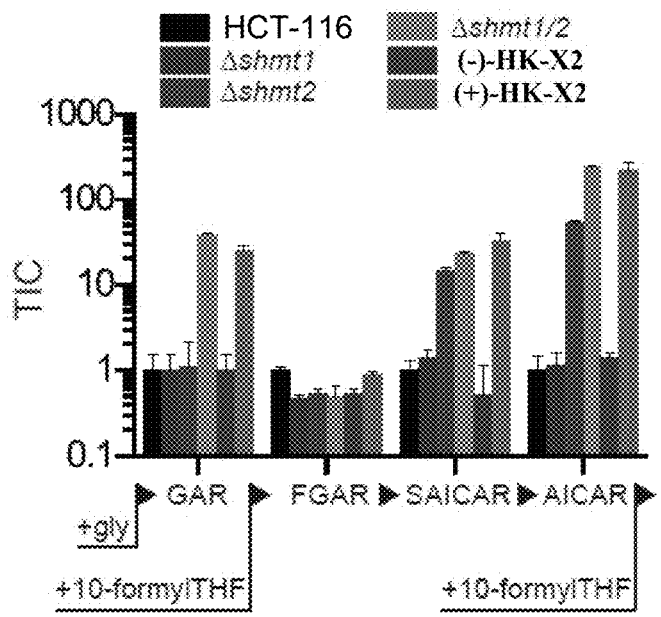
Figure 10E:
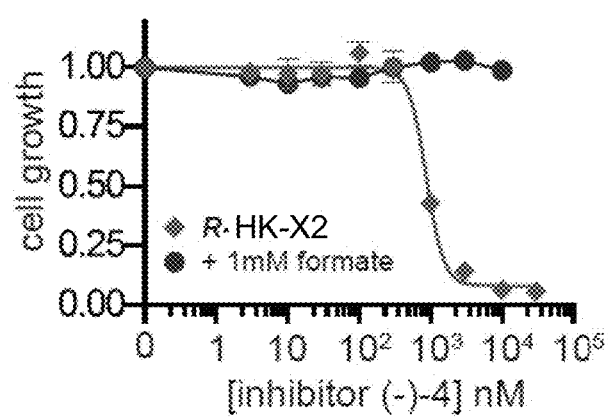

Inhibition of cellular SHMT activity can be monitored by isotope tracers and LC-MS. U-$^{13}$C serine is catabolized in the mitochondria by SHMT2 into U-$^{13}$C-glycine and a $^{13}$C-5,10-methylene-THF (FIG. 10A). Glycine is further incorporated into downstream metabolites such as glutathione and purines, whereas the folate 1C unit can be exported to the cytosol for incorporation into purines and thymidine. In addition, glycine and a 1C unit can recombine to make partially labeled serine via SHMT1 or SHMT2. To assess target engagement, the effects of SHMT genetic manipulations to pharmacological treatment with HK-X2 were compared. Serine media consumption was inhibited in both HCT-116 SHMT1/2 double deletion cells and WT cells treated with (+)-HK-X2 (FIG. 10B). Glycine production from serine and subsequent incorporation into glutathione or ADP was completely blocked in SHMT1/2 double deletion cells as evidenced by the missing M+2 labeling fraction (FIG. 10C). Nearly complete blockade was observed in WT cells treated with (+)-HK-X2 but not (−)-HK-X2. Drug treatment also blocked recombination of glycine and 10-formyl-THF to reform serine. Genetic deletion of SHMT1/2, and to a lesser extent SHMT2, results in buildup of purine biosynthetic intermediates upstream of steps requiring 10-formyl-THF as a substrate (FIG. 10D). Such buildup is also seen with (+)-HK-X2. Thus, HK-X2 phenocopies, in an enantioselective manner, the metabolic consequences of SHMT genetic deletion.

Figure 10F:
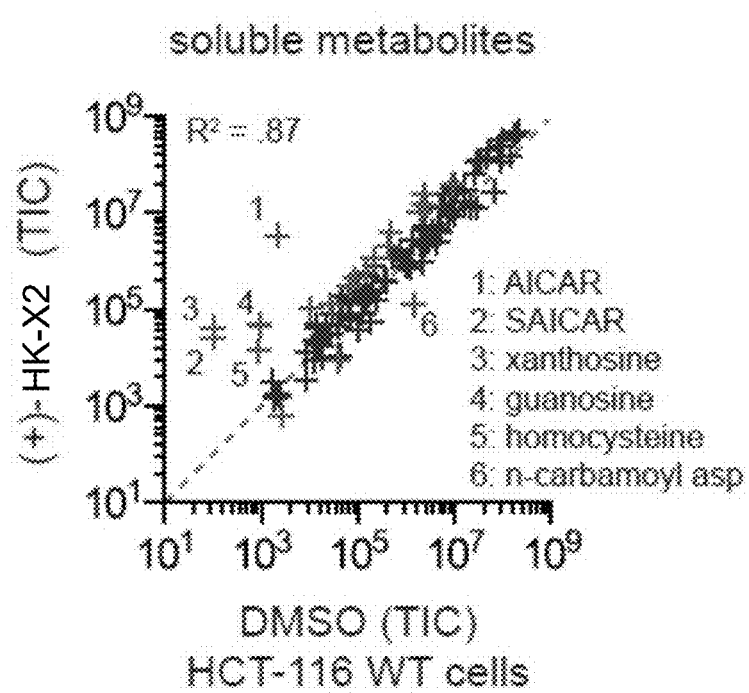
Figure 10G:
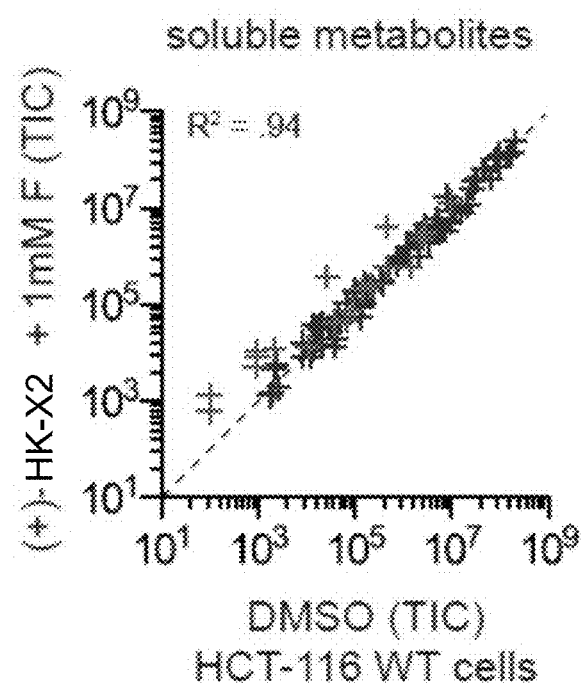

To assess the selectivity of the metabolic effects of HK-X2, untargeted LC-MS analysis on soluble metabolites from drug-treated cells was performed (FIG. 10F). In addition to purine intermediates, a buildup of purine salvage products (xanthosine, guanosine), whose increase is consistent with purine insufficiency, was observed. Buildup of homocysteine, a classic marker of 1C deficiency was further observed. Depletion of the pyrimidine intermediate N-carbamoyl-aspartate was also observed, likely reflecting feedback inhibition of aspartate transcarbamoylase by excess pyrimidines in the purine starved cells. Importantly, there were no other large changes in metabolism suggestive of off-target effects. Moreover, the changes in metabolite abundances were rescued by formate (FIG. 10F) and metabolite abundances in SHMT1/2 double deletion cells closely matched those from WT cells treated with (+)-HK-X2. Thus, at doses sufficient to robustly inhibit SHMT1 and SHMT2 in cell culture, (+)-HK-X2 selectively targets 1C metabolism.

Example 18: Cancer Cell Sensitivity to SHMT Inhibition

Figure 11A:
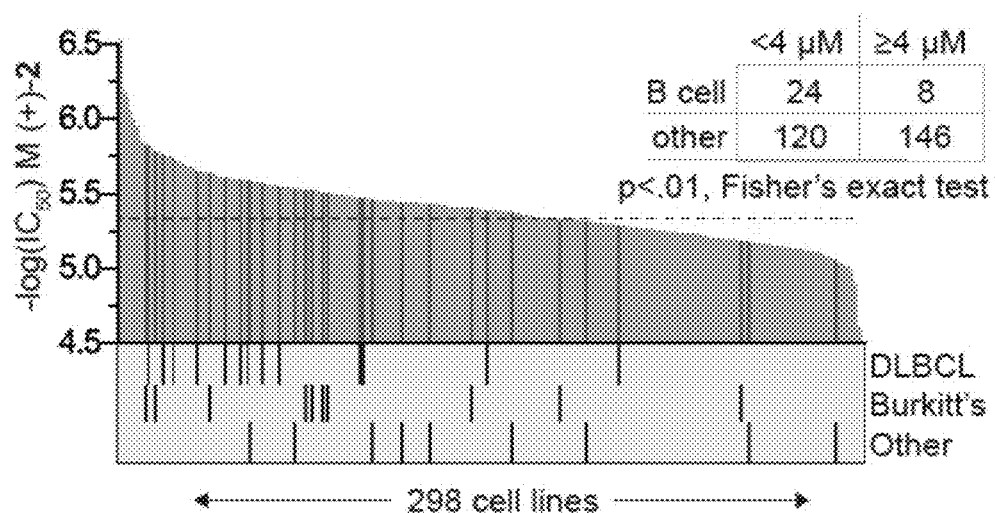
Figure 11B:
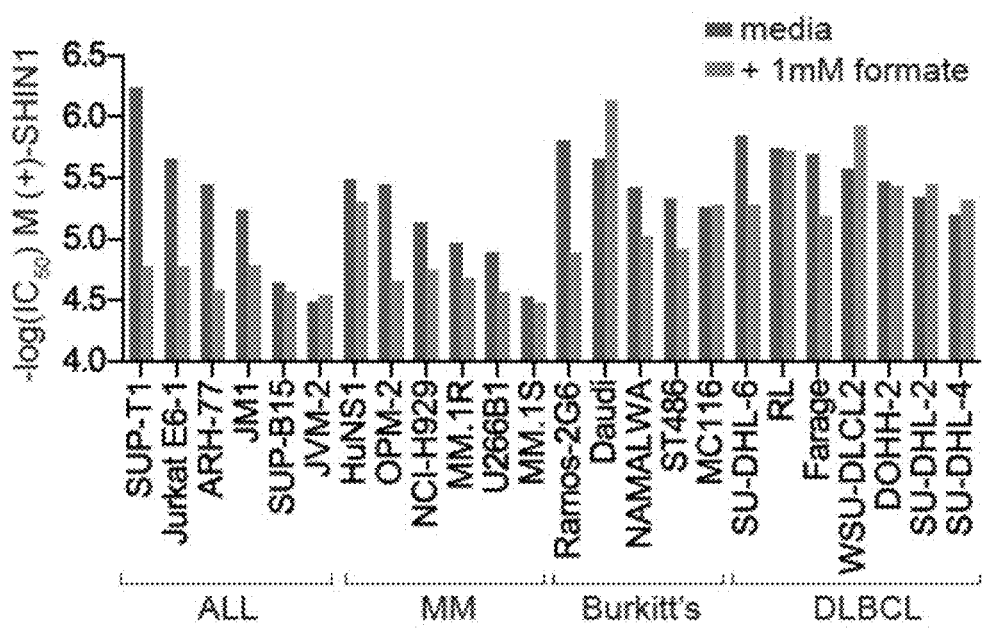

A panel of nearly 300 human cancer cell lines was screened for growth in the presence of the (+)-enantiomer of HK-X1 (FIG. 11A). The median $IC_{50}$ was 4 µM. Cell lines of B-cell lymphoma origin were enriched in the more sensitive half of cells (p<0.001, Fisher's Exact Test). This effect was driven by a pronounced sensitivity of Burkitt's and DLBCL lymphomas (FIG. 11A). A set of hematological cancer lines was then screened with (+)-HK-X2, supplemented with and without formate to test for rescue (FIG. 11B). Like HCT-116 cells, cell lines of T-cell origin such as Acute Lymphocytic Leukemia (ALL) cells, were largely rescued from the antigrowth effects of (+)-HK-X2 by formate. In contrast, formate failed to rescue the growth of B-cell lymphoma lines.

Figure 11C:
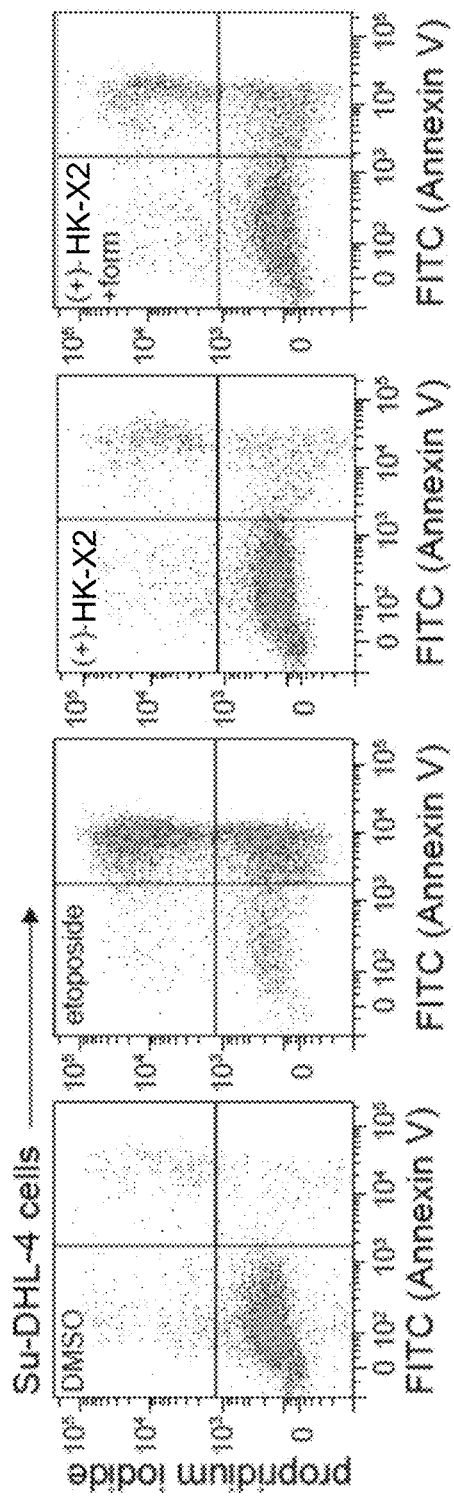
Figure 11D:
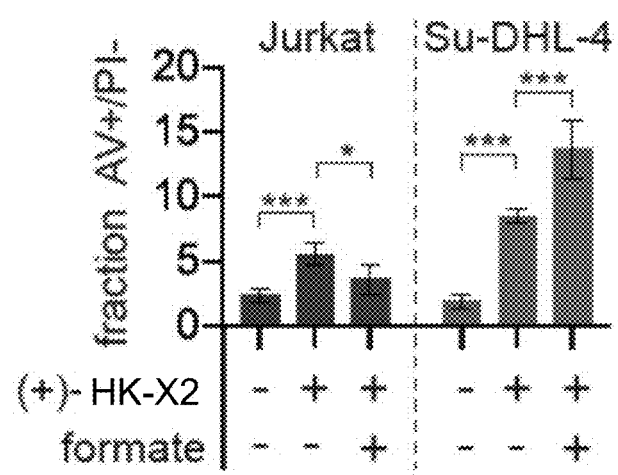

To explore this surprising lack of rescue further, flow cytometry was used to analyze the effect of (+)-HK-X2, with and without formate, on the DLBCL cell line Su-DHL-4. HK-X2 itself induced apoptosis as measured by Annexin V surface staining (FIGS. 11C and 11D). Apoptosis was enhanced by co-treatment with formate. In contrast, as expected, formate rescued Jurkat E6-1 leukemia cells from apoptosis (FIG. 11C). Without wishing to be bound by theory, it is hypothesized that the failure of formate to rescue growth in the DLBCL cell lines is due to a requirement for both glycine and 1C units made by SHMT in these cells. When glycine is limiting, formate can enhance the cytotoxicity of SHMT inhibition. For example, formate augments the effect of HK-X2 in HCT-116 cells in glycine-free media. Mechanistically, by supplying 5,10-methylene-THF, formate may drives residual SHMT enzymatic function in the glycine-consuming direction. Alternatively, whereas cells may have the machinery to sense 1C deficiency and safely pause growth (e.g. due to AICAR activation of AMPK), they may lack comparable mechanisms for surviving glycine limitation.

Example 19: Defective Glycine Uptake in DLBCL

Figure 12A:
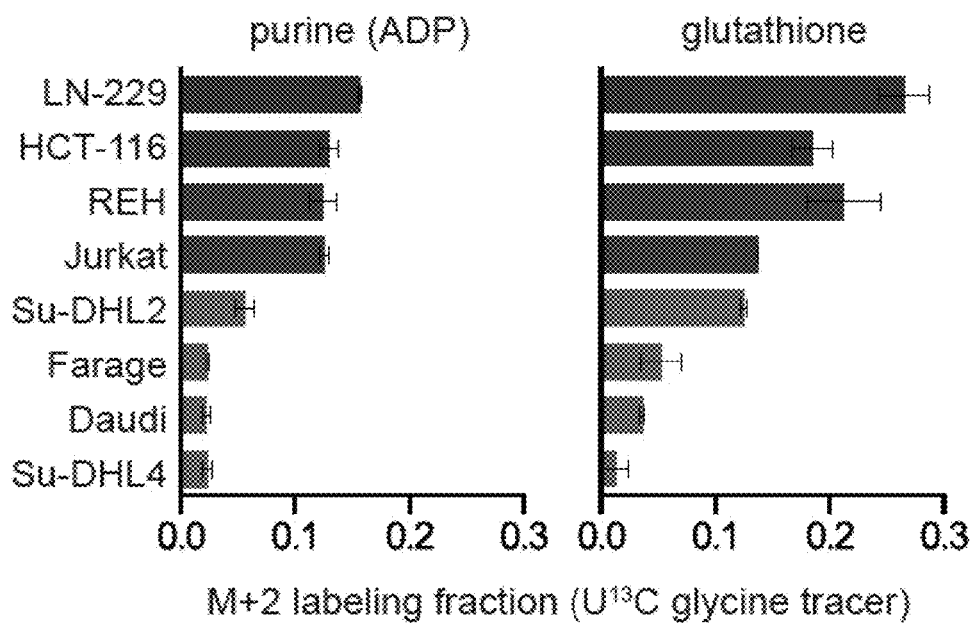

The inability of formate to rescue the antigrowth effects of enantiomerically pure HK-X2 ((+)-HK-X2) in DLBCL raised the question of whether HK-X2 activity in these cells was on target. If so, it was hypothesized that the cells might require SHMT not only for 1C units, but also to produce glycine. Indeed, SHMT2 loss causes glycine auxotrophy. Here, however, the cells were cultured in RPMI, which contains glycine (10 mg/L, 130 µM). Accordingly, the goal of this experiment is to understand if DLBCL and other B-cell lines might be deficient in glycine uptake. Compared to adherent cancer cell lines, and hematological cancer lines that were rescued by formate, B-cell cancer lines uptake glycine and incorporate it into downstream metabolites such as purines and glutathione at lower rates (FIG. 12A).

Figure 12B:
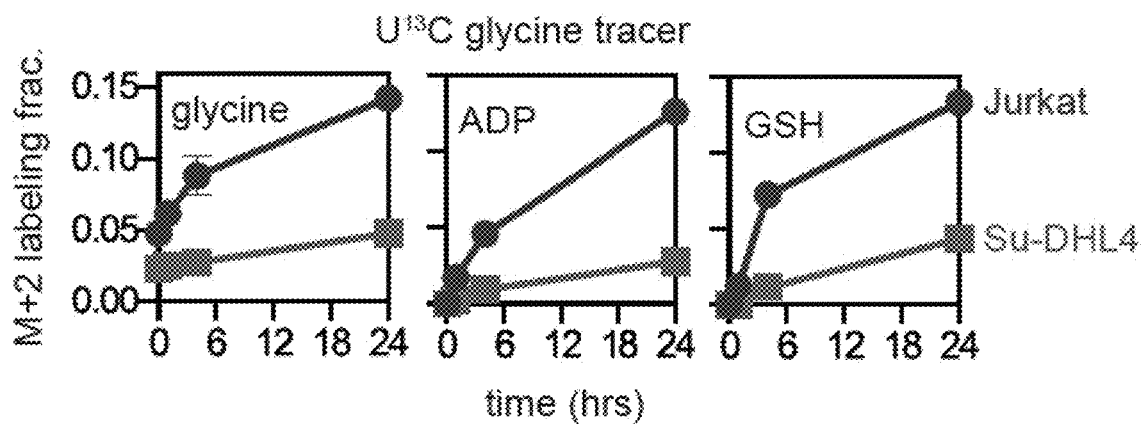
Figure 12C:
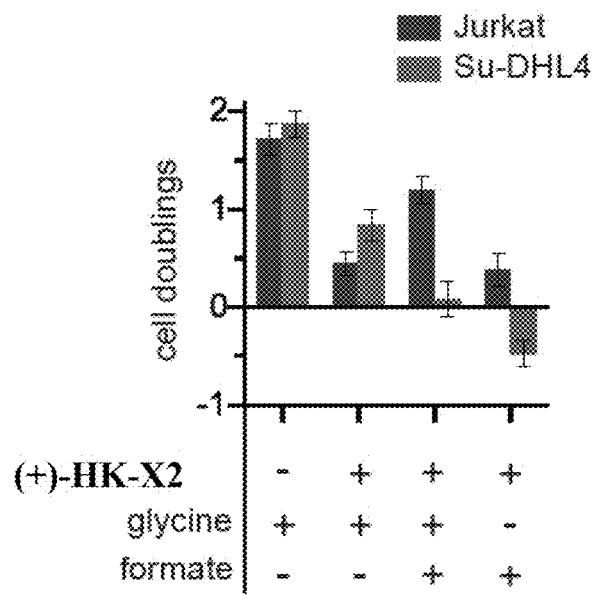
Figure 12D:
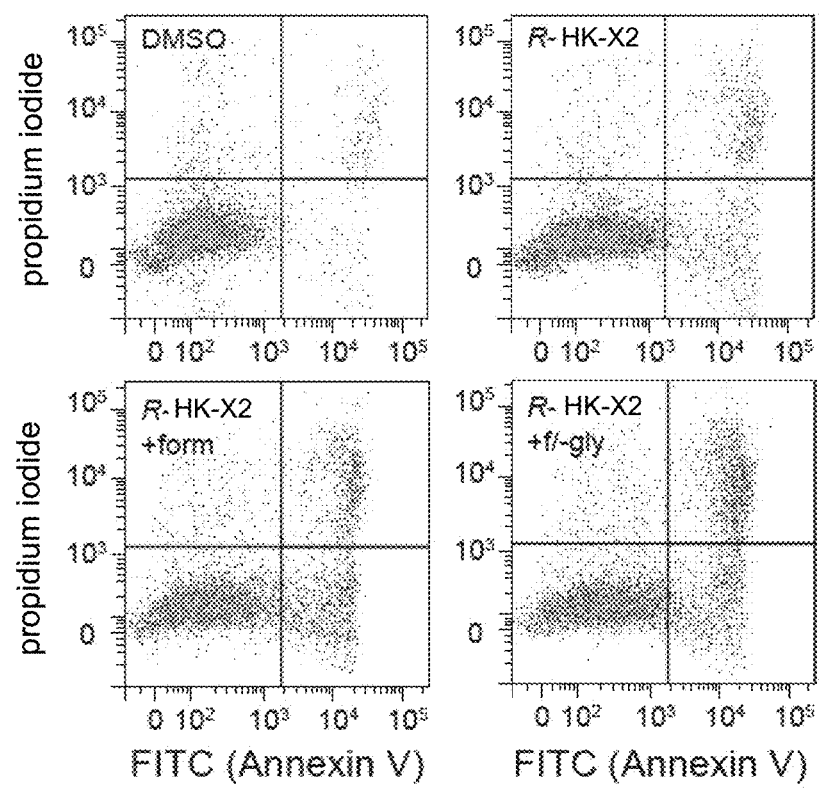
Figure 12E:
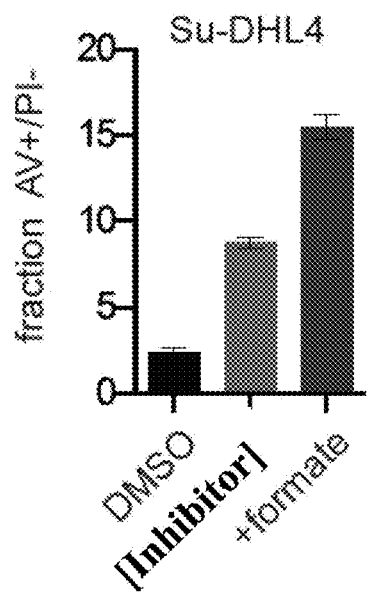

The defect in glycine uptake was particularly profound in certain DLBCL lines, such as Su-DHL4 which is sensitive to HK-X2 and not rescued by formate (FIG. 12B). Jurkat cells are actually more sensitive to HX-X2 than SuDHL4 cells, but their growth can largely be rescued by formate (FIG. 12C). In contrast, cell growth is further decreased in Su-DHL4 cells by addition of formate. This can be further exacerbated by removal of glycine from the media. The toxic effects of formate in the presence of HK-X2 are likely due to the resulting methylene-THF shifting the thermodynamics of the SHMT reaction in the direction of glycine consumption. Using flow cytometry, apoptosis of Su-DHL4 cells were studied with AnnexinV surface staining (FIGS. 12D and 12E). With inhibitor alone, the apoptotic fraction of cells was increased from 2% to 8% and further doubled in the presence of formate to 15%.

Figure 12F:
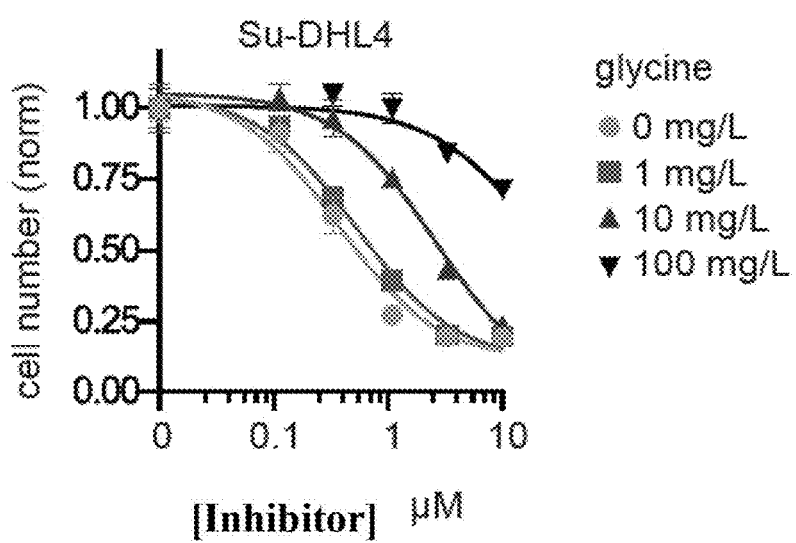
Figure 12G:
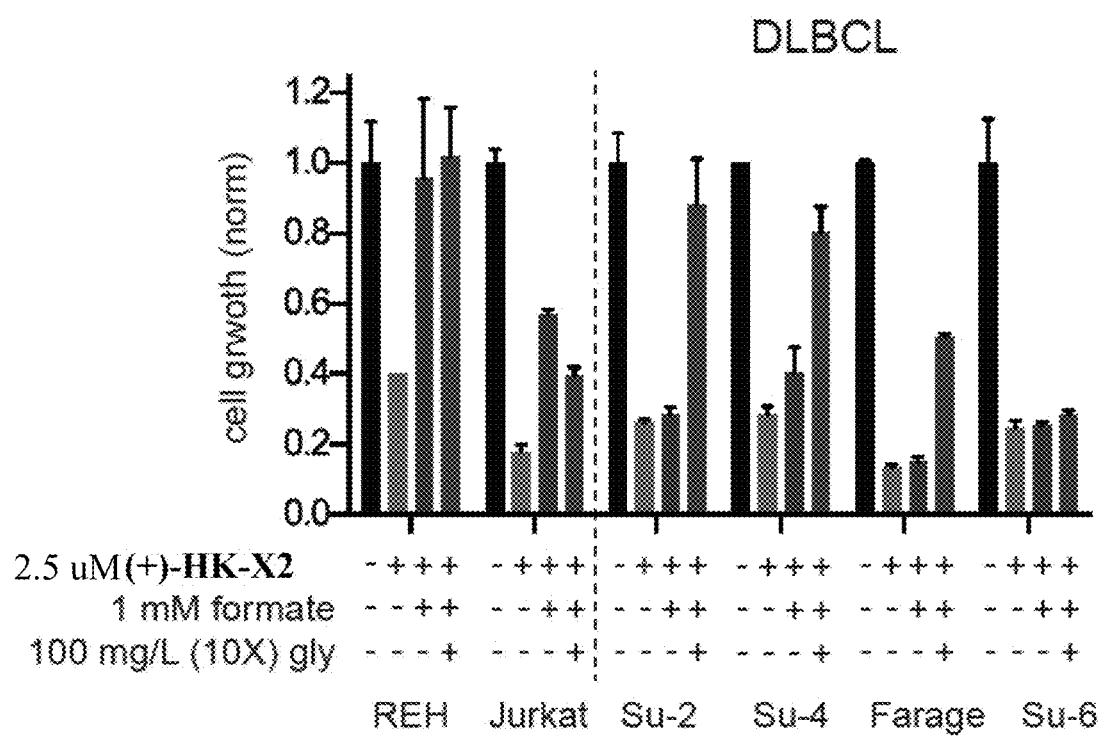

To confirm the hypothesis that glycine availability was limiting in Su-DHL4 cells and to explain the synergistic cell killing effects of HK-X2 in combination with formate, how varying RPMI glycine concentration would alter the cell response to the SHMT inhibitor, e.g., HK-X2, was studied. In SuDHL4 cells, the $IC_{50}$ of HK-X2 was highly dependent upon the glycine concentration. Increasing or decreasing glycine by 10-fold compared to standard RPMI markedly shifted the HK-X2 $IC_{50}$ values (FIG. 12F). For Jurkat cells, little dependence upon extracellular glycine concentrations was observed. Across a set of DLBCL cell lines, supplying both formate and supra-physiologic glycine generally rescued cell growth, indicating on-target HK-X2 activity with both products of the SHMT reaction being required (FIG. 12G).

Figure 14A:
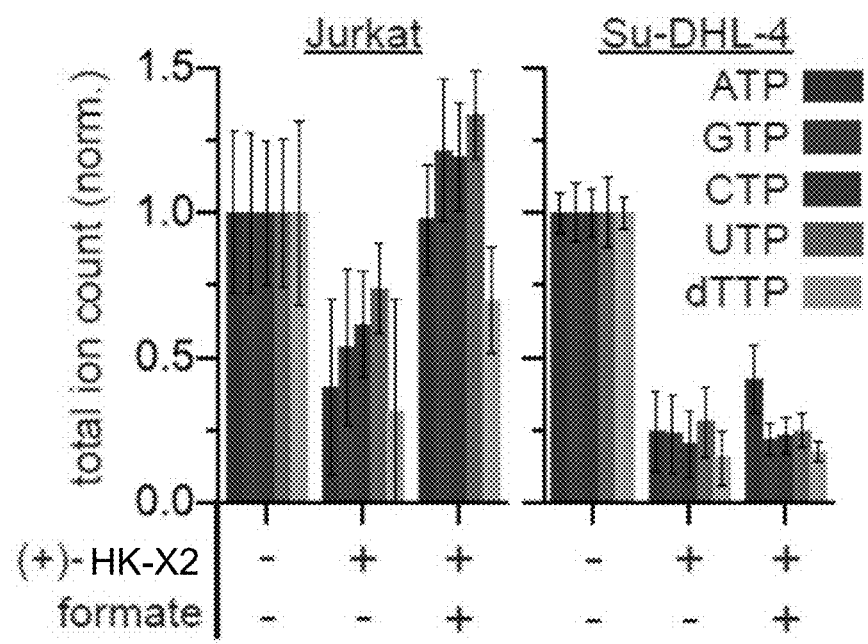
Figure 14B:
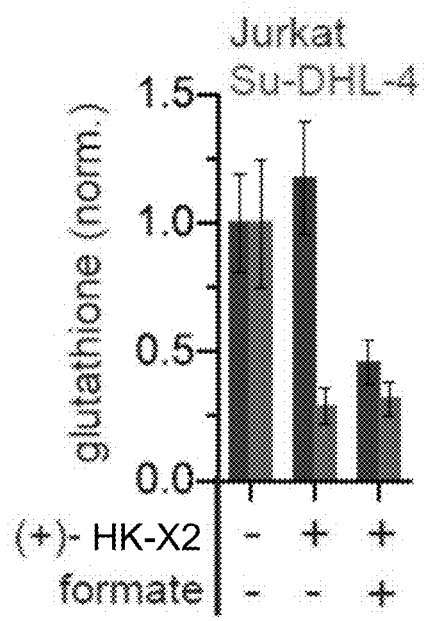
Figure 14C:
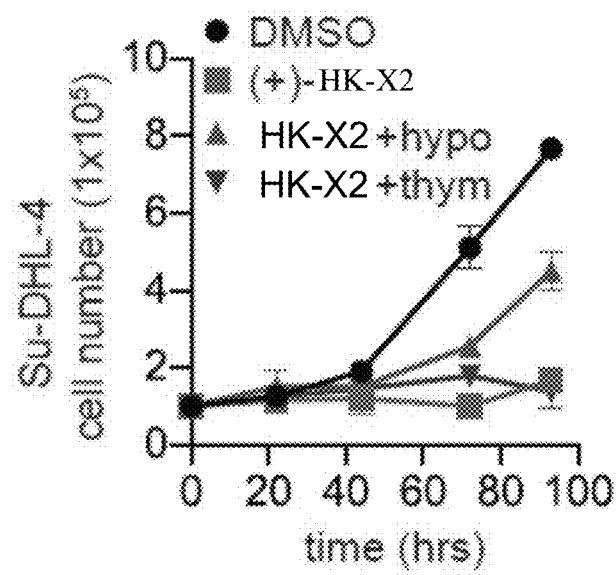
Figure 14D:
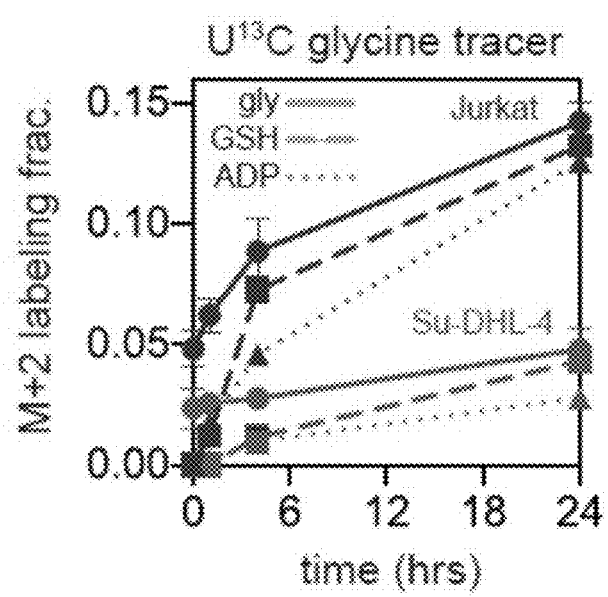
Figure 14E:
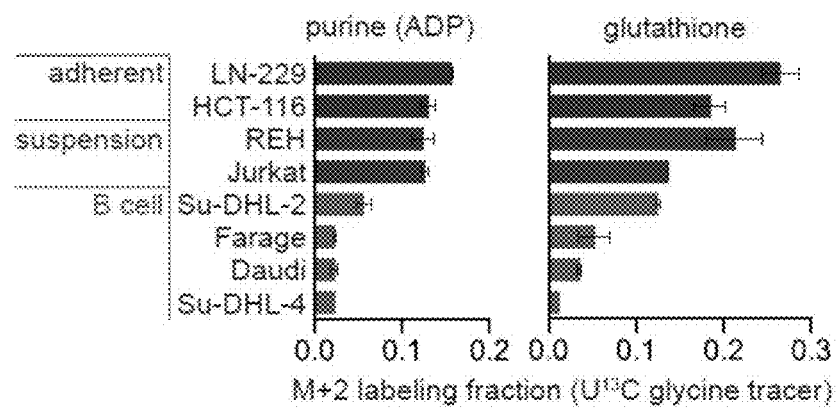

HK-X2 induced glycine deficiency in DLBCL cells, even though they were cultured in complete media with glycine (RPMI, 10 mg/L glycine=130 µM). This suggested that glycine uptake is intrinsically impaired in these cells. Using U-$^{13}$C-glycine, the kinetics of extracellular glycine incorporation into cells and downstream metabolic products was monitored (FIG. 14D). Labeling of intracellular glycine products, such as glutathione and ADP, was markedly less in Su-DHL-4 cells than Jurkat cells. In a larger set of cell lines, composed of both other hematological cancer and adherent cell lines, steady state labeling of intracellular metabolites from glycine was significantly lower in B-cell lymphoma cell lines (FIG. 14E).

Given the apparent glycine shortage in these B cells upon HK-X2 treatment, extracellular glycine levels were augmented, and response to drug was evaluated. First, the concentration of glycine in RPMI was altered and response to drug observed. A reduction of glycine in the media modestly improved the potency of HK-X2, indicating that the cells were sensitive to extracellular glycine. More strikingly, increasing the media glycine by 10-fold substantially rescued the cells from HK-X2. In contrast, in Jurkat cells, a small amount of extracellular glycine was sufficient and more did not further rescue the cells from HK-X2. Across a set of DLBCL cell lines, representing both ABC and GBC subtypes, supplying both formate and supra-physiologic glycine (100 mg/L, 1.3 mM) generally rescued cell growth (FIG. 12G). These results indicate the importance of both products of the SHMT reaction, glycine and folate 1C units, for the proliferation of DLBCL cell lines.

Figure 14F:
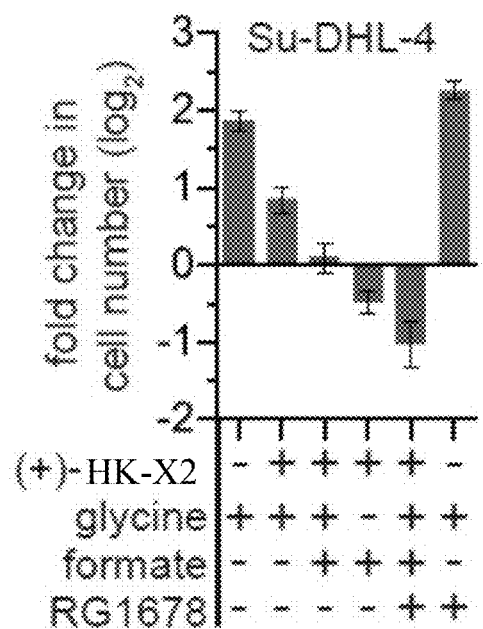
Figure 14G:
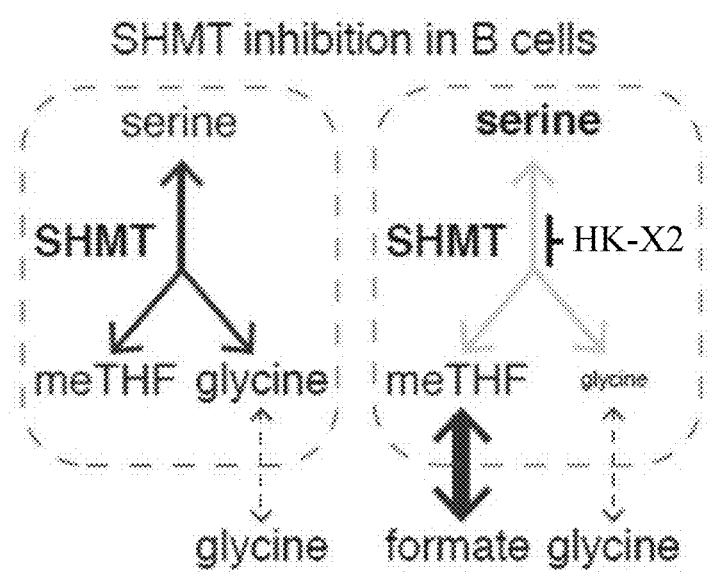

Knowing that manipulating glycine could augment the efficacy of HK-X2, different mechanisms of decreasing glycine were tested. When formate was added, HK-X2 was transformed from being a drug that slowed cell growth to one that was fully cytostatic (FIG. 14F). Further removing glycine caused significant cell death. Interestingly, combining the glycine reuptake transporter 1 (GlyT1) (SLC6A9) inhibitor RG1678 with HK-X2 led to even greater cell death, even in the presence of media glycine (FIG. 14F). These results suggest that the low level of glycine uptake in these cells is mediated by GlyT1 and that combinations of formate, SHMT inhibitor, and/or GlyT1 inhibitor may selectively target these cells.

Example 20: DLBCL Cells Require SHMT to Make Glycine for Purine Synthesis

The inability of formate to rescue the antigrowth effects of HK-X2 in DLBCL cell lines suggested that glycine may be limiting in these cells. To explore this hypothesis, the metabolic effects of HK-X2 in DLBCL and Jurkat cells treated with (+)-HK-X2 (72 h, 5 µM) with and without formate were characterized. In Jurkat and DLBCL cell lines Su-DHL-4 and Su-DHL-2, HK-X2 treatment led to a large reduction in nucleotide triphosphates (FIG. 14A). This can be rationalized as reflecting impaired purine synthesis, which requires both 1C units and glycine, with pyrimidines also falling due to endogenous mechanisms that balance their levels with those of purines. There is also a component of energy stress, particularly in Su-DHL-4 cells, as nucleotide monophosphates were increased, not decreased. Consistent with 1C limitation, dTTP, whose synthesis requires a folate 1C unit, was more depleted than other pyrimidines.

Formate supplementation restored nucleotide levels in Jurkat but not DLBCL cell lines. It was confirmed that formate rescues folate 1C levels in DLBCL cells, as the AICAR accumulation induced by (+)-HK-X2 is fully reversed. Thus, while nucleotide synthesis in HK-X2-treated Jurkat cells is solely limited by 1C units, an additional factor is lacking in DLBCL cells. Consistent with glycine being the second factor missing in DLBCL cells, (+)-HK-X2 treatment depleted the glycine-containing redox defense tripeptide glutathione (FIG. 14B). Strikingly, while HK-X2 alone did not alter glutathione in Jurkat cells, formate addition caused glutathione depletion. This further validates that, when SHMT is inhibited, provision of excess 1C units can cause glycine stress. Glutathione supplementation did not rescue growth. Based on these results, it was hypothesized that growth in SHMT-inhibited DLBCL cells might be restored with purine supplementation which would simultaneously alleviate IC and glycine metabolic stress. Growth was partially rescued in Su-DHL-4 cells treated with hypoxanthine. Thymidine, which rescues the effects of the classical antifolate pemetrexed but does not contain glycine, had no benefit in HK-X2-treated DLBCL cells (FIG. 14C). Thus, HK-X2 blocks cell growth through a progressive depletion of purines leading to loss of nucleotide triphosphates. Restoration of purines levels restores growth.

Whether glycine shortage might also impact protein synthesis was next examined Severe amino acid shortages lead to loss of cognate tRNA charging and thus ribosome stalling, which can be measured using ribosome profiling. Ribosome profiling on Su-DHL-4 cells treated with (+)-HK-X2 was performed. Untreated Su-DHL-4 cells growing in RPMI did not show evidence of glycyl-tRNA insufficiency; no enrichment for these codons was observed. Furthermore, no difference in glycine codon occupancy was observed between treated and control cells. Collectively, these results suggest a hierarchy in the sensitivity of different intracellular metabolic products to glycine levels: glutathione synthesis is most sensitive, followed by purine synthesis, with protein synthesis most resistant. This hierarchy is consistent with biochemical measurements of the KM values of the relevant enzymes: the glycyl-tRNA amino acid synthase has a lower KM for glycine (15 µM) than that found in glycinamide ribonucleotide synthetase (45 µM) or glutathione synthetase (452 µM).

Example 21: Liver Microsome Assay

Male CD-1 mouse liver microsomes were obtained from commercial sources (Corning #452701). The following master solution was prepared before compound addition:

| Reagent | Stock Concentration | Volume | Final Concentration |
| --- | --- | --- | --- |
| Phosphate buffer | 200 mM | 200 µL | 100 mM |
| Ultra-pure $H_2O$ | — | 64 µL | — |
| $MgCl_2$ solution | 50 mM | 40 µL | 5 mM |
| Alamethacin | 5 mg/mL | 2 µL | 25 ug/mL |
| Microsomes | 20 mg/mL | 10 µL | 0.5 mg/mL |

Two separate experiments were performed as follows: a) With Cofactors (NADPH and UDPGA): 40 µL of 10 mM NADPH and 40 µL of 20 mM UDPGA were added to the incubations. The final concentrations of microsomes, NADPH and UDPGA were 0.5 mg/mL, 1 mM and 2 mM, respectively. b) Without Cofactors (NADPH and UDPGA): 10 µL of 20 mg/mL liver microsomes and 80 µL of ultra-pure water were added to the incubations. The final concentration of microsomes was 0.5 mg/mL. The mixture was pre-warmed at 37° C. for 5 minutes.

The reaction was started with the addition of 4 µL of 200 µM control compound or test compound solution. Verapamil was used as positive control in this study. The final concentration of test compound or control compound was 2 µM. The incubation solution was incubated in water bath at 37° C. Aliquots of 50 µL were taken from the reaction solution at 0.5, 5, 15, 30, 45 and 60 minutes. The reaction was stopped by the addition of 5 volumes of cold acetonitrile with IS (100 nM alprazolam, 200 nM caffeine and 100 nM tolbutamide). Samples were centrifuged at 3,220 g for 40 minutes. Aliquot of 100 µL of the supernatant was mixed with 100 µL of ultra-pure $H_2O$ and then used for LC-MS/MS analysis. The in vitro half-life (in vitro t1/2) was determined from the slope value of the LC-MS signal of the test compound. The data are reported in Table 6.

TABLE 6

Metabolic Stability of Test Compounds in Pooled Male Mouse Liver Microsomes

| Compound No./Structure | t1/2 Replicate 1 | $CL_{int}$ (µL/min/mg protein) (replicate 1) | t1/2 Replicate 2 | $CL_{int}$ (µL/min/mg protein) (replicate 2) |
| --- | --- | --- | --- | --- |
| 1 | 2.32 | 596.63 | 1.79 | 776.05 |
| 71 | 4.86 | 285.28 | 6.84 | 202.99 |
| 11 | 1.82 | 763.82 | 2.56 | 541.48 |

TABLE 6-continued

Metabolic Stability of Test Compounds in Pooled Male Mouse Liver Microsomes

| Compound No./Structure | t1/2 Replicate 1 | $CL_{int}$ (μL/min/mg protein) (replicate 1) | t1/2 Replicate 2 | $CL_{int}$ (μL/min/mg protein) (replicate 2) |
|---|---|---|---|---|
| 74 | 20.40 | 67.95 | 20.40 | 67.96 |
| HK-X3 | 15.09 | 91.87 | 14.70 | 94.28 |
| (F₃C, F₃C, Br-substituted pyrazolopyran structure) | 15.79 | 87.77 | 19.39 | 71.47 |

Other SHMT inhibitors, such as compounds of any of Formulae (I)-(IX), are evaluated in similar assays, such as the assays set forth in Examples 10-19.

All publications and patents cited herein are hereby incorporated by reference in their entirety.

Those skilled in the art will recognize, or be able to ascertain using no more than routine experimentation, many equivalents to the specific embodiments of the subject matters in this disclosure described herein. Such equivalents are intended to be encompassed by the following claims.

REFERENCES

Pavlova N N, Thompson C B (2016) The Emerging Hallmarks of Cancer Metabolism. Cell Metab 23(1):27-47.

Schulze A, Harris A L (2012) How cancer metabolism is tuned for proliferation and vulnerable to disruption. Nature 491(7424):364-373.

Labuschagne C F, van den Broek N J F, Mackay G M, Vousden K H, Maddocks O D K (2014) Serine, but Not Glycine, Supports One-Carbon Metabolism and Proliferation of Cancer Cells. CellReports:1-11.

Jain M, et al. (2012) Metabolite Profiling Identifies a Key Role for Glycine in Rapid Cancer Cell Proliferation. Science 336(6084):1040-1044.

Possemato R, et al. (2011) Functional genomics reveal that the serine synthesis pathway is essential in breast cancer. Nature 476(7360):346-350.

Locasale J W, et al. (2011) Phosphoglycerate dehydrogenase diverts glycolytic flux and contributes to oncogenesis. Nat Genet 43(9):869-874.

Lee G Y, et al. (2014) Comparative oncogenomics identifies PSMB4 and SHMT2 as potential cancer driver genes. Cancer Res 74(11):3114-3126.

Nilsson R, et al. (2014) Metabolic enzyme expression highlights a key role for MTHFD2 and the mitochondrial folate pathway in cancer. Nature Communications 5:3128.

Ben-Sabra I, Hoxhaj G, Ricoult S, Asara J M (2016) mTORC1 induces purine synthesis through control of the mitochondrial tetrahydrofolate cycle. Science 351(6274):728-732.

Ducker G S, et al. (2016) Reversal of Cytosolic One-Carbon Flux Compensates for Loss of the Mitochondrial Folate Pathway. Cell Metab 23(6):1140-1153.

Lewis C A, et al. (2014) Tracing compartmentalized NADPH metabolism in the cytosol and mitochondria of Mammalian cells. Mol Cell 55(2):253-263.

Tibbetts A S, Appling D R (2010) Compartmentalization of Mammalian Folate-Mediated One-Carbon Metabolism. Annu Rev Nutr 30(1):57-81.

Patel H, Pietro E D, MacKenzie R E (2003) Mammalian fibroblasts lacking mitochondrial NAD+-dependent methylenetetrahydrofolate dehydrogenase-cyclohydrolase are glycine auxotrophs. J Biol Chem 278(21):19436-19441.

Ducker G S, Rabinowitz J D (2017) One-Carbon Metabolism in Health and Disease. Cell Metab 25(1):27-42.

Loayza-Puch F, et al. (2016) Tumour-specific proline vulnerability uncovered by differential ribosome codon reading. Nature Publishing Group 530(7591):490-494.

Zhao R, Goldman I D (2003) Resistance to antifolates. 22(47):7431-7457.

Longley D B, Harkin D P, Johnston P G (2003) 5-Fluorouracil: mechanisms of action and clinical strategies. Nat Rev Cancer 3(5):330-338.

Pacold M E, et al. (2016) A PHGDH inhibitor reveals coordination of serine synthesis and one-carbon unit fate. Nat Chem Biol 12(6):452-458.

Wang Q, et al. (2017) Rational Design of Selective Allosteric Inhibitors of PHGDH and Serine Synthesis with Anti-tumor Activity. Cell Chem Biol 24(1):55-65.

Mullarky E, et al. (2016) Identification of a small molecule inhibitor of 3-phosphoglycerate dehydrogenase to target serine biosynthesis in cancers. Proc Natl Acad Sci USA 113(7):1778-1783.

Witschel M, Stelzer F, Hutzler J, Qu T (2013) Pyrazolopyrans having herbicidal and pharmaceutical properties. (61/656,025).

Witschel M C, et al. (2015) Inhibitors of plasmodial serine hydroxymethyltransferase (SHMT): cocrystal structures of pyrazolopyrans with potent blood- and liver-stage activities. J Med Chem 58(7):3117-3130.

Marani M, et al. (2016) A pyrazolopyran derivative preferentially inhibits the activity of human cytosolic serine hydroxymethyltransferase and induces cell death in lung cancer cells. Oncotarget 7(4):4570-4583.

Rabinowitz J D, Kim H, Ducker G S, Ghergurovich J M, The Trustees Of Princeton University (2016) Shmt inhibitors.

Ma E H, et al. (2017) Serine Is an Essential Metabolite for Effector T Cell Expansion. *Cell Metab:*1-14.

Cockrell G M, et al. (2013) New Paradigm for Allosteric Regulation of *Escherichia coli* Aspartate Transcarbamoylase. *Biochemistry* 52(45):8036-8047.

Cader M Z, et al. (2007) Crystal structure of human wildtype and S581L-mutant glycyl-tRNA synthetase, an enzyme underlying distal spinal muscular atrophy. *FEBS Lett* 581(16):2959-2964.

Antle V D, et al. (1996) Substrate specificity of glycinamide ribonucleotide synthetase from chicken liver. *J Biol Chem* 271(14):8192-8195.

Njalsson R, et al. (2001) Cooperative Binding of γ-Glutamyl Substrate to Human Glutathione Synthetase. *Biochemical and Biophysical Research Communications* 289(1):80-84.

Harvey R J, Yee B K (2013) Glycine transporters as novel therapeutic targets in schizophrenia, alcohol dependence and pain. *Nat Rev Drug Discov* 12(11):866-885.

Farber S (1948) Temporary remissions in acute leukemia in children produced by folid acid antagonist, 4-aminopteroyl-glutamic acid (aminopterin). *New England Journal of Medicine* 238(787-793): 1-7.

Eggert U S, et al. (2004) Parallel Chemical Genetic and Genome-Wide RNAi Screens Identify Cytokinesis Inhibitors and Targets. *Plos Biol* 2(12):e379-9.

Guertin D A, et al. (2006) Ablation in mice of the mTORC components raptor, rictor, or mLST8 reveals that mTORC2 is required for signaling to Akt-FOXO and PKCalpha, but not S6K1. *Dev Cell* 11(6):859-871.

Kiriyama Y, et al. (1989) Biochemical characterization of U937 cells resistant to L-asparaginase: the role of asparagine synthetase. *Leukemia* 3(4):294-297.

Pui C-H, Evans W E (2006) Treatment of acute lymphoblastic leukemia. *N Engl J Med* 354(2):166-178.

Ducker, G. S. et al. Reversal of Cytosolic One-Carbon Flux Compensates for Loss of the Mitochondrial Folate Pathway. Cell Metab 23, 1140-1153 (2016).

Lamarre, S. G. et al. An isotope-dilution, GC-MS assay for formate and its application to human and animal metabolism. Amino Acids 46, 1885-1891 (2014).

Lu, W. et al. Metabolomic Analysis via Reversed-Phase Ion-Pairing Liquid Chromatography Coupled to a Stand Alone Orbitrap Mass Spectrometer. Anal. Chem. 82, 3212-3221 (2010).

Clasquin, M. F., Melamud, E. & Rabinowitz, J. D. LC-MS Data Processing with MAVEN: A Metabolomic Analysis and Visualization Engine. (John Wiley & Sons, Inc., 2002). doi:10.1002/0471250953.bi1411s37

Ran, F. A. et al. Double nicking by RNA-guided CRISPR Cas9 for enhanced genome editing specificity. Cell 154, 1380-1389 (2013).

Ran, F. A. et al. Genome engineering using the CRISPR-Cas9 system. Nat Protoc 8, 2281-2308 (2013).

The invention claimed is:

1. A method for treating a hematological malignancy in a mammalian subject in need thereof, comprising administering to the subject an effective amount of a compound of Formula (I):

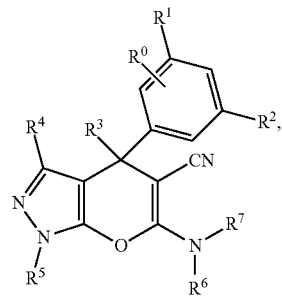

or a pharmaceutically acceptable salt thereof, wherein:

$R^0$, $R^1$ and $R^2$ are each independently selected from the group consisting of —H, halogen, hydroxyl, nitro, nitrile, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)R^{12}$, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl, and substituted or unsubstituted haloalkoxy; provided that, at least one of $R^0$, $R^1$ and $R^2$ is selected from the group consisting of substituted or unsubstituted alkenyl, and substituted or unsubstituted alkynyl;

$R^3$ is selected from the group consisting of —H, halogen, hydroxyl, nitro, nitrile, —$SOR^{11}$, —$S(O)_2R^{11}$, —$S(O)_2NR^{10}R^{12}$, —$OR^{11}$, —$OC(O)R^{12}$, —$C(O)OR^{12}$, —$C(O)R^{11}$, —$C(O)NR^{10}R^{12}$, —$NR^{10}R^{12}$, —$N(R^{12})C(O)R^{11}$, —$NS(O)_2R^{12}$, substituted or unsubstituted alkyl, substituted or unsubstituted cycloalkyl, substituted or unsubstituted heterocyclyl, substituted or unsubstituted aryl, substituted or unsubstituted heteroaryl, substituted or unsubstituted arylalkyl, substituted or unsubstituted heteroarylalkyl, substituted or unsubstituted haloalkyl, and substituted or unsubstituted haloalkoxy;

$R^4$ is selected from the group consisting of —H, substituted or unsubstituted alkyl, substituted or unsubstituted cycloalkyl, substituted or unsubstituted aryl, substituted or unsubstituted heteroaryl, substituted or unsubstituted arylalkyl, and substituted or unsubstituted heteroarylalkyl;

$R^5$, $R^6$ and $R^7$ are each independently selected from the group consisting of —H, —$C(O)R^{11}$, substituted or unsubstituted alkyl, substituted or unsubstituted cycloalkyl, substituted or unsubstituted aryl, substituted or unsubstituted heteroaryl, substituted or unsubstituted arylalkyl, and substituted or unsubstituted heteroarylalkyl; or $R^5$ is selected from any of the foregoing and $R^6$ and $R^7$ taken together with the nitrogen atom to which they are attached form a substituted or unsubstituted 3-6 membered ring;

each occurrence of $R^{11}$ is independently selected from the group consisting of substituted or unsubstituted alkyl, substituted or unsubstituted cycloalkyl, substituted or unsubstituted heterocyclyl, substituted or unsubstituted aryl, and substituted or unsubstituted heteroaryl; and each occurrence of $R^{10}$ and $R^{12}$ is independently selected from the group consisting of —H, substituted or unsubstituted alkyl, substituted or unsubstituted cycloalkyl, substituted or unsubstituted heterocyclyl, substituted or unsubstituted aryl, and substituted or unsubstituted heteroaryl.

2. The method according to claim 1, wherein the compound is a compound of formula (II):

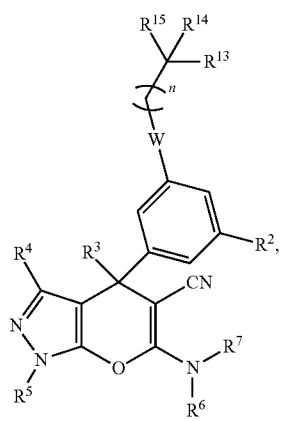

(II)

or a pharmaceutically acceptable salt thereof, wherein:

W represents —CR$^{16}$═CR$^{16}$— or —C≡C—;

n is 0, 1, 2, 3, or 4;

$R^{13}$, $R^{14}$, and $R^{15}$ are independently selected from the group consisting of hydrogen, —OH, halogen, optionally substituted alkyl, optionally substituted haloalkyl, —OR$^a$, —OC(O)R$^b$, —C(O)NR$^a$R$^b$, and —NR$^a$R$^b$; or $R^{13}$ and $R^{14}$ together with the atom to which they are attached form a 4-7 membered heterocyclic ring comprising 1 or 2 heteroatoms selected from the group consisting of NR$^a$, O, S, SO, or SO$_2$; wherein the heterocyclic ring is optionally substituted with one or more substituents independently selected from the group consisting of oxo and optionally substituted alkyl; and $R^{16}$, R$^a$ and R$^b$, independently at each occurrence, are H or optionally substituted alkyl.

3. The method according to claim 2, wherein W is —C≡C—.

4. The method according to claim 2, wherein $R^{13}$, $R^{14}$, and $R^{15}$ are independently selected from the group consisting of hydrogen, —OH, halogen, optionally substituted alkyl, optionally substituted haloalkyl, —OR$^a$, —OC(O)R$^b$, —C(O)NR$^a$R$^b$, and —NR$^a$R$^b$, wherein R$^a$ and R$^b$, independently at each occurrence, are H or optionally substituted alkyl.

5. The method according to claim 1, wherein the compound is a compound of formula (III):

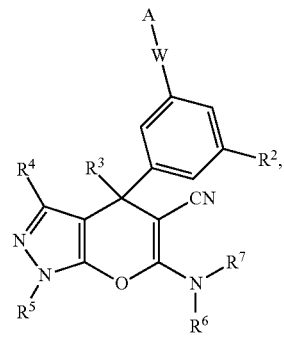

(III)

or a pharmaceutically acceptable salt thereof, wherein:

W represents —CR$^{16}$═CR$^{16}$— or —C≡C—;

$R^{16}$ is H or optionally substituted alkyl; and

A represents optionally substituted aryl or optionally substituted heteroaryl.

6. The method according to claim 5, wherein W is —C≡C—.

7. The method according to claim 5, wherein A is aryl, optionally substituted with one or more substituents independently selected from the group consisting of —OH, halogen, optionally substituted alkyl, optionally substituted haloalkyl, —OR$^a$, —OC(O)R$^b$, —C(O)NR$^a$R$^b$, and —NR$^a$R$^b$, wherein R$^a$ and R$^b$, independently at each occurrence, are H or optionally substituted alkyl.

8. The method according to claim 7, wherein A is phenyl, optionally substituted with one or more substituents independently selected from the group consisting of —CH$_2$OH, —OH, —CF$_3$, —COOH, —F, —CH$_2$NH$_2$, —CONH$_2$, and —NH$_2$.

9. The method according to claim 5, wherein A is heteroaryl, optionally substituted with one or more substituents independently selected from the group consisting of —OH, halogen, optionally substituted alkyl, optionally substituted haloalkyl, —OR$^a$, —OC(O)R$^b$, —C(O)NR$^a$R$^b$, and —NR$^a$R$^b$, wherein R$^a$ and R$^b$, independently at each occurrence, are H or optionally substituted alkyl.

10. The method according to claim 9, wherein A is an optionally substituted heteroaryl containing 1-4 N atoms.

11. The method according to claim 2, wherein:

$R^2$ is nitro, —F, —Cl, —OCH$_3$, —CCl$_3$, or —CF$_3$;

$R^3$ is selected from the group consisting of isopropyl, cyclopropyl, and cyclobutyl;

$R^4$ is methyl or isopropyl; and $R^5$, $R^6$ and $R^7$ are each independently selected from the group consisting of —H, alkyl, phenyl, and —COCH$_3$.

12. The method according to claim 1, wherein:

$R^0$ is —H;

one of $R^1$ and $R^2$ is substituted or unsubstituted alkenyl, or substituted or unsubstituted alkynyl; the other is independently selected from the group consisting of —H, halogen, hydroxyl, nitro, nitrile, —OR$^{11}$, substituted or unsubstituted alkyl, substituted or unsubstituted alkenyl, substituted or unsubstituted alkynyl, substituted or unsubstituted haloalkyl, or substituted or unsubstituted haloalkoxy;

$R^3$ is selected from the group consisting of isopropyl, cyclopropyl, and cyclobutyl;

$R^4$ is methyl or isopropyl; and $R^5$, $R^6$ and $R^7$ are each independently selected from the group consisting of —H, alkyl, phenyl, and —COCH$_3$.

13. The method according to claim 1, wherein:
$R^0$ is —H;
one of $R^1$ and $R^2$ is substituted or unsubstituted alkenyl or substituted or unsubstituted alkynyl; the other is independently selected from the group consisting of —H, methoxy, fluoro, chloro, bromo, hydroxyl, nitro, nitrile, substituted or unsubstituted alkyl, —CCl$_3$, and —CF$_3$;
$R^3$ is cyclobutyl or iso-propyl;
$R^4$ is methyl;
$R^5$ and $R^6$ are each independently selected from the group consisting of —H, alkyl, and phenyl; and
$R^7$ is —H.

14. The method of claim 1, wherein the compound is represented by the following structural formula:

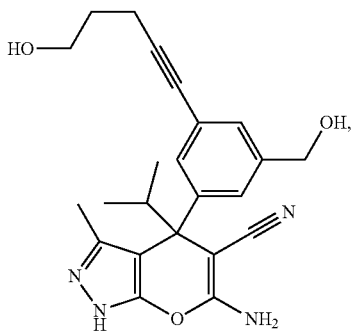

or a pharmaceutically acceptable salt thereof.

15. The method of claim 1, wherein the hematological malignancy is a pediatric leukemia, adult leukemia, or lymphoma.

16. The method of claim 1, wherein the mammalian subject is a human subject.

17. The method of claim 1, wherein the hematological malignancy is a leukemia.

18. The method of claim 17, wherein the leukemia is acute lymphoblastic leukemia (ALL), acute myelogenous leukemia (AML), chronic lymphocytic leukemia (CLL), chronic myelogenous leukemia (CIVIL) or acute monocytic leukemia (AMoL).

19. The method of claim 1, wherein the hematological malignancy is a B-cell lymphoma.

20. The method of claim 19, wherein the B-cell lymphoma is a diffuse large B-cell lymphoma, Burkitt lymphoma, follicular lymphoma, marginal zone B-cell lymphoma, extranodal marginal zone lymphoma, mucosa-associated lymphatic tissue lymphoma, small lymphocytic lymphoma, or mantle cell lymphoma.

21. The method of claim 1, wherein the hematological malignancy is a T-cell lymphoma.

22. The method of claim 1, wherein the hematological malignancy is a NK-cell lymphoma.

* * * * *

UNITED STATES PATENT AND TRADEMARK OFFICE
CERTIFICATE OF CORRECTION

PATENT NO. : 10,584,132 B2
APPLICATION NO. : 16/103375
DATED : March 10, 2020
INVENTOR(S) : Joshua D. Rabinowitz et al.

Page 1 of 1

It is certified that error appears in the above-identified patent and that said Letters Patent is hereby corrected as shown below:

In the Claims

In Claim 18, Column 166, Lines 11-12, delete:
"chronic myelogenous leukemia (CIVIL)"
And insert:
-- chronic myelogenous leukemia (CML) --

Signed and Sealed this
Nineteenth Day of May, 2020

Andrei Iancu
*Director of the United States Patent and Trademark Office*